(12) United States Patent
Morag et al.

(10) Patent No.: US 7,809,584 B2
(45) Date of Patent: Oct. 5, 2010

(54) MESSAGE AND PROGRAM SYSTEM SUPPORTING COMMUNICATION

(75) Inventors: Assaf Morag, Palo Alto, CA (US); Gary Gannot, El Cerrito, CA (US); Ofir Baharav, Ramat-Sharon (IL)

(73) Assignee: McKesson Information Solutions LLC, Alpharetta, GA (US)

( * ) Notice: Subject to any disclaimer, the term of this patent is extended or adjusted under 35 U.S.C. 154(b) by 915 days.

(21) Appl. No.: 11/526,205

(22) Filed: Sep. 21, 2006

(65) Prior Publication Data
US 2007/0124173 A1 May 31, 2007

Related U.S. Application Data

(63) Continuation of application No. 09/394,341, filed on Sep. 13, 1999, now abandoned.

(51) Int. Cl.
G06Q 10/00 (2006.01)
G06Q 99/00 (2006.01)
(52) U.S. Cl. .................. 705/2; 705/3; 705/51
(58) Field of Classification Search .............. 705/2, 705/3, 51
See application file for complete search history.

(56) References Cited

U.S. PATENT DOCUMENTS

| | | | |
|---|---|---|---|
| 4,491,725 A | 1/1985 | Pritchard | |
| 4,513,382 A | 4/1985 | Faulkner, Jr. | |
| 4,873,687 A | 10/1989 | Breu | |
| 5,255,187 A | 10/1993 | Sorensen | |
| 5,277,188 A | 1/1994 | Selker | |
| 5,301,105 A | 4/1994 | Cummings, Jr. | |
| 5,469,353 A | 11/1995 | Pinsky et al. | |
| 5,542,420 A | 8/1996 | Goldman et al. | |

(Continued)

FOREIGN PATENT DOCUMENTS

EP  0 591 439 B1  3/1999

(Continued)

OTHER PUBLICATIONS

David Pryor, *It takes a "health" village on the Internet*, Health Management Technology, Feb. 1997, one page.

(Continued)

*Primary Examiner*—Gerald J. O'Connor
*Assistant Examiner*—Maroun Kanaan
(74) *Attorney, Agent, or Firm*—Alston & Bird LLP

(57) ABSTRACT

A method is provided for facilitating messaging upon a network involving a physician(s), a patient(s) and a workflow engine. Each physician and patient may operate a computer for receiving/sending messages upon the network. The workflow engine may also access the network for receiving/sending messages. The method may include using a first medical message wizard by the patient on a computer, a medical profiler process performed by the workflow engine and a second medical message wizard usable by a first physician on a computer. Additionally, a service provider(s) and a client(s) may operate a computer for receiving/sending messages upon the network and a service-flow engine may access the network for receiving/sending messages. The method may further include using a first service message interface by the client on a computer, a service profiler process performed by the service-flow engine and a second service message interface usable by a first service provider.

62 Claims, 86 Drawing Sheets

U.S. PATENT DOCUMENTS

| | | | |
|---|---|---|---|
| 5,594,638 | A | 1/1997 | Iliff |
| 5,619,991 | A | 4/1997 | Sloane |
| 5,630,125 | A | 5/1997 | Zellweger |
| 5,660,176 | A | 8/1997 | Iliff |
| 5,666,492 | A | 9/1997 | Rhodes et al. |
| 5,711,297 | A | 1/1998 | Iliff |
| 5,724,968 | A | 3/1998 | Iliff |
| 5,737,539 | A | 4/1998 | Edelson et al. |
| 5,748,907 | A | 5/1998 | Crane |
| 5,758,095 | A | 5/1998 | Albaum et al. |
| 5,797,515 | A | 8/1998 | Liff et al. |
| 5,823,948 | A | 10/1998 | Ross, Jr. et al. |
| 5,825,881 | A | 10/1998 | Colvin, Sr. |
| 5,845,255 | A | 12/1998 | Mayaud |
| 5,851,182 | A | 12/1998 | Sahadevan |
| 5,868,669 | A | 2/1999 | Iliff |
| 5,890,129 | A | 3/1999 | Spurgeon |
| 5,897,493 | A | 4/1999 | Brown |
| 5,911,687 | A | 6/1999 | Sato et al. |
| 5,987,480 | A | 11/1999 | Donohue et al. |
| 5,991,731 | A | 11/1999 | Colon et al. |
| 6,006,191 | A | 12/1999 | DiRienzo |
| 6,014,631 | A | 1/2000 | Teagarden et al. |
| 6,039,688 | A | 3/2000 | Douglas |
| 6,112,247 | A | 8/2000 | Williams |
| 6,149,585 | A | 11/2000 | Gray |
| 6,154,444 | A | 11/2000 | Masuo et al. |
| 6,253,326 | B1 | 6/2001 | Lincke et al. |
| 6,256,613 | B1 | 7/2001 | Falchuk et al. |
| 6,302,844 | B1 | 10/2001 | Walker et al. |
| 6,330,491 | B1 | 12/2001 | Lion |
| 6,343,318 | B1 | 1/2002 | Hawkins et al. |
| 6,405,037 | B1 | 6/2002 | Rossmann |
| 6,493,427 | B1 | 12/2002 | Kobylevsky et al. |
| 6,584,445 | B2 | 6/2003 | Papageorge |
| 7,251,609 | B1 | 7/2007 | McAlindon et al. |
| 2001/0037219 | A1 | 11/2001 | Malik |
| 2002/0065682 | A1 | 5/2002 | Goldenberg |
| 2003/0018495 | A1 | 1/2003 | Sussman |
| 2003/0028399 | A1 | 2/2003 | Davis et al. |

FOREIGN PATENT DOCUMENTS

| | | |
|---|---|---|
| JP | 9-19467 | 9/1997 |
| WO | WO 95/29455 | 11/1995 |
| WO | WO 98/40835 | 9/1998 |
| WO | WO 98/41943 | 9/1998 |

OTHER PUBLICATIONS

Richard N. Shiffman, *Design and Implementation of a System for Computer-Assisted Telephone Triage in Pediatrics*, Fourteenth Annual Symposium on Computer Applications in Medical Care, A Conference of the American Medical Informatics Association, Nov. 4-7, 1990, pp. 826-830.

Hisakazu Ogura, Koji Yamamoto, Hiroshi Furutani, Yasuhiro Kitzaoe, Masahisa Hirakawa, Etsuro Sagara, *On-line Prescription Order and Prescription Support in an Integrated Hospital Information System*, Medical Informatics, Jan. 1985, vol. 10, No. 4, pp. 287-299.

http://www.netsys.com/firewalls/firewalls-9712/0445; The Intelligent Hacker's Choice: Systems, Networks, Administration since 1977; Re: Secure POP/IMAP; Michael W. Chalkley (mikech@avana.net); Tue, Dec. 16, 1997 10:56:50-0500.

www.mymd.com; Home • Contact • Feedback • Site Map • Search; Copyright © 1998-2003 Telemedicine Group, Inc. All rights reserved.

Notice of Panel Decision from Pre-Appeal Brief Review (Proceed to Board) mailed Mar. 8, 2010 in connection with related U.S. Appl. No. 11/525,521, filed Sep. 21, 2006.

Final Office Action mailed Aug. 5, 2009 in connection with related U.S. Appl. No. 11/525,521, filed Sep. 21, 2006.

Notice of Panel Decision from Pre-Appeal Brief Review (Re-Open Prosecution) mailed Jul. 21, 2009 in connection with related U.S. Appl. No. 11/525,521, filed Sep. 21, 2006.

Final Office Action mailed Apr. 3, 2009 in connection with related U.S. Appl. No. 11/525,521, filed Sep. 21, 2006.

Office Action mailed Oct. 17, 2008 in connection with related U.S. Appl. No. 11/525,521, filed Sep. 21, 2006.

Final Office Action mailed Mar. 2, 2010 in connection with related U.S. Appl. No. 10/359,414, filed Feb. 5, 2003.

Office Action mailed Sep. 2, 2009 in connection with related U.S. Appl. No. 10/359,414, filed Feb. 5, 2003.

Office Action mailed Mar. 4, 2009 in connection with related U.S. Appl. No. 10/359,414, filed Feb. 5, 2003.

Advisory Action mailed Dec. 15, 2008 in connection with related U.S. Appl. No. 10/359,414, filed Feb. 5, 2003.

Final Office Action mailed Aug. 20, 2008 in connection with related U.S. Appl. No. 10/359,414, filed Feb. 5, 2003.

Office Action mailed Dec. 31, 2007 in connection with related U.S. Appl. No. 10/359,414, filed Feb. 5, 2003.

Office Action mailed Nov. 24, 2009 in connection with related U.S. Appl. No. 10/017,165, filed Dec. 14, 2001.

Final Office Action mailed Jun. 8, 2009 in connection with related U.S. Appl. No. 10/017,165, filed Dec. 14, 2001.

Office Action mailed Jan. 20, 2008 in connection with related U.S. Appl. No. 10/017,165, filed Dec. 14, 2001.

Office Action (Restriction Requirement) mailed Mar. 24, 2006 in connection with related U.S. Appl. No. 09/937,364, filed Sep. 21, 2001 (Application abandoned).

Office Action mailed Mar. 21, 2006 in connection with related U.S. Appl. No. 09/394,341, filed Sep. 13, 2999 (Application abandoned).

Final Office Action mailed Sep. 23, 2003 in connection with related U.S. Appl. No. 09/394,341, filed Sep. 13, 2999 (Application abandoned).

Office Action mailed Apr. 3, 2003 in connection with related U.S. Appl. No. 09/394,341, filed Sep. 13, 2999 (Application abandoned).

"Merck-Medco Announces Interactive Web Site," News Release, Oct. 27, 1998.

"Merck-Medco and Physicians' Online Pilot New Suite of Internet Applications to Facilitate Physician and Pharmacist Communications at the Point of Prescribing," Business Wire, Oct. 22, 1999.

Kenneth D. Mandl, Issac S. Kohane, and Allan M. Brandt; Electronic Patient-Physician Communication: Problems and Promise; Annals of Internal Medicine; Sep. 15, 1998.

Xin Li, Daniel J. Valentino, George J. So, Robert Lufkin, Ricky K. Taira; *A World Wide Web Telemedicine System*; Proceedings of the SPIE; vol. 2711; Feb. 13, 1996.

"The Cornwall Dermatology Electronic Referral and Image Transfer Project," Journal of Telemedicine and Telecare, J. Telemed. Telcare UK, vol. 5, Suppl. 1, pp. 85-86.

Silvia Miksch, Kenneth Cheng, Barbara Hayes-Roth, "An Intelligent Assistant for Patient Health Care," Proceedings of the First International Conference on Autonomous Agents, pp. 458-465.

John M. Herron and Howard Yonas, "A Multi-Location, Teleradiology System for Emergency Triage Consultation," Proceedings of the SPIE—The International Society for Optical Engineering, Proc. SPIE—Int. Soc. Opt. Eng. (USA), vol. 2711, pp, 408-414.

Catherine C. Marshall and Frank M. Shipman III, "Spatial Hypertext and the Practice of Information Triage," Eighth ACM Conference on Hypertext and the Practice of Information Triage, Hypertext 1997, pp. 124-133.

Hong-Mei Chen and David Y.Y.Yun, "High-Performance Telemedicine Information Management," Journal of Parallel and Distributed Computing, vol. 56, No. 3, pp. 235-250.

Claims Triage [insurance claims overpayments], Best's Review-Property/Casualty Insurance Edition, Mar. 1999, vol. 99, No. 11, pp. 105-106.

"Claims Triage," Best's Review—Life/Health Insurance Edition, Feb. 1999, vol. 99, No. 10, pp. 81-82.

"Prioritizing Patients for Intensive Care: Triage With Analytic Hierarchy Process Model," 1997 Proceedings Decision Sciences Institute, 1997 28th Annual Meeting, vol. 2, pp. 958-960.

Naoki Ohboshi, Hisayuki Masui, Yahiko Kambayashi, Takashi Takahashi, "A Study of Medical Emergency Workflow," Computer Methods and Programs in Biomedicine, vol. 55, No. 3, pp. 177-190.

James R. Warren, "Better, More Cost-Effective Intake Interviews," IEEE Intelligent Systems, vol. 13, No. 1, pp. 40-48.

Alejandro Pazos Sierra and Antonio Blanco Ferro, "Mestriman: An Expert System for Medical Triage and Clinical Management of Patients in Catastrophes," Expert Systems with Applications, vol. 6, No. 4, pp. 449-457.

T. Timpka and T. Buur, "Medical Reasoning and Patient Requests in Decision-Making for Female Genitourinary Infections," Methods of Information in Medicine, vol. 30, No. 3, pp. 215-220.

B. Iiuet, C. Rollands and J. Martin, "A Methodology for Information Analysis of Emergency and Triage Units in Hospital Information Systems," Medical Informatics, vol. 8, No. 4, pp. 255-264.

Thomas P. Landau and Robert S. Ledley, "Decision Theory Model of the Emergency Medical Triage Process," Computers in Biology and Medicine, vol. 12, No. 1, pp. 27-42.

H.R. Oldfield, Jr. "Automated Multiphasic Health Testing: A Diagnosis in Three Parts," Journal of Clinical Engineering, vol. 3, No. 2, pp. 113-117.

Allen R. Wenner, M.D., "Electronic Patient Record. Decision Support in the Waiting Room," Toward an Electronic Patient Record 1997. Conference and Exposition Proceedings in Nashville, TN, Apr. 26-May 3, 1997, vol. 3, pp. 240-241.

Martin R. Stytz, Sheila B. Banks, Brina W. Garcia and Gayl M. Godsell-Stytz, "Distributed Virtual Environment for Emergency Medical Training," Proceedings of the SPIE—The International Society for Optical Engineering, Proc. SPIE—Int. Soc. Opt. Eng. (USA), vol. 3085, pp. 174-184.

Dr. Gerald Pitts, "Virtual Reality: Triage Training Extraordinaire," Simulators International XII. Proceedings of the 1995 Simulation Multi Conference, pp. 332-337.

Yadin David, "TeleHealth: Current Practices and Future Directions," Proceedings of the SPIE—The International Society for Optical Engineering, Proc. SPIE—Int. Soc. Opt. Eng. (USA), vol. 2618, pp. 2-8.

Audrie C. M. Dumay, "Triage Simulation in a Virtual Environment," Interactive Technology and the New Paradigm for Healthcare Medicine Meets Virtual Reality III Proceedings, pp. 101-111.

Robert B. Fraser, Ph.D., "An Expert System for the Diagnosis, Treatment, and Triage of Head Injuries in Remote Environments," Medical Informatics Europe 1991 Proceedings, pp. 275-279.

Michael M. Laks, M.D., Charles B. Cairns, M.D., and Harry P. Selker, M.D., "An on-line Computerized ECG Program for the Prediction of Acute Ischemic Heart Disease," Proceedings Computers in Cardiology, Jerusalem, Israel, Sep. 19-22, 1989, (Cat. No. 89CH2932-2) pp. 505-508.

M. Michael Shabot, M.D., Mark Lobue, B.A., Beverly J. Leyerle, R.N., "Use of Automatic Computerized Intensity-Intervention Scores to Measure the Appropriateness of ICU Utilization," Proceedings of the Eleventh Annual Symposium on Computer Applications in Medical Care, 1987, (Cat. No. 87CH2446-3) pp. 671-675.

Charles L. Rogerson, Ph.D., "Towards a Case-Mix Information System for the Emergency Department," Proceedings of the Eighth Annual Symposium on Computer Applications in Medical Care, Sep. 1984, (Cat. No. 84CH2090-9) pp. 514-517.

William J. Sacco, Ph.D., Howard R. Champion, M.D., "The Application of Computer-Based Techniques to the Development of Injury Severity Indices," Proceedings of the Fifth Annual Symposium on Computer Application in Medical Care, 1981, pp. 989-993.

Bruce F. Berg, "Examining Models for Coordinating Health-Care to the Elderly," Computers, Environment and Urban Systems, vol. 6, No. 2, pp. 97-109.

Thomas E. Miller and Scott Reents, "The Health Care Industry in Transition. The Online Mandate to Change," Internet Strategies Group, Cyber Dialogue Inc., Jul. 1998, pp. 1-17.

Stephen J. Denelsky, "e-health Getting Connected in a Digital Age," Health Care Information Services, Oct. 1998, pp. 1-41.

"ProxyMed Partners With Renaissance Interactive to Develop Physician Office Web Portal on Microsoft Platform," Excite News, Jun. 1999, one page.

"Synetic Announces Two Key Agreements," www.newsalert.com, Business Wire, May 1999, two pages.

H. Moreland, R.N., M. Johnston, and D. Sharp, "Demonstration of the Tele-Triage System (C) a Microcomputer-Based Telephone Triage Program for Use by R.N.'s in Ambulatory Care Settings or Physicians' Offices," Proceedings of the Sixth Annual Symposium on Computer Applications in Medical Care, 1982, p. 637.

S.B. Henry, R.N., J.G. Schreiner, M.A., D. Borchelt, R.N. and M.A. Musen, M.D., "A Needs Analysis for Computer-Based Telephone Triage in a Community AIDS Clinic," Sixteenth Annual Symposium on Computer Applications in Medical Care, Nov. 8-11, pp. 59-63.

Christina A. Van Hoorebeke, "Implementation of an After-Hours Triage and Utilization Control System," Proceedings of the Twentieth Hawaii International Conference on System Sciences 197, 1987, vol. 3, pp. 201-204.

Margaret Sabin, "Telephone Triage Improves Demand Management Effectiveness," Healthcare Financial Management, Aug. 1998, vol. 52, No. 8, pp. 49-51.

Larry Frisch, M.D. and Allen R. Wenner M.D., Automated Telephone Interviewing to Improve Health Care Access, Proceedings Toward an Electronic Patient Record 1996, Twelfth International Symposium on the Creation of Electronic Health Record System and Global Conference on Patient Cards, part vol. 2, pp. 529-535, vol. 2.

Robert C. Beveridge, MD, "ED and Ambulatory Database: a Canadian Perspective," Proceedings Toward an Electronic Patient Record 1996. Twelfth International Symposium on the Creation of Electronic Health Record System and Global Conference on patient Cards, part 1, vol. 1, p. 164.

Final Office Action mailed Jun. 1, 2010 in connection with related U.S. Appl. No. 11/525,521, Filed Sep. 21, 2006.

Final Office Action mailed May 25, 2010 in connection with related U.S. Appl. No. 10/017,165, filed Dec. 14, 2001.

Advisory Action mailed Jun. 16, 2010 in connection with related U.S. Appl. No. 10/359,414, filed Feb. 5, 2003.

Prior U.S. Appl. No. 09/394,341, filed Sep. 13, 1999 (abandoned).

ver. 12

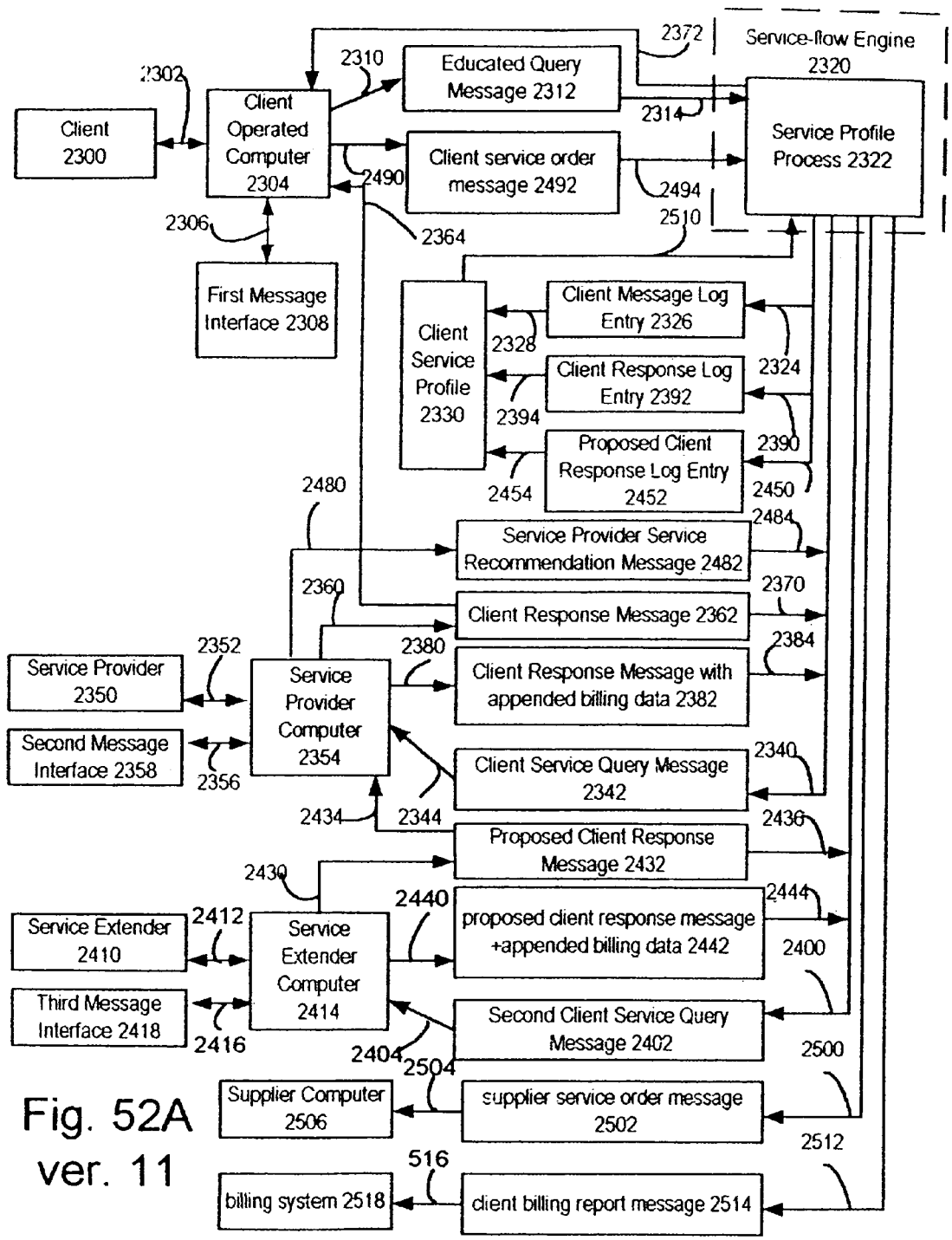
Fig. 52A ver. 11 ver. 2

MESSAGE AND PROGRAM SYSTEM SUPPORTING COMMUNICATION

This application is a continuation of U.S. patent application Ser. No. 09/394,341, filed Sep. 13, 1999, which is herein incorporated by reference in its entirety for all purposes.

TECHNICAL FIELD

This invention relates to a messaging communication method and program system supporting communication between patients and physicians, physician extenders including nurses, and the ordering of prescriptions, alternatively supporting communication between clients, service providers, service extenders including service assistants and the ordering of services.

DESCRIPTION OF THE PRIOR ART

FIG. 1 depicts prior art human-computer interfaces capable of supporting messaging upon communications networks. One exemplary prior art computer system includes a display screen 2 in an enclosure 4, audio speakers 6 and 8, a second enclosure 10 housing a removable media drive 12. Keyboard 14 is interfaced via physical transport mechanism 16 to the computer. Selector device 18 is interfaced via physical transport mechanism 20 to the computer. Audio microphone 22 is interfaced via physical transport mechanism 24 to the computer. The computer system interfaces via physical transport mechanism 30 to network 32.

Certain exemplary prior art handheld computer interfaces are often single enclosures 40 incorporating a miniature display screen 42 with buttons 44 and a pointing device 46. The computer enclosure 40 is often held in one hand, while the pointing device 46 is held with the other hand. Wireless communications port 48 can both transmit 50 signals and receive 38 signals transmitted by wireless transceiver interface 36, which interfaces to network 32 via physical transport mechanism 34. Other exemplary uses of such devices include mounting enclosure 40 on a wrist- or arm-band, thus freeing one hand.

Other exemplary prior art computer systems include but are not limited to devices incorporating one or more audio speakers such as 6 or 8, at least one audio microphone 22, which may or may not possess a display screen 2, but often possess a miniature display screen 42 and often several buttons 44 or keyboard 14. Cellular telephones, both hand held and vehicle-mounted, possessing all these features are readily available connecting to either local wireless networks or larger national and international networks, in some cases through orbiting satellite transceivers 36, which use separate carriers 34 to further interface to ground base stations which provide high bandwidth gateways to large Wide Area Networks (WANs), including the Internet and the World Wide Web.

These exemplary devices are often capable of receiving messages, such as e-mail and paging messages. Many of these exemplary devices are capable of audio exchanges in a fashion similar to a telephone with a telephone messaging center. Many of these exemplary devices may further support the loading and adding of programs to provide upgraded services and new service capabilities. Many of these systems possess the ability to retain such loaded or added programs after the power to the module has been turned off.

Such devices have been used to further provide a communication avenue between patients and physicians, through email and paging-style messages. Paging a doctor with a short message such as "Water has broken" may give an adequate portrayal of some situations such as the imminence of labor in childbirth. However, such a messaging system could not adequately portray the circumstances regarding a potential breach birth.

Traditional telephones have often been used to permit a physician and patient to communicate. However, there are problems with such devices. Telephones without answering or message centers require that both patient and physician be available at essentially the same time, which is often difficult to arrange. Telephones, even with messaging centers, still have problems. Often the stored messages are short in duration. Even when the messages may be quite long, patients do not tend to give concise, clear and complete verbal medical descriptions of exactly the relevant conditions needed to describe their medical condition. This leads to a situation of question and answers, often with the patient and/or doctor having to wait significant amounts of time between each "bounce" before there is enough information in front of the physician to respond with a consultation. Further, physicians must listen through their patients messages, often wasting time trying to sort through the words to determine the observed medical conditions. This is an inefficient use of the physicians' time.

Email exchanges between patients and physicians can provide greater amounts of information. However, there is a tendency to waste both patient and doctor time for several reasons. First, patients do not tend to write concise, clear and complete medical descriptions of exactly the relevant conditions needed to describe their medical condition. This is understandable, most people are not trained enough at medicine to know what a physician will need to know. This again leads to question and answer situations, often with the patient and doctor having to wait significant amounts of time between each "bounce" before there is enough information in front of the physician to respond with a consultation. Further, physicians must read what their patients have written, often wasting time trying to sort through the words to determine the observed medical conditions. This is an inefficient use of the physicians' time.

The devices mentioned above have also been used to further provide a communication avenue between clients and service providers for various kinds of service support, through email and paging-style messages. Brief messages such as "flat tire" may convey adequate information in some circumstances but would be fundamentally inadequate in situations based around mission critical technologies such as aircraft.

Consider a commonly occurring scenario in the airline industry. A technician in an isolated location finds an intermittent failure in testing a system possessing electromechanical, fluidic and airfoil control components, by way of example. The determination of the proper course of action involves decisions regarding each of these areas of the aircraft's technologists, combined with an understanding of the reliability history of the system involved and the relevant government and airline regulations. Client such as the local airport technician need access to high level, integrated service provider responses.

Traditional telephones have often been used to permit a service provider and client to communicate. However, there are problems with such devices. Telephones without answering or message centers require that both client and service provider be available at essentially the same time, which is often difficult to arrange or involve the clients waiting for extended periods of time "on hold". Telephones, even with messaging centers, still have problems. Often the stored messages are short in duration. Even when the messages may be quite long, clients do not tend to give concise, clear and complete verbal service descriptions of exactly the relevant conditions needed to describe their service condition. This leads to a situation of question and answers, often with the client and/or doctor having to wait significant amounts of time between each "bounce" before there is enough information in front of the service provider to respond with a consultation. Also, the expertise of the service providers may vary greatly, making the omission of specific questions possible, limiting the utility of the direct contact. Further, service providers must listen through their clients messages, often wasting time trying to sort through the words to determine the observed service conditions. This is an inefficient use of the service providers' time.

Email exchanges between clients and service providers can provide greater amounts of information. However, there is a tendency to waste both client and doctor time for several reasons. First, clients do not tend to write concise, clear and complete service descriptions of exactly the relevant conditions needed to describe their service condition. This is understandable, most people are not trained enough in the service area's technology to know what a service provider will need to know. This again leads to question and answer situations, often with the client and doctor having to wait significant amounts of time between each "bounce" before there is enough information in front of the service provider to respond with a consultation. Further, service providers must read what their clients have written, often wasting time trying to sort through the words to determine the observed service conditions. This is an inefficient use of the service providers' time.

FIG. 2 depicts a generic prior art block of a messaging communications system supporting the online ordering of prescriptions by physicians interacting with pharmacies. Email and other messaging systems have been used to provide a limited form of automation for the placing of prescription orders with various pharmacies possessing online message capabilities. Physician 100 interacts 102 with a physician-operated computer 104, which may be a desktop, notebook, or handheld computer, possibly embedded in a cellular telephone. The physician operated computer 104 sends a specialized message, a prescription ordering message, using physical transport mechanism 106 to a network 108, which is controlled and accessed 110 by network server 112. Network server 112 accesses 114 medical databases and patient database 116. Network server 112 then sends a specialized pharmaceutical order message to a pharmacy computer 120 which is linked 118 to the same network 110.

There is a central problem with such systems. The patient is not part of the interaction. The patient cannot choose whether to order the prescription. The patient cannot choose which pharmacy or where the pharmacy sends the prescription, or whether a traditional brick and mortar pharmacy is preferred. The patient cannot choose between different brands.

SUMMARY OF THE INVENTION

One aspect of this invention embodies a method of messaging upon a network involving at least one physician, at least one patient and a workflow engine. Each physician operates a computer, which from time to time is capable of receiving and sending messages upon the network at a corresponding address on the network. Each patient operates a computer, which from time to time, is capable of receiving and sending messages upon the network at a corresponding address on the network. The workflow engine accesses the network for receiving and sending messages upon the network using at least one workflow engine address on the network. The method comprises using a first medical message wizard by the patient on the patient operated computer, a medical profiler process performed by the workflow engine and a second medical message wizard by the first physician on the physician operated computer at the first corresponding physician address.

Using the first medical message wizard by the patient is further comprised of generating an educated query message and sending the educated query message to the medical profiler address. Performing the medical profiler process by the workflow engine is further comprised of receiving the educated query message at the medical profiler address; processing the received educated query message; generating a patient message log entry in a medical profile of the patient; generating a patient medical query message; sending the patient medical query message to a first physician with the corresponding physician address. Using the second medical message wizard by the first physician is further comprised of receiving the patient medical query message; processing the patient medical query message; generating a physician-viewable patient medical query message; and displaying a physician-viewable patient medical query message.

This embodiment of the invention has several advantageous characteristics: It minimizes the need for extensive typing for the patient. It decreases the need for message "ping-pong" between patient and physician due to insufficient information in the patient's messages to the physician. It allows the physician to read in an optimized format, which minimizes the physician's reading time. In many cases, the physician will not need to poll a chart pool, because the medical profile will cover the required information. There is no need for phone tag with patients.

A further aspect of this invention involves further embodiments of the first messaging wizard, medical profiler process and second messaging wizard. The second medical message wizard further comprises responding to the physician-viewable patient medical query message; generating a patient response message; sending the patient response message; and copying the patient response message with an appended physician billing data to the workflow engine. Responding to the physician-viewable patient medical query message creates a first-physician response. Generating a patient response message from the physician-viewable patient medical query message and the first-physician response. Sending the patient response message to the patient at the corresponding patient address.

The medical profiler process further comprises: receiving the copied patient response message with the appended physician billing data; processing the received, copied patient response message with the appended physician billing data; generating a patient response log entry in the medical profile of the patient. Processing the received, copied patient response message with the appended physician billing data creates a processed, received, copied patient response message with the appended physician billing data. The generating a patient response log entry in the medical profile of the patient is from the processed, received, copied patient response message with the appended physician billing data.

The first message wizard further comprises: receiving the patient response message; processing the received patient response message to create a processed, received patient response message; and displaying the processed, received patient response message.

This aspect of the invention is advantageous for several reasons. It supports the physician responding to the optimized educated query of the patient. It supports the automated logging of physician responses with billing information at the workflow engine. It supports the patient receiving the physician's response.

Further embodiments of this invention advantageously support the use of authentication keys insuring secure communications between patient and workflow engine, between patient and physician and between physician and workflow engine.

Further embodiments of this invention advantageously support physician extenders, including nurses, physician assistants and administrators.

Further embodiments of this invention advantageously support prescriptions involving, not only the physician, workflow engine and pharmacy, but also the patient. This is advantageous for several reasons. The patient takes part in the prescription-ordering interaction. The patient can choose whether to order the prescription. The patient can choose which pharmacy to purchase the prescription from. The patient can choose where the pharmacy sends the prescription. The patient can choose whether a traditional brick and mortar pharmacy is preferred. The patient can choose between different brands.

Another aspect of this invention embodies a computer program residing on a computer readable medium accessible by the patient operated computer capable of receiving patient response messages and sending messages to a workflow engine. It includes code for receiving the patient response message with an embedded prescription; code for displaying the received patient response message; code for responding to the patient response message; code for sending the patient prescription message to the workflow engine. The code for responding to the patient response message further includes code for generating a patient prescription message from the embedded prescription.

This aspect of the invention is advantageous for several reasons. The patient takes part in the prescription-ordering interaction. The patient can choose whether to order the prescription. The patient can choose which pharmacy to purchase the prescription from. The patient can choose where the pharmacy sends the prescription. The patient can choose whether a traditional brick and mortar pharmacy is preferred. The patient can choose between different brands.

Another aspect of this invention embodies a method of messaging upon a network involving at least one service provider, at least one client and a service-flow engine. Each service provider operates a computer, which from time to time is capable of receiving and sending messages upon the network at a corresponding address on the network. Each client operates a computer, which from time to time, is capable of receiving and sending messages upon the network at a corresponding address on the network. The service-flow engine accesses the network for receiving and sending messages upon the network using at least one service-flow engine address on the network. The method comprises using a first service message interface by the client on the client operated computer, a service profiler process performed by the service-flow engine and a second service message interface by the first service provider on the service provider operated computer at the first corresponding service provider address.

Using the first service message interface by the client is further comprised of generating an educated query message and sending the educated query message to the service profiler address. Performing the service profiler process by the service-flow engine is further comprised of receiving the educated query message at the service profiler address; processing the received educated query message; generating a client message log entry in a service profile of the client; generating a client service query message; sending the client service query message to a first service provider with the corresponding service provider address. Using the second service message interface by the first service provider is further comprised of receiving the client service query message; processing the client service query message; generating a service provider-viewable client service query message; and displaying a service provider-viewable client service query message.

This embodiment of the invention has several advantageous characteristics: It minimizes the need for extensive typing for the client. It decreases the need for message "ping-pong" between client and service provider due to insufficient information in the client's messages to the service provider. It allows the service provider to read in an optimized format, which minimizes the service provider's reading time. In many cases, the service provider will not need to poll a chart pool, because the service profile will cover the required information. There is no need for phone tag with clients.

A further aspect of this invention involves further embodiments of the first message interface, service profiler process and second message interface. The second service message interface further comprising responding to the service provider-viewable client service query message; generating a client response message; sending the client response message; and copying the client response message with an appended service provider billing data to the service-flow engine. Responding to the service provider-viewable client service query message creates a first-service provider response. Generating a client response message from the service provider-viewable client service query message and the first-service provider response. Sending the client response message to the client at the corresponding client address.

The service profiler process further comprises: receiving the copied client response message with the appended service provider billing data; processing the received, copied client response message with the appended service provider billing data; generating a client response log entry in the service profile of the client. Processing the received, copied client response message with the appended service provider billing data creates a processed, received, copied client response message with the appended service provider billing data. The generating a client response log entry in the service profile of the client is from the processed, received, copied client response message with the appended service provider billing data.

The first message interface further comprises: receiving the client response message; processing the received client response message to create a processed, received client response message; and displaying the processed, received client response message.

This aspect of the invention is advantageous for several reasons. It supports the service provider responding to the optimized educated query of the client. It supports the automated logging of service provider responses with billing information at the service-flow engine. It supports the client receiving the service provider's response.

Further embodiments of this invention advantageously support the use of authentication keys insuring secure communications between client and service-flow engine, between client and service provider and between service provider and service-flow engine.

Further embodiments of this invention advantageously support service extenders, including service assistants, service provider assistants and administrators.

Further embodiments of this invention advantageously supports service recommendations involving the service provider, service-flow engine and supplier, but also the client. This is advantageous for several reasons. The client takes part in the service recommendation-ordering interaction. The client can choose whether to order the service recommendation. The client can choose which supplier to purchase the service recommendation from. The client can choose where the supplier sends the service recommendation. The client can choose whether a traditional brick and mortar supplier is preferred. The client can choose between different brands.

Another aspect of this invention embodies a computer program residing on a computer readable medium accessible by the client operated computer capable of receiving client response messages and sending messages to a service-flow engine. It includes code for receiving the client response message with an embedded service recommendation; code for displaying the received client response message; code for responding to the client response message; code for sending the client service recommendation message to the service-flow engine. The code for responding to the client response message further includes code for generating a client service recommendation message from the embedded service recommendation.

This aspect of the invention is advantageous for several reasons. The client takes part in the service recommendation-ordering interaction. The client can choose whether to order the recommended service(s). The client can choose which supplier to purchase the recommended service(s) from. The client can choose where the supplier delivers the recommended service(s). The client can choose whether a traditional brick and mortar supplier is preferred. The client can choose between different brands.

These and other advantages of the present invention will become apparent upon reading the following detailed descriptions and studying the various figures of the drawings.

BRIEF DESCRIPTION OF THE DRAWINGS

FIG. 52A depicts an interactive flow between a client using a first message interface, service profiler performing a service profiler process and service provider using a second message interface in accordance with a further embodiment of the invention;

DETAILED DESCRIPTION OF THE INVENTION

Figure 1:
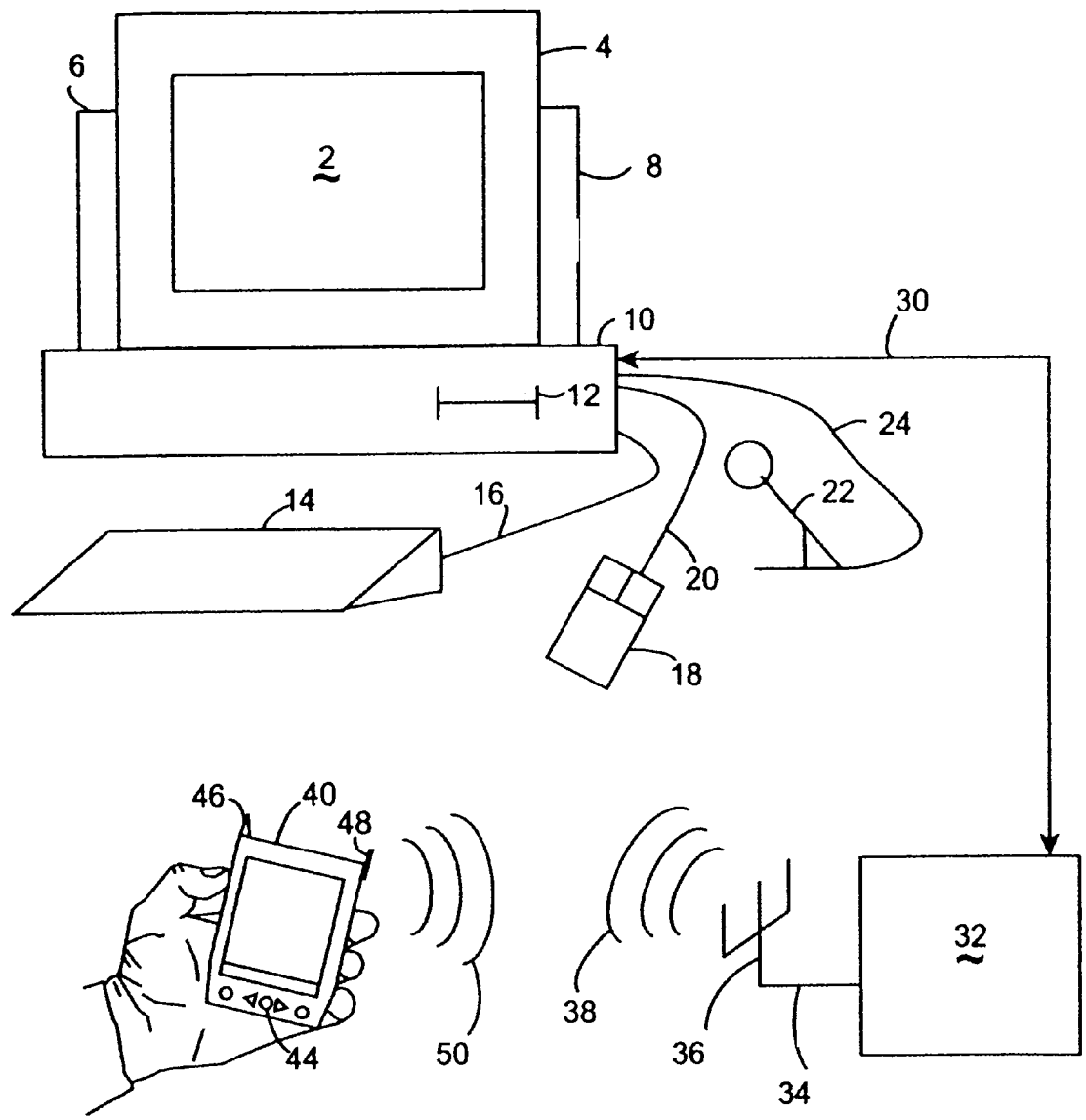
FIG. 1 depicts prior art human-computer interface capable of supporting messaging upon communications networks.
Figure 2:
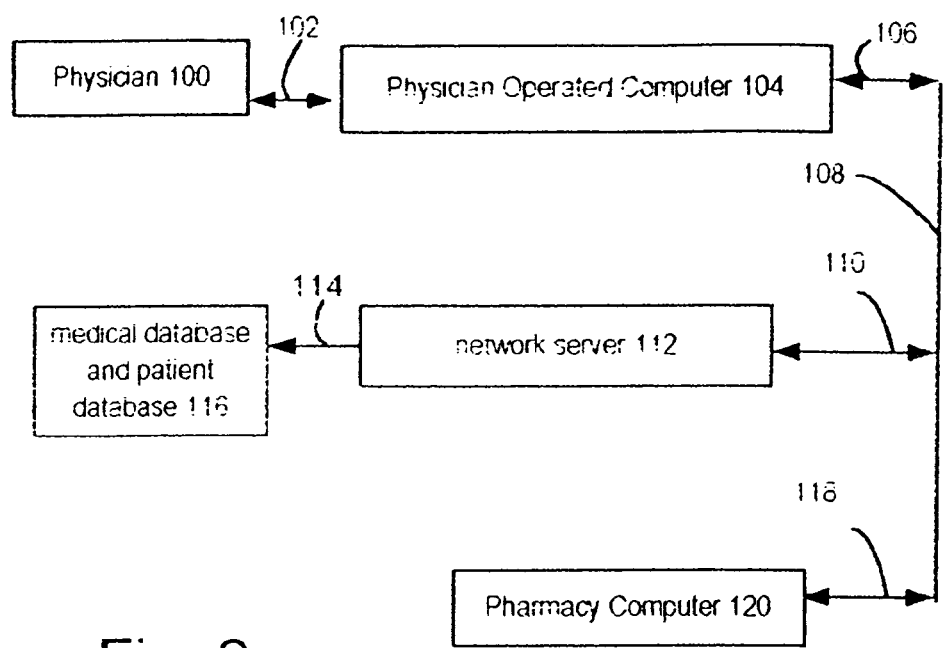
FIG. 2 depicts a generic prior art block of a messaging communications system supporting the online ordering of prescriptions by physicians interacting with pharmacies.

FIGS. 1 and 2 refer to prior art and were previously discussed in the Background of the invention.

Discussion of Primary Terms as Used Herein:

A message will refer to a communication session with a source and a destination whose contents can be described in a digital fashion. Examples of messages include but are not limited to phone mail, email and pager messages.

A medical profile of a patient is a collection of information residing in some computer accessible media which from time to time a computer may be able to access.

The medical profiler process is the system-wide activities which are performed in an automated fashion by the workflow engine to facilitate the medical communication between patients, physicians, physician extenders and pharmacies to support at least the following: medical queries, replies and transactions involved in prescriptions.

The workflow engine is the mechanism performing the collection of operations known as the medical profiler process. It has at least one address on the network shared with patients, physicians, physician extenders and pharmacies. Note that this shared network may in fact be partitioned into a collection of networks, each possessing gateways, firewalls and the like as is well known in the art. Note that the workflow engine may include but is not limited to one computer, and in fact, in certain embodiments preferably involves more than one server computer as will be discussed later.

A patient as used herein will have two components of meaning: the first component being the entity about whose health the medical profile, query messages, response message and prescriptions are directed; the second is the responsible adult acting for the patient in all the transactions, such as generating the query messages, receiving and considering the response messages and ordering the prescriptions. Note that a list of the first component entities includes but is not limited to pets, trees, children, the physically incapacitated, the mentally incapacitated and the emotionally incapacitated.

Figure 3A:
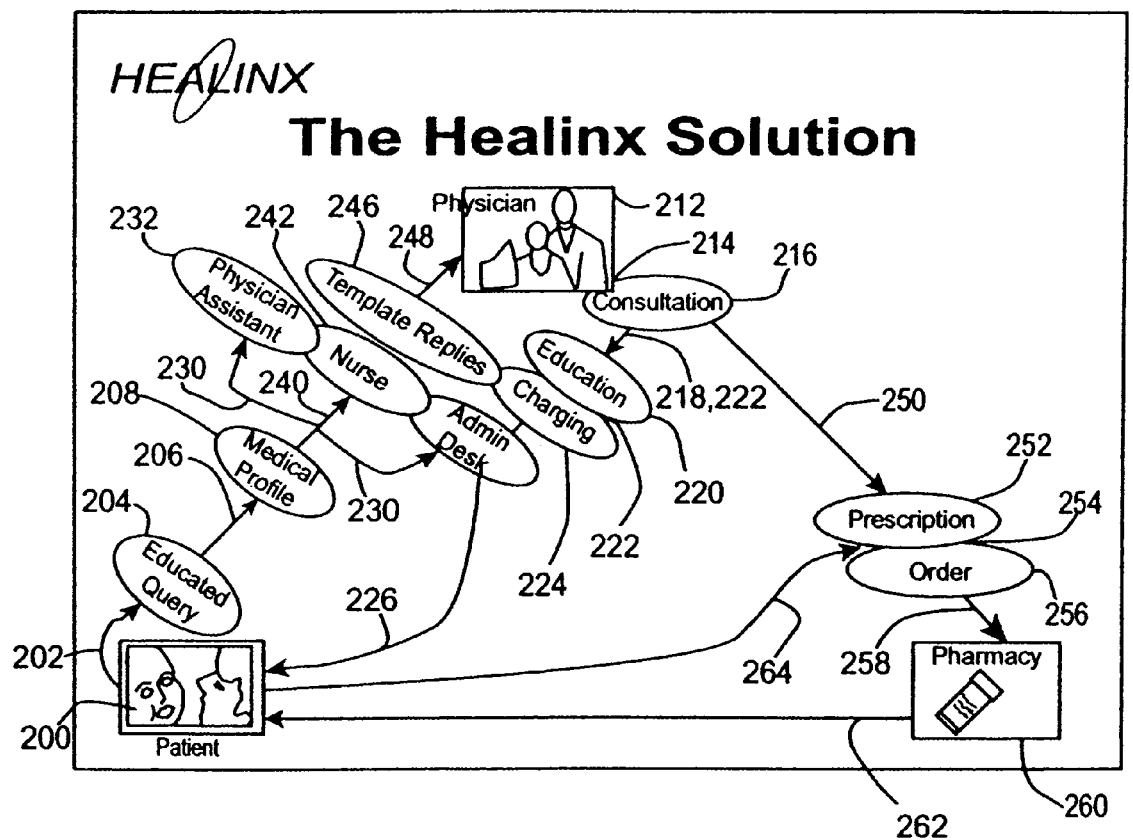
FIG. 3A depicts a flow diagram of an embodiment of the invention in accordance with certain embodiments.

FIG. 3A depicts a flow diagram of an embodiment of the invention in accordance with certain embodiments. There are two main flows of information likely to be prevalent with users of this invention. The most common flow would be a patient 200 initiate 202 query 204, where the patient will launch an electronic message 206. These messages can sub-categorized in four main groups-Request a refill, Schedule an appointment, Consult symptoms with the physician 212 and page the physician 212. The second possible flow is initiation of messages by the clinic/physician 212 aimed at broadcasting information to patients 200.

At the time of registration or post sending the first consultation/refill request the patient 200 is being asked to fill in his/her medical profile 208. Medical profile 208 would contain the patient 200's medication list, allergies, problems and demographics. The medical profile 208 is then validated by the patient 200's medical staff and is approved. Once approved the medical profile 208 is locked and the patient 200 may not alter the profile. The profile 208 is updated automatically by transactions made by the workflow engine or by the patient's medical staff. In the event that the patient 200 wants to edit the medical profile 208 then the patient initiates a query 204 to the medical staff informing them that the profile needs corrections. The medical staff can with one click approve the patient query 204 and update the profile 208.

FIG. 3A portrays the typical flow of a patient 200 initiated query 204. The patient 200 through the use of a wizard 202, initiates an educated query 204.

Using a problem-related database and knowledge of the patient medical profile 208, the application generates a problem specific questioner (form). This form is both problem and patient 200 specific. The form is advantageous in that it removes the need for a great deal of typing on behalf of the patient 200. It is further advantageous in decreasing the need for message ping pong between the patient 200 and the physician 212 due to insufficient data. It is further advantageous in allowing the physician 212 to read a more readable and intelligent format than that of a patient 200 free text waffle.

The next step in the flow of the message is attaching the summary of the patient medical record or as we call it 'medical profile' 208 to the message. The patient 200 initiates the medical profile at the point of registration to the workflow engine or at the time of the first refill/consult request. The patient 200 is asked by the workflow engine to fill in his/her medical profile i.e. problems allergies and medications. This medical profile 208 is interactive and will be later validated by the nurse 242 or physician 212. Once validated for the first time it is locked and the patient 200 can no longer tamper with the data. Any prescription 252 sent through the workflow engine automatically updates the medical profile 208. The patient 200 may add data to the 'locked' medical profile 208 but that data will not be embedded in the medical profile 208 prior to the physician 212 or his staff validating the new data. The workflow engine attaches the medical profile 208 to any patient related document thus avoids the need for a chart pull at the point of care, plus it allows the patient 200 to present the medical profile 208 to foreign physicians 21.2 when on the move.

The workflow engine then takes the message and the medical profile 208 attached and routes it to the proper physician extender according to the type of message sent. As an example, a refill messages would be routed to the nurse 242, an urgent scheduling query will also get to the nurse 242, a non-urgent query will be routed to the scheduling desk. This process allows the physician 212 to share the workload with his extenders.

Each member of the physician's staff can create his own canned replies 246. These are replies that were typed once by the staff were saved and may be pasted with two clicks to message bodies of future replies. With many physicians complaining about repetitious replies to their patients this tool allows both the saving of time and a reduction in typing need. The pasted 'canned replies' are then editable and customizable.

Once edited and filled by the medical staff the messages are routed to the physician 212 who in most cases needs to do nothing more then approve his staff's work and in a single click send the message to the patient 200. The physician 212 at this stage may determine a fee for the service and add educational material 220 and pointers (from a library) to sites of further patient education. The workflow engine notifies the patient 200 via regular e-mail (patient@aol.com) that a message is waiting for him in his Healinx inbox and provides an hyperlink to lead the patient 200 to his Healinx inbox.

The physician/physician extender may also prescribe medication and attach it to the outgoing message, this in turn checks the medication using a licensed database against the patient's medical profile for drug/drug, drug/allergy conflicts and alerts the physician. It also allows us to attach education material to the prescription alerting the patient 200 for possible side effects and actions that should or should not be taken with the prescribed medication. Education material 220 taken from the database is attached to the prescription and can be viewed by the patient 200.

The patient 200 reading the message views the embedded prescription and has the choice of ordering 264 the prescription in the pharmacy of his choice to be delivered from an online pharmacy 260 or to be picked up from his favorite brick and mortar traditional pharmacy 260. In addition in the event that the patient 200 is on the move then he may choose with a single click the closest pharmacy 260 and the prescription will be electronically shipped to that pharmacy 260 at no extra cost or hassle.

Physicians 212 may set the workflow engine to allow patient 200 paging, the message 204 typed by the patient 200 will be sent to the physician 212 over pager or phone. The physician 212 can then request 214 additional information such as the patient medical profile and initiate a call back 216 to the patient 200. The physician 212 may set up the times of day he willing to be accessible by pager and the pricing per beep dependant on the time of day.

Further embodiments of the invention support the workflow engine creating routing chains of physician extenders starting with a first physician extender proceeding through successor physician extenders until the routing chain terminates with a physician reviewing the collective proposed patient response. The routing chain may be generated by the workflow engine based upon the patient's educated query message.

Further embodiments of the invention support the workflow engine creating routing trees of physicians with patent query messages starting with a source list of physicians, possibly routing to intermediate physicians and culminating in a first physician who reviews the collective physician responses to their respective patient medical queries.

Using outsourced solutions, the patients 200 can monitor their readings of blood pressure, sugar level, or other monitoring and transmit it to Healinx. We then take the readings and imbed these in the patient medical profile 208. If abnormal readings are found both patient 200 and physician 212 are notified.

Through an embedded database and the patient's medical profile 208 the workflow engine searches for patient 200 as to who should schedule a preventive examination. As an example the workflow engine would remind all women 25-45 to schedule a mammogram. The workflow engine will hold a customized preventive health calendar per patient 200 and remind that patient 200 to schedule an appointment if needed.

Through the medical profile 208 of patient 200's the workflow engine will allow clinics to search for certain patient characteristics. Using this filter the clinic can rapidly create variable patient mailing lists to which they can mail at once. For example in the event that the clinic seeks to contact all males aged 25-45 who are smokers that take Prozac.

Further embodiments of the invention include the capability for a vendor to author templates and routing them through an authoring tool. Templates would be descriptions of the most common customer queries. The templates would support the customer diagnostics of the problem and allow the customer to provide a comprehensive description of the problem encountered.

The customer can then be provided with the most common solutions to the diagnosis. And allow the client to choose whether the off-the-shelf reply is adequate or not. If not then the customer may send the query to the vendor. For premium pricing the customer may page and get an immediate phone response.

Identifying the template used allows triage of the mail into the most adequate department for reply. This allows the people in charge of replying to customize their replies and paste these in the message body. The message according to its severity can then be sent to a supervisor for approval or directly to the patient 200.

The vendor may attach a prescription (the spare part needed) and allow the patient 200 to choose the most convenient service center. The order is then sent to a service center of the customer's 200 choice and authorization and pricing of the entire service are controlled by the vendor.

Figure 3B:
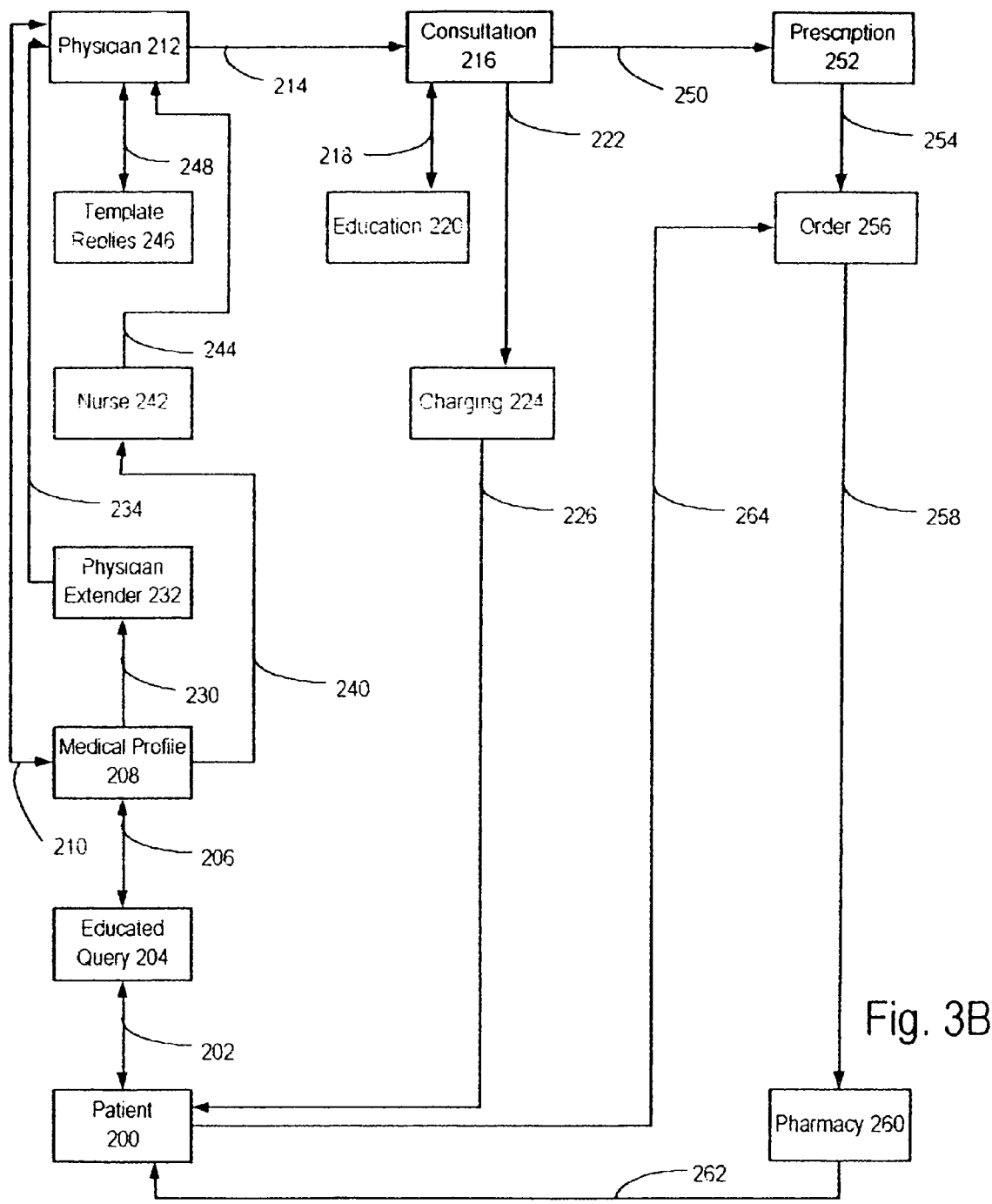
FIG. 3B depicts a more detailed flow diagram of an embodiment of the invention in accordance with certain embodiments.

FIG. 3B depicts a flow diagram of an embodiment of the invention in accordance with certain embodiments. Patient 200 is the primary initiator of this invention. Arrow 202 depicts the interactions of patient 200 to create the educated query message 204. The educated query message 204 is an optimized medical query directed by the patient to address concerns and conditions involving the patient. Arrow 206 depicts the sending of educated query message 204 to the medical profile 208 which is managed by the medical profiler process. The workflow engine performs the various medical profiler process operations. More will be said about the workflow engine shortly. Arrow 210 depicts interactive communication between the workflow engine 208 and the physicians 212 primarily regarding the medical profiler. Physicians 212 are the central destination of patient generated educated medical query messages as sent by 210 from the medical profiler process to the physician 212. Arrow 214 depicts the response of physician 212 to the educated query message, generating a consultative response 216. Consultation 216 provides the basis of the patient response message 226. Arrow 218 depicts the inclusion of the physician consultative response 216 with educational material 220. Educational material 220 is included in certain, but not all cases, to meet mandated regulations as well as provide the physicians a mechanism to distribute standard material regarding various conditions and treatments. Arrow 222 depicts the workflow engine activities required to incorporate the consultative response and included materials 220 with billing information (charging) 224. Charging 224 performs tasks of notifying a patient medical profile of the consultative transaction, what was the query, response, educational materials included and the medical service expenses. Arrow 226 depicts the actual patent response message derived from 224 query, physician response, educational materials included and the medical service expenses sent to patient 200.

Arrow 230 depicts the message information flow from the workflow engine to physician extender 232. Physician extenders 232 perform a number of medical service tasks under the direction of physicians 212. Arrow 234 depicts the sending of proposed patient response messages generated by physician extenders 232 to a physician 212. Arrow 240 depicts another message information flow from the workflow engine to a nurse 242. While nurses are physician extenders, a nurse 242 performs a specific additional task distinguishing them from other physician extenders, such as physician assistants and administrators. Nurse 242 can propose prescription refills for example. Arrow 244 depicts the sending of proposed patient response message, which may further include proposed embedded prescription refills, from nurse 242 to physician 246.

Physician 212 performs a review on the proposed patient response messages from physician extenders, including nurses, as delivered by arrows 234 and 244. Template replies 246 offer the capability for physicians to optimize the quality and efficiency of response in making many standard replies. Arrow 248 depicts the interaction between template replies 246 and physician 212.

Arrow 250 depicts the information and activity flow based upon the consultative response 216 and the placing of a prescription message 252. Prescription message 252 is created based upon the physician's consultative response 216, which in turn is based upon the patient's medical query message and possibly a nurse's proposed prescription refill. Arrow 254 depicts sending a prescription message 252 to ordering process 256. Patient 200 receives the patent response message 226, and may respond by ordering the embedded prescription, which is depicted by arrow 264 indicating a patient prescription message sent to ordering process 256. Ordering process 256 waits until both the physician prescription message 254 and patient prescription message 264 have been received and processed before the order 258 is actually placed with pharmacy 260. Pharmacy 260 sends the prescription to patient 300 as indicated by arrow 362.

Figure 4:
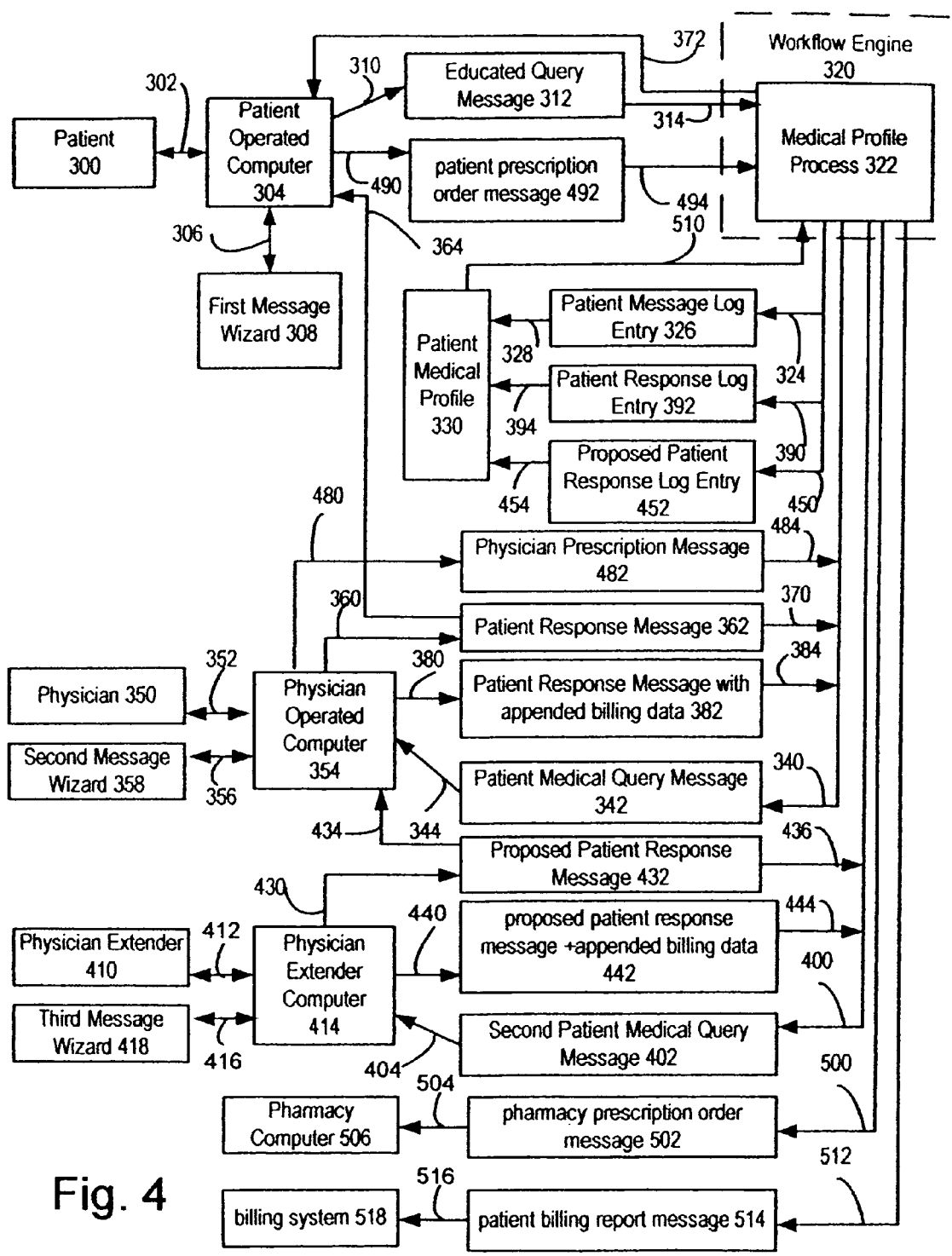
FIG. 4 depicts an interactive flow between a patient using a first messaging wizard, medical profiler performing a medical profiler process and physician using a second messaging wizard in accordance with an embodiment of the invention.

FIG. 4 depicts an interactive flow between a patient using a first messaging wizard, workflow engine performing a medical profiler process and physician using a second messaging wizard in accordance with an embodiment of the invention. Patient 300 interacts 302 with patient operated computer 304, which can access 306 and perform the operations of first messaging wizard 308. Physician 350 interacts 352 with physician operated computer 354, which can access 356 and perform the operations of second messaging wizard 358. Physician extender 400 interacts 402 with physician extender operated computer 404, which can access 406 and perform the operations of second messaging wizard 408.

Patient 300 using first messaging wizard 308 on patient operated computer 304 generates 310 educated query message 312 and sends it 314 to workflow engine 320 where it is received by medical profiler process 322. Medical profiler process 322 generates 324 patient message log entry 326, which is added 328 to the patient medical profile 330. Medical profiler process 322 further generates 340 patient medical query message 342, which is sent 344 to physician operated computer 354.

Physician 350 using second messaging wizard 358 on physician operated computer 354 receives and responds to the patient medical query message 342, generating 360 a patient response message 362, which in certain embodiments is sent 364 directly to the patient operated computer 304. In certain alternative embodiments, patient response message 362 is sent 370 to the workflow engine, where the medical profiler process 322 then sends 372 a version to the patient operated computer 304. Physician 350 using second messaging wizard 358 on physician operated computer 354 further responds to the patient medical query message 342, generating a patient response message with appended physician billing data 382, which is sent 384 to the workflow engine, where the medical profiler process 322 then generates 390 a patient response log entry 392 which is added 394 to the patient medical profile 330.

In certain situations, a prescription is embedded into patient response message 362 by the physician 350 using second messaging wizard 358 on physician operated computer 354 in response to the patient medical query message 342, which embedded into the patient response message 362. Physician 350 using second messaging wizard 358 on physician operated computer 354 also generates 480 physician prescription message 482, which is sent 484 to the workflow engine using the medical profiler process 322. Patient 300 using first messaging wizard 308 on patient operated computer 304 generates 490 patient prescription order message 492 and sends it 494 to workflow engine 320 where it is received by medical profiler process 322. Once both physician prescription message 482 and patient prescription order message 492 have been received and authenticated, the medial profiler process 322 generates 500 a pharmacy prescription order message 502 which is sent 504 to the pharmacy computer 506.

Medical profiler process 322 accesses 510 the patient medical profile 330 to generate 512 patient billing report message 514 which is sent 516 to billing system 518. Note that the billing system 518 in certain embodiments is a separate system element external to the workflow engine. In certain alternative embodiments, billing system 518 resides within the operations performed by the workflow engine. In certain further embodiments, billing system 518 is part of the medical profiler process.

Medical profiler process 322 further generates 400 a second patient medical query message 402, which is sent 404 to physician extender operated computer 414. Physician extender 410 using third messaging wizard 418 on physician operated computer 414 receives and responds to the second patient medical query message 412, generating 430 a proposed patient response message 432, which is sent 434 directly to the physician operated computer 354, where it is inserted into the patient medical query message 342. In certain alternative embodiments, patient response message 432 is sent 436 to the workflow engine, where the medical profiler process 322 then sends a version to the physician operated computer 354. Physician extender 410 using third messaging wizard 418 on physician operated computer 414 further responds 440 to the second patient medical query message 402, generating a proposed patient response message with appended physician extender billing data 442, which is sent 444 to the workflow engine, where the medical profiler process 322 then generates 450 a proposed patient response with appended physician extender billing data log entry 452 which is added 454 to the patient medical profile 330.

Note that in the flowcharts included herein, the starting operation of a flowchart may perform operations to allocate systems resources for use by the subsequent operations of the flowchart in certain embodiments. The starting operation of a flowchart may further perform initialize systems resources in certain embodiments.

Note also that in the flowcharts included herein, the terminating or exit operation of a flowchart may perform operations to release allocated systems resources used by the subsequent operations of the flowchart in certain embodiments. The terminating operation of a flowchart may further perform a "return" operation in certain embodiments. Alternatively, the terminating operation of a flowchart may not perform a "return" operation in certain embodiments.

Figure 5:
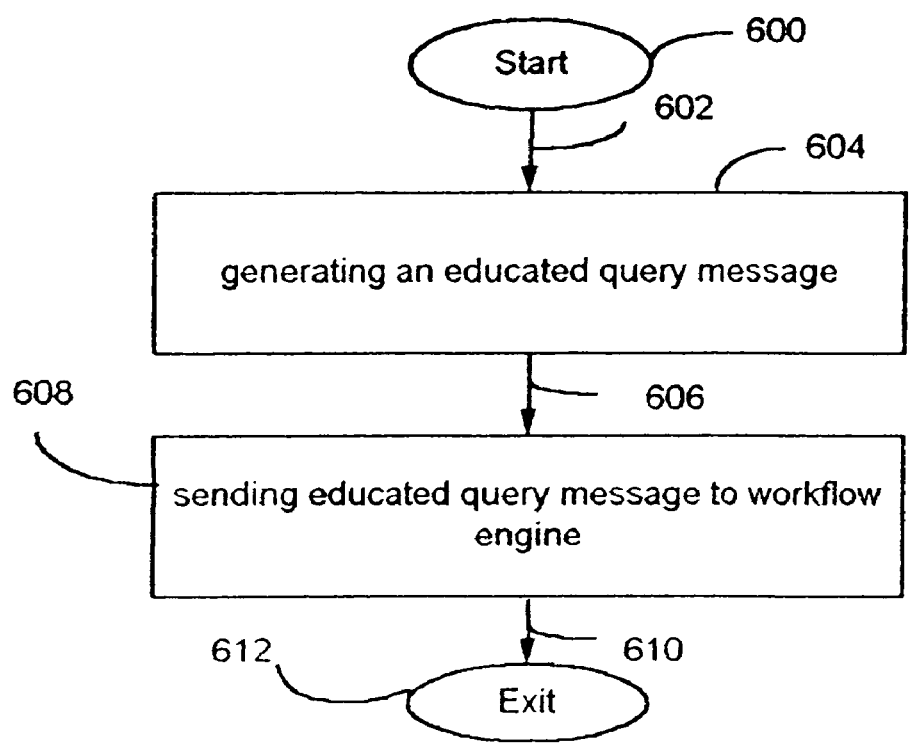
FIG. 5 depicts a flowchart of operations supporting the generation and sending of an educated query by a patient using the first messaging wizard in accordance with embodiments supporting FIG. 4.

FIG. 5 depicts a flowchart of operations supporting the generation and sending of an educated query by a patient using the first messaging wizard in accordance with embodiments supporting FIG. 4. Operation 600 starts the operations of this flowchart. Arrow 602 directs the flow of execution from operation 600 to operation 604. Operation 604 performs generating of an educated query message. Arrow 606 directs execution from operation 604 to operation 608. Operation 608 performs sending the educated query message to the workflow engine. Arrow 610 directs execution from operation 608 to operation 612. Operation 612 terminates the operations of this flowchart.

Figure 6:
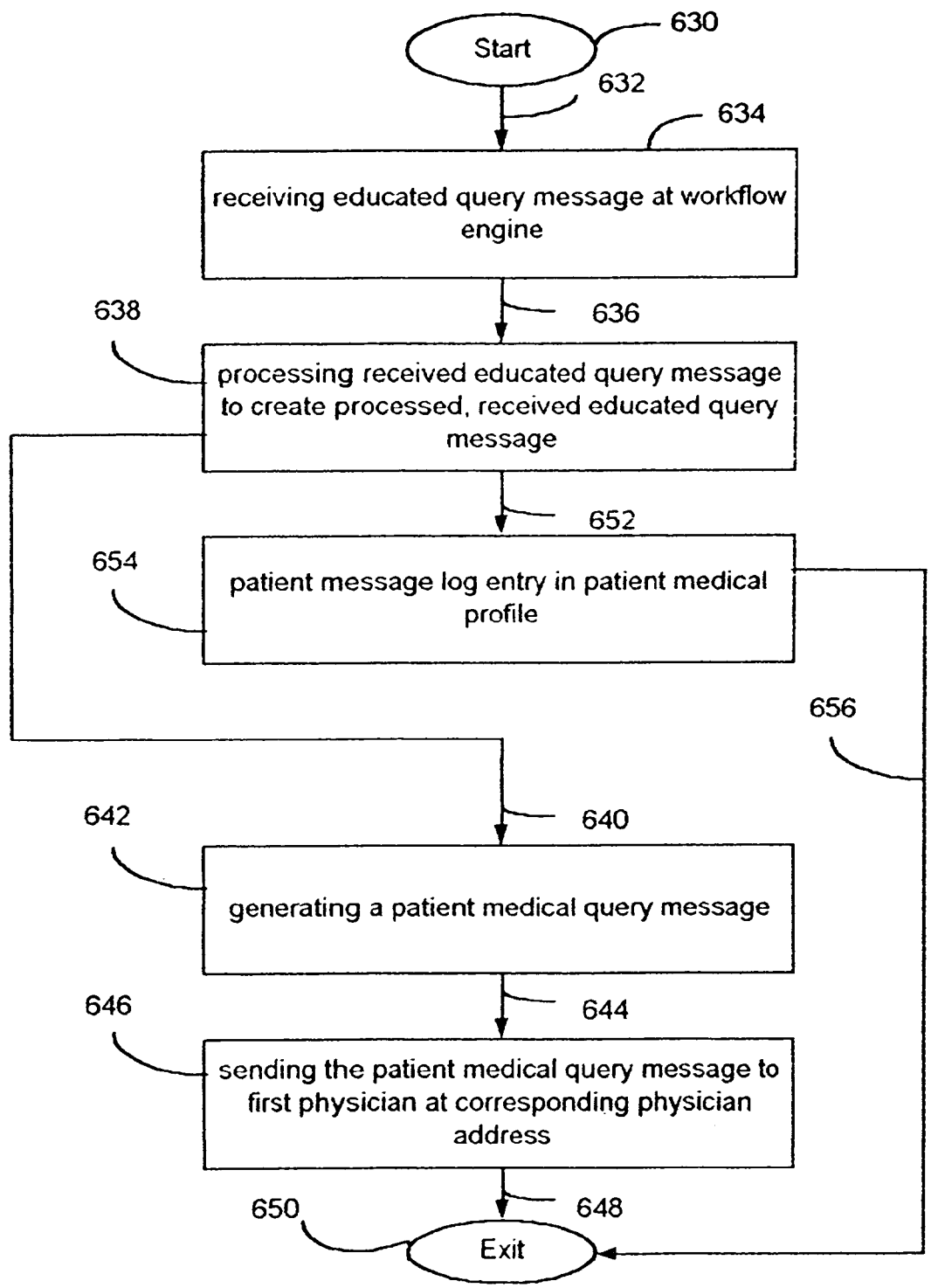
FIG. 6 depicts a flowchart of operations supporting the reception, processing, logging of the educated query message from the patient, and the generation and sending of the patient medical query message to a physician by the medical profiler process performed by the medical profiler in accordance with embodiments supporting FIG. 4.

FIG. 6 depicts a flowchart of operations supporting the reception, processing, logging of the educated query message from the patient, and the generation and sending of the patient medical query message to a physician by the medical profiler process performed by the workflow engine in accordance with embodiments supporting FIG. 4. Operation 630 starts the operations of this flowchart. Arrow 632 directs the flow of execution from operation 630 to operation 634. Operation 634 performs receiving the educated query message at the workflow engine. Arrow 636 directs execution from operation 634 to operation 638. Operation 638 performs processing the received educated query message to create the processed, received educated query message. Arrow 640 directs execution from operation 638 to operation 642. Operation 642 performs generating a patient medical query message. Arrow 644 directs execution from operation 642 to operation 646. Operation 646 performs sending the patient medical query message to first physician at corresponding physician address. Arrow 648 directs execution from operation 646 to operation 650. Operation 650 terminates the operations of this flowchart.

In certain embodiments, operation 646 further includes selecting a first physician. In certain further embodiments, operation 646 further includes selecting a first physician based upon the received educated query message. In certain further embodiments, operation 646 further includes selecting a first physician based upon the processed, received educated query message.

Arrow 652 directs the flow of execution from starting operation 638 to operation 654. Operation 654 performs generating a patient message log entry in the patient medical profile. Arrow 656 directs execution from operation 654 to operation 650.

Figure 7:
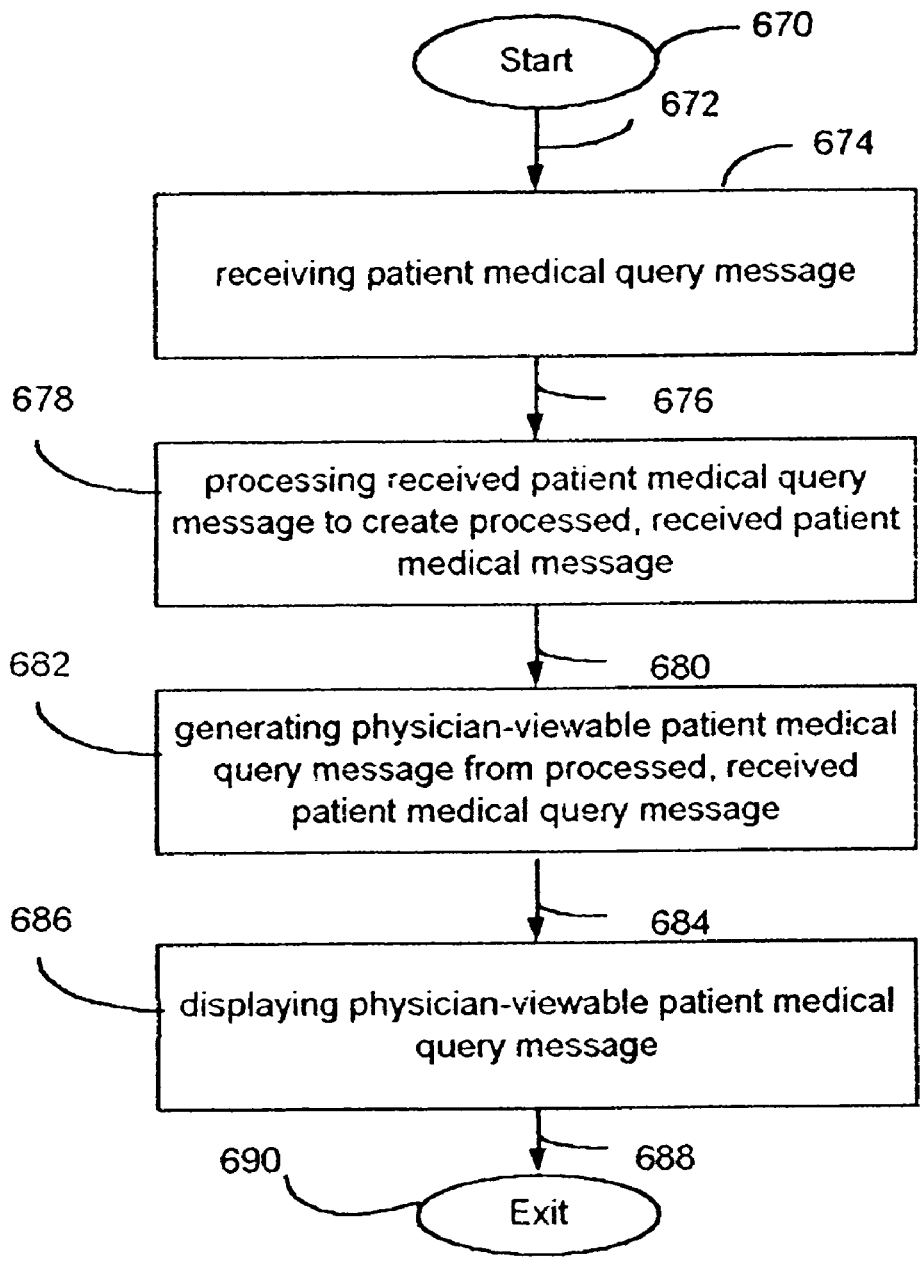
FIG. 7 depicts a flowchart of operations supporting reception, processing and viewing the patient medical query message by the second message wizard for the physician in accordance with embodiments supporting FIG. 4.

FIG. 7 depicts a flowchart of operations supporting reception, processing and viewing the patient medical query message by the second message wizard for the physician in accordance with embodiments supporting FIG. 4. Operation 670 starts the operations of this flowchart. Arrow 672 directs the flow of execution from operation 670 to operation 674. Operation 674 performs receiving the patient query message. Arrow 676 directs execution from operation 674 to operation 678. Operation 678 performs processing the received patient medical query message to create the processed, received patient medical message. Arrow 680 directs execution from operation 678 to operation 682. Operation 682 performs generating a physician-viewable patient medical query message from the processed, received patient medical query message. Arrow 684 directs execution from operation 682 to operation 686. Operation 686 performs displaying the physician-viewable patient medical query message. Arrow 688 directs execution from operation 686 to operation 690. Operation 690 terminates the operations of this flowchart.

Figure 8:
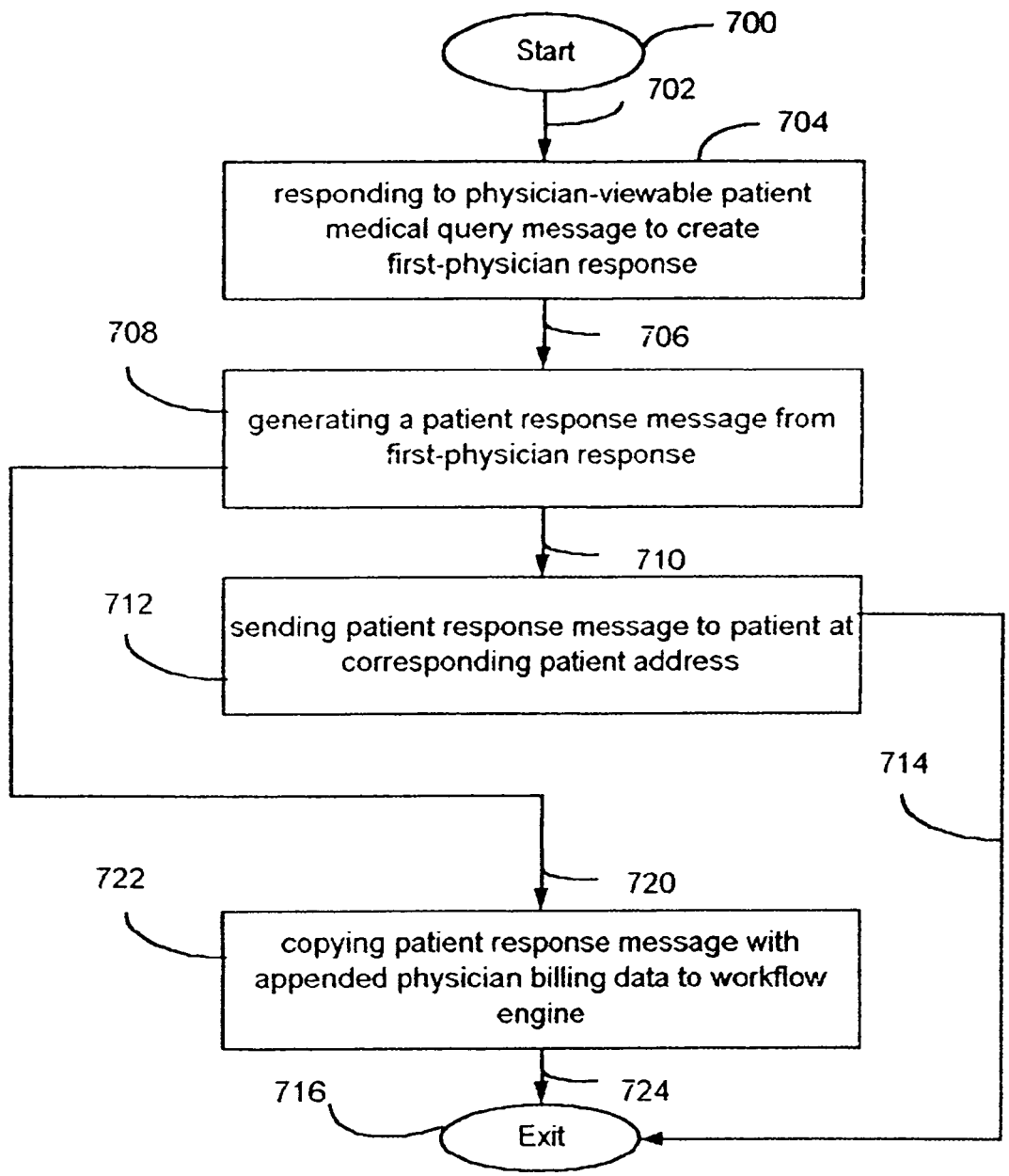
FIG. 8 depicts a flowchart of operations supporting reception, generation and sending a patient response message, as well as copying the patient response message with an appended physician billing data to the medical profiler address in accordance with embodiments supporting FIG. 4.

FIG. 8 depicts a flowchart of operations supporting reception, generation and sending a patient response message, as well as copying the patient response message with an appended physician billing data to the workflow engine in accordance with embodiments supporting FIG. 4. Operation 700 starts the operations of this flowchart. Arrow 702 directs the flow of execution from operation 700 to operation 704. Operation 704 performs responding to the physician-viewable patient medical query message to create a first-physician response. Arrow 706 directs execution from operation 704 to operation 708. Operation 708 performs generating a patient response message from the first-physician response. Arrow 710 directs execution from operation 708 to operation 712. Operation 712 performs sending the patient response message to the patient at the corresponding patient address. Arrow 714 directs execution from operation 712 to operation 716. Operation 716 terminates the operations of this flowchart.

Arrow 720 directs the flow of execution from starting operation 708 to operation 722. Operation 722 performs copying the patient response message with appended physician billing data to workflow engine. Arrow 724 directs execution from operation 722 to operation 716.

Figure 9:
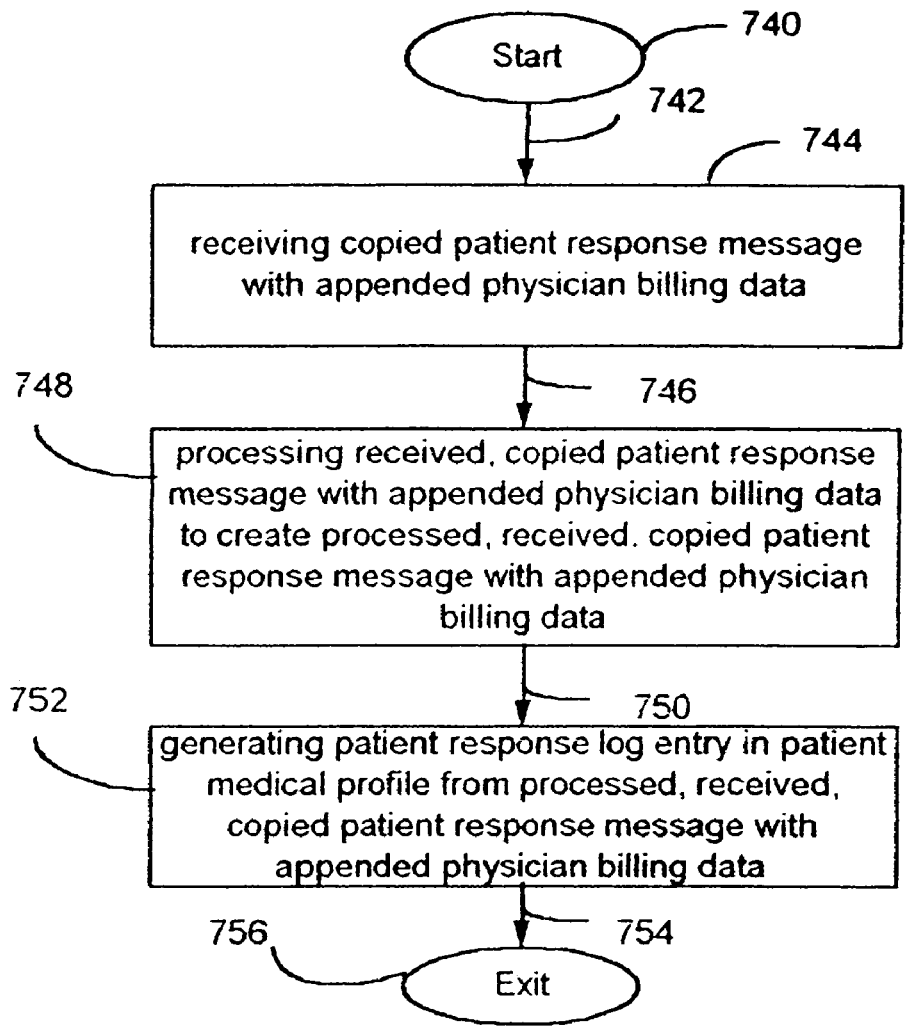
FIG. 9 depicts a flowchart of operations supporting the reception, processing, logging the copied patient response message with an appended physician billing data by the medical profiler process performed by the medical profiler in accordance with embodiments supporting FIG. 4.

FIG. 9 depicts a flowchart of operations supporting the reception, processing, logging the copied patient response message with an appended physician billing data by the medical profiler process performed by the workflow engine in accordance with embodiments supporting FIG. 4. Operation 740 starts the operations of this flowchart. Arrow 742 directs the flow of execution from operation 740 to operation 744. Operation 744 performs receiving the copied patient response message with appended physician billing data. Arrow 746 directs execution from operation 744 to operation 748. Operation 748 performs processing the received, copied patient response message with appended physician billing data to create the processed, received, copied patient response message with appended physician billing data. Arrow 750 directs execution from operation 748 to operation 752. Operation 752 performs generating a patient response log entry in patient medical profile from the processed, received, copied patient response message with appended physician billing data. Arrow 754 directs execution from operation 752 to operation 756. Operation 756 terminates the operations of this flowchart.

Figure 10:
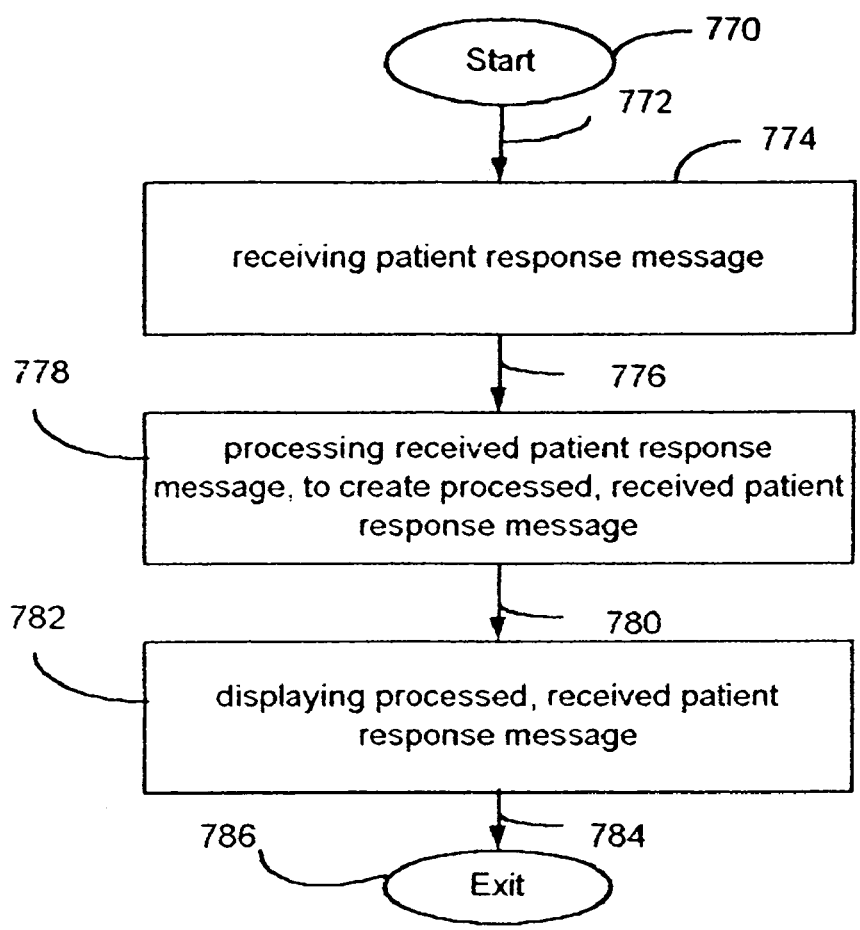
FIG. 10 depicts a flowchart of operations supporting reception, processing and display of the patient response message using the first messaging wizard on the patient operated computer in accordance with embodiments supporting FIG. 4.

FIG. 10 depicts a flowchart of operations supporting reception, processing and display of the patient response message using the first messaging wizard on the patient operated computer in accordance with embodiments supporting FIG. 4. Operation Q0 starts the operations of this flowchart. Arrow 772 directs the flow of execution from operation 770 to operation 774. Operation 774 performs receiving the patient response message. Arrow 776 directs execution from operation 774 to operation 778. Operation 778 performs processing the received patient response message, to create a processed, received patient response message. Arrow 780 directs execution from operation 778 to operation 782. Operation 782 performs displaying the processed, received patient response message. Arrow 784 directs execution from operation 782 to operation 786. Operation 786 terminates the operations of this flowchart.

Figure 11:
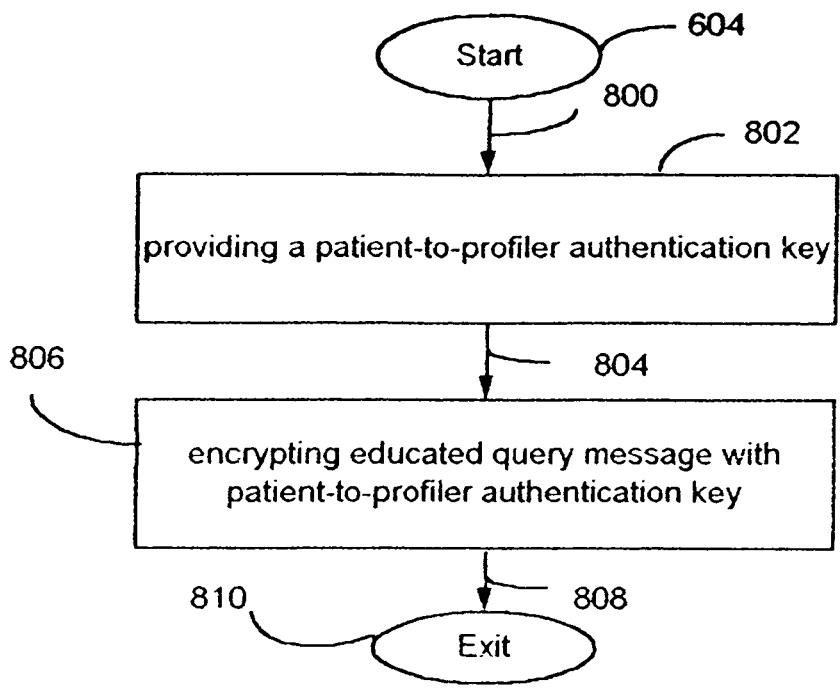
FIG. 11 depicts a flowchart of further details regarding operation 604, generation of an educated query message by the first messaging wizard in accordance with embodiments supporting FIG. 5.

FIG. 11 depicts a flowchart of further details regarding operation 604, generation of an educated query message by the first messaging wizard in accordance with embodiments supporting FIG. 5. Arrow 800 directs the flow of execution from starting operation 604 to operation 802. Operation 802 performs providing a patient-to-profiler authentication key. Arrow 804 directs execution from operation 802 to operation 806. Operation 806 performs encrypting the educated query message with patient-to-profiler authentication key. Arrow 808 directs execution from operation 806 to operation 810. Operation 810 terminates the operations of this flowchart.

Figure 12:
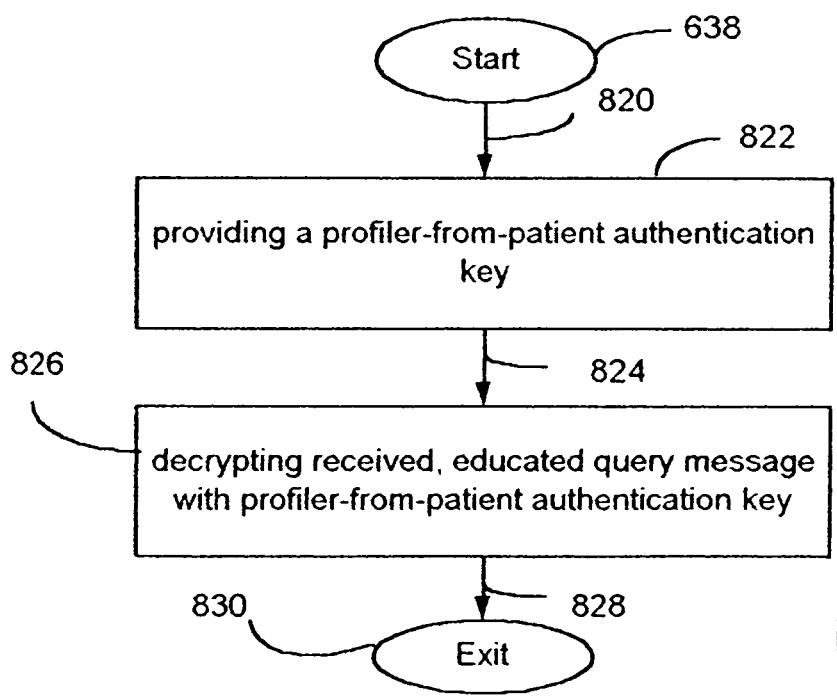
FIG. 12 depicts a flowchart of further details regarding operation 638, processing the educated query message using the medical profiler process performed by the medical profiler in accordance with embodiments supporting FIG. 6.

FIG. 12 depicts a flowchart of further details regarding operation 638, processing the educated query message using the medical profiler process performed by the workflow engine in accordance with embodiments supporting FIG. 6. Arrow 820 directs the flow of execution from starting operation 638 to operation 822. Operation 822 performs providing a profiler-from-patient authentication key. Arrow 824 directs execution from operation 822 to operation 826. Operation 826 performs decrypting the received, educated query message with profiler-from-patient authentication key. Arrow 828 directs execution from operation 826 to operation 830. Operation 830 terminates the operations of this flowchart.

Figure 13:
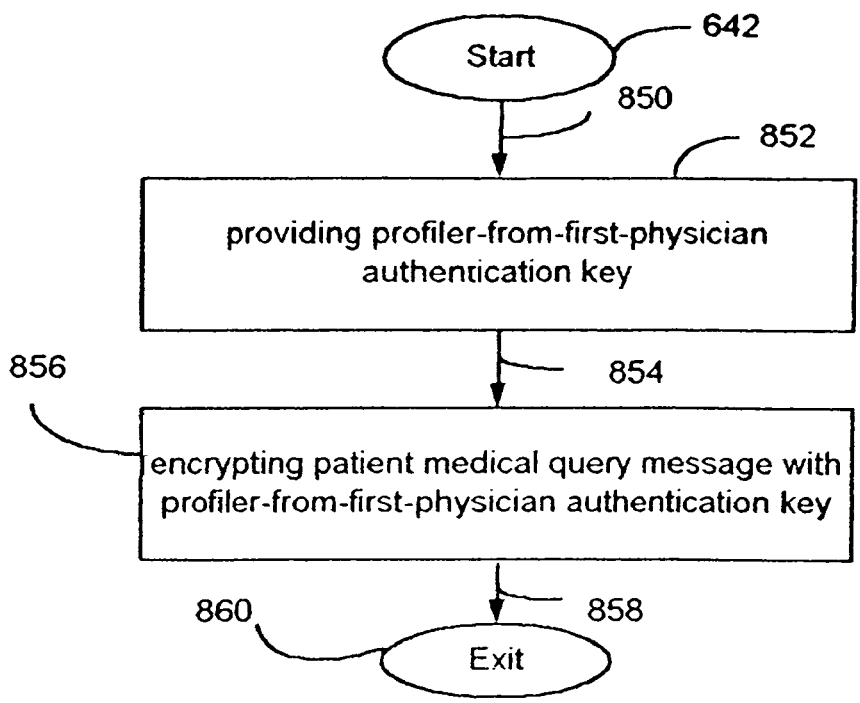
FIG. 13 depicts a flowchart of further details regarding operation 642, generation of a patient medical query message by the medical profiler process performed by the medical profiler in accordance with embodiments supporting FIG. 6.

FIG. 13 depicts a flowchart of further details regarding operation 642, generation of a patient medical query message by the medical profiler process performed by the workflow engine in accordance with embodiments supporting FIG. 6. Arrow 850 directs the flow of execution from starting operation 642 to operation 852. Operation 852 performs providing profiler-from-first-physician authentication key. Arrow 854 directs execution from operation 852 to operation 856. Operation 856 performs encrypting patient medical query message with profiler-from-first-physician authentication key. Arrow 858 directs execution from operation 856 to operation 860. Operation 860 terminates the operations of this flowchart.

Figure 14:
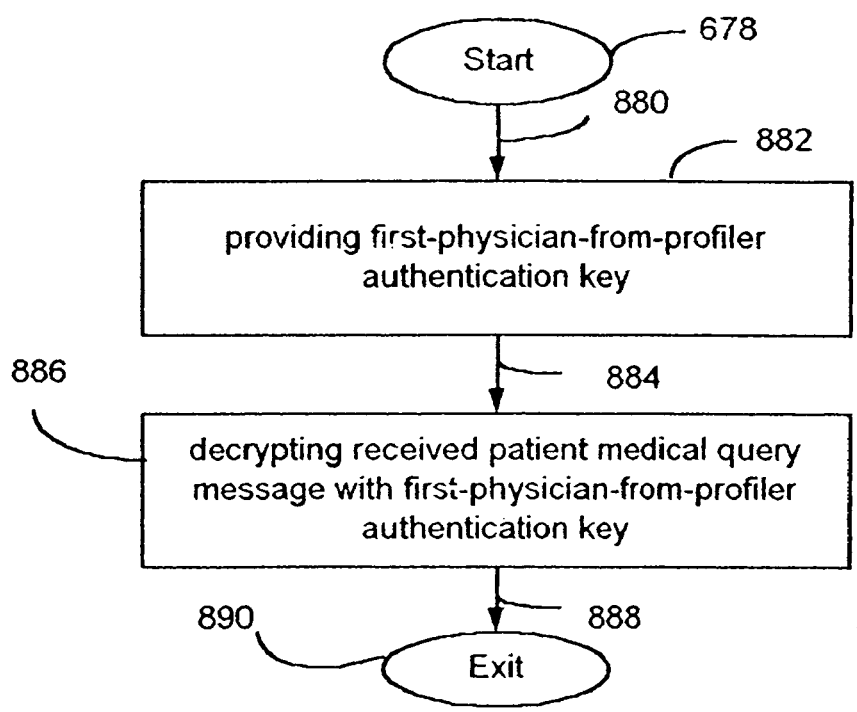
FIG. 14 depicts a flowchart of further details regarding operation 678, processing the received patient medical query message by the second messaging wizard in accordance with embodiments supporting FIG. 7.

FIG. 14 depicts a flowchart of further details regarding operation 678, processing the received patient medical query message by the second messaging wizard in accordance with embodiments supporting FIG. 7. Arrow 880 directs the flow of execution from starting operation 678 to operation 882. Operation 882 performs providing a first-physician-from-profiler authentication key. Arrow 884 directs execution from operation 882 to operation 886. Operation 886 performs decrypting the received patient medical query message with the first-physician-from-profiler authentication key. Arrow 888 directs execution from operation 886 to operation 890. Operation 890 terminates the operations of this flowchart.

Figure 15:
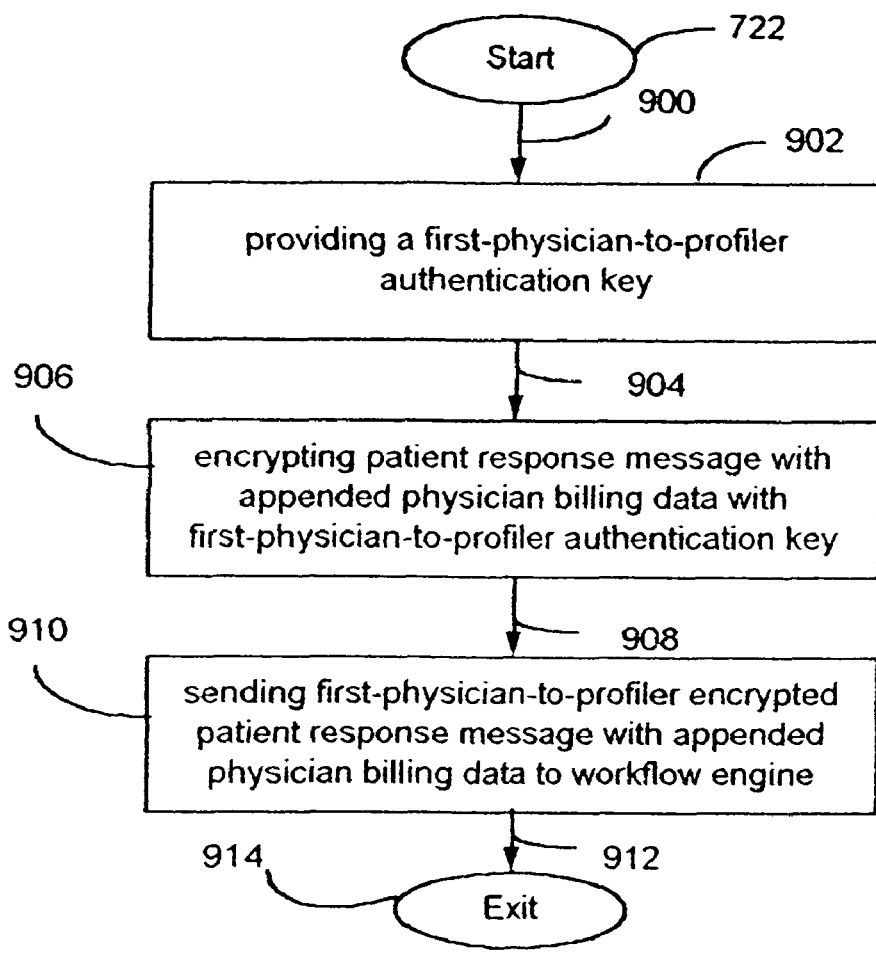
FIG. 15 depicts a flowchart of further details regarding operation 722, copying the patient response message with appended physician billing data to the medical profiler by the second messaging wizard in accordance with embodiments supporting FIG. 8.

FIG. 15 depicts a flowchart of further details regarding operation 722, copying the patient response message with appended physician billing data to the workflow engine by the second messaging wizard in accordance with embodiments supporting FIG. 8. Arrow 900 directs the flow of execution from starting operation 722 to operation 902. Operation 902 performs providing a first-physician-to-profiler authentication key. Arrow 904 directs execution from operation 902 to operation 906. Operation 906 performs encrypting the patient response message with appended physician billing data with the first-physician-to-profiler authentication key. Arrow 908 directs execution from operation 906 to operation 910. Operation 910 performs sending first-physician-to-profiler encrypted patient response message with appended physician billing data to the workflow engine. Arrow 912 directs execution from operation 910 to operation 914. Operation 914 terminates the operations of this flowchart.

Figure 16:
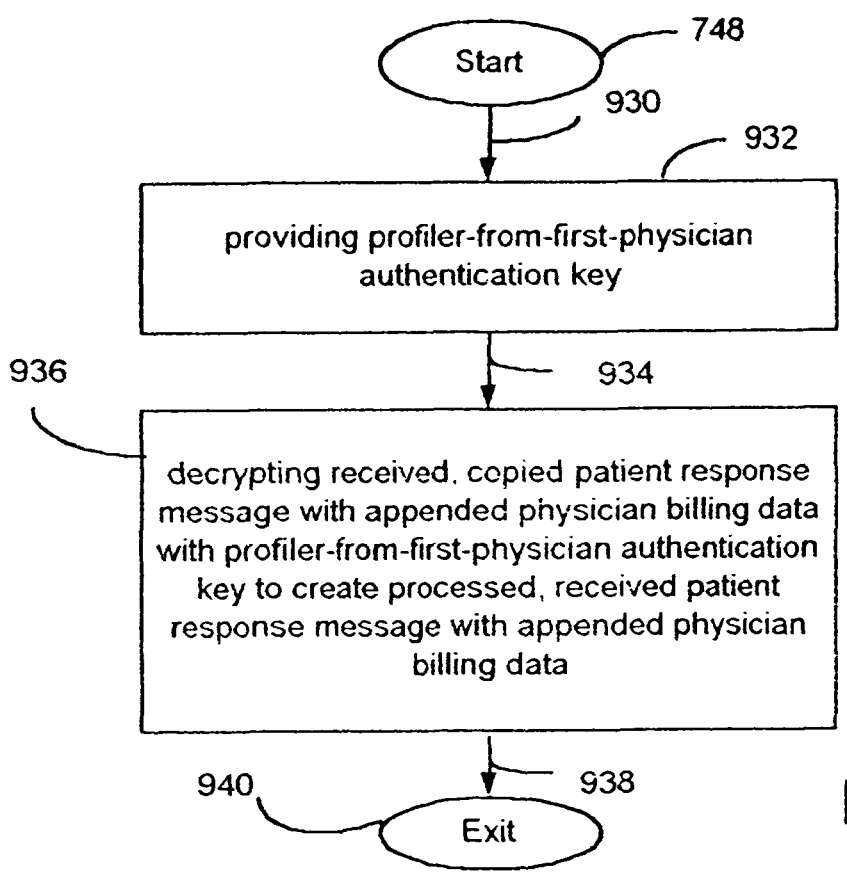
FIG. 16 depicts a flowchart of further details regarding operation 748, processing the received, copied the patient response message with appended physician billing data using the medical profiler process performed by the medical profiler in accordance with embodiments supporting FIG. 9.

FIG. 16 depicts a flowchart of further details regarding operation 748, processing the received, copied the patient response message with appended physician billing data using the medical profiler process performed by the workflow engine in accordance with embodiments supporting FIG. 9. Arrow 930 directs the flow of execution from starting operation 748 to operation 932. Operation 932 performs providing a profiler-from-first-physician authentication key. Arrow 934 directs execution from operation 932 to operation 936. Operation 936 performs decrypting the received, copied patient response message with appended physician billing data with the profiler-from-first physician authentication key to create the processed, received patient response message with appended physician billing data. Arrow 938 directs execution from operation 936 to operation 940. Operation 940 terminates the operations of this flowchart.

Figure 17:
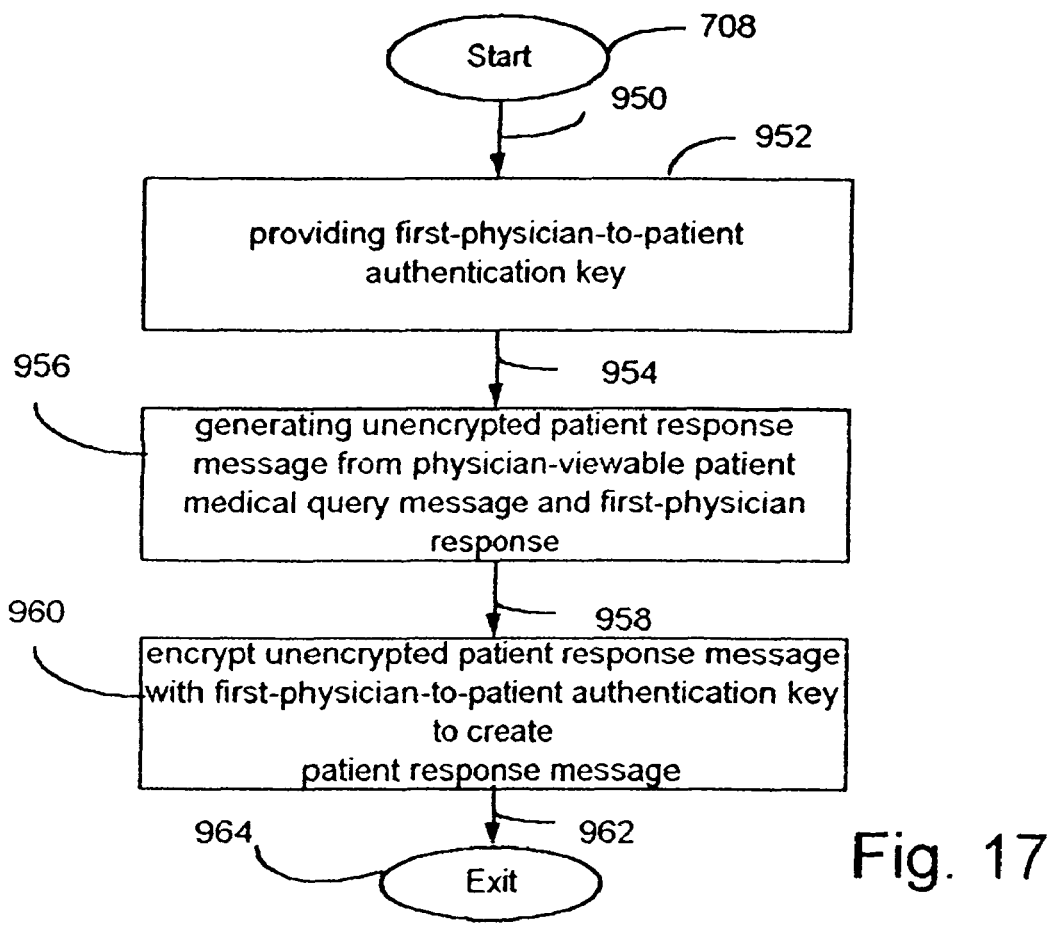
FIG. 17 depicts a flowchart of further details regarding operation 708, generating patient response message using the second message wizard in accordance with embodiments supporting FIG. 8.

FIG. 17 depicts a flowchart of further details regarding operation 708, generating patient response message using the second message wizard in accordance with embodiments supporting FIG. 8. Arrow 950 directs the flow of execution from starting operation 708 to operation 952. Operation 952 performs providing first-physician-to-patient authentication key. Arrow 954 directs execution from operation 952 to operation 956. Operation 956 performs generating an unencrypted patient response message from the physician-viewable patient medical query message and the first-physician response. Arrow 958 directs execution from operation 956 to operation 960. Operation 960 performs encrypt the unencrypted patient response message with the first-physician-to-patient authentication key to create the patient response message. Arrow 962 directs execution from operation 960 to operation 964. Operation 964 terminates the operations of this flowchart.

Note that operations 952 and 956 may be performed either in the order presented by this flowchart, or in certain alternative embodiments, in the reverse order to that shown, or further alternatively, concurrently with each other.

Figure 18:
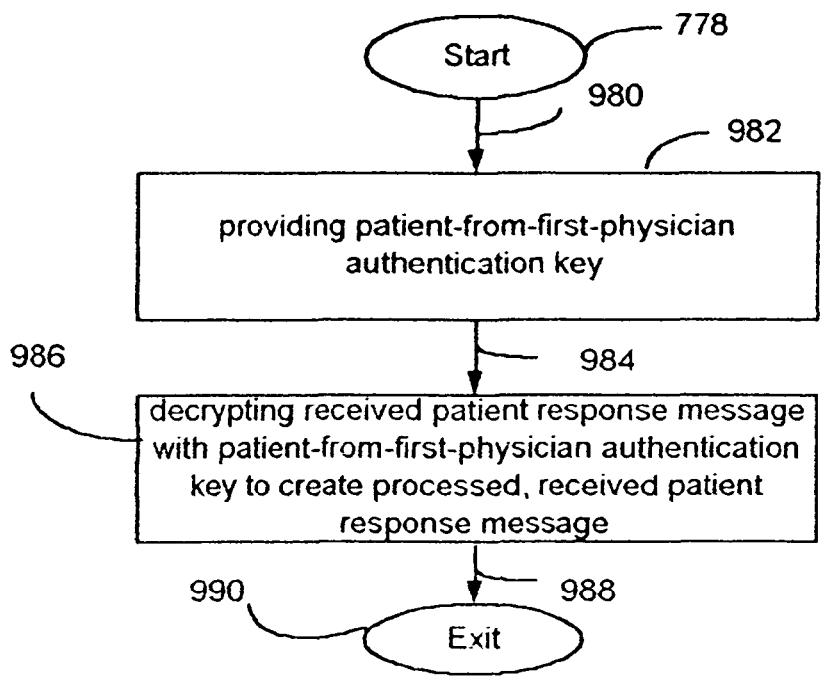
FIG. 18 depicts a flowchart of further details regarding operation 778, processing the received patient response message using the first message wizard in accordance with embodiments supporting FIG. 10.

FIG. 18 depicts a flowchart of further details regarding operation 778, processing the received patient response message using the first message wizard in accordance with embodiments supporting FIG. 10. Arrow 980 directs the flow of execution from starting operation 778 to operation 982. Operation 982 performs providing a patient-from-first-physician authentication key. Arrow 984 directs execution from operation 982 to operation 986. Operation 986 performs decrypting the received patient response message with the patient-from-first-physician authentication key to create the processed, received patient response message. Arrow 988 directs execution from operation 986 to operation 990. Operation 990 terminates the operations of this flowchart.

Figure 19:
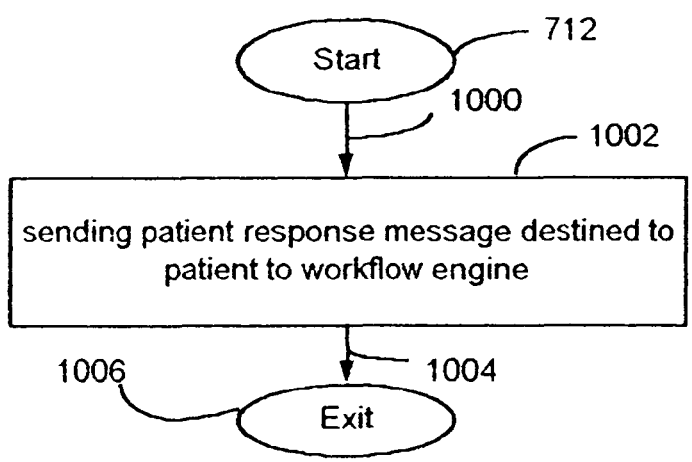
FIG. 19 depicts a flowchart of further details regarding operation 712, sending the patient response message with appended physician billing data using the medical profiler process performed by the medical profiler in accordance with embodiments supporting FIG. 8.

FIG. 19 depicts a flowchart of further details regarding operation 712, sending the patient response message with appended physician billing data using the medical profiler process performed by the workflow engine in accordance with embodiments supporting FIG. 8. Arrow 1000 directs the flow of execution from starting operation 712 to operation 1002. Operation 1002 performs sending patient response message destined to patient to workflow engine. Arrow 1004 directs execution from operation 1002 to operation 1006. Operation 1006 terminates the operations of this flowchart.

Figure 20:
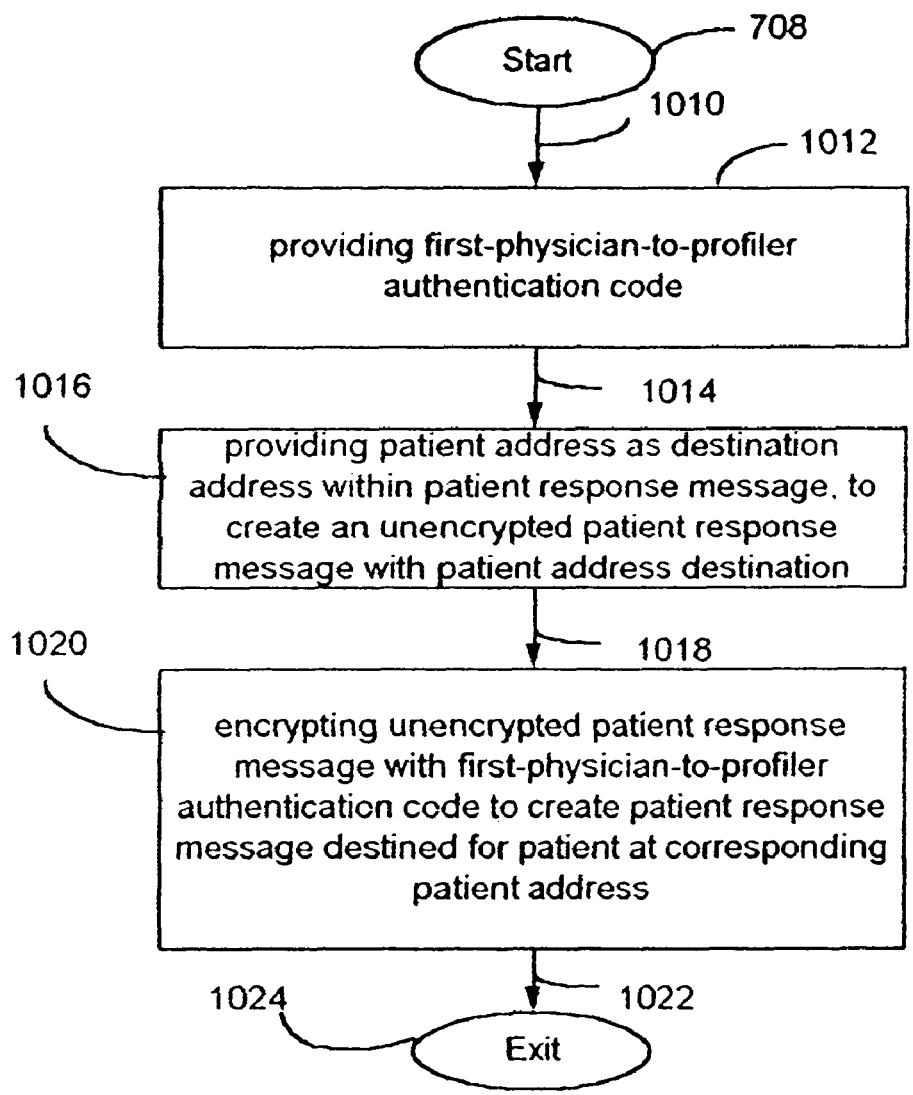
FIG. 20 depicts a flowchart of further details regarding operation 708, generating the patient response message using the second message wizard in accordance with embodiments supporting FIG. 8.

FIG. 20 depicts a flowchart of further details regarding operation 708, generating the patient response message using the second message wizard in accordance with embodiments supporting FIG. 8. Arrow 1010 directs the flow of execution from starting operation 708 to operation 1012. Operation 1012 performs providing the first-physician-to-profiler authentication code. Arrow 1014 directs execution from operation 1012 to operation 1016. Operation 1016 performs providing the patient address as destination address within the patient response message, to create an unencrypted patient response message with patient address destination. Arrow 1018 directs execution from operation 1016 to operation 1020. Operation 1020 performs encrypting the unencrypted patient response message with the first-physician-to-profiler authentication code to create the patient response message destined for the patient at the corresponding patient address. Arrow 1022 directs execution from operation 1020 to operation 1024. Operation 1024 terminates the operations of this flowchart.

Note that operations 1012 and 1016 in certain alternative embodiments may be performed in reverse order, and in certain further alternative embodiments, may be concurrently performed.

Figure 21:
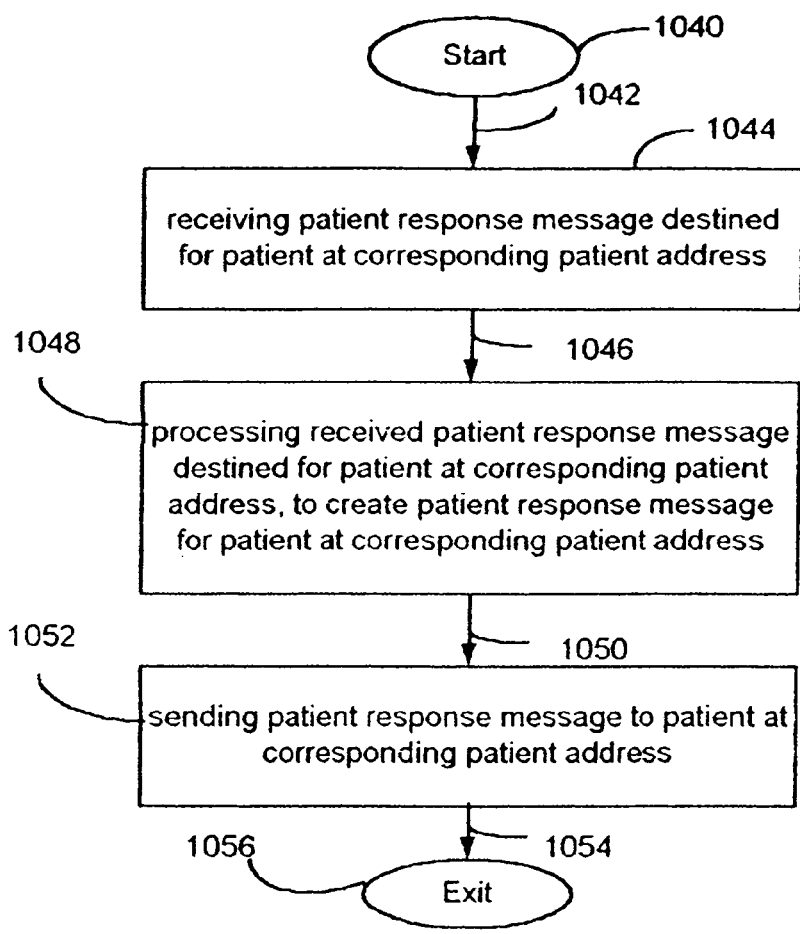
FIG. 21 depicts a flowchart of operations of the medical profiler process performed by the medical profiler in accordance with alternative embodiments supporting FIG. 4.

FIG. 21 depicts a flowchart of operations of the medical profiler process performed by the workflow engine in accordance with alternative embodiments supporting FIG. 4. Operation 1040 starts the operations of this flowchart. Arrow 1042 directs the flow of execution from operation 1040 to operation 1044. Operation 1044 performs receiving the patient response message destined for the patient at the corresponding patient address. Arrow 1046 directs execution from operation 1044 to operation 1048. Operation 1048 performs processing the received patient response message destined for the patient at the corresponding patient address, to create the patient response message for the patient at the corresponding patient address. Arrow 1050 directs execution from operation 1048 to operation 1052. Operation 1052 performs sending the patient response message to the patient at the corresponding patient address. Arrow 1054 directs execution from operation 1052 to operation 1056. Operation 1056 terminates the operations of this flowchart.

Figure 22:
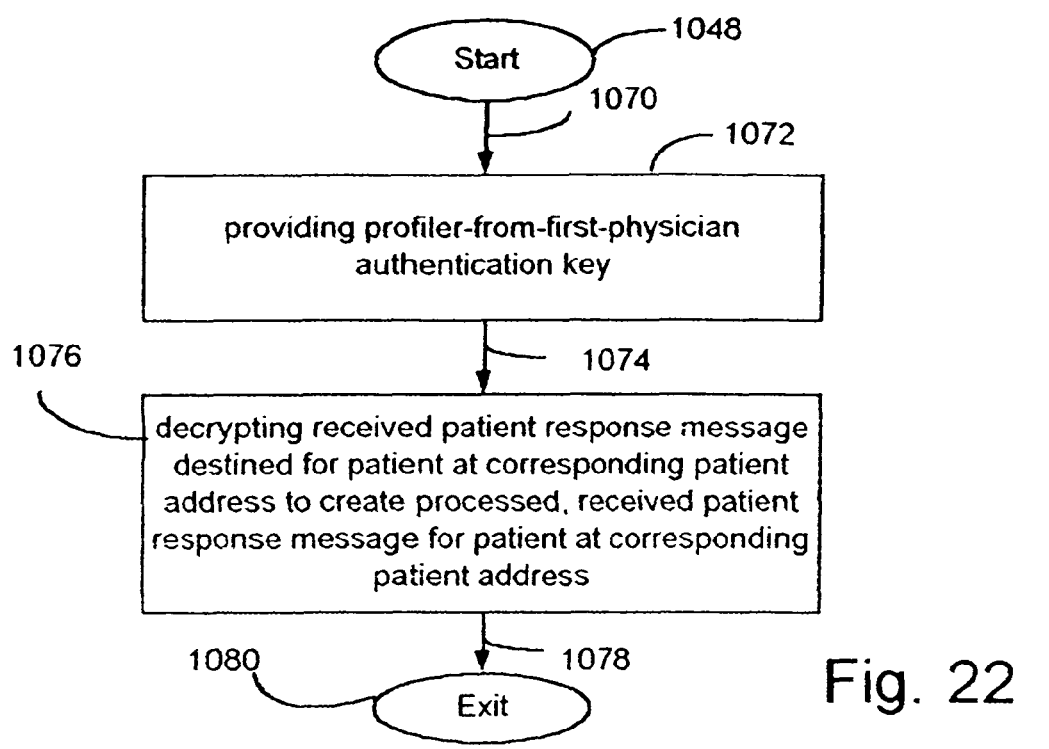
FIG. 22 depicts a flowchart of further details regarding operation 1048, processing the patient response message destined for the patient using the medical profiler process performed by the medical profiler in accordance with embodiments supporting FIG. 21.

FIG. 22 depicts a flowchart of further details regarding operation 1048, processing the patient response message destined for the patient using the medical profiler process performed by the workflow engine in accordance with embodiments supporting FIG. 21. Arrow 1070 directs the flow of execution from starting operation 1048 to operation 1072. Operation 1072 performs providing a profiler-from-first-physician authentication key. Arrow 1074 directs execution from operation 1072 to operation 1076. Operation 1076 performs decrypting the received patient response message destined for the patient at the corresponding patient address to create the processed, received patient response message for the patient at the corresponding patient address. Arrow 1078 directs execution from operation 1076 to operation 1080. Operation 1080 terminates the operations of this flowchart.

Figure 23:
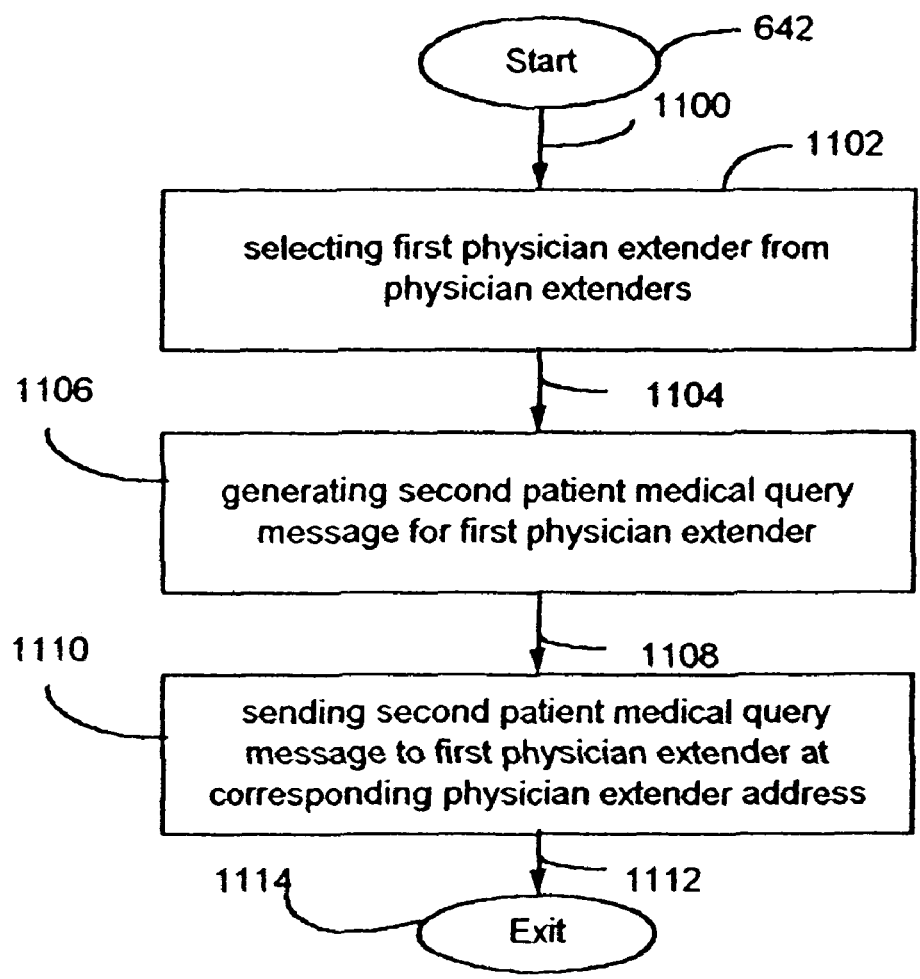
FIG. 23 depicts a flowchart of further details regarding operation 642, generating a patient medical query message using the medical profiler process performed by the medical profiler in accordance with embodiments.

FIG. 23 depicts a flowchart of further details regarding operation 642, generating a patient medical query message using the medical profiler process performed by the workflow engine in accordance with embodiments. Arrow 1100 directs the flow of execution from starting operation 642 to operation 1102. Operation 1102 performs selecting a first physician extender from the physician extenders. Arrow 1104 directs execution from operation 1102 to operation 1106. Operation 1106 performs generating a second patient medical query message for the first physician extender. Arrow 1108 directs execution from operation 1106 to operation 1110. Operation 1110 performs sending the second patient medical query message to the first physician extender at the corresponding physician extender address. Arrow 1112 directs execution from operation 1110 to operation 1114. Operation 1114 terminates the operations of this flowchart.

Note that in certain embodiments, operation 1102 is based upon the received educated query message. In certain further embodiments, operation 1102 is based upon the processed, received educated query message.

Figure 24:
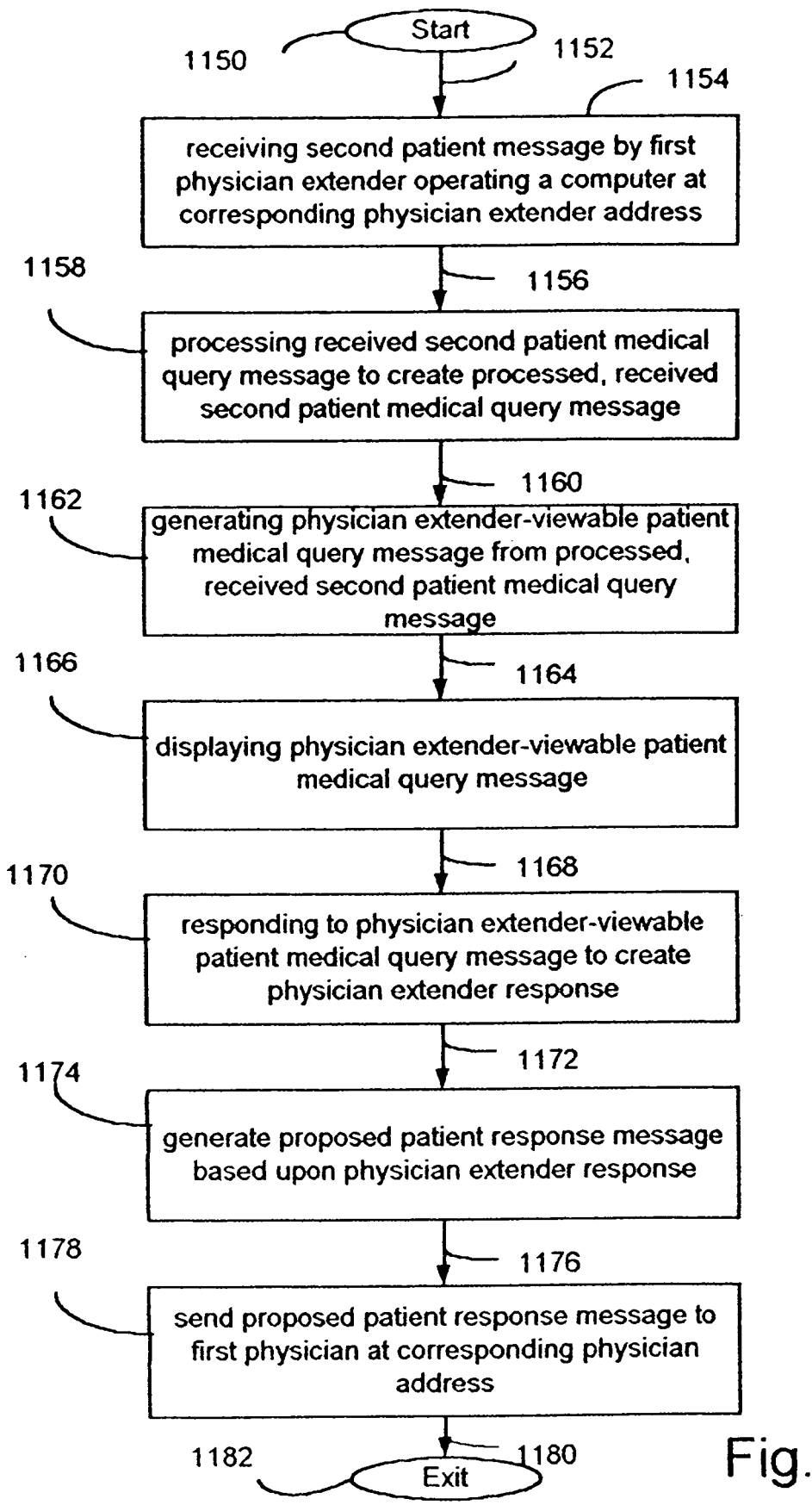
FIG. 24 depicts a flowchart of operations using the third message wizard on the physician extender computer in accordance with embodiments supporting FIG. 9.

FIG. 24 depicts a flowchart of operations using the third message wizard on the physician extender computer in accordance with embodiments supporting FIG. 9. Operation 1150 starts the operations of this flowchart. Arrow 1152 directs the flow of execution from operation 1150 to operation 1154. Operation 1154 performs receiving a second patient message by first physician extender operating a computer at the corresponding physician extender address. Arrow 1156 directs execution from operation 1154 to operation 1158. Operation 1158 performs processing the received second patient medical query message to create a processed, received second patient medical query message. Arrow 1160 directs execution from operation 1158 to operation 1162. Operation 1162 performs generating a physician extender-viewable patient medical query message from the processed, received second patient medical query message. Arrow 1164 directs execution from operation 1162 to operation 1166. Operation 1166 performs displaying the physician extender-viewable medical query message. Arrow 1168 directs execution from operation 1166 to operation 1170. Operation 1170 performs responding to the physician extender-viewable medical query message to create a physician extender response. Arrow 1172 directs execution from operation 1170 to operation 1174. Operation 1174 performs generating the proposed patient response message from physician extender response. Arrow 1176 directs execution from operation 1174 to operation 1178. Operation 1178 performs sending the proposed patient response message to the first physician at the corresponding physician address. Arrow 1180 directs execution from operation 1178 to operation 1182. Operation 1182 terminates the operations of this flowchart.

Figure 25:
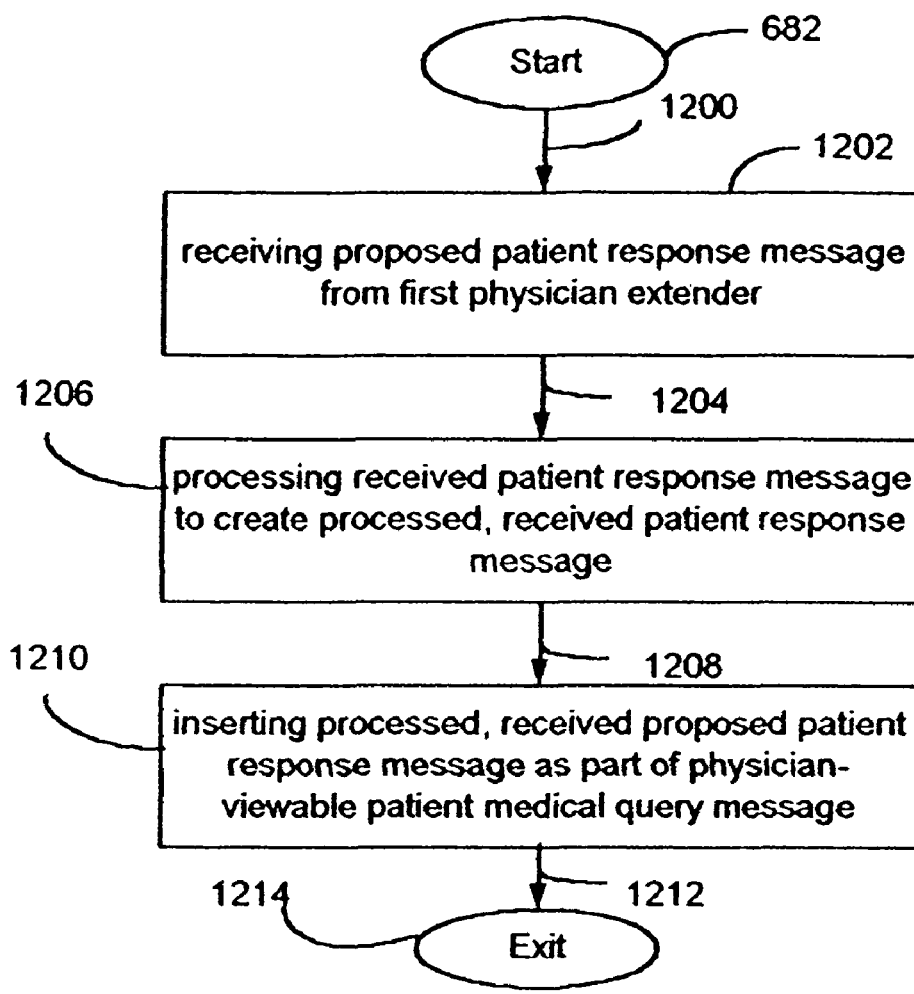
FIG. 25 depicts a flowchart of further details regarding operation 602, generating the physician-viewable patient medical query message in accordance with embodiments supporting FIG. 7.

FIG. 25 depicts a flowchart of further details regarding operation 682, generating the physician-viewable patient medical query message in accordance with embodiments supporting FIG. 7. Arrow 1200 directs the flow of execution from starting operation 682 to operation 1202. Operation 1202 performs receiving proposed patient response message from first physician extender. Arrow 1204 directs execution from operation 1202 to operation 1206. Operation 1206 performs processing the received patient response message to create processed, received patient response message. Arrow 1208 directs execution from operation 1206 to operation 1210. Operation 1210 performs inserting the processed, received proposed patient response message as part of the physician-viewable patient medical query message. Arrow 1212 directs execution from operation 1210 to operation 1214. Operation 1214 terminates the operations of this flowchart.

Figure 26:
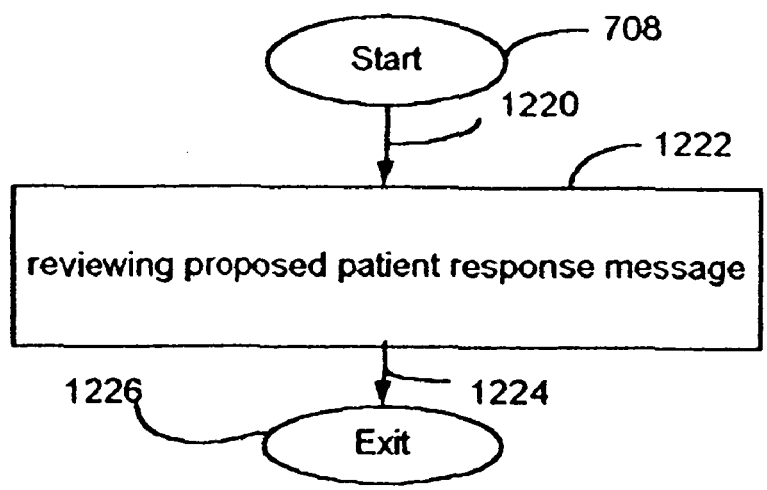
FIG. 26 depicts a flowchart of further details regarding operation 708, generating the patient response message using the second message wizard in accordance with embodiments supporting FIG. 8.

FIG. 26 depicts a flowchart of further details regarding operation 708, generating the patient response message using the second message wizard in accordance with certain embodiments. Arrow 1220 directs the flow of execution from starting operation 708 to operation 1222. Operation 1222 performs reviewing the proposed patient response message. Arrow 1224 directs execution from operation 1222 to operation 1226. Operation 1226 terminates the operations of this flowchart.

Figure 27:
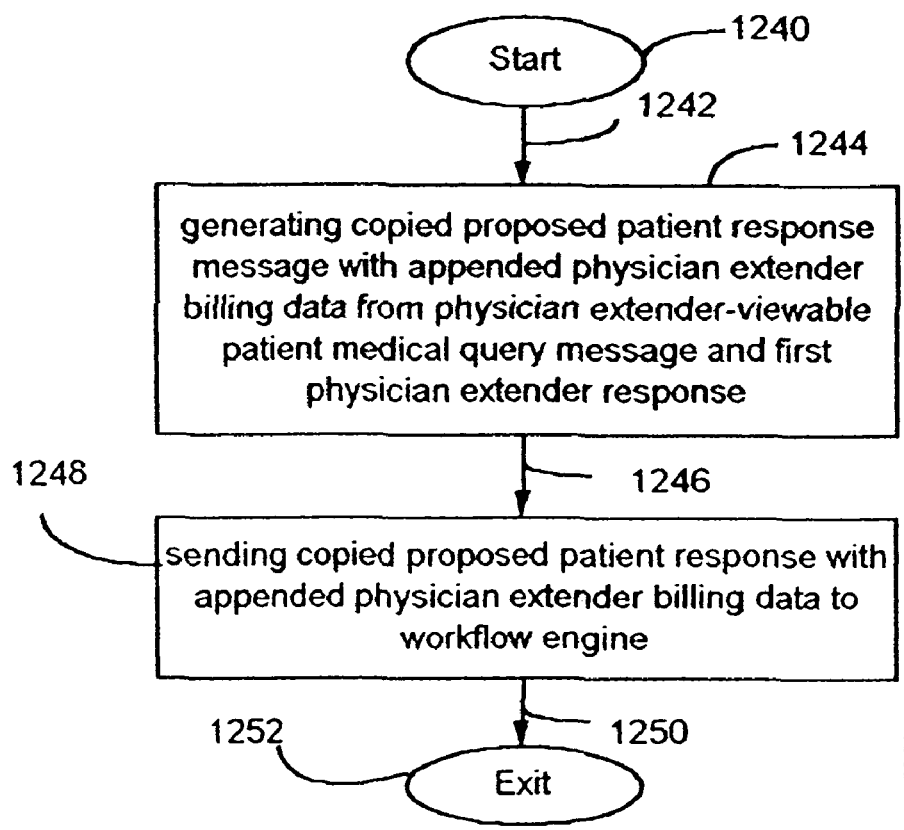
FIG. 27 depicts a flowchart of further operations embodying the third message wizard in accordance with certain embodiments.

FIG. 27 depicts a flowchart of further operations embodying the third message wizard in accordance with certain embodiments. Arrow 1240 directs the flow of execution from starting operation 1240 to operation 1242. Operation 1242 performs generating a copied proposed patient response message with appended physician extender billing data from the physician extender-viewable patient medical query message and first physician extender response. Arrow 1244 directs execution from operation 1242 to operation 1246. Operation 1246 performs sending copied proposed patient response with appended physician extender billing data to workflow engine. Arrow 1248 directs execution from operation 1246 to operation 1250. Operation 1250 terminates the operations of this flowchart.

Figure 28:
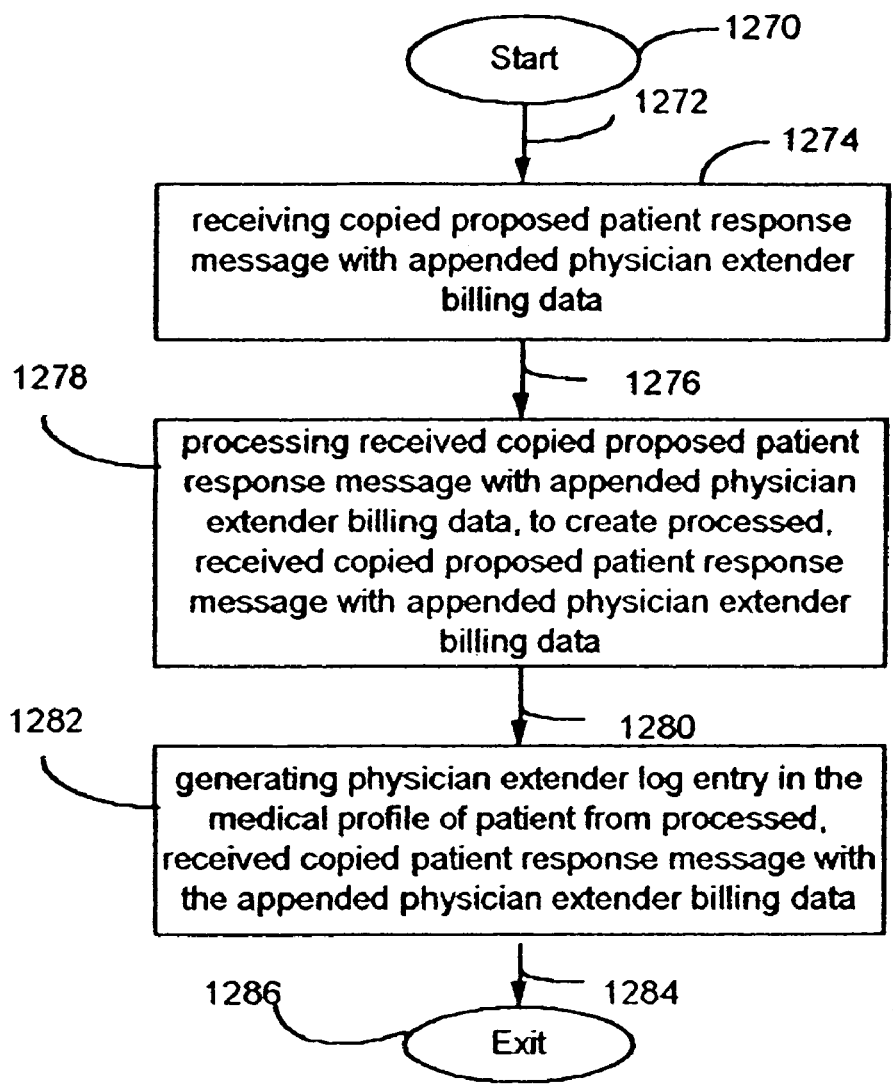
FIG. 28 depicts a flowchart of further operations embodied in the message profiler process in accordance with certain embodiments.

FIG. 28 depicts a flowchart of further operations embodied in the message profiler process in accordance with certain embodiments. Operation 1270 starts the operations of this flowchart. Arrow 1272 directs the flow of execution from operation 1270 to operation 1274. Operation 1274 performs receiving the copied proposed patient response message with the appended physician extender billing data. Arrow 1276 directs execution from operation 1274 to operation 1278. Operation 1278 performs processing the received copied proposed patient response message with the appended physician extender billing data, to create a processed, received copied proposed patient response message with the appended physician extender billing data. Arrow 1280 directs execution from operation 1278 to operation 1282. Operation 1282 performs generating a physician extender log entry in the medical profile of the patient from the processed, received copied patient response message with the appended physician extender billing data. Arrow 1284 directs execution from operation 1282 to operation 1286. Operation 1286 terminates the operations of this flowchart.

Figure 29:
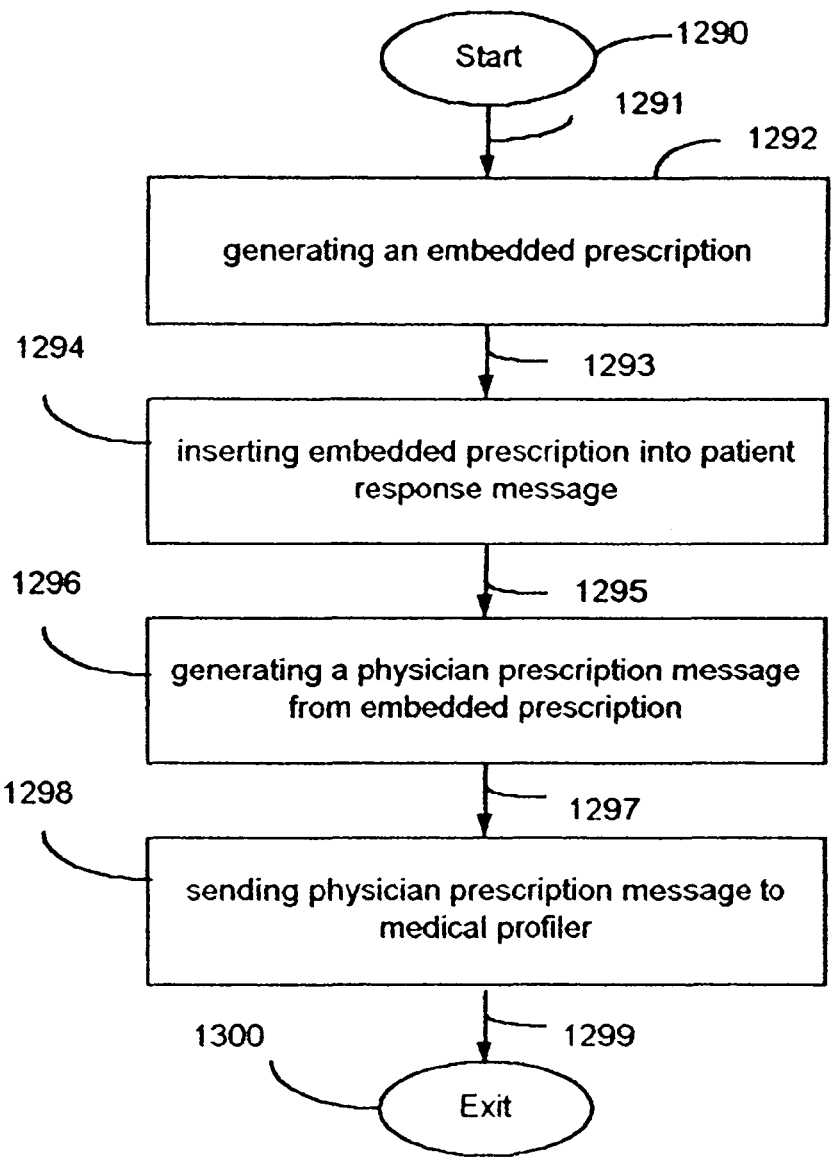
FIG. 29 depicts a flowchart of further operations embodied in a second messaging wizard in accordance with certain embodiments supporting prescriptions.

FIG. 29 depicts a flowchart of further operations embodied in a second messaging wizard in accordance with certain embodiments supporting prescriptions. Operation 1290 starts the operations of this flowchart. Arrow 1291 directs the flow of execution from operation 1290 to operation 1292. Operation 1292 performs generating an embedded prescription. Arrow 1293 directs execution from operation 1292 to operation 1294. Operation 1294 performs inserting the embedded prescription into patient response message. Arrow 1295 directs execution from operation 1294 to operation 1296. Operation 1296 performs generating a physician prescription message from the embedded prescription. Arrow 1297 directs execution from operation 1296 to operation 1298. Operation 1298 performs sending the physician prescription message to the workflow engine. Arrow 1299 directs execution from operation 1298 to operation 1300. Operation 1300 terminates the operations of this flowchart.

Figure 30:
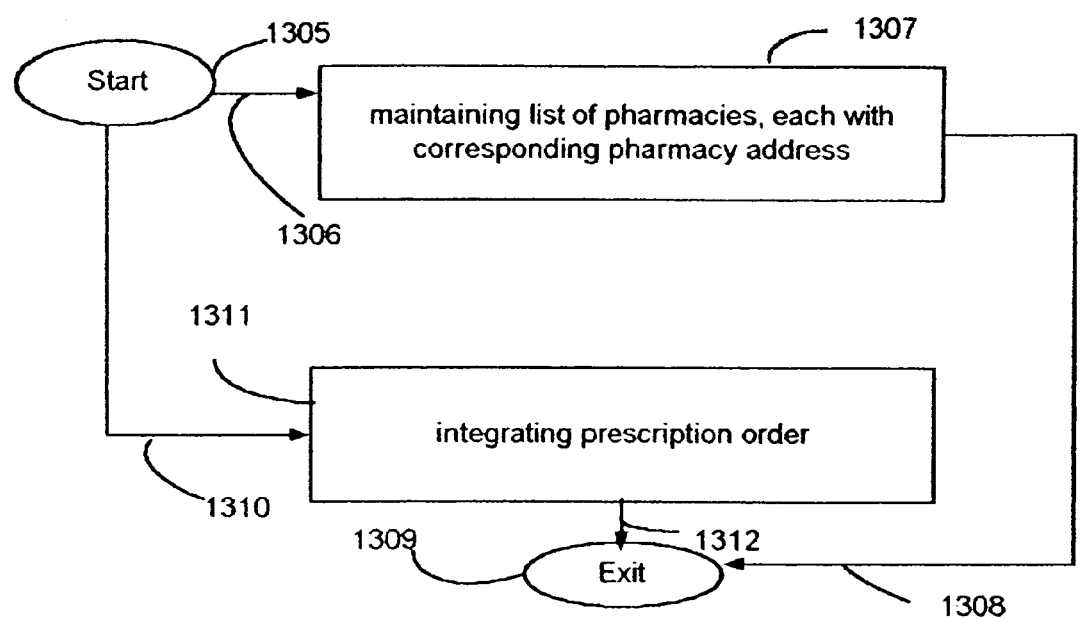
FIG. 30 depicts a flowchart of further operations embodied in a medical profiler in accordance with certain embodiments supporting prescriptions.

FIG. 30 depicts a flowchart of further operations embodied in a medical profiler in accordance with certain embodiments supporting prescriptions. Operation 1305 starts the operations of this flowchart. Arrow 1306 directs the flow of execution from operation 1305 to operation 1307. Operation 1307 performs maintaining a list of pharmacies, each with a corresponding pharmacy address. Arrow 1308 directs execution from operation 1307 to operation 1309. Operation 1309 terminates the operations of this flowchart.

Arrow 1310 directs the flow of execution from starting operation 1305 to operation 1311. Operation 1311 performs integrating a prescription order. Arrow 1312 directs execution from operation 1311 to operation 1309. Operation 1309 terminates the operations of this flowchart.

Note that arrows 1306 and 1310 may be concurrently active, the pharmacy list may be undergoing maintenance operations and the integration of prescription orders may be performed concurrently on either the same computer or distinct computers according to various embodiments of the invention.

Figure 30A:
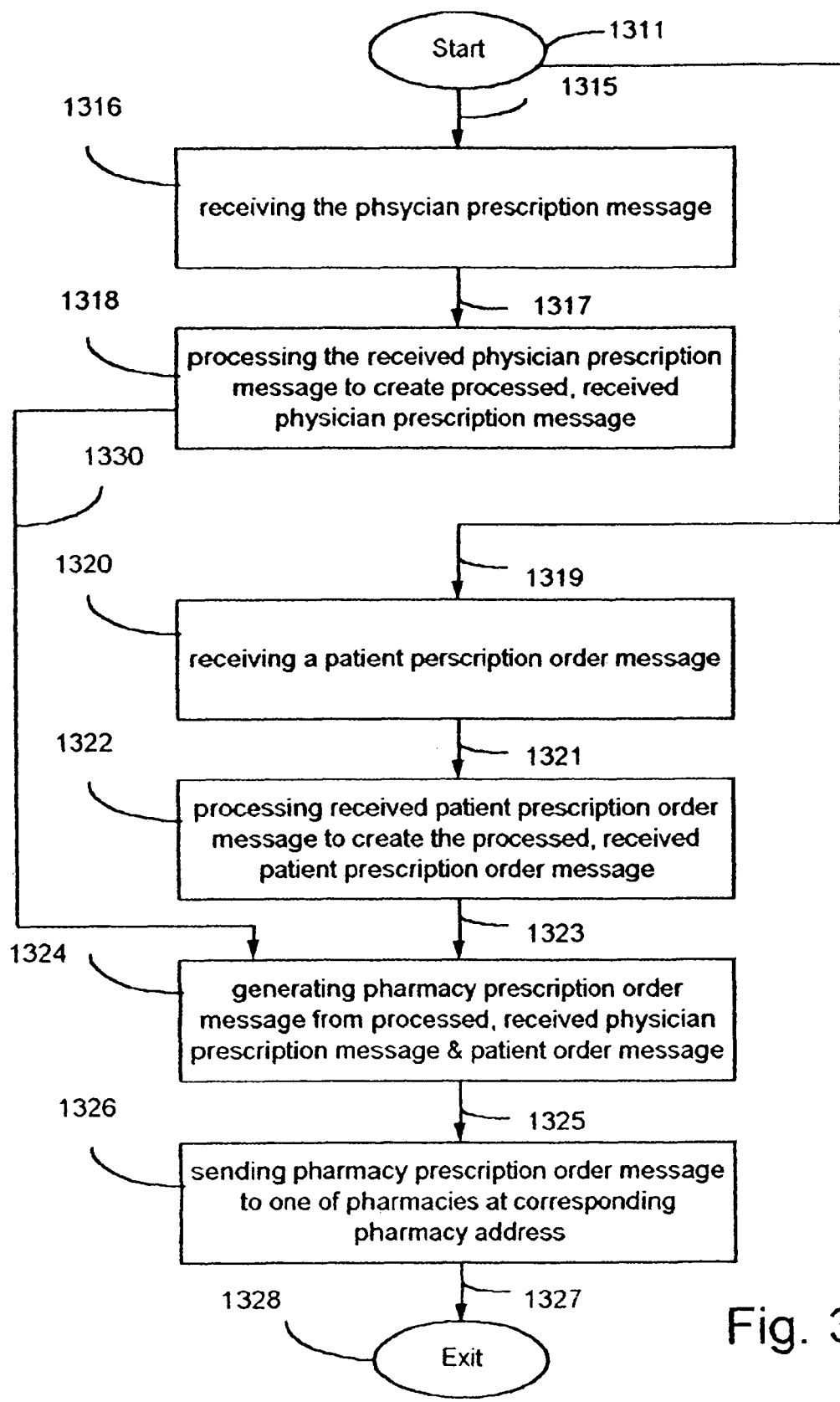
FIG. 30A depicts a flowchart of further details regarding operation 1311, integrating a prescription order in the medical profiler process in accordance with embodiments supporting FIG. 30.

FIG. 30A depicts a flowchart of further details regarding operation 1311, integrating a prescription order in the medical profiler process in accordance with embodiments supporting FIG. 30. Arrow 1315 directs the flow of execution from the starting of operation 1311 to operation 1316. Operation 1316 performs receiving the physician prescription message. Arrow 1317 directs execution from operation 1316 to operation 1318. Operation 1318 performs processing the received physician prescription message, to create a processed, received physician prescription message.

Arrow 1319 directs execution from operation 1311 to operation 1320. Operation 1320 performs receiving a patient prescription order message. Arrow 1321 directs execution from operation 1320 to operation 1322. Operation 1322 performs processing the received patient prescription order message to create a processed, received patient prescription order message.

Arrow 1323 directs execution from operation 1322 to operation 1324. Arrow 1330 directs execution from operation 1318 to operation 1324. Note that in certain embodiments, both arrows 1323 and 1330 must perform their flow of execution before operation 1324 can execute. Operation 1324 performs generating a pharmacy prescription order message from the processed, received physician prescription message and the processed, received patient prescription order message. Arrow 1325 directs execution from operation 1324 to operation 1326. Operation 1326 performs sending the pharmacy prescription order message to one of the pharmacies at the corresponding pharmacy address. Arrow 1327 directs execution from operation 1326 to operation 1328. Operation 1328 terminates the operations of this flowchart.

Figure 31:
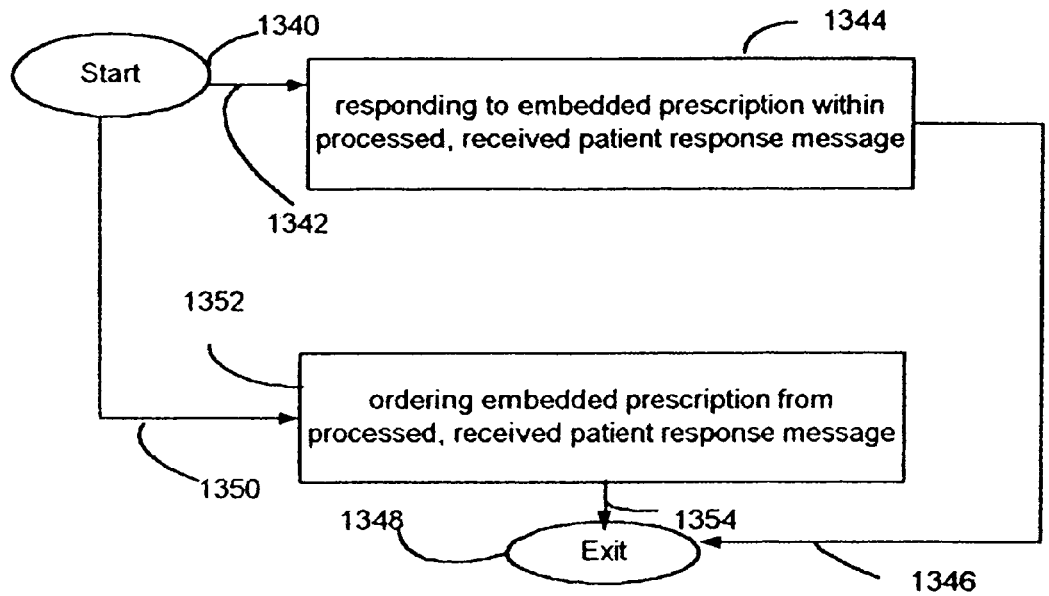
FIG. 31 depicts a flowchart of further operations embodied in the first messaging wizard in accordance with certain embodiments supporting prescriptions.

FIG. 31 depicts a flowchart of further operations embodied in the first messaging wizard in accordance with certain embodiments supporting prescriptions. Operation 1340 starts the operations of this flowchart. Arrow 1342 directs the flow of execution from operation 1340 to operation 1344. Operation 1344 performs responding to the embedded prescription within the processed, received patient response message. Arrow 1346 directs execution from operation 1344 to operation 1348. Operation 1348 terminates the operations of this flowchart.

Arrow 1350 directs the flow of execution from starting operation 1340 to operation 1352. Operation 1352 performs ordering the embedded prescription from the processed, received patient response message. Arrow 1354 directs execution from operation 1352 to operation 1348. Operation 1348 terminates the operations of this flowchart.

Note that in certain embodiments, the starting operation may act as a branching mechanism. Such a mechanism can be driven by patient choices via a user interface, such as buttons or pull down menus being selected or pushed.

Figure 32:
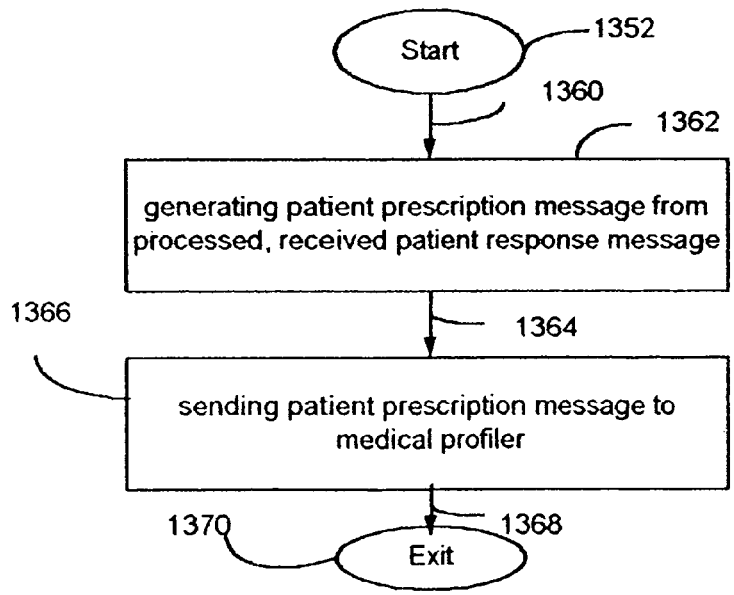
FIG. 32 depicts a flowchart of further details of operation 1352, ordering the embedded prescription of FIG. 31.

FIG. 32 depicts a flowchart of further details of operation 1352, ordering the embedded prescription of FIG. 31. Arrow 1360 directs the flow of execution from starting operation 1352 to operation 1362. Operation 1362 performs generating a patient prescription message from the processed, received patient response message. Arrow 1364 directs execution from operation 1362 to operation 1366. Operation 1366 performs sending the patient prescription message to the workflow engine. Arrow 1368 directs execution from operation 1366 to operation 1370. Operation 1370 terminates the operations of this flowchart.

Figure 33:
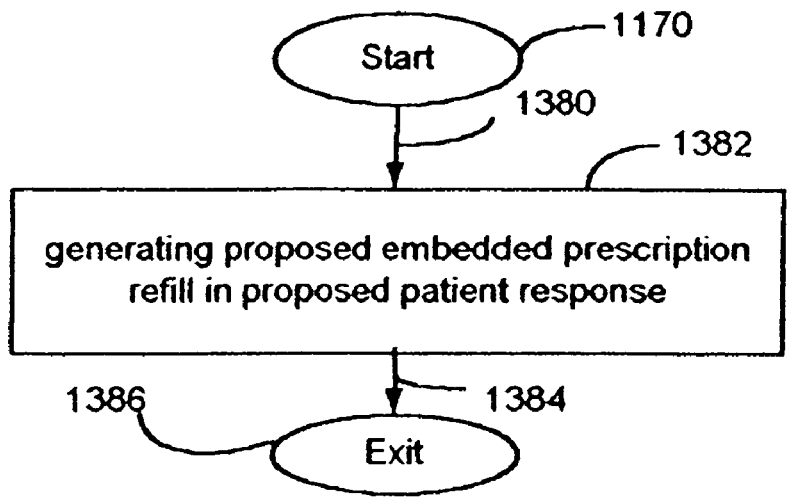
FIG. 33 depicts a flowchart of further details of operation 1170 of FIG. 25.

FIG. 33 depicts a flowchart of further details of operation 1170 of FIG. 25. Arrow 1380 directs the flow of execution from starting operation 1170 to operation 1382. Operation 1382 performs generating a proposed embedded prescription refill in the proposed patient response. Arrow 1384 directs execution from operation 1382 to operation 1386. Operation 1386 terminates the operations of this flowchart.

Figure 34:
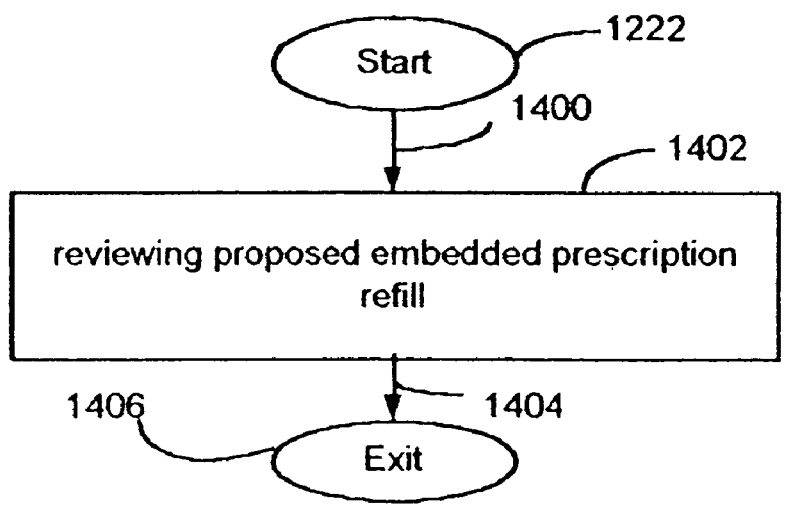
FIG. 34 depicts a flowchart of further details of operation 1222 of FIG. 27.

FIG. 34 depicts a flowchart of further details of operation 1222 of FIG. 27. Arrow 1400 directs the flow of execution from starting operation 1222 to operation 1402. Operation 1402 performs reviewing the proposed embedded prescription refill. Arrow 1404 directs execution from operation 1402 to operation 1406. Operation 1406 terminates the operations of this flowchart.

Figure 35:
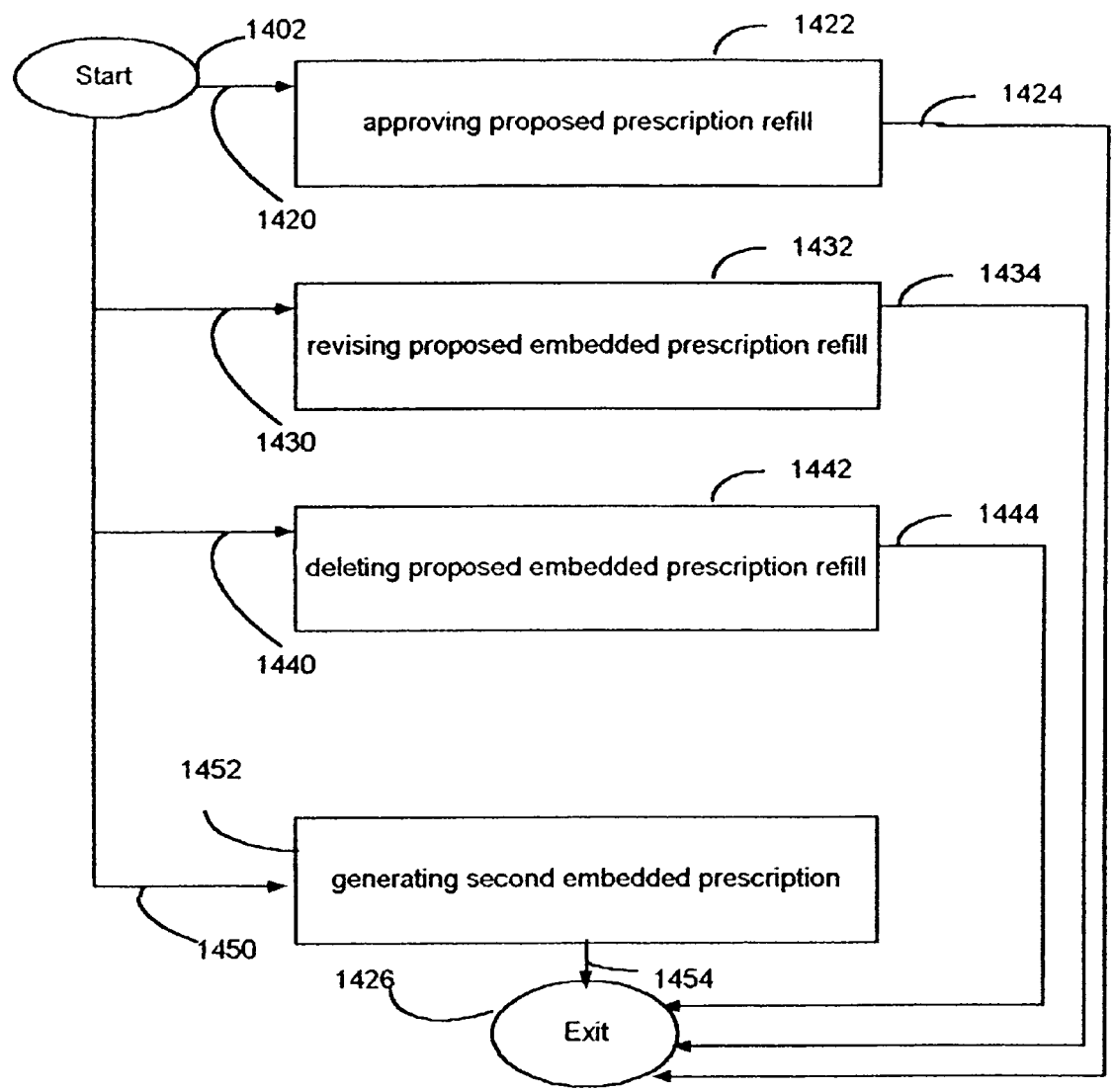
FIG. 35 depicts a flowchart of further details of operation 1402 of FIG. 34.

FIG. 35 depicts a flowchart of further details of operation 1402 of FIG. 34. Arrow 1420 directs the flow of execution from starting operation 1402 to operation 1422. Operation 1422 performs approving the proposed prescription refill. Arrow 1424 directs execution from operation 1422 to operation 1426. Operation 1426 terminates the operations of this flowchart.

Arrow 1430 directs the flow of execution from starting operation 1402 to operation 1432. Operation 1432 performs revising the proposed embedded prescription refill. Arrow 1434 directs execution from operation 1432 to operation 1426. Operation 1426 terminates the operations of this flowchart.

Arrow 1440 directs the flow of execution from starting operation 1402 to operation 1442. Operation 1442 performs deleting the proposed embedded prescription refill. Arrow 1444 directs execution from operation 1442 to operation 1426. Operation 1426 terminates the operations of this flowchart.

Arrow 1450 directs the flow of execution from starting operation 1402 to operation 1452. Operation 1452 performs generating a second embedded prescription. Arrow 1454 directs execution from operation 1452 to operation 1426. Operation 1426 terminates the operations of this flowchart.

Note that in certain embodiments, the starting operation may act as a branching mechanism. Such a mechanism can be driven by patient choices via a user interface, such as buttons or pull down menus being selected or pushed.

Figure 36:
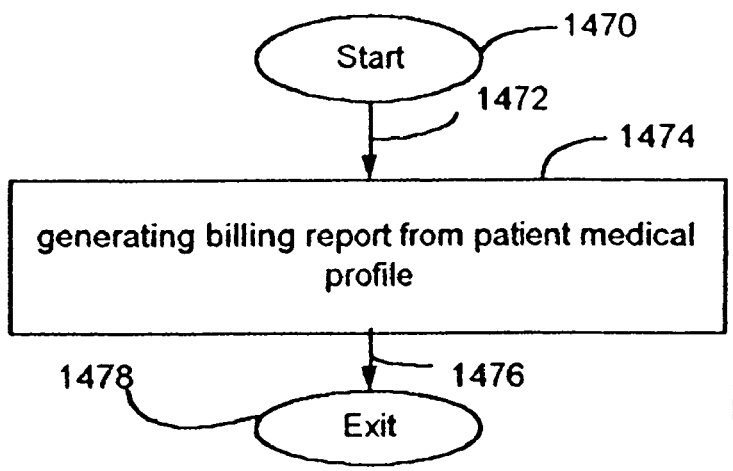
FIG. 36 depicts a flowchart of further operations embodying the message profiler process in accordance with certain embodiments supporting billing patients.

FIG. 36 depicts a flowchart of further operations embodying the message profiler process in accordance with certain embodiments supporting billing patients. Operation 1470 starts the operations of this flowchart. Arrow 1472 directs the flow of execution from operation 1470 to operation 1474. Operation 1474 performs generating a billing report from the patient medical profile. Arrow 1476 directs execution from operation 1474 to operation 1478. Operation 1478 terminates the operations of this flowchart.

Figure 37:
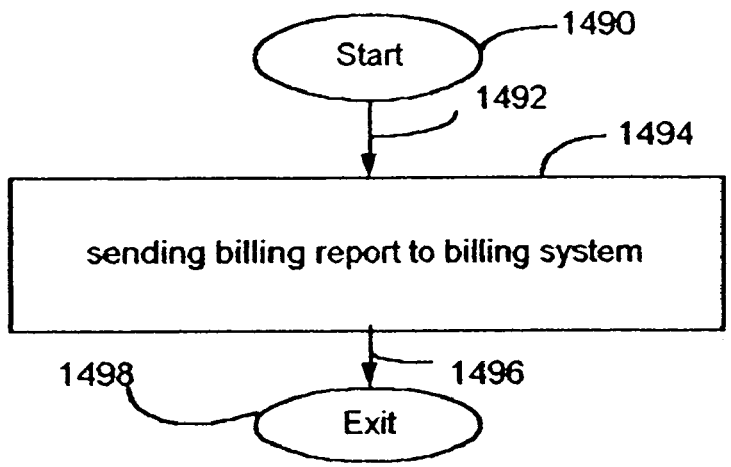
FIG. 37 depicts a flowchart of further operations embodying the message profiler process in accordance with certain embodiments further supporting billing patients.

FIG. 37 depicts a flowchart of further operations embodying the message profiler process in accordance with certain embodiments further supporting billing patients. Operation 1490 starts the operations of this flowchart. Arrow 1492 directs the flow of execution from operation 1490 to operation 1494. Operation 1494 performs sending the billing report to the billing system. Arrow 1496 directs execution from operation 1494 to operation 1498. Operation 1498 terminates the operations of this flowchart.

Figure 38:
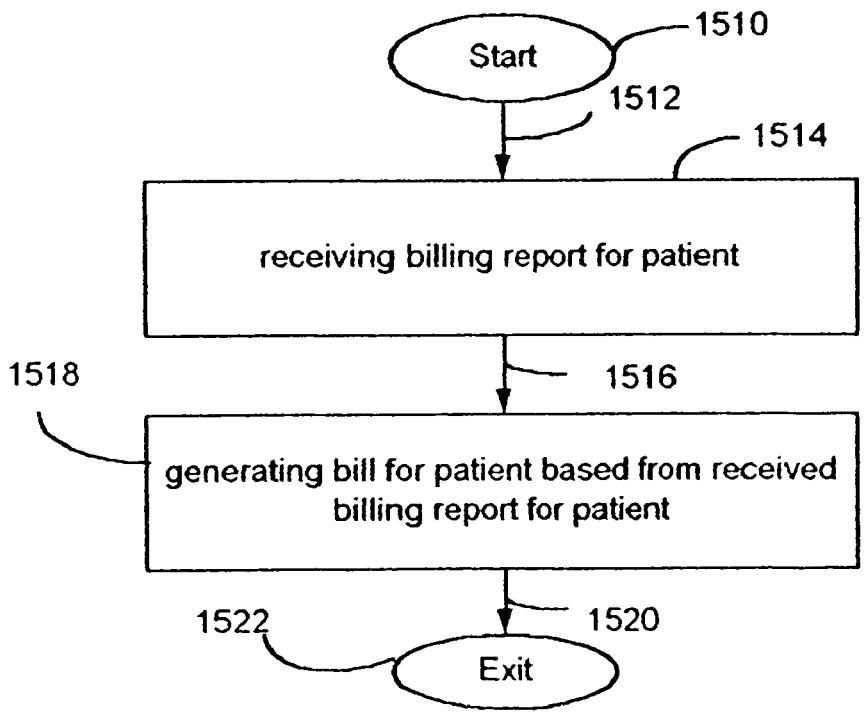
FIG. 38 depicts a flowchart of further operations embodying a billing process in accordance with certain embodiments.

FIG. 38 depicts a flowchart of further operations embodying a billing process in accordance with certain embodiments. Operation 1510 starts the operations of this flowchart. Arrow 1512 directs the flow of execution from operation 1510 to operation 1514. Operation 1514 performs receiving the billing report for the patient. Arrow 1516 directs execution from operation 1514 to operation 1518. Operation 1518 performs generating a bill for the patient based from the received billing report for the patient. Arrow 1520 directs execution from operation 1518 to operation 1522. Operation 1522 terminates the operations of this flowchart. ###

Figure 39:
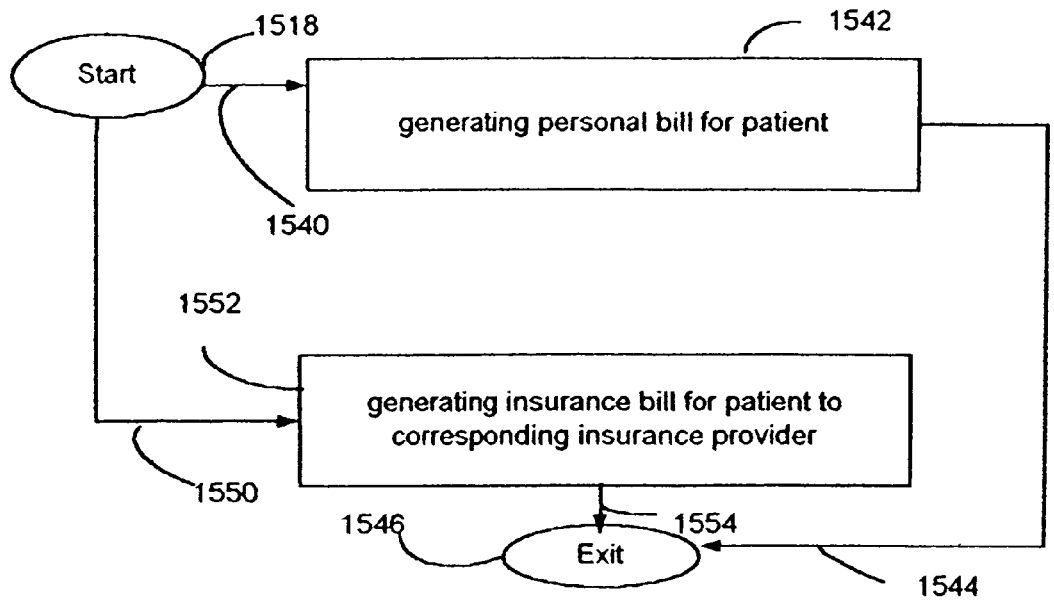
FIG. 39 depicts a flowchart of further details of operation 1518 of FIG. 38.

FIG. 39 depicts a flowchart of further details of operation 1518 of FIG. 38. Arrow 1540 directs the flow of execution from starting operation 1518 to operation 1542. Operation 1542 performs generating a personal bill for the patient. Arrow 1544 directs execution from operation 1542 to operation 1546. Operation 1546 terminates the operations of this flowchart.

Arrow 1550 directs the flow of execution from starting operation 1518 to operation 1552. Operation 1552 performs generating an insurance bill for the patient to corresponding insurance provider. Arrow 1554 directs execution from operation 1552 to operation 1546. Operation 1546 terminates the operations of this flowchart.

Note that a patient may not have insurance, so that in such circumstances, no insurance bills would be generated. Note also, that in certain circumstances, there may be an overall insuring, such as a governmental agency, fully paying for the health costs. In such circumstances, no personal medical bill might be generated. In certain alternative embodiments, the performing of these operations might not lead to output of one or the other kinds of medical bills.

Figure 40:
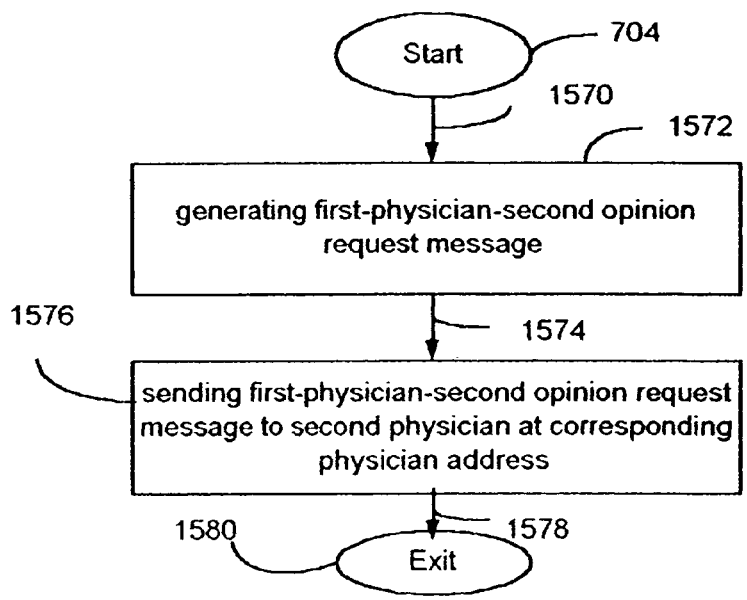
FIG. 40 depicts a flowchart of further details of operation 708 of FIG. 8 supporting a physician requesting a second opinion in accordance with certain embodiments.

FIG. 40 depicts a flowchart of further details of operation 708 of FIG. 8 supporting a physician requesting a second opinion in accordance with certain embodiments. Arrow 1570 directs the flow of execution from starting operation 704 to operation 1572. Operation 1572 performs generating a first-physician-second opinion request message. Arrow 1574 directs execution from operation 1572 to operation 1576. Operation 1576 performs sending the first-physician-second opinion request message to the second physician at the corresponding physician address. Arrow 1578 directs execution from operation 1576 to operation 1580. Operation 1580 terminates the operations of this flowchart.

Figure 41:
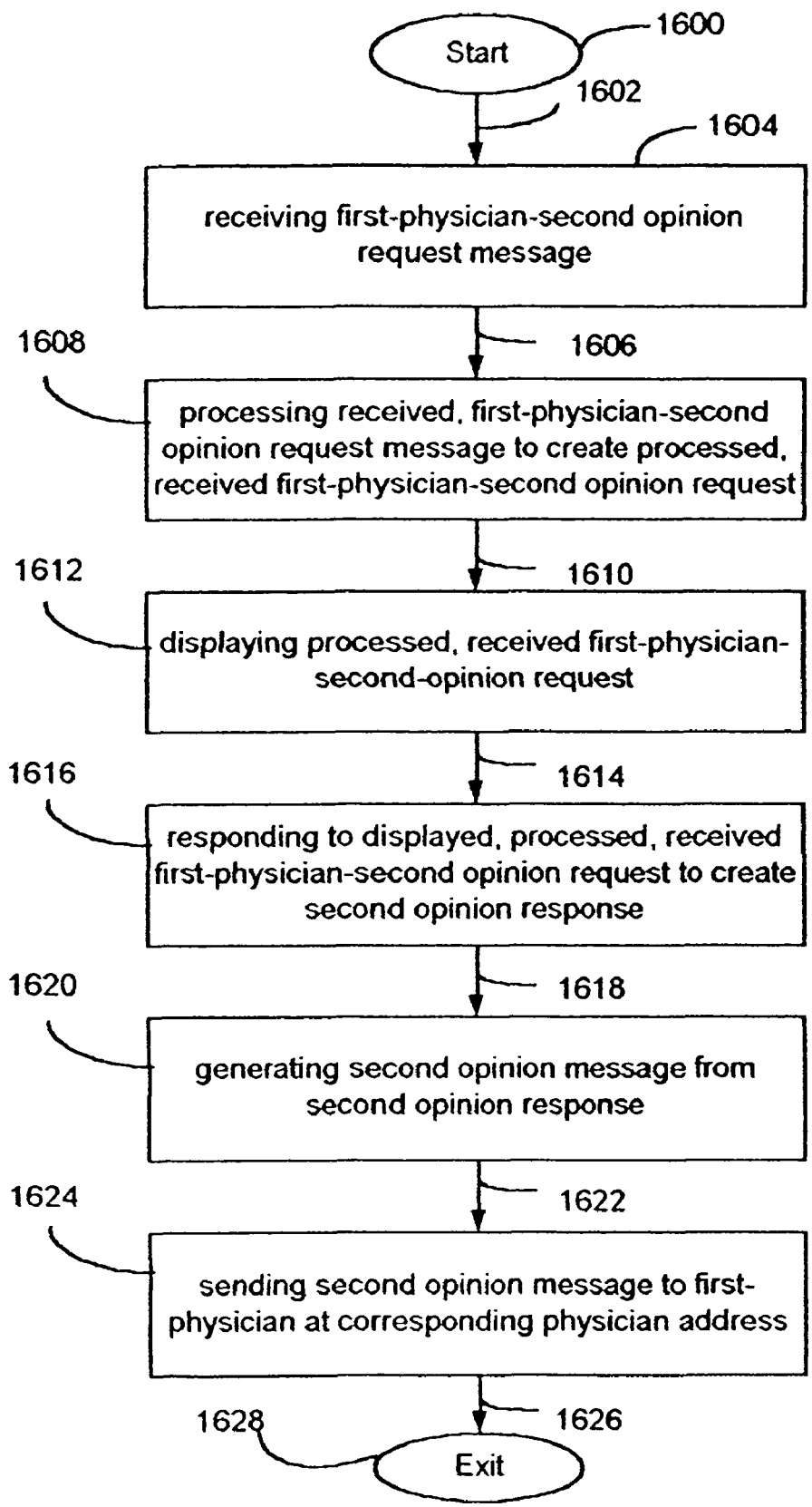
FIG. 41 depicts a flowchart of operations embodied in the second message wizard supporting a second physician and a second opinion request in accordance with certain embodiments.

FIG. 41 depicts a flowchart of operations embodied in the second message wizard supporting a second physician and a second opinion request in accordance with certain embodiments. Operation 1600 starts the operations of this flowchart. Arrow 1602 directs the flow of execution from operation 1600 to operation 1604. Operation 1604 performs receiving the first-physician-second opinion request message. Arrow 1606 directs execution from operation 1604 to operation 1608. Operation 1608 performs processing the received, first-physician-second opinion request message to create the processed, received first-physician-second opinion request. Arrow 1610 directs execution from operation 1608 to operation 1612. Operation 1612 performs displaying the processed, received first-physician-second-opinion request. Arrow 1614 directs execution from operation 1612 to operation 1616. Operation 1616 performs responding to the displayed, processed, received first-physician-second opinion request to create a second opinion response. Arrow 1618 directs execution from operation 1616 to operation 1620. Operation 1620 performs generating a second opinion message from the second opinion response. Arrow 1622 directs execution from operation 1620 to operation 1624. Operation 1624 performs sending the second opinion message to the first-physician at the corresponding physician address. Arrow 1626 directs execution from operation 1624 to operation 1628. Operation 1628 terminates the operations of this flowchart.

Figure 42:
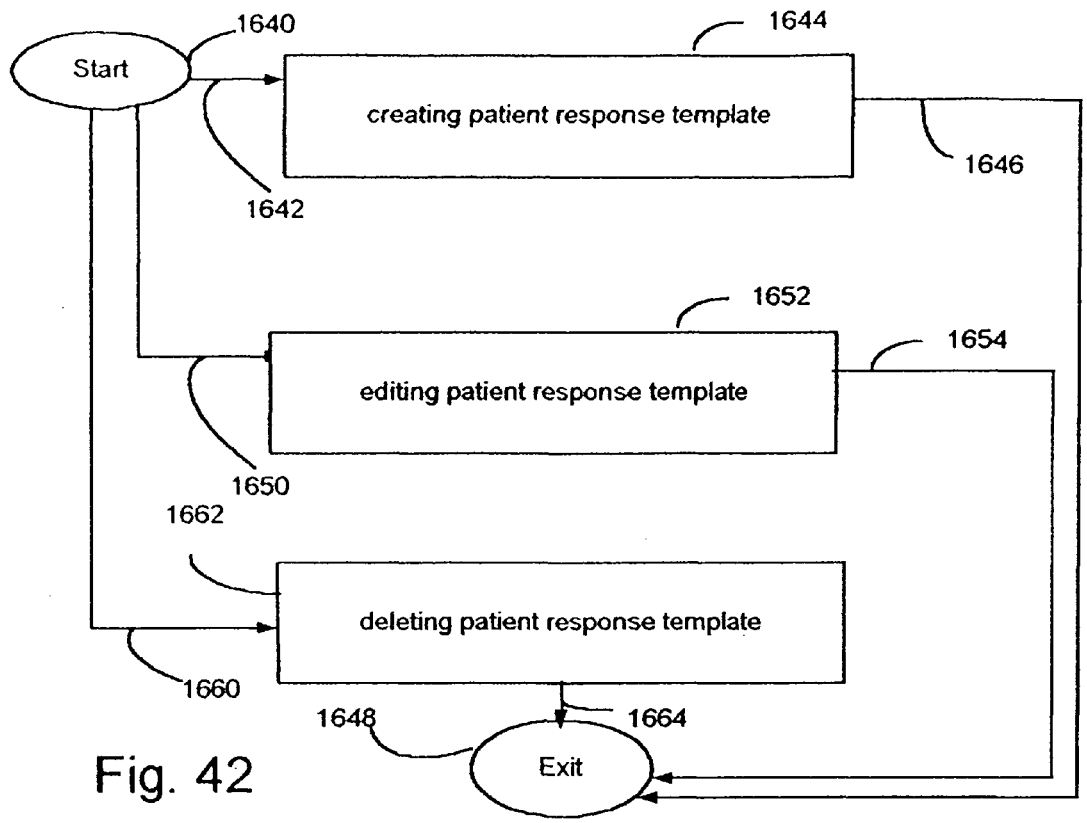
FIG. 42 depicts a flowchart of operations embodied in a second message wizard supporting maintaining a collection of patient response templates in accordance with certain embodiments.

FIG. 42 depicts a flowchart of operations embodied in a second message wizard supporting maintaining a collection of patient response templates in accordance with certain embodiments. Operation 1640 starts the operations of this flowchart. Arrow 1642 directs the flow of execution from operation 1640 to operation 1644. Operation 1644 performs creating a patient response template. Arrow 1646 directs execution from operation 1644 to operation 1648. Operation 1648 terminates the operations of this flowchart.

Arrow 1650 directs the flow of execution from starting operation 1640 to operation 1652. Operation 1652 performs editing one of the patient response templates. Arrow 1654 directs execution from operation 1652 to operation 1648. Operation 1648 terminates the operations of this flowchart.

Arrow 1660 directs the flow of execution from starting operation 1640 to operation 1662. Operation 1662 performs deleting one of the patient response templates. Arrow 1664 directs execution from operation 1662 to operation 1648. Operation 1648 terminates the operations of this flowchart.

Note that in certain embodiments, the starting operation may act as a branching mechanism. Such a mechanism can be driven by patient choices via a user interface, such as buttons or pull down menus being selected or pushed.

Figure 43:
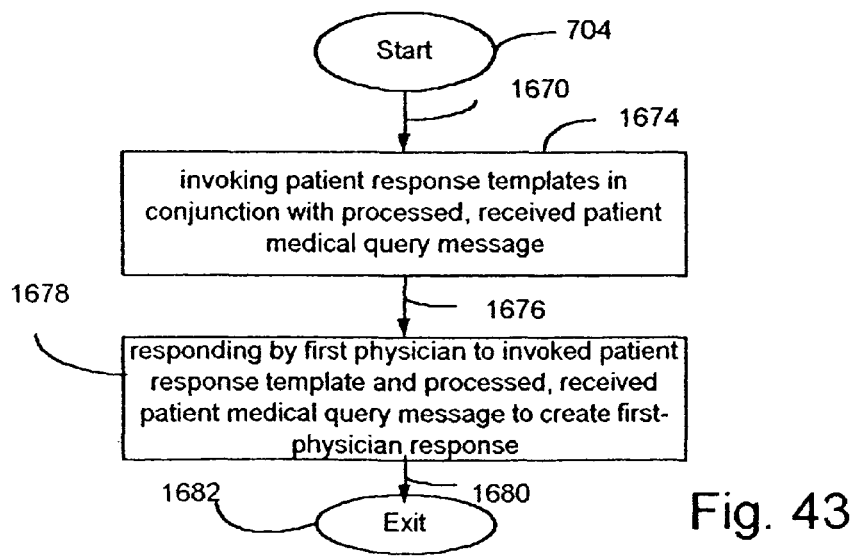
FIG. 43 depicts a flowchart of further details of operation 704 of FIG. 8 supporting use of a patient response template to create a first-physician response in accordance with certain embodiments.

FIG. 43 depicts a flowchart of further details of operation 704 of FIG. 8 supporting use of a patient response template to create a first-physician response in accordance with certain embodiments. Arrow 1670 directs the flow of execution from starting operation 704 to operation 1672. Operation 1672 performs invoking one of the patient response templates in conjunction with the processed, received patient medical query message. Arrow 1674 directs execution from operation 1672 to operation 1676. Operation 1676 performs responding by first physician to invoked patient response template and processed, received patient medical query message to create the first-physician response. Arrow 1678 directs execution from operation 1676 to operation 1680. Operation 1680 terminates the operations of this flowchart.

Figure 44:
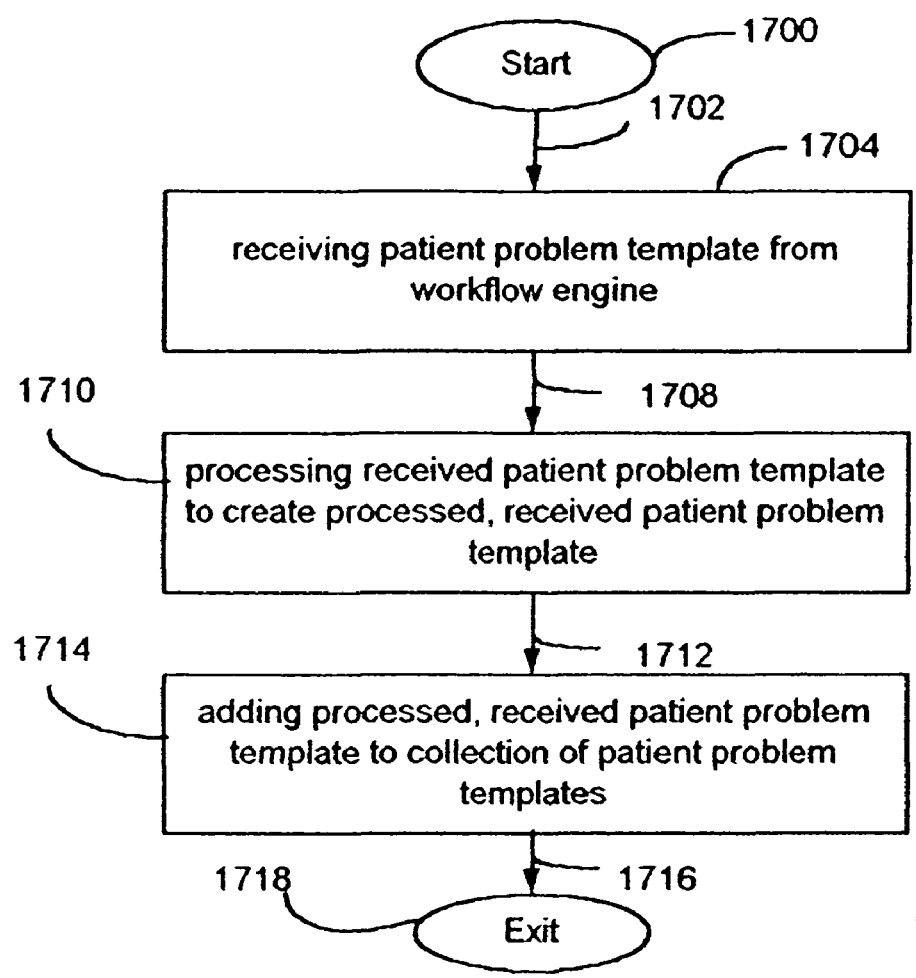
FIG. 44 depicts a flowchart of operations embodied in a first messaging wizard to support maintaining a collection of patient problem templates in accordance with certain embodiments.

FIG. 44 depicts a flowchart of operations embodied in a first messaging wizard to support maintaining a collection of patient problem templates in accordance with certain embodiments. Operation 1700 starts the operations of this flowchart. Arrow 1702 directs the flow of execution from operation 1700 to operation 1704. Operation 1704 performs receiving the patient problem template from workflow engine. Arrow 1706 directs execution from operation 1704 to operation 1708. Operation 1708 performs processing the received patient problem template to create a processed, received patient problem template. Arrow 1710 directs execution from operation 1708 to operation 1712. Operation 1712 performs adding the processed, received patient problem template to the collection of patient problem templates. Arrow 1714 directs execution from operation 1712 to operation 1716. Operation 1716 terminates the operations of this flowchart.

Figure 45:
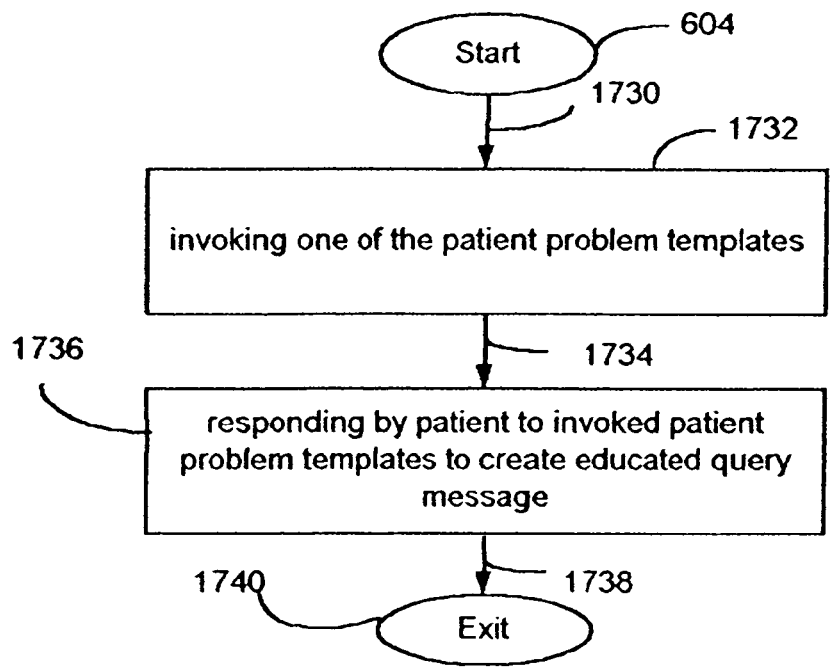
FIG. 45 depicts a flowchart of further details of operation 604 of FIG. 5 supporting use of a patient problem template to create an educated medical query using a first medical wizard in accordance with certain embodiments.

FIG. 45 depicts a flowchart of further details of operation 604 of FIG. 5 supporting use of a patient problem template to create an educated medical query using a first medical wizard in accordance with certain embodiments. Arrow 1730 directs the flow of execution from starting operation 604 to operation 1732. Operation 1732 performs invoking one of the patient problem templates. Arrow 1734 directs execution from operation 1732 to operation 1736. Operation 1736 performs responding by patient to invoked patient problem templates to create the educated query message. Arrow 1738 directs execution from operation 1736 to operation 1740. Operation 1740 terminates the operations of 1520 this flowchart.

Figure 46:
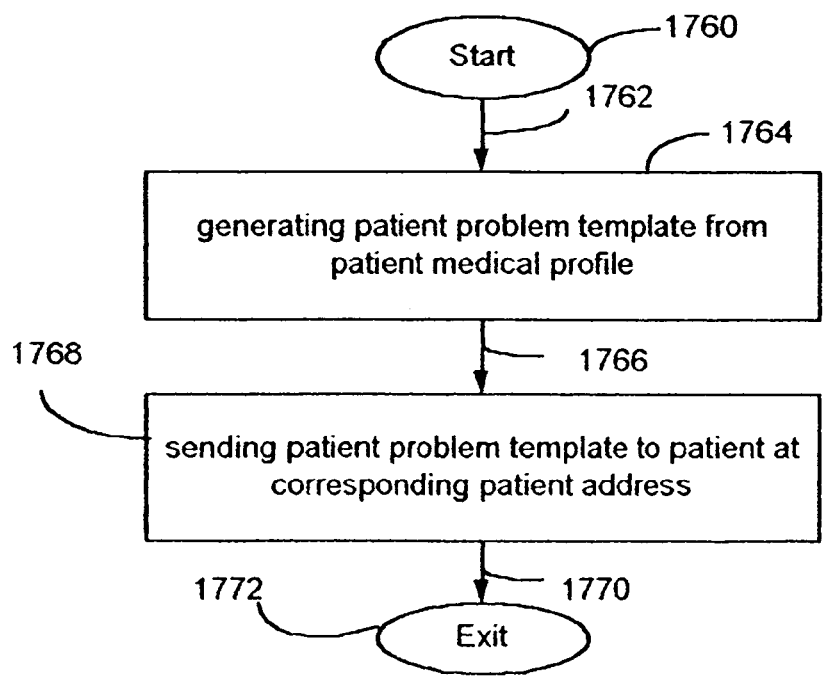
FIG. 46 depicts a flowchart of operations embodied in a medical profiler process to generate and send patient problem templates to patients in accordance with certain embodiments.

FIG. 46 depicts a flowchart of operations embodied in a medical profiler process performed by a workflow engine to generate and send patient problem templates to patients in accordance with certain embodiments. Operation 1760 starts the operations of this flowchart. Arrow 1762 directs the flow of execution from operation 1760 to operation 1764. Operation 1764 performs generating a patient problem template from the patient medical profile. Arrow 1766 directs execution from operation 1764 to operation 1768. Operation 1768 performs sending the patient problem template to the patient at the corresponding patient address. Arrow 1770 directs execution from operation 1768 to operation 1772. Operation 1772 terminates the operations of this flowchart.

Figure 47:
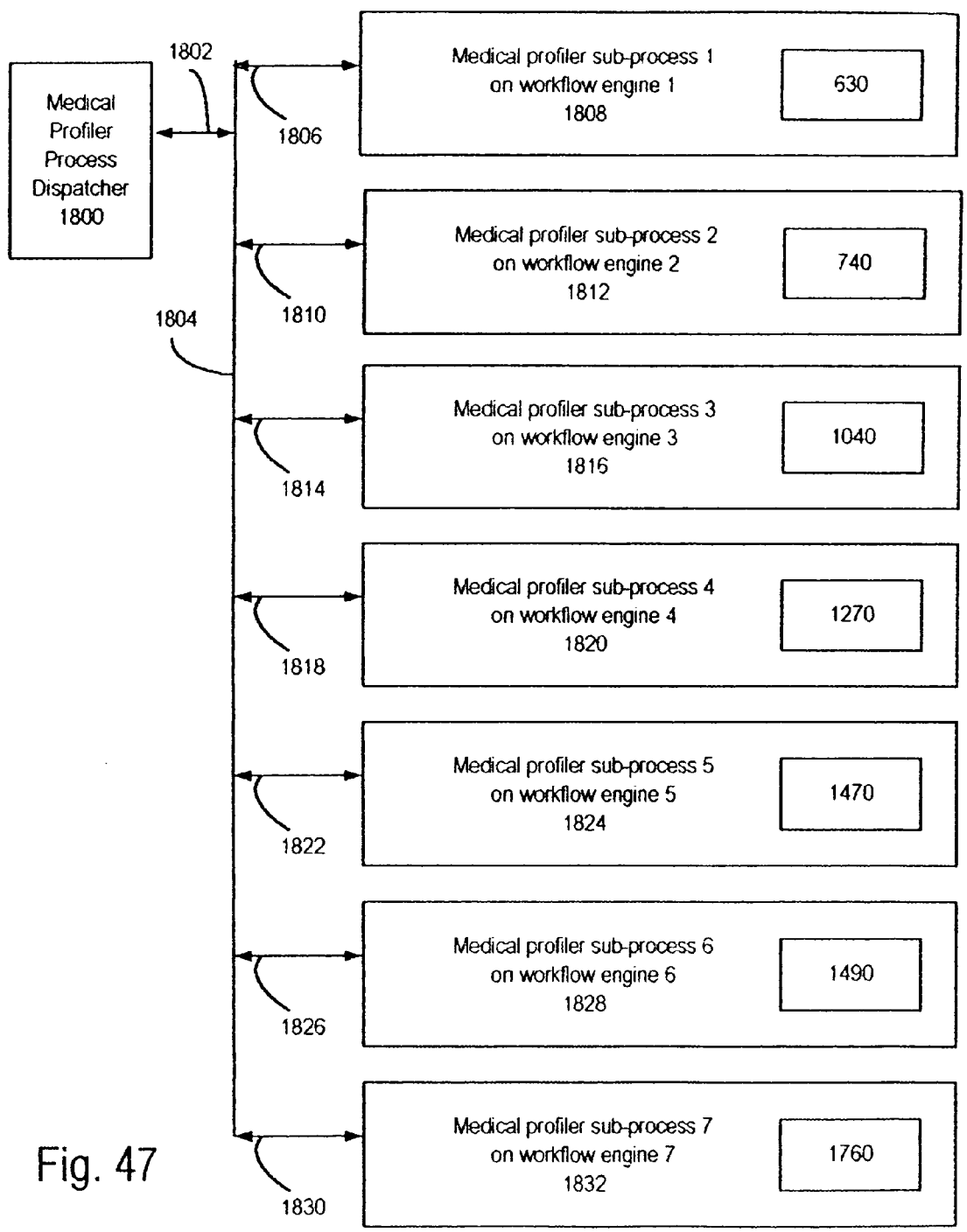
FIG. 47 depicts a flow diagram of a medical profiler process in accordance with certain embodiments.

FIG. 47 depicts a flow diagram of a medical profiler process in accordance with certain embodiments. Box 1800 designates a Medical Profiler Process Dispatcher. This communicates via physical transport mechanism 1802 to network 1804. Box 1808 designates Medical profiler sub-process 1 on workflow engine 1, performing the operation 630 of FIG. 6. This communicates via physical transport mechanism 1806 to network 1804. Box 1812 designates Medical profiler sub-process 2 on workflow engine 2, performing the operation 740 of FIG. 9. This communicates via physical transport mechanism 1810 to network 1804. Box 1816 designates Medical profiler sub-process 3 on workflow engine 3, performing the operation 1040 of FIG. 21. This communicates via physical transport mechanism 1814 to network 1804. Box 1820 designates Medical profiler sub-process 4 on workflow engine 4, performing the operation 1270 of FIG. 28. This communicates via physical transport mechanism 1818 to network 1804. Box 1824 designates Medical profiler sub-process 5 on workflow engine 5, performing the operation 1470 of FIG. 36. This communicates via physical transport mechanism 1822 to network 1804. Box 1828 designates Medical profiler sub-process 6 on workflow engine 6, performing the operation 1490 of FIG. 37. This communicates via physical transport mechanism 1826 to network 1804. Box 1832 designates Medical profiler sub-process 7 on workflow engine 7, performing the operation 1760 of FIG. 46. This communicates via physical transport mechanism 1830 to network 1804.

Note that in certain alternative embodiments, collections of these sub-processes may preferably reside on a single workflow engine. Note that in certain other embodiments, multiple workflow engines may be performing a given sub-process.

Figure 48:
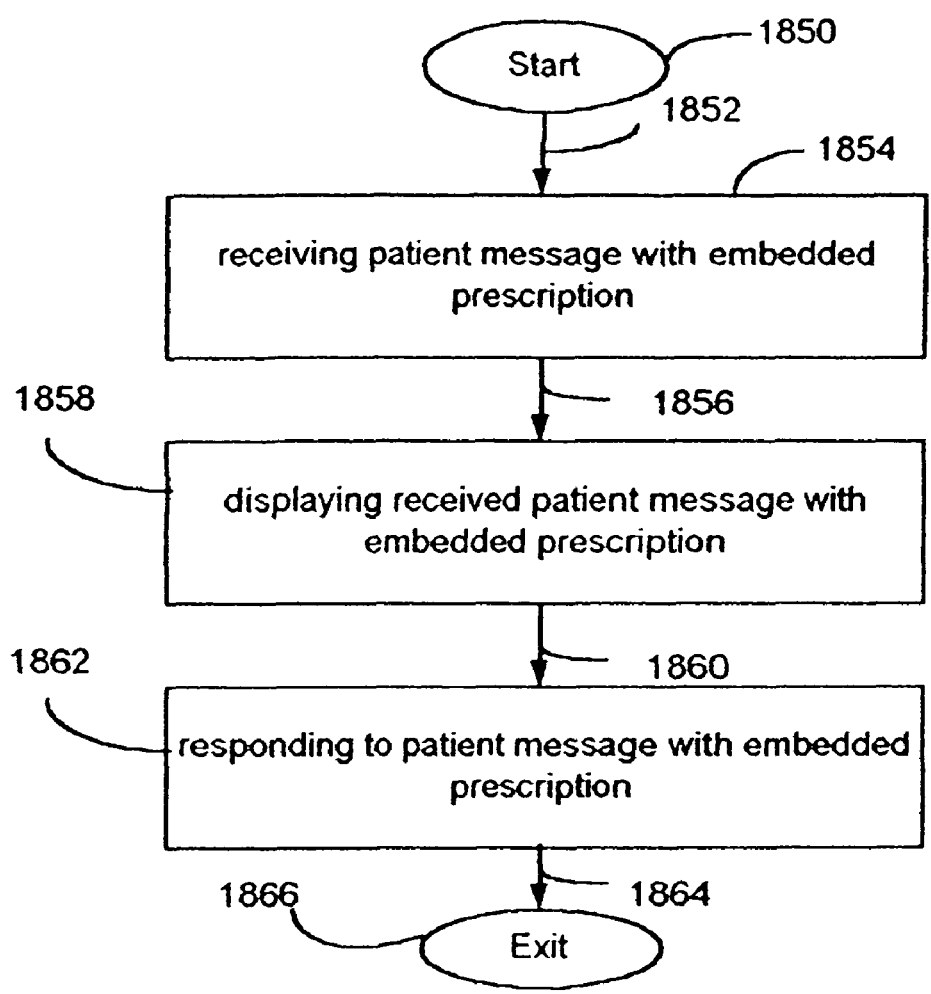
FIG. 48 depicts a flow diagram of a computer program capable of receiving a message from a physician containing a prescription and responding to the message containing the prescription by generating and sending a prescription order message in accordance with certain embodiments in accordance with an aspect of the invention.

FIG. 48 depicts a flow diagram of a computer program capable of receiving a message from a physician containing a prescription and responding to the message containing the prescription in accordance with an aspect of the invention. Operation 1850 starts the operations of this flowchart. Arrow 1852 directs the flow of execution from operation 1850 to operation 1854. Operation 1854 performs receiving the patient message with an embedded prescription. Arrow 1856 directs execution from operation 1854 to operation 1858. Operation 1858 performs displaying the received patient message with embedded prescription. Arrow 1860 directs execution from operation 1858 to operation 1862. Operation 1862 performs responding to the patient message with embedded prescription. Arrow 1864 directs execution from operation 1862 to operation 1866. Operation 1866 terminates the operations of this flowchart.

Figure 49:
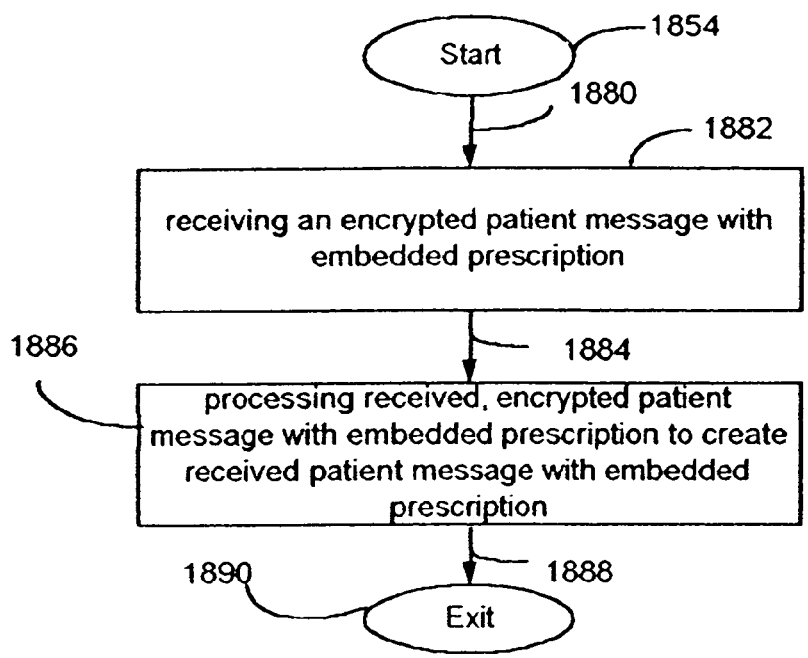
FIG. 49 depicts a flowchart of further details of the code of 1854 of FIG. 48 supporting receiving a patient response message with an embedded prescription in accordance with certain embodiments.

FIG. 49 depicts a flowchart of further details of the code of 1854 of FIG. 48 supporting receiving a patient message with an embedded prescription in accordance with certain embodiments. Arrow 1880 directs the flow of execution from starting operation 1854 to operation 1882. Operation 1882 performs receiving an encrypted patient message with embedded prescription. Arrow 1884 directs execution from operation 1882 to operation 1886. Operation 1886 performs processing the received, encrypted patient message with embedded prescription to create the received patient message with embedded prescription. Arrow 1888 directs execution from operation 1886 to operation 1890. Operation 1890 terminates the operations of this flowchart.

Figure 50:
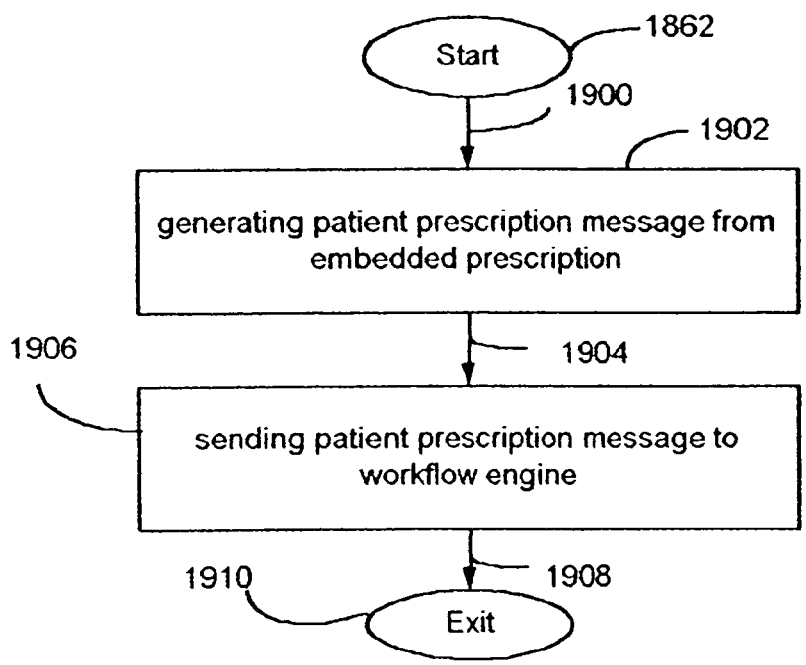
FIG. 50 depicts a flowchart of further details of the code of 1862 of FIG. 48 supporting responding to the patient response message in accordance with certain embodiments.

FIG. 50 depicts a flowchart of further details of the code of 1862 of FIG. 48 supporting responding to the patient response message in accordance with certain embodiments. Arrow 1900 directs the flow of execution from starting operation 1862 to operation 1902. Operation 1902 performs generating a patient prescription message from said embedded prescription. Arrow 1904 directs execution from operation 1902 to operation 1906. Operation 1906 performs sending said patient prescription message to said workflow engine. Arrow 1908 directs execution from operation 1906 to operation 1910. Operation 1910 terminates the operations of this flowchart.

Figure 50A:
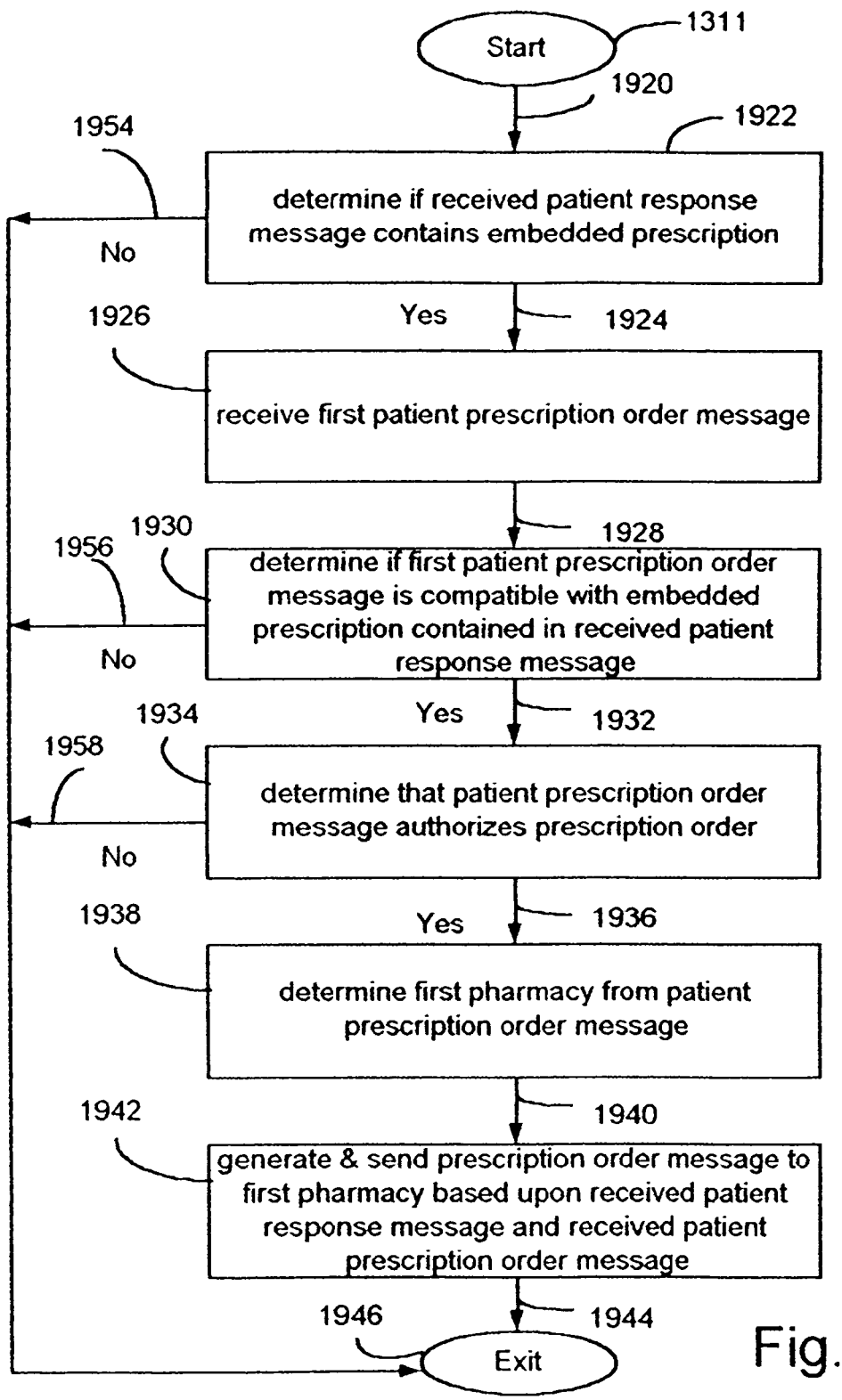
FIG. 50A depicts a flowchart of further details of 1311 of FIG. 30 supporting integrating a prescription order in accordance with certain embodiments.

FIG. 50A depicts a flowchart of further details of 1311 of FIG. 30 supporting integrating a prescription order in accordance with certain embodiments.

Arrow 1920 directs the flow of execution from starting operation 1311 to operation 1922. Operation 1922 determines if the received patient response message contains an embedded prescription. Arrow 1924 directs execution from operation 1922 to operation 1926. Arrow 1924 directs execution when the determination is ☐Yes☐ to operation 1926. Arrow 1954 directs execution when the determination is ☐No☐ to operation 1946.

Operation 1926 performs receiving the patient prescription order message from the first patient. Arrow 1928 directs execution from operation 1926 to operation 1930. Operation 1930 determines if the patient prescription order message from the first patient is compatible with the embedded prescription contained in the received patient response message. Arrow 1932 directs execution from operation 1930 to operation 1934. Arrow 1932 directs execution when the determination is ☐Yes☐ to operation 1934. Arrow 1956 directs execution when the determination is ☐No☐ to operation 1946.

Operation 1934 determines if the patient prescription order received from the first patient authorizes the prescription order. Arrow 1936 directs execution from operation 1934 to operation 1938. Arrow 1936 directs execution when the determination is ☐Yes☐ to operation 1938. Arrow 1958 directs execution when the determination is ☐No☐ to operation 1946.

Operation 1938 determines a first pharmacy from the patient prescription order. Arrow 1940 directs execution from operation 1938 to operation 1942. Operation 1942 performs generates and sends the prescription order message to the first pharmacy based upon the received patient response message and the received patient prescription order message. Arrow 1944 directs execution from operation 1942 to operation 1946. Operation 1946 terminates the operations of this flowchart.

Figure 50B:
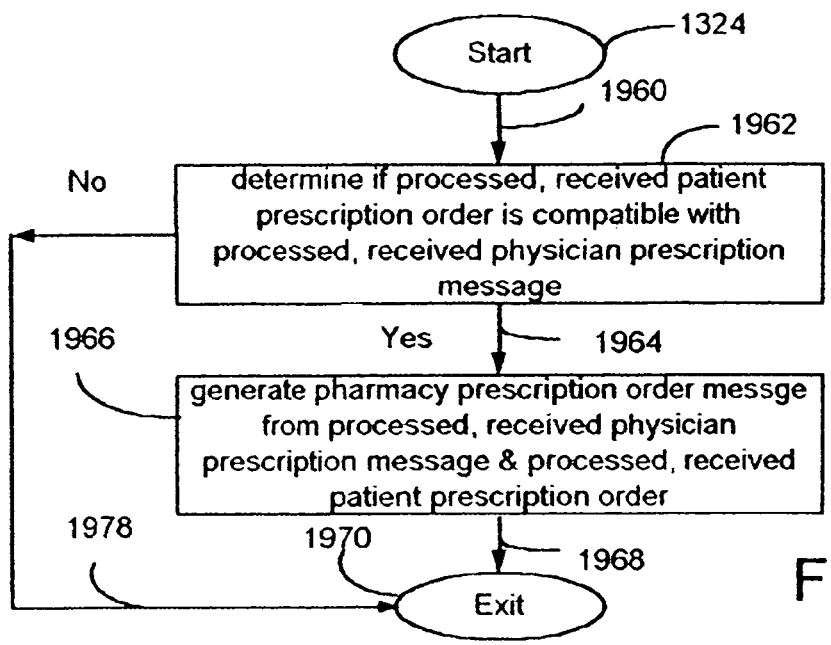
FIG. 50B depicts a flowchart of further details of 1324 of FIG. 30A supporting generating a pharmacy prescription order in accordance with certain embodiments.

FIG. 50B depicts a flowchart of further details of 1324 of FIG. 30A supporting generating a pharmacy prescription order in accordance with certain embodiments.

Arrow 1960 directs the flow of execution from starting operation 1324 to operation 1962. Operation 1962 determines if the processed, received patient prescription order is compatible with the processed, received physician prescription. Arrow 1964 directs execution when the determination is 'Yes' to operation 1966. Arrow 1978 directs usage when the determination is 'No' to operation 1970.

Operation 1966 generates a pharmacy prescription order message from the processed, received physician prescription message and the processed, received patient prescription order. Arrow 1968 directs execution from operation 1966 to operation 1970. Operation 1970 terminates the operations of this flowchart.

Figure 50C:
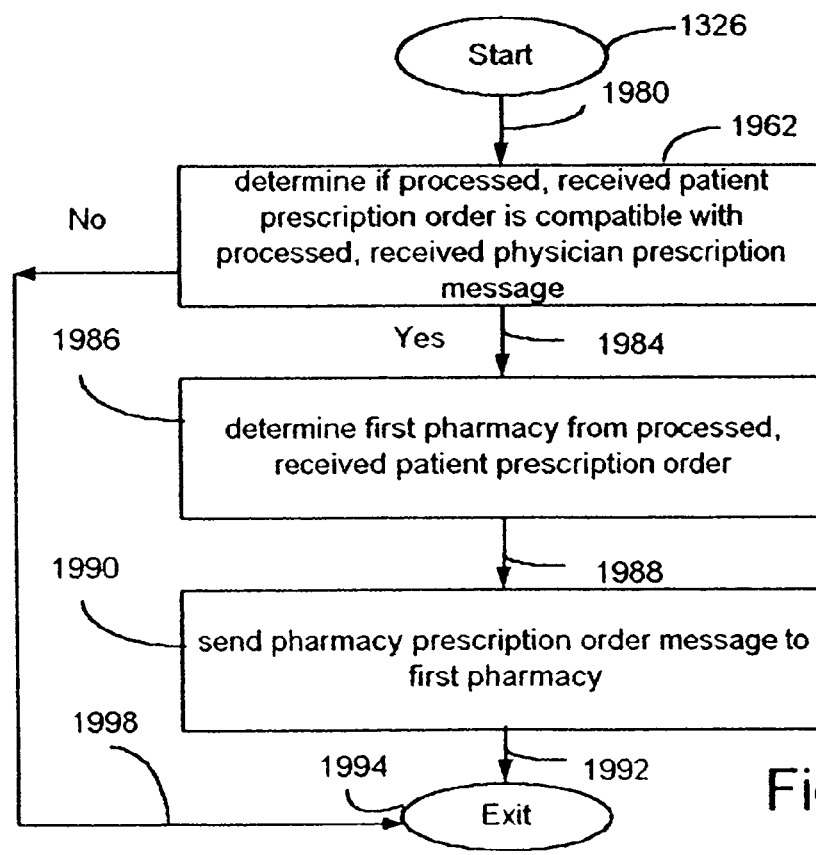
FIG. 50C depicts a flowchart of further details of 1326 of FIG. 30A supporting sending a pharmacy prescription order to a pharmacy in accordance with certain embodiments.

FIG. 50C depicts a flowchart of further details of 1326 of FIG. 30A supporting sending a pharmacy prescription order to a pharmacy in accordance with certain embodiments.

Arrow 1980 directs the flow of execution from starting operation 1326 to operation 1962. Operation 1962 determines if the processed, received patient prescription order is compatible with the processed, received physician prescription. Arrow 1984 directs execution from operation 1962 to operation 1986. Arrow 1984 directs execution when the determination is ☐Yes☐ to operation 1986. Arrow 1998 directs usage when the determination is ☐No☐ to operation 1994.

Operation 1986 performs determine the first pharmacy from the processed, received patient prescription order. Arrow 1988 directs execution from operation 1986 to operation 1990. Operation 1990 performs sending the pharmacy prescription order message to the first pharmacy. Arrow 1992 directs execution from operation 1990 to operation 1994. Operation 1994 terminates the operations of this flowchart.

Figure 50D:
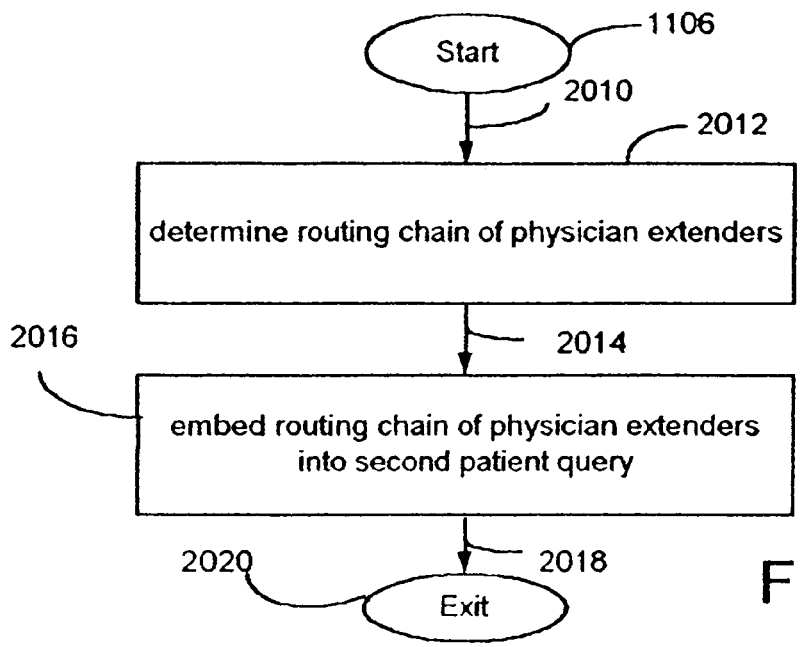
FIG. 50D depicts a flowchart of further details of 1106 of FIG. 23 supporting determining a routing chain of physician extenders and embedding the routing chain into a second patient query in accordance with certain embodiments.

FIG. 50D depicts a flowchart of further details of 1106 of FIG. 23 supporting determining a routing chain of physician extenders and embedding the routing chain into a second patient query in accordance with certain embodiments.

Arrow 2010 directs the flow of execution from starting operation 1106 to operation 2012. Operation 2012 determines a routing chain of physician extenders. Arrow 2014 directs execution from operation 2012 to operation 2016. Operation 2016 embeds the routing chain of physician extenders into the second medical query. Arrow 2018 directs execution from operation 2016 to operation 2020. Operation 2020 terminates the operations of this flowchart.

Note that a routing chain of physician extenders is a collection of at least one physician extender to whom the second patient query will be routed after the first physician extender has added their proposed response to the patient query.

Figure 50E:
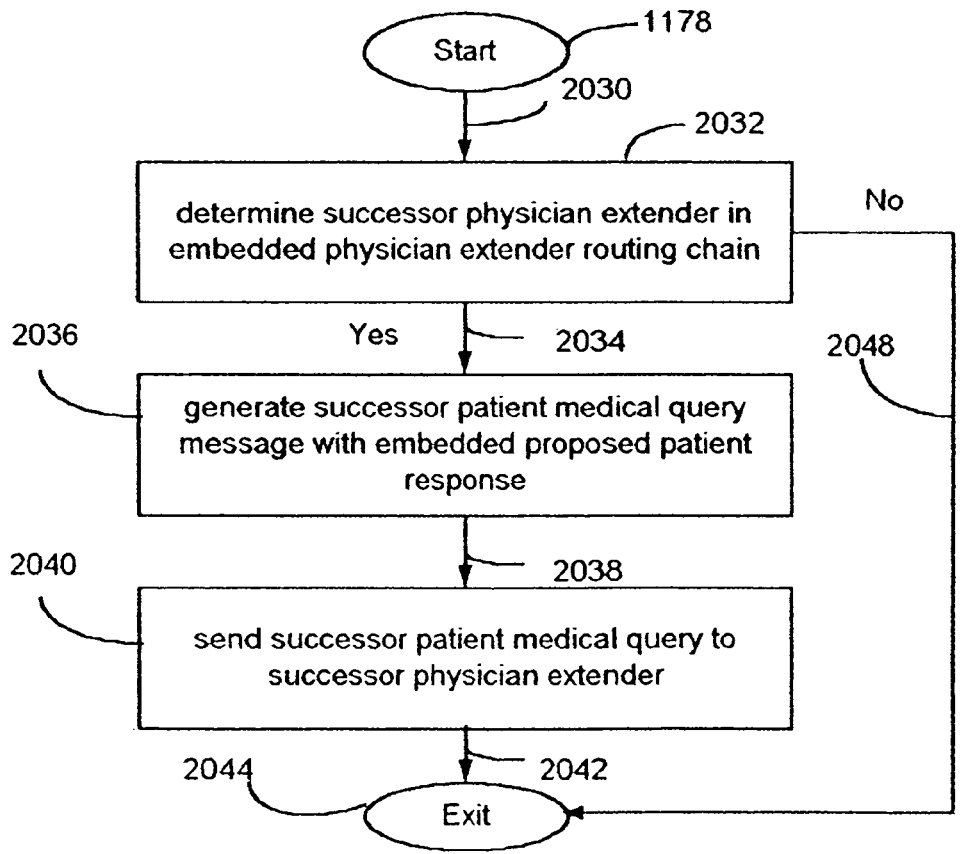
FIG. 50E depicts a flowchart of further details of 1178 of FIG. 24 supporting determining successor physician extenders in an embedded physician extender routing chain, generating a successor medical query message with embedded proposed patient response and sending the successor patient medical query to the successor physician extender.

FIG. 50E depicts a flowchart of further details of 1178 of FIG. 24 supporting determining successor physician extenders in an embedded physician extender routing chain, generating a successor medical query message with embedded proposed patient response and sending the successor patient medical query to the successor physician extender.

Arrow 2030 directs the flow of execution from starting operation 1178 to operation 2032. Operation 2032 determines if there is a successor physician extender in the embedded physician extender chain. Arrow 2034 directs execution from operation 2032 to operation 2036. Arrow 2034 directs execution when the determination is ☐Yes☐ to operation 2032. Arrow 2048 directs execution when the determination is ☐No☐ to operation 2044.

Operation 2036 generates the successor medical query message with the embedded proposed patient response. Arrow 2038 directs execution from operation 2036 to operation 2040. Operation 2040 send the successor patient medical query to the successor physician extender. Arrow 2042 directs execution from operation 2040 to operation 2044. Operation 2044 terminates the operations of this flowchart.

Figure 50F:
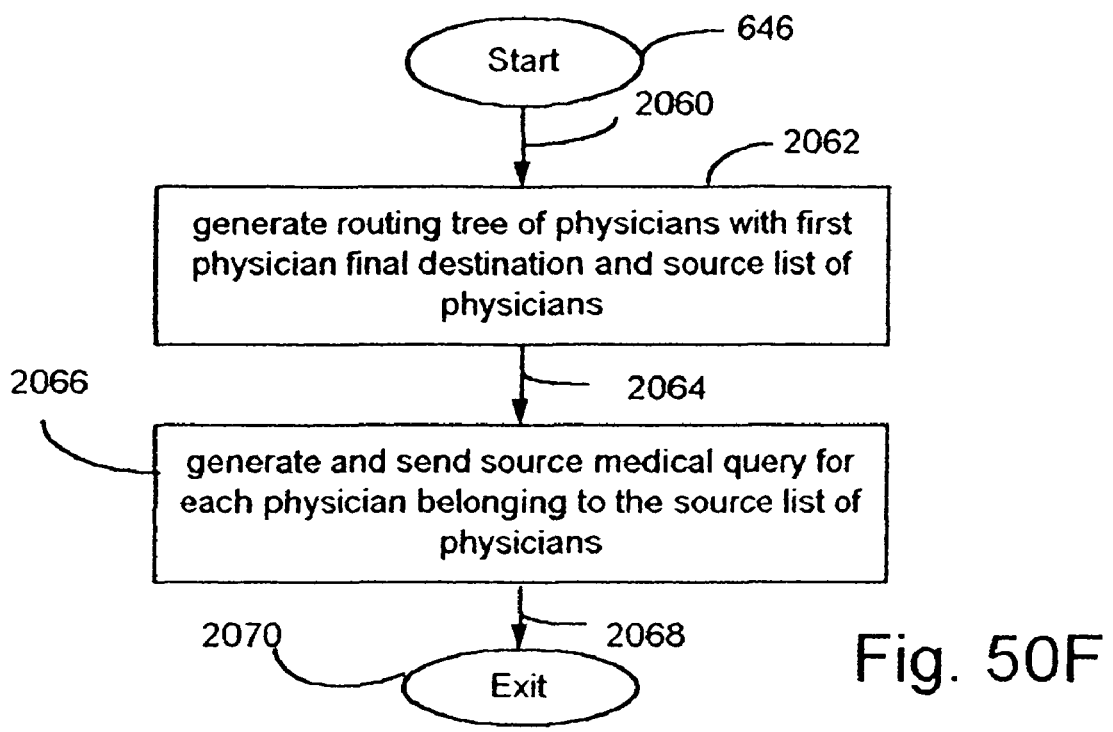
FIG. 50F depicts a flowchart of further details of 646 of FIG. 6 supporting generating a routing tree of physicians with first physician final destination and source list of physicians, generating and sending a source medical query to each physician included in the physician source list.

FIG. 50F depicts a flowchart of further details of 646 of FIG. 6 supporting generating a routing tree of physicians with first physician final destination and source list of physicians, generating and sending a source medical query to each physician included in the physician source list.

Arrow 2060 directs the flow of execution from starting operation 646 to operation 2062. Operation 2062 performs generating a routing tree of physicians with the first physician the final destination of the routing tree and a source list of physicians of the routing tree. Arrow 2064 directs execution from operation 2062 to operation 2066. Operation 2066 performs generating and sending a source medical query for and to each physician belonging to the source list of the routing tree. Arrow 2068 directs execution from operation 2066 to operation 2070. Operation 2070 terminates the operations of this flowchart.

Additional Discussion of Primary Terms as Used Herein:

A service profile of a client is a collection of information residing in some computer accessible media which from time to time a computer may be able to access.

The service profiler process is the system-wide activities which are performed in an automated fashion by the service-flow engine to facilitate the service communication between clients, service providers, service extenders and suppliers to support at least the following: service queries, replies and transactions involved in service recommendations.

The service-flow engine is the mechanism performing the collection of operations known as the service profiler process. It has at least one address on the network shared with clients, service providers, service extenders and suppliers. Note that this shared network may in fact be partitioned into a collection of networks, each possessing gateways, firewalls and the like as is well known in the art. Note that the service-flow engine may include but is not limited to one computer, and in fact, in certain embodiments preferably involves more than one server computer as will be discussed later.

A client as used herein will have two components of meaning: The first component being the entity about whom the service profile, query messages, response message and service recommendations are directed; the second is a responsible individual acting for the client in all the transactions, such as generating the query messages, receiving and considering the response messages and ordering the service recommendations. Note that a list of the first component entities includes but is not limited to people, corporations, companies, organizations, as well as real estate, machinery including but not limited to automobiles, computer systems, web sites, software, telephones, communications networks and systems.

Further embodiments of the invention support the service-flow engine creating routing chains of service extenders starting with a first service extender proceeding through successor service provider extenders until the routing chain terminates with a service provider reviewing the collective proposed client response. The routing chain may be generated by the service-flow engine based upon the client's educated query message.

Further embodiments of the invention support the service-flow engine creating routing trees of service providers with patent query messages starting with a source list of service providers, possibly routing to intermediate service providers and culminating in a first service provider who reviews the collective service provider responses to their respective client service queries.

Figure 51:
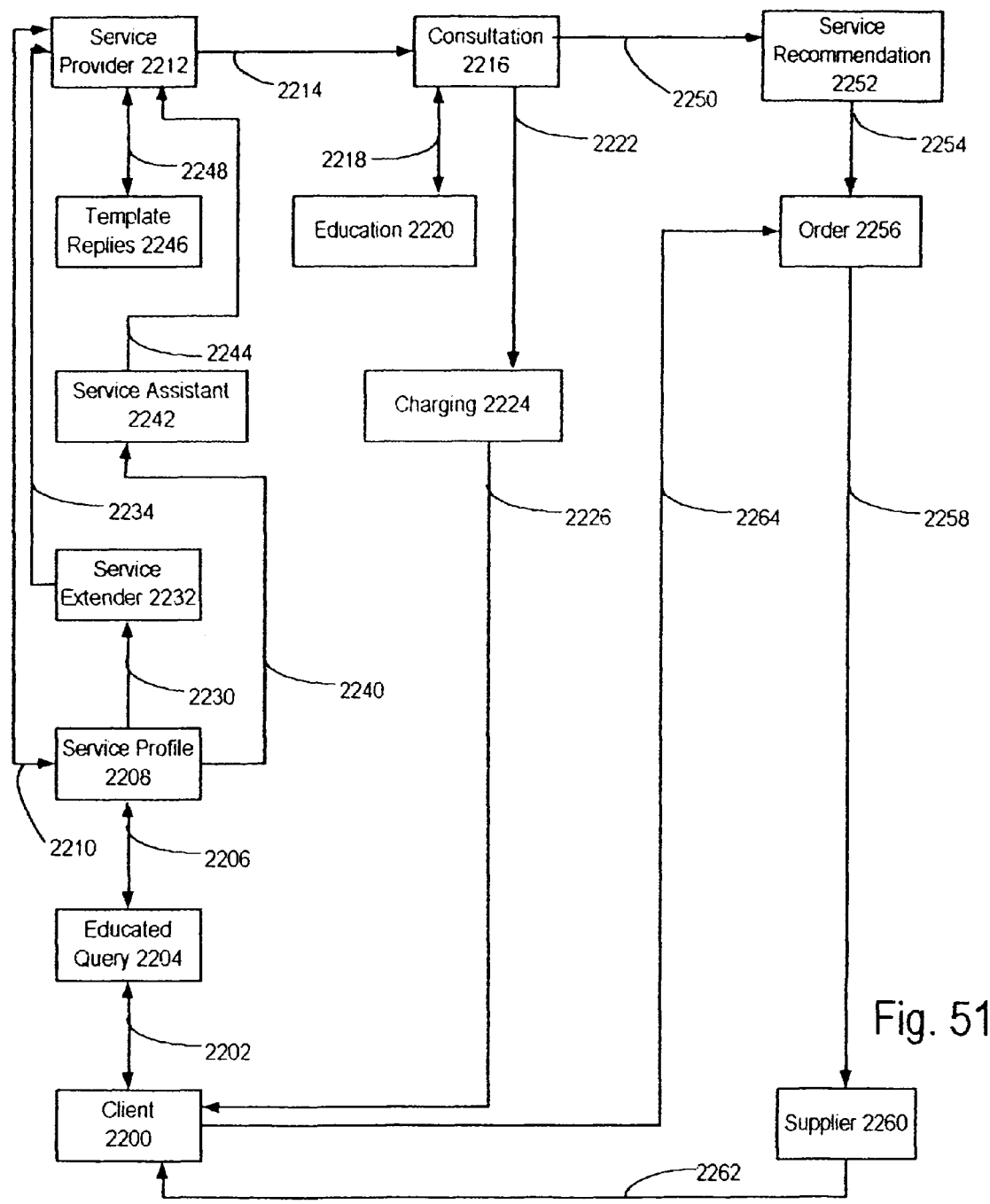
FIG. 51 depicts a more detailed flow diagram of an embodiment of the invention in accordance with certain embodiments.

FIG. 51 depicts a flow diagram of an embodiment of the invention in accordance with certain embodiments. Client 2200 is the primary initiator of this invention. Arrow 2202 depicts the interactions of client 2200 to create the educated query message 2204. The educated query message 2204 is an optimized service query directed by the client to address concerns and conditions involving the client. Arrow 2206 depicts the sending of educated query message 2204 to the service profile 2208 which is managed by the service profiler process. The service-flow engine performs the various service profiler process operations. More will be said about the service-flow engine shortly. Arrow 2210 depicts interactive communication between the service-flow engine 2208 and the service providers 2212 primarily regarding the service profiler. Service providers 2212 are the central destination of client generated educated service query messages as sent by 2210 from the service profiler process to the service provider 2212. Arrow 2214 depicts the response of service provider 2212 to the educated query message, generating a consultative response 2216. Consultation 2216 provides the basis of the client response message 2226. Arrow 2218 depicts the inclusion of the service provider consultative response 2216 with educational material 2220. Educational material 2220 is included in certain, but not all cases, to meet mandated regulations as well as provide the service providers a mechanism to distribute standard material regarding various conditions and treatments. Arrow 2222 depicts the service-flow engine activities required to incorporate the consultative response and included materials 2220 with billing information (charging) 2224. Charging 2224 performs tasks of notifying a client service profile of the consultative transaction, what was the query, response, educational materials included and the service expenses. Arrow 2226 depicts the actual patent response message derived from 2224 query, service provider response, educational materials included and the service expenses sent to client 2200.

Arrow 2230 depicts the message information flow from the service-flow engine to service extender 2232. Service extenders 2232 perform a number of service tasks under the direction of service providers 2212. Arrow 2234 depicts the sending of proposed client response messages generated by service extenders 2232 to a service provider 2212. Arrow 2240 depicts another message information flow from the service-flow engine to a service assistant 2242. While service assistants are service extenders, a service assistant 2242 performs a specific additional task distinguishing them from other service extenders, such as service provider assistants and administrators. Service assistant 2242 can propose service recommendation refills for example. Arrow 2244 depicts the sending of proposed client response message, which may further include proposed embedded service recommendation refills, from service assistant 2242 to service provider 2246.

Service provider 2212 performs a review on the proposed client response messages from service extenders, including service assistants, as delivered by arrows 2234 and 2244. Template replies 2246 offer the capability for service providers to optimize the quality and efficiency of response in making many standard replies. Arrow 2248 depicts the interaction between template replies 2246 and service provider 2212.

Arrow 2250 depicts the information and activity flow based upon the consultative response 2216 and the placing of a service recommendation message 2252. Service recommendation message 2252 is created based upon the service provider's consultative response 2216, which in turn is based upon the client's service query message and possibly a service assistant's proposed service recommendation refill. Arrow 2254 depicts sending a service recommendation message 2252 to ordering process 2256. Client 2200 receives the patent response message 2226, and may respond by ordering the embedded service recommendation, which is depicted by arrow 2264 indicating a client service recommendation message sent to ordering process 2256. Ordering process 2256 waits until both the service provider service recommendation message 2254 and client service recommendation message 2264 have been received and processed before the order 2258 is actually placed with supplier 2260. Supplier 2260 sends the service recommendation to client 2300 as indicated by arrow 2362.

Figure 52:
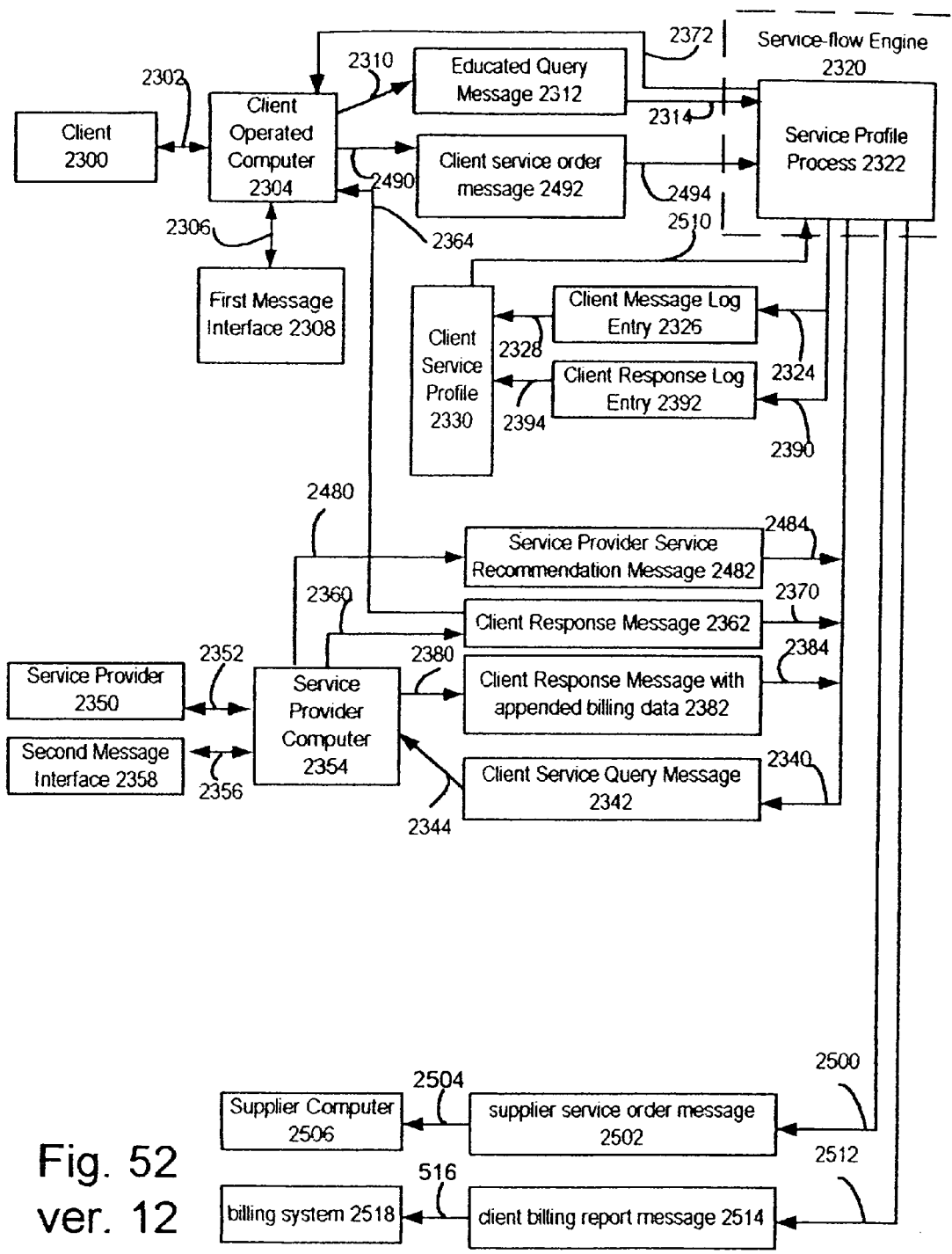
FIG. 52 depicts an interactive flow between a client using a first message interface, service profiler performing a service profiler process and service provider using a second message interface in accordance with an embodiment of the invention.

FIG. 52 depicts an interactive flow between a client using a first message interface, service-flow engine performing a service profiler process and service provider using a second message interface in accordance with an embodiment of the invention. Client 2300 interacts 2302 with client operated computer 2304, which can access 2306 and perform the operations of first message interface 2308. Service provider 2350 interacts 2352 with service provider operated computer 2354, which can access 2356 and perform the operations of second message interface 2358. Service extender 2400 interacts 2402 with service extender operated computer 2404, which can access 2406 and perform the operations of second message interface 2408.

Client 2300 using first message interface 2308 on client operated computer 2304 generates 2310 educated query message 2312 and sends it 2314 to service-flow engine 2320 where it is received by service profiler process 2322. Service profiler process 2322 generates 2324 client message log entry 2326, which is added 2328 to the client service profile 2330. Service profiler process 2322 further generates 2340 client service query message 2342, which is sent 2344 to service provider operated computer 2354.

Service provider 2350 using second message interface 2358 on service provider operated computer 2354 receives and responds to the client service query message 2342, generating 2360 a client response message 2362, which in certain embodiments is sent 2364 directly to the client operated computer 2304. In certain alternative embodiments, client response message 2362 is sent 2370 to the service-flow engine, where the service profiler process 2322 then sends 2372 a version to the client operated computer 2304. Service provider 2350 using second message interface 2358 on service provider operated computer 2354 further responds to the client service query message 2342, generating a client response message with appended service provider billing data 2382, which is sent 2384 to the service-flow engine, where the service profiler process 2322 then generates 2390 a client response log entry 2392 which is added 2394 to the client service profile 2330.

In certain situations, a service recommendation is embedded into client response message 2362 by the service provider 2350 using second message interface 2358 on service provider operated computer 2354 in response to the client service query message 2342, which embedded into the client response message 2362. Service provider 2350 using second message interface 2358 on service provider operated computer 2354 also generates 2480 service provider service recommendation message 2482, which is sent 2484 to the service-flow engine using the service profiler process 2322. Client 2300 using first message interface 2308 on client operated computer 2304 generates 2490 client order message 2492 and sends it 2494 to service-flow engine 2320 where it is received by service profiler process 2322. Once both service provider service recommendation message 2482 and client order message 2492 have been received and authenticated, the medial profiler process 2322 generates 2500 a supplier service order message 2502 which is sent 2504 to the supplier computer 2506.

Service profiler process 2322 accesses 2510 the client service profile 2330 to generate 2512 client billing report message 2514 which is sent 2516 to billing system 2518. Note that the billing system 2518 in certain embodiments is a separate system element external to the service-flow engine. In certain alternative embodiments, billing system 2518 resides within the operations performed by the service-flow engine. In certain further embodiments, billing system 2518 is part of the service profiler process.

Note that in the flowcharts included herein, the starting operation of a flowchart may perform operations to allocate systems resources for use by the subsequent operations of the flowchart in certain embodiments. The starting operation of a flowchart may further perform initialize systems resources in certain embodiments.

Note also that in the flowcharts included herein, the terminating or exit operation of a flowchart may perform operations to release allocated systems resources used by the subsequent operations of the flowchart in certain embodiments. The terminating operation of a flowchart may further perform a "return" operation in certain embodiments. Alternatively, the terminating operation of a flowchart may not perform a "return" operation in certain embodiments.

FIG. 52A depicts an interactive flow between a client using a first message interface, service-flow engine performing a service profiler process and service provider using a second message interface in accordance with a further embodiment of the invention. Client 2300 interacts 2302 with client operated computer 2304, which can access 2306 and perform the operations of first message interface 2308. Service provider 2350 interacts 2352 with service provider operated computer 2354, which can access 2356 and perform the operations of second message interface 2358. Service extender 2400 interacts 2402 with service extender operated computer 2404, which can access 2406 and perform the operations of second message interface 2408.

Client 2300 using first message interface 2308 on client operated computer 2304 generates 2310 educated query message 2312 and sends it 2314 to service-flow engine 2320 where it is received by service profiler process 2322. Service profiler process 2322 generates 2324 client message log entry 2326, which is added 2328 to the client service profile 2330.

Service profiler process 2322 further generates 2340 client service query message 2342, which is sent 2344 to service provider operated computer 2354.

Service provider 2350 using second message interface 2358 on service provider operated computer 2354 receives and responds to the client service query message 2342, generating 2360 a client response message 2362, which in certain embodiments is sent 2364 directly to the client operated computer 2304. In certain alternative embodiments, client response message 2362 is sent 2370 to the service-flow engine, where the service profiler process 2322 then sends 2372 a version to the client operated computer 2304. Service provider 2350 using second message interface 2358 on service provider operated computer 2354 further responds to the client service query message 2342, generating a client response message with appended service provider billing data 2382, which is sent 2384 to the service-flow engine, where the service profiler process 2322 then generates 2390 a client response log entry 2392 which is added 2394 to the client service profile 2330.

In certain situations, a service recommendation is embedded into client response message 2362 by the service provider 2350 using second message interface 2358 on service provider operated computer 2354 in response to the client service query message 2342, which embedded into the client response message 2362. Service provider 2350 using second message interface 2358 on service provider operated computer 2354 also generates 2480 service provider service recommendation message 2482, which is sent 2484 to the service-flow engine using the service profiler process 2322. Client 2300 using first message interface 2308 on client operated computer 2304 generates 2490 client order message 2492 and sends it 2494 to service-flow engine 2320 where it is received by service profiler process 2322. Once both service provider service recommendation message 2482 and client order message 2492 have been received and authenticated, the medial profiler process 2322 generates 2500 a supplier service order message 2502 which is sent 2504 to the supplier computer 2506.

Service profiler process 2322 accesses 2510 the client service profile 2330 to generate 2512 client billing report message 2514 which is sent 2516 to billing system 2518. Note that the billing system 2518 in certain embodiments is a separate system element external to the service-flow engine. In certain alternative embodiments, billing system 2518 resides within the operations performed by the service-flow engine. In certain further embodiments, billing system 2518 is part of the service profiler process.

Service profiler process 2322 further generates 2400 a second client service query message 2402, which is sent 2404 to service extender operated computer 2414. Service extender 2410 using third message interface 2418 on service provider operated computer 2414 receives and responds to the second client service query message 2412, generating 2430 a proposed client response message 2432, which is sent 2434 directly to the service provider operated computer 2354, where it is inserted into the client service query message 2342. In certain alternative embodiments, client response message 2432 is sent 2436 to the service-flow engine, where the service profiler process 2322 then sends a version to the service provider operated computer 2354. Service extender 2410 using third message interface 2418 on service provider operated computer 2414 further responds 2440 to the second client service query message 2402, generating a proposed client response message with appended service extender billing data 2442, which is sent 2444 to the service-flow engine, where the 1915 service profiler process 2322 then generates 2450 a proposed client response with appended service extender billing data log entry 2452 which is added 2454 to the client service profile 2330.

Figure 53:
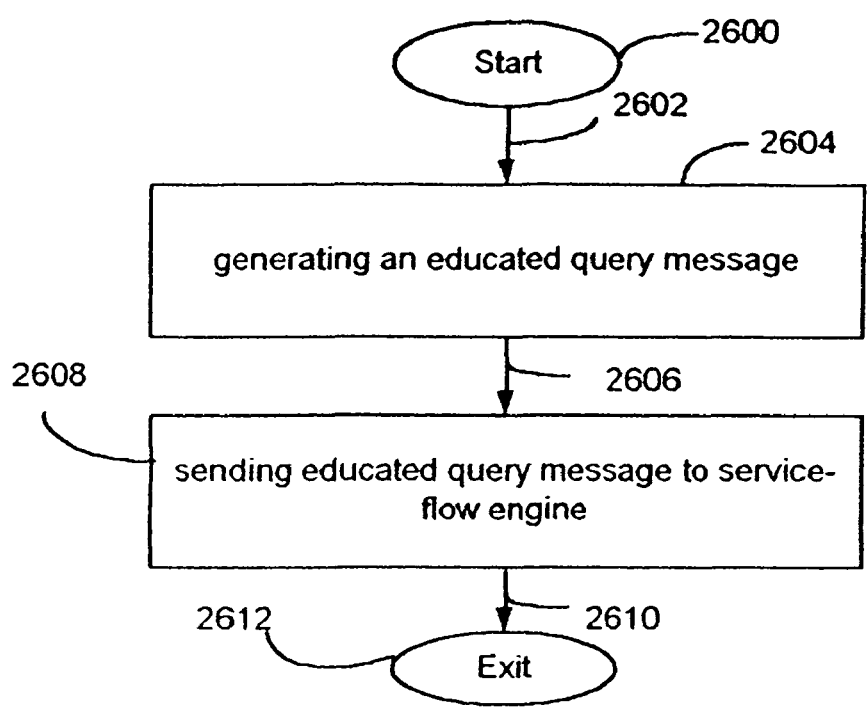
FIG. 53 depicts a flowchart of operations supporting the generation and sending of an educated query by a client using the first message interface in accordance with embodiments supporting FIG. 52.

FIG. 53 depicts a flowchart of operations supporting the generation and sending of an educated query by a client using the first message interface in 1920 accordance with embodiments supporting FIG. 52. Operation 2600 starts the operations of this flowchart. Arrow 2602 directs the flow of execution from operation 2600 to operation 2604. Operation 2604 performs generating of an educated query message. Arrow 2606 directs execution from operation 2604 to operation 2608. Operation 2608 performs sending the educated query message 1925 to the service-flow engine. Arrow 2610 directs execution from operation 2608 to operation 2612. Operation 2612 terminates the operations of this flowchart.

Figure 54:
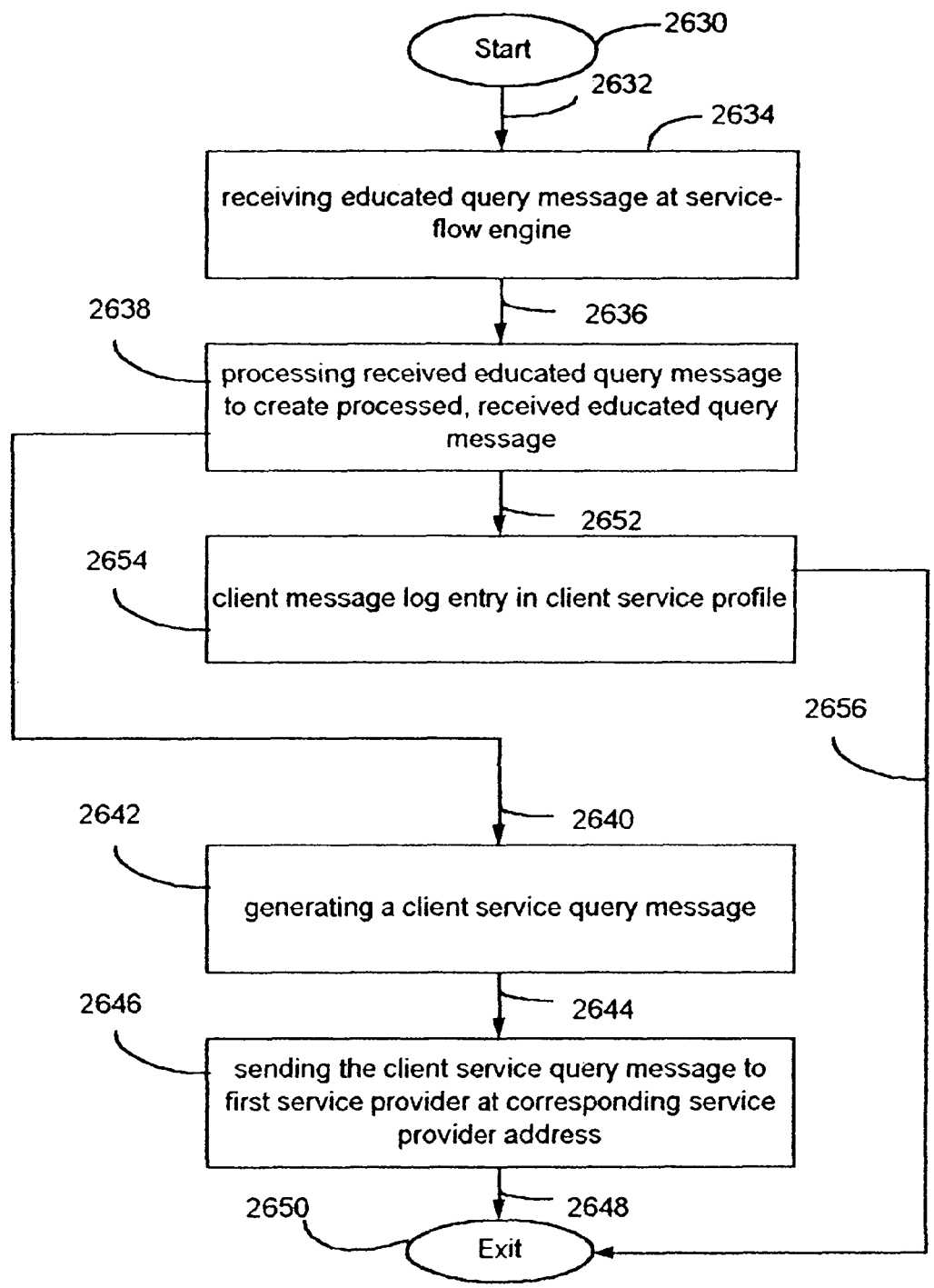
FIG. 54 depicts a flowchart of operations supporting the reception, processing, logging of the educated query message from the client, and the generation and sending of the client service query message to a service provider by the service profiler process performed by the service profiler in accordance with embodiments supporting FIG. 52.

FIG. 54 depicts a flowchart of operations supporting the reception, processing, logging of the educated query message from the client, and the generation and sending of the client service query message to a service provider by the service profiler process performed by the service-flow engine in accordance with embodiments supporting FIG. 52. Operation 2630 starts the operations of this flowchart. Arrow 2632 directs the flow of execution from operation 2630 to operation 2634. Operation 2634 performs receiving the educated query message at the service-flow engine. Arrow 2636 directs execution from operation 2634 to operation 2638. Operation 2638 performs processing the received educated query message to create the processed, received educated query message. Arrow 2640 directs execution from operation 2638 to operation 2642. Operation 2642 performs generating a client service query message. Arrow 2644 directs execution from operation 2642 to operation 2646. Operation 2646 performs sending the client service query message to first service provider at corresponding service provider address. Arrow 2648 directs execution from operation 2646 to operation 2650. Operation 2650 terminates the operations of this flowchart.

In certain embodiments, operation 646 further includes selecting a first service provider. In certain further embodiments, operation 646 further includes selecting a first service provider based upon the received educated query message. In certain further embodiments, operation 646 further includes selecting a first service provider based upon the processed, received educated query message.

Arrow 2652 directs the flow of execution from starting operation 2638 to operation 2654. Operation 2654 performs generating a client message log entry in the client service profile. Arrow 2656 directs execution from operation 2654 to operation 2650.

Figure 55:
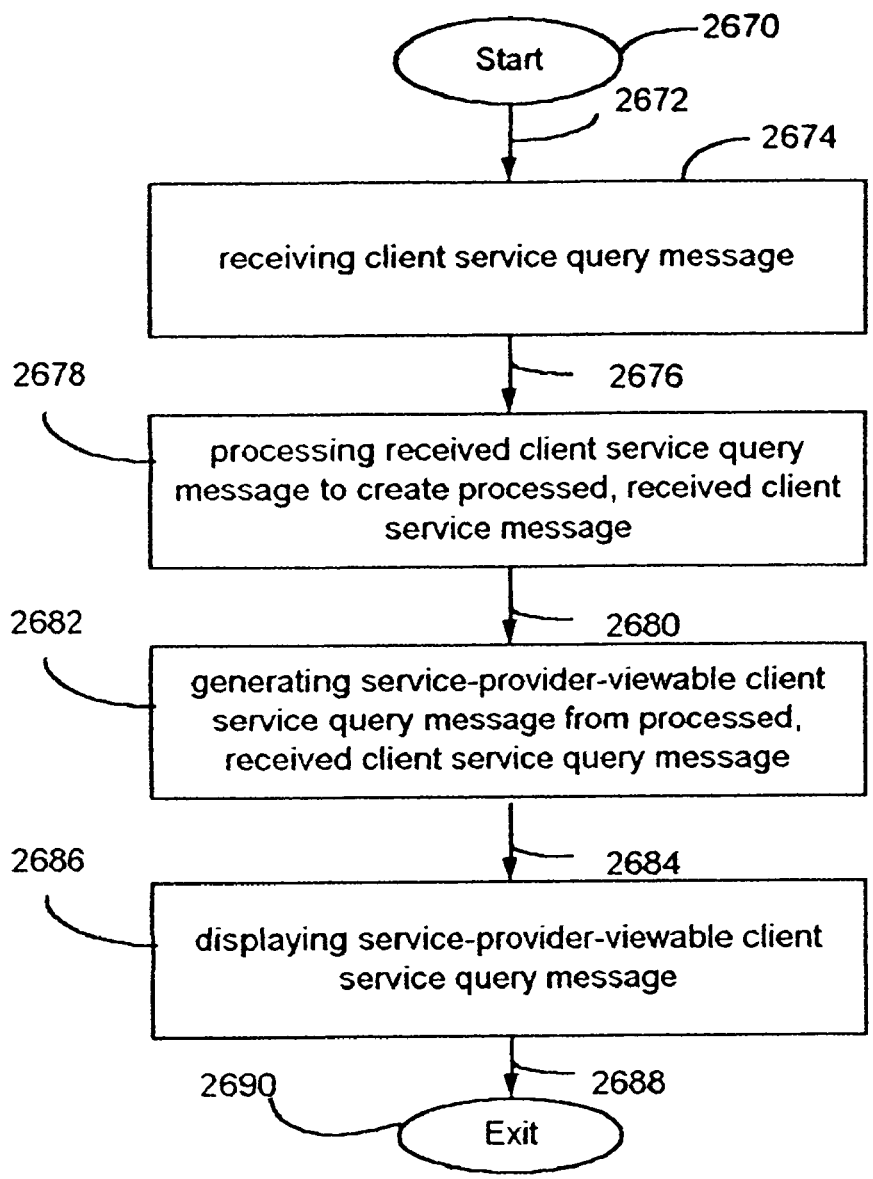
FIG. 55 depicts a flowchart of operations supporting reception, processing and viewing the client service query message by the second message interface for the service provider in accordance with embodiments supporting FIG. 52.

FIG. 55 depicts a flowchart of operations supporting reception, processing and viewing the client service query message by the second message interface for the service provider in accordance with embodiments supporting FIG. 52. Operation 2670 starts the operations of this flowchart. Arrow 2672 directs the flow of execution from operation 2670 to operation 2674. Operation 2674 performs receiving the client query message. Arrow 2676 directs execution from operation 2674 to operation 2678. Operation 2678 performs processing the received client service query message to create the processed, received client service message. Arrow 2680 directs execution from operation 2678 to operation 2682. Operation 2682 performs generating a service-provider-viewable client service query message from the processed, received client service query message. Arrow 2684 directs execution from operation 2682 to operation 2686. Operation 2686 performs displaying the service-provider-viewable client service query message. Arrow 2688 directs execution from operation 2686 to operation 2690. Operation 2690 terminates the operations of this flowchart.

Figure 56:
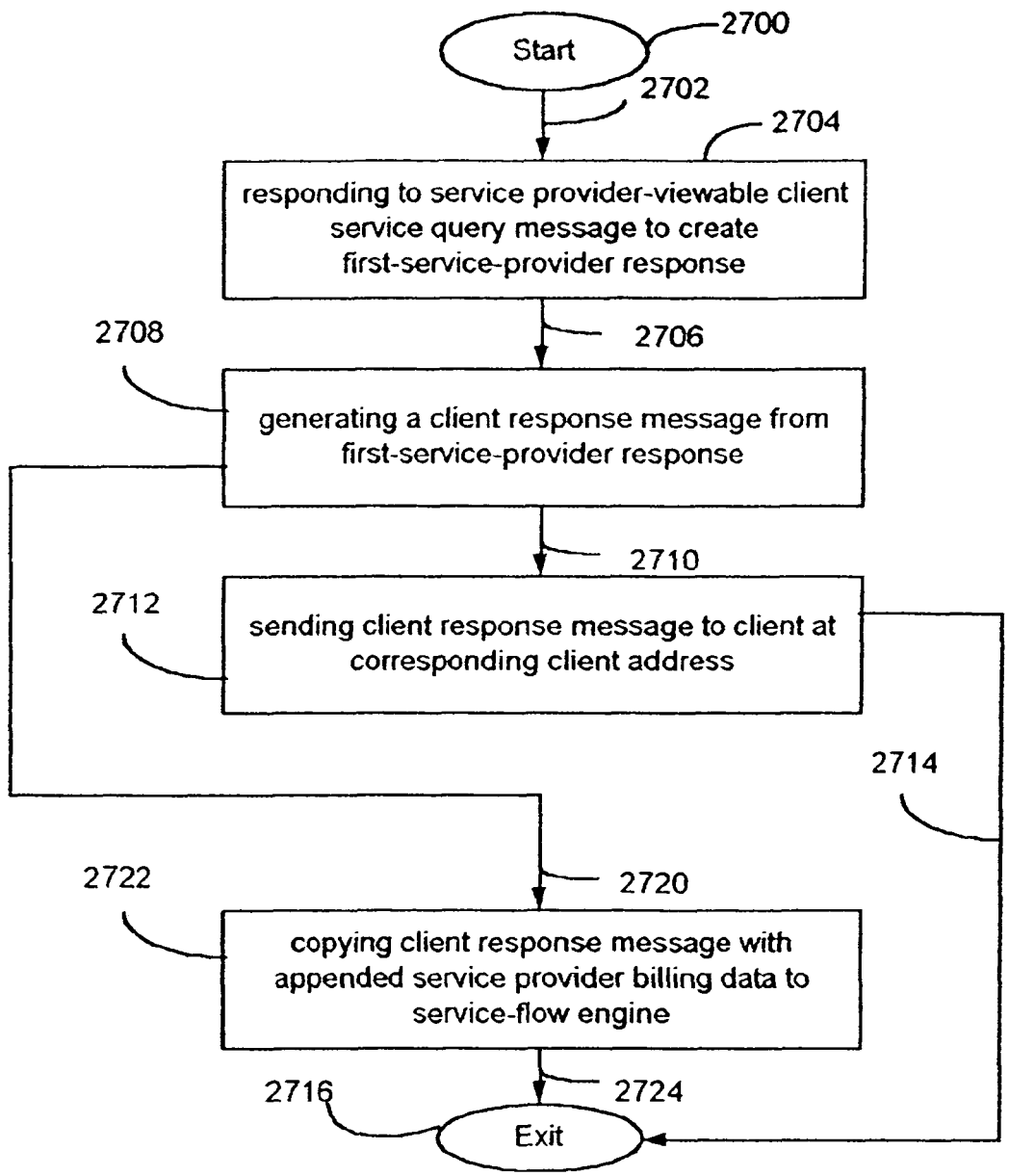
FIG. 56 depicts a flowchart of operations supporting reception, generation and sending a client response message, as well as copying the client response message with an appended service provider billing data to the service profiler address in accordance with embodiments supporting FIG. 52.

FIG. 56 depicts a flowchart of operations supporting reception, generation and sending a client response message, as well as copying the client response message with an appended service provider billing data to the service-flow engine in accordance with embodiments supporting FIG. 52. Operation 2700 starts the operations of this flowchart. Arrow 2702 directs the flow of execution from operation 2700 to operation 2704. Operation 2704 performs responding to the service-provider-viewable client service query message to create a first-service-provider response. Arrow 2706 directs execution from operation 2704 to operation 2708. Operation 2708 performs generating a client response message from the first-service-provider response. Arrow 2710 directs execution from operation 2708 to operation 2712. Operation 2712 performs sending the client response message to the client at the corresponding client address. Arrow 2714 directs execution from operation 2712 to operation 2716. Operation 2716 terminates the operations of this flowchart.

Arrow 2720 directs the flow of execution from starting operation 2708 to operation 2722. Operation 2722 performs copying the client response message with appended service provider billing data to service-flow engine. Arrow 2724 directs execution from operation 2722 to operation 2716.

Figure 57:
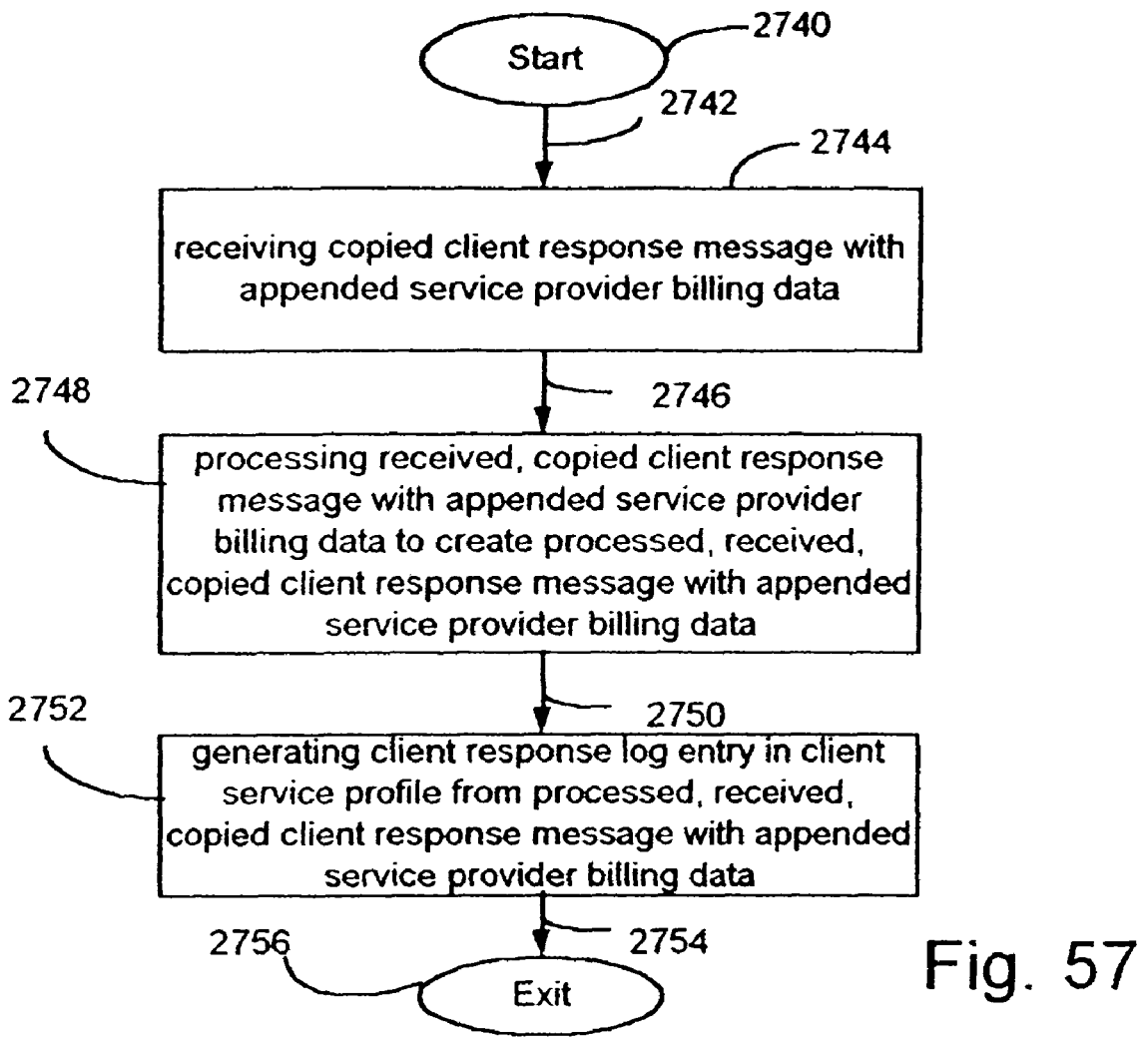
FIG. 57 depicts a flowchart of operations supporting the reception, processing, logging the copied client response message with an appended service provider billing data by the service profiler process performed by the service profiler in accordance with embodiments supporting FIG. 52.

FIG. 57 depicts a flowchart of operations supporting the reception, processing, logging the copied client response message with an appended service provider billing data by the service profiler process performed by the service-flow engine in accordance with embodiments supporting FIG. 52. Operation 2740 starts the operations of this flowchart. Arrow 2742 directs the flow of execution from operation 2740 to operation 2744. Operation 2744 performs receiving the copied client response message with appended service provider billing data. Arrow 2746 directs execution from operation 2744 to operation 2748. Operation 2748 performs processing the received, copied client response message with appended service provider billing data to create the processed, received, copied client response message with appended service provider billing data. Arrow 2750 directs execution from operation 2748 to operation 2752. Operation 2752 performs generating a client response log entry in client service profile from the processed, received, copied client response message with appended service provider billing data. Arrow 2754 directs execution from operation 2752 to operation 2756. Operation 2756 terminates the operations of this flowchart.

Figure 58:
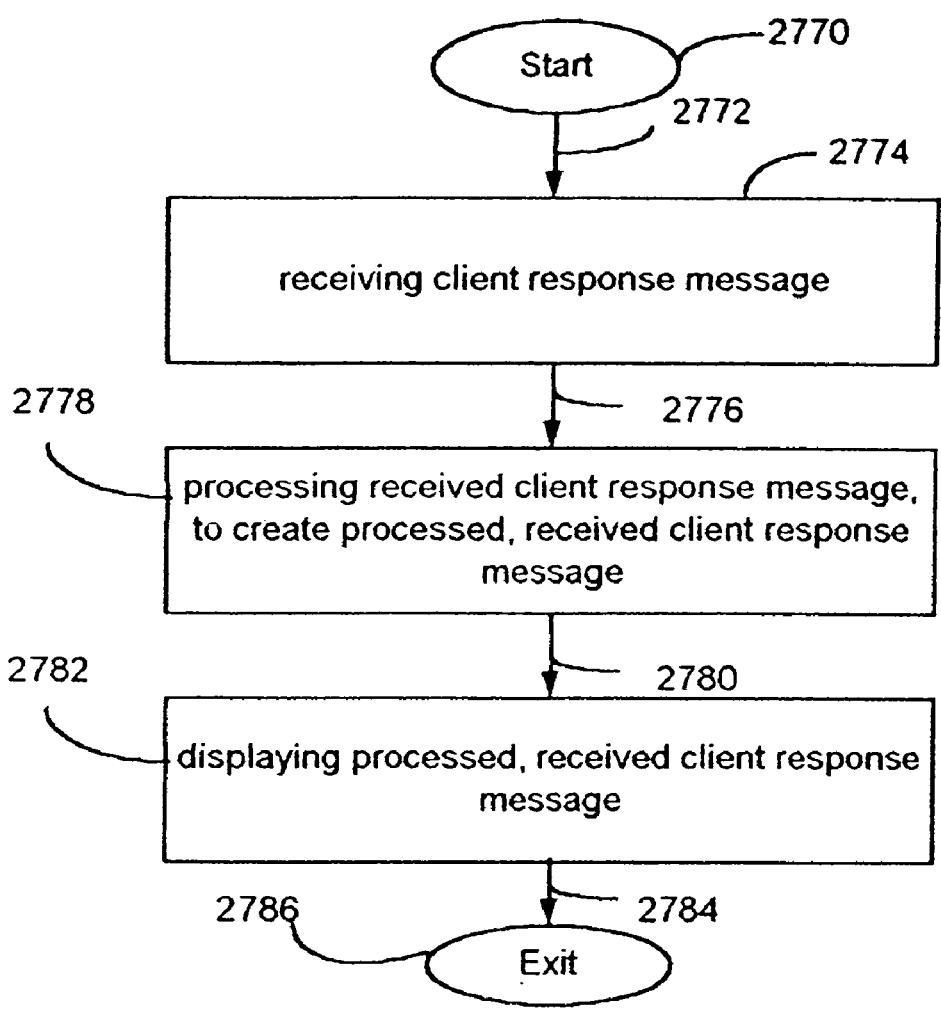
FIG. 58 depicts a flowchart of operations supporting reception, processing and display of the client response message using the first message interface on the client operated computer in accordance with embodiments supporting FIG. 52.

FIG. 58 depicts a flowchart of operations supporting reception, processing and display of the client response message using the first message interface on the client operated computer in accordance with embodiments supporting FIG. 52. Operation 2770 starts the operations of this flowchart. Arrow 2772 directs the flow of execution from operation 2770 to operation 2774. Operation 2774 performs receiving the client response message. Arrow 2776 directs execution from operation 2774 to operation 2778. Operation 2778 performs processing the received client response message, to create a processed, received client response message. Arrow 2780 directs execution from operation 2778 to operation 2782. Operation 2782 performs displaying the processed, received client response message. Arrow 2784 directs execution from operation 2782 to operation 2786. Operation 2786 terminates the operations of this flowchart.

Figure 59:
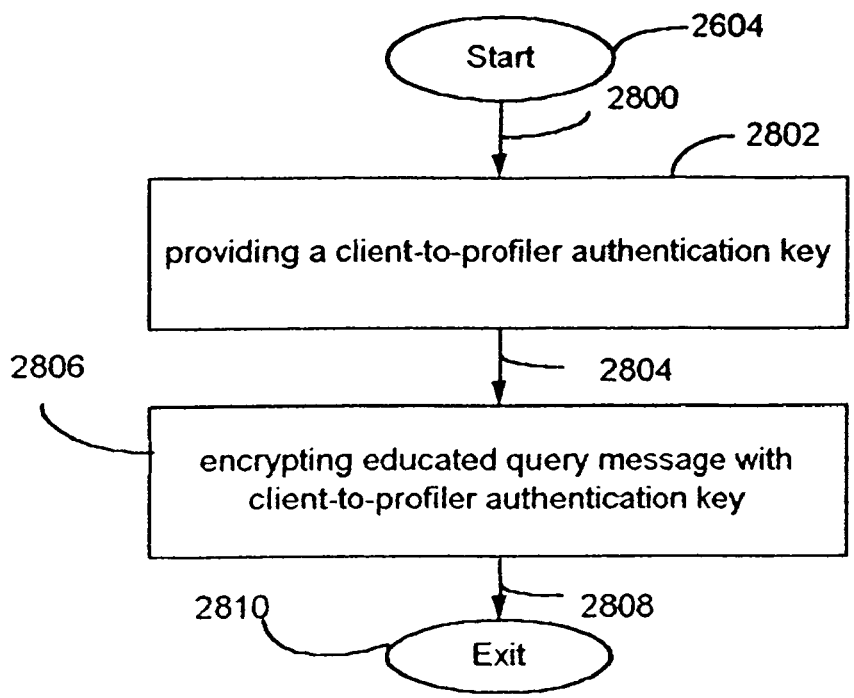
FIG. 59 depicts a flowchart of further details regarding operation 2604, generation of an educated query message by the first message interface in accordance with embodiments supporting FIG. 53.

FIG. 59 depicts a flowchart of further details regarding operation 2604, generation of an educated query message by the first message interface in accordance with embodiments supporting FIG. 53. Arrow 2800 directs the flow of execution from starting operation 2604 to operation 2802. Operation 2802 performs providing a client-to-profiler authentication key. Arrow 2804 directs execution from operation 2802 to operation 2806. Operation 2806 performs encrypting the educated query message with client-to-profiler authentication key. Arrow 2808 directs execution from operation 2806 to operation 2810. Operation 2810 terminates the operations of this flowchart.

Figure 60:
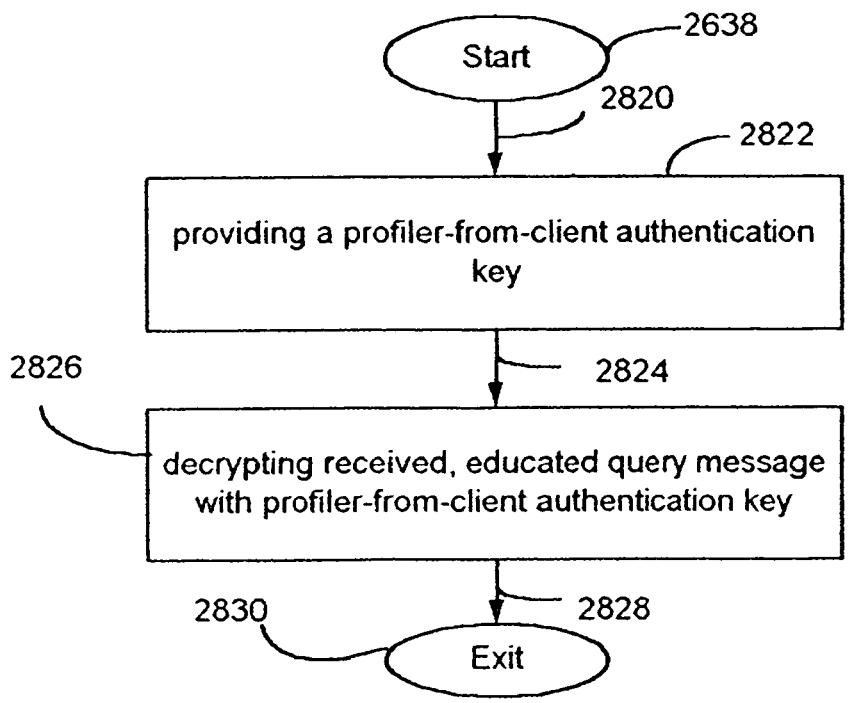
FIG. 60 depicts a flowchart of further details regarding operation 2638, processing the educated query message using the service profiler process performed by the service profiler in accordance with embodiments supporting FIG. 54.

FIG. 60 depicts a flowchart of further details regarding operation 2638, processing the educated query message using the service profiler process performed by the service-flow engine in accordance with embodiments supporting FIG. 54. Arrow 2820 directs the flow of execution from starting operation 2638 to operation 2822. Operation 2822 performs providing a profiler-from-client authentication key. Arrow 2824 directs execution from operation 2822 to operation 2826. Operation 2826 performs decrypting the received, educated query message with profiler-from-client authentication key. Arrow 2828 directs execution from operation 2826 to operation 2830. Operation 2830 terminates the operations of this flowchart.

Figure 61:
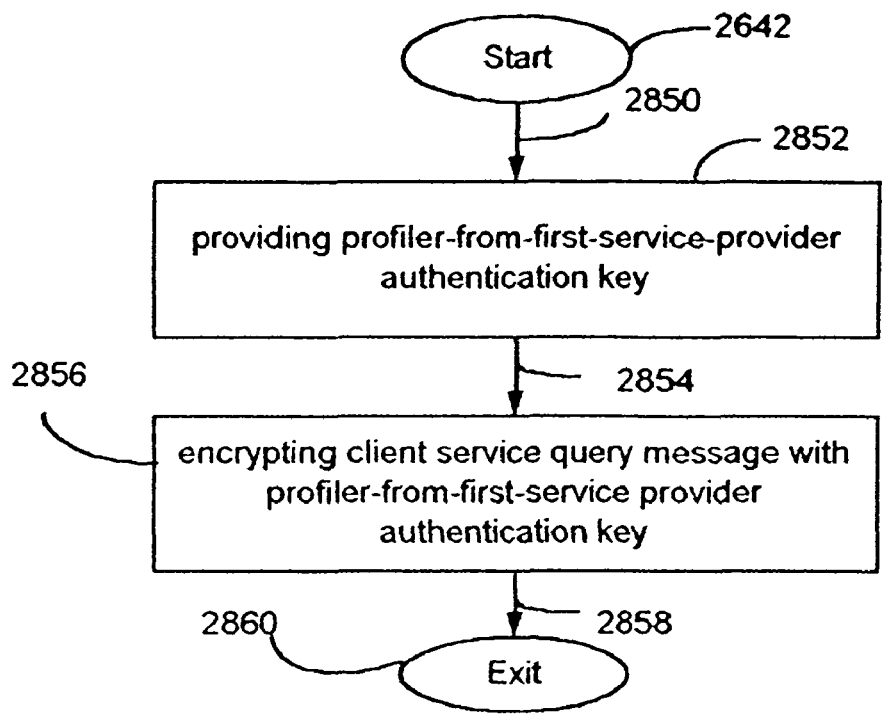
FIG. 61 depicts a flowchart of further details regarding operation 2642, generation of a client service query message by the service profiler process performed by the service profiler in accordance with embodiments supporting FIG. 54.

FIG. 61 depicts a flowchart of further details regarding operation 2642, generation of a client service query message by the service profiler process performed by the service-flow engine in accordance with embodiments supporting FIG. 54. Arrow 2850 directs the flow of execution from starting operation 2642 to operation 2852. Operation 2852 performs providing profiler-from-first-service-provider authentication key. Arrow 2854 directs execution from operation 2852 to operation 2856. Operation 2856 performs encrypting client service query message with profiler-from-first-service-provider authentication key. Arrow 2858 directs execution from operation 2856 to operation 2860. Operation 2860 terminates the operations of this flowchart.

Figure 62:
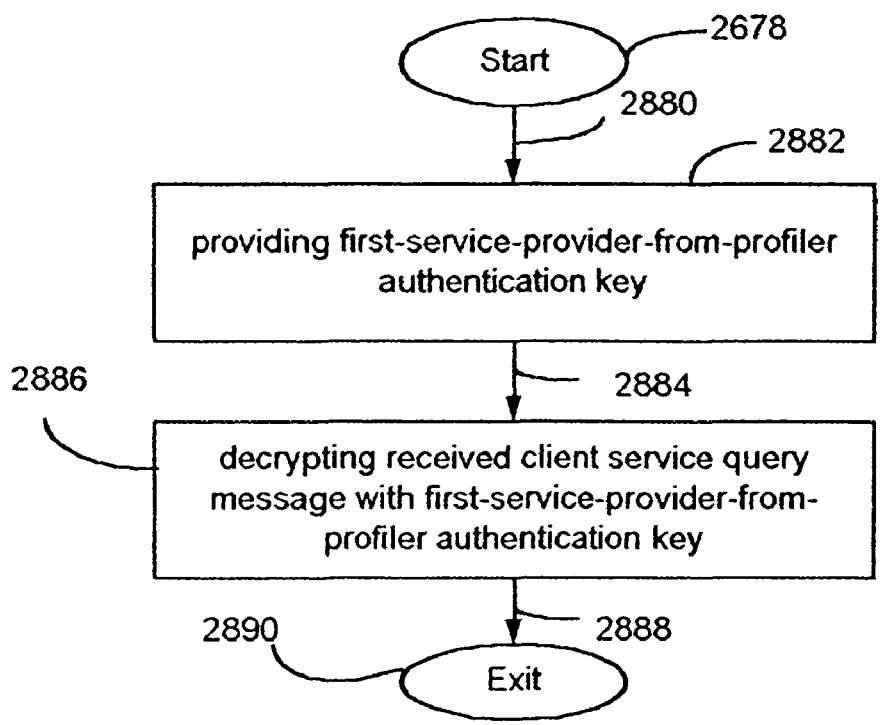
FIG. 62 depicts a flowchart of further details regarding operation 2678, processing the received client service query message by the second message interface in accordance with embodiments supporting FIG. 55.

FIG. 62 depicts a flowchart of further details regarding operation 2678, processing the received client service query message by the second message interface in accordance with embodiments supporting FIG. 55. Arrow 2880 directs the flow of execution from starting operation 2678 to operation 2882. Operation 2882 performs providing a first-service-provider-from-profiler authentication key. Arrow 2884 directs execution from operation 2882 to operation 2886. Operation 2886 performs decrypting the received client service query message with the first-service-provider-from-profiler authentication key. Arrow 2888 directs execution from operation 2886 to operation 2890. Operation 2890 terminates the operations of this flowchart.

Figure 63:
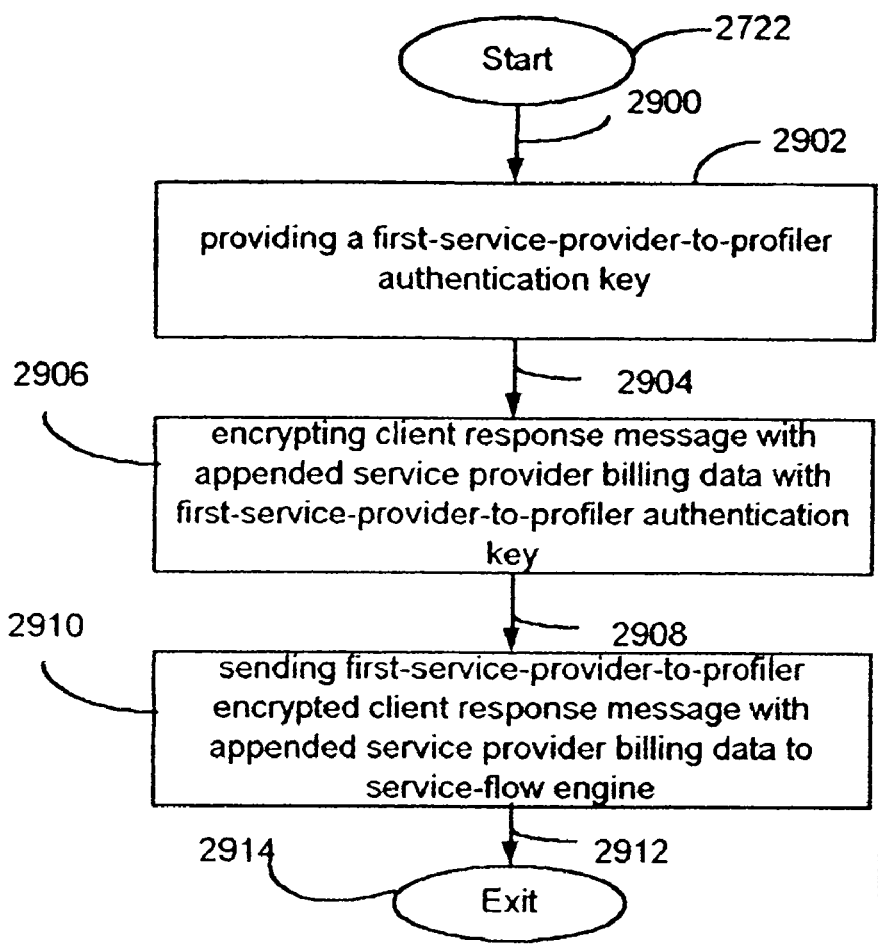
FIG. 63 depicts a flowchart of further details regarding operation 2722, copying the client response message with appended service provider billing data to the service profiler by the second message interface in accordance with embodiments supporting FIG. 56.

FIG. 63 depicts a flowchart of further details regarding operation 2722, copying the client response message with appended service provider billing data to the service-flow engine by the second message interface in accordance with embodiments supporting FIG. 56. Arrow 2900 directs the flow of execution from starting operation 2722 to operation 2902. Operation 2902 performs providing a first-service-provider-to-profiler authentication key. Arrow 2904 directs execution from operation 2902 to operation 2906. Operation 2906 performs encrypting the client response message with appended service provider billing data with the first-service-provider-to-profiler authentication key. Arrow 2908 directs execution from operation 2906 to operation 2910. Operation 2910 performs sending first-service-provider-to-profiler encrypted client response message with appended service provider billing data to the service-flow engine.

Arrow 2912 directs execution from operation 2910 to operation 2914. Operation 2914 terminates the operations of this flowchart.

Figure 64:
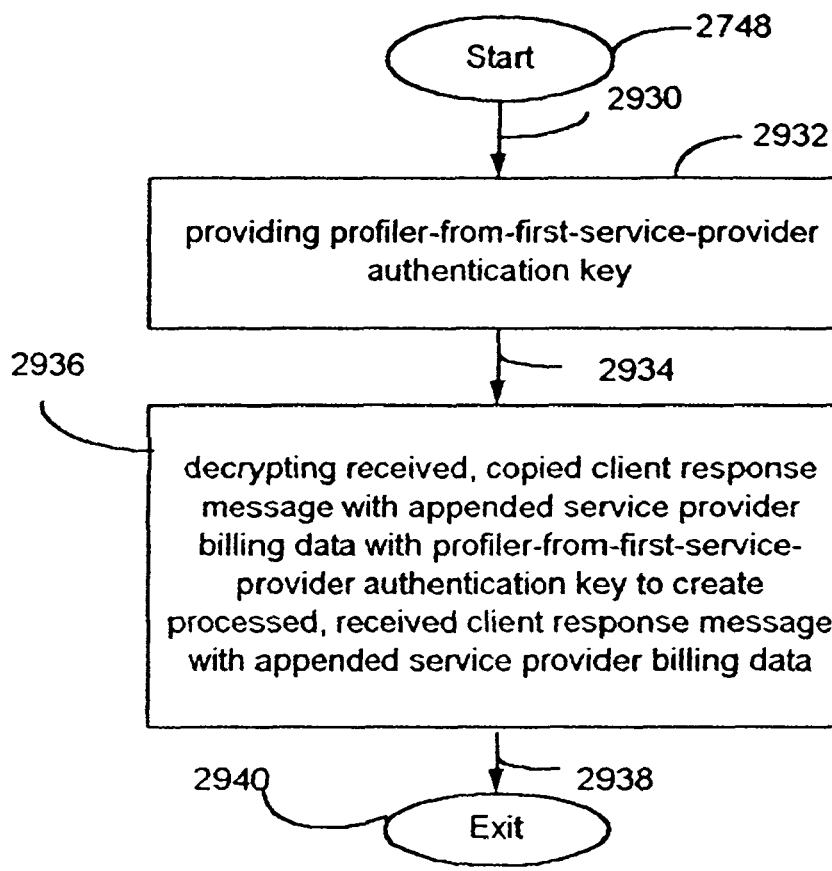
FIG. 64 depicts a flowchart of further details regarding operation 2748, processing the received, copied the client response message with appended service provider billing data using the service profiler process performed by the service profiler in accordance with embodiments supporting FIG. 57.

FIG. 64 depicts a flowchart of further details regarding operation 2748, processing the received, copied the client response message with appended service provider billing data using the service profiler process performed by the service-flow engine in accordance with embodiments supporting FIG. 57. Arrow 2930 directs the flow of execution from starting operation 2748 to operation 2932. Operation 2932 performs providing a profiler-from-first-service-provider authentication key. Arrow 2934 directs execution from operation 2932 to operation 2936. Operation 2936 performs decrypting the received, copied client response message with appended service provider billing data with the profiler-from-first service provider authentication key to create the processed, received client response message with appended service provider billing data. Arrow 2938 directs execution from operation 2936 to operation 2940. Operation 2940 terminates the operations of this flowchart.

Figure 65:
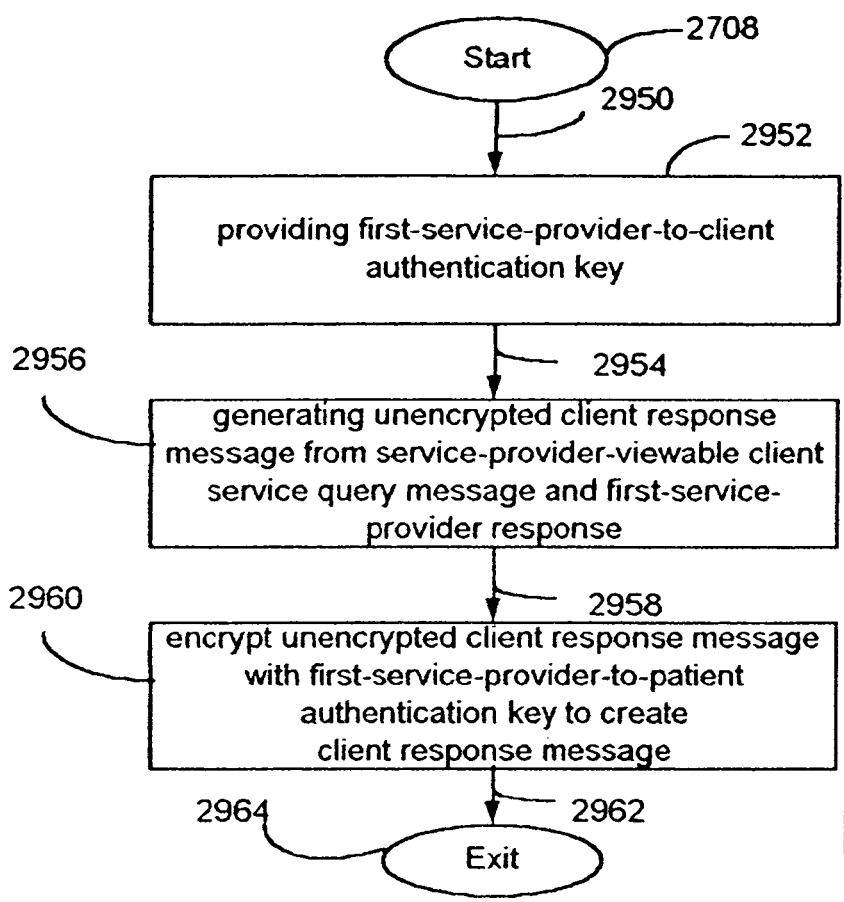
FIG. 65 depicts a flowchart of further details regarding operation 2708, generating client response message using the second message interface in accordance with embodiments supporting FIG. 56.

FIG. 65 depicts a flowchart of further details regarding operation 2708, generating client response message using the second message interface in accordance with embodiments supporting FIG. 56. Arrow 2950 directs the flow of execution from starting operation 2708 to operation 2952. Operation 2952 performs providing first-service-provider-to-client authentication key. Arrow 2954 directs execution from operation 2952 to operation 2956. Operation 2956 performs generating an unencrypted client response message from the service-provider-viewable client service query message and the first-service-provider response. Arrow 2958 directs execution from operation 2956 to operation 2960. Operation 2960 performs encrypt the unencrypted client response message with the first-service-provider-to-client authentication key to create the client response message. Arrow 2962 directs execution from operation 2960 to operation 2964. Operation 2964 terminates the operations of this flowchart.

Note that operations 2952 and 2956 may be performed either in the order presented by this flowchart, or in certain alternative embodiments, in the reverse order to that shown, or further alternatively, concurrently with each other.

Figure 66:
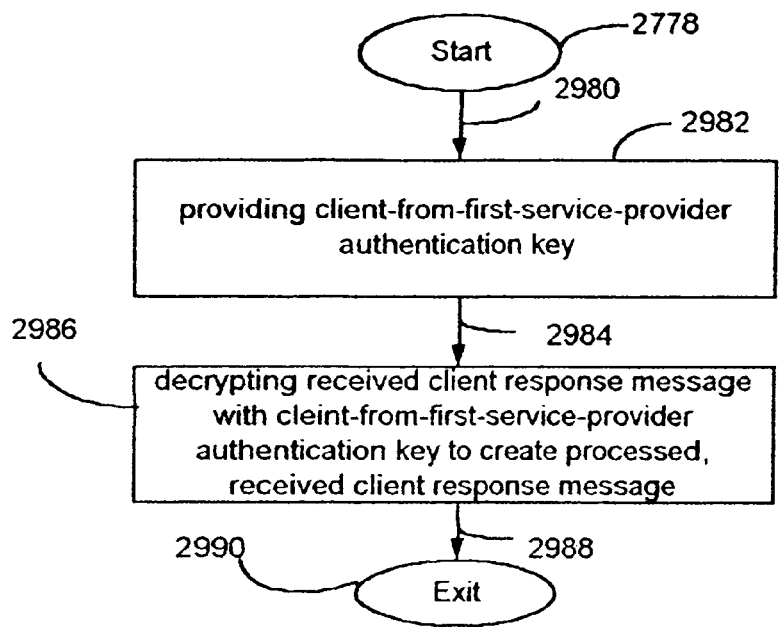
FIG. 66 depicts a flowchart of further details regarding operation 2778, processing the received client response message using the first message interface in accordance with embodiments supporting FIG. 58.

FIG. 66 depicts a flowchart of further details regarding operation 2778, processing the received client response message using the first message interface in accordance with embodiments supporting FIG. 58. Arrow 2980 directs the flow of execution from starting operation 2778 to operation 2982. Operation 2982 performs providing a client-from-first-service-provider authentication key. Arrow 2984 directs execution from operation 2982 to operation 2986. Operation 2986 performs decrypting the received client response message with the client-from-first-service-provider authentication key to create the processed, received client response message. Arrow 2988 directs execution from operation 2986 to operation 2990. Operation 2990 terminates the operations of this flowchart.

Figure 67:
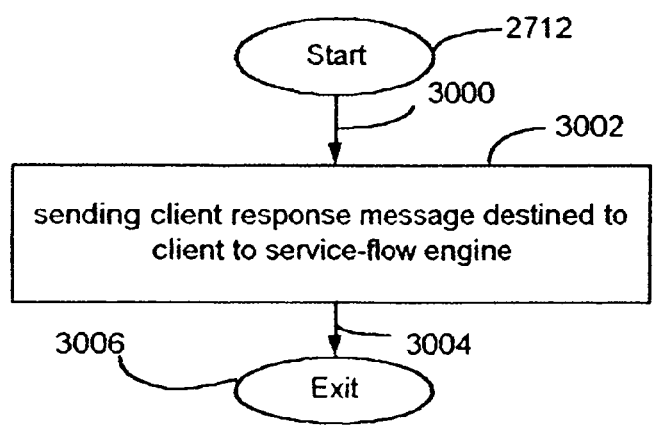
FIG. 67 depicts a flowchart of further details regarding operation 2712, sending the client response message with appended service provider billing data using the service profiler process performed by the service profiler in accordance with embodiments supporting FIG. 56.

FIG. 67 depicts a flowchart of further details regarding operation 2712, sending the client response message with appended service provider billing data using the service profiler process performed by the service-flow engine in accordance with embodiments supporting FIG. 56. Arrow 3000 directs the flow of execution from starting operation 2712 to operation 3002. Operation 3002 performs sending client response message destined to client to service-flow engine. Arrow 3004 directs execution from operation 3002 to operation 3006. Operation 3006 terminates the operations of this flowchart.

Figure 68:
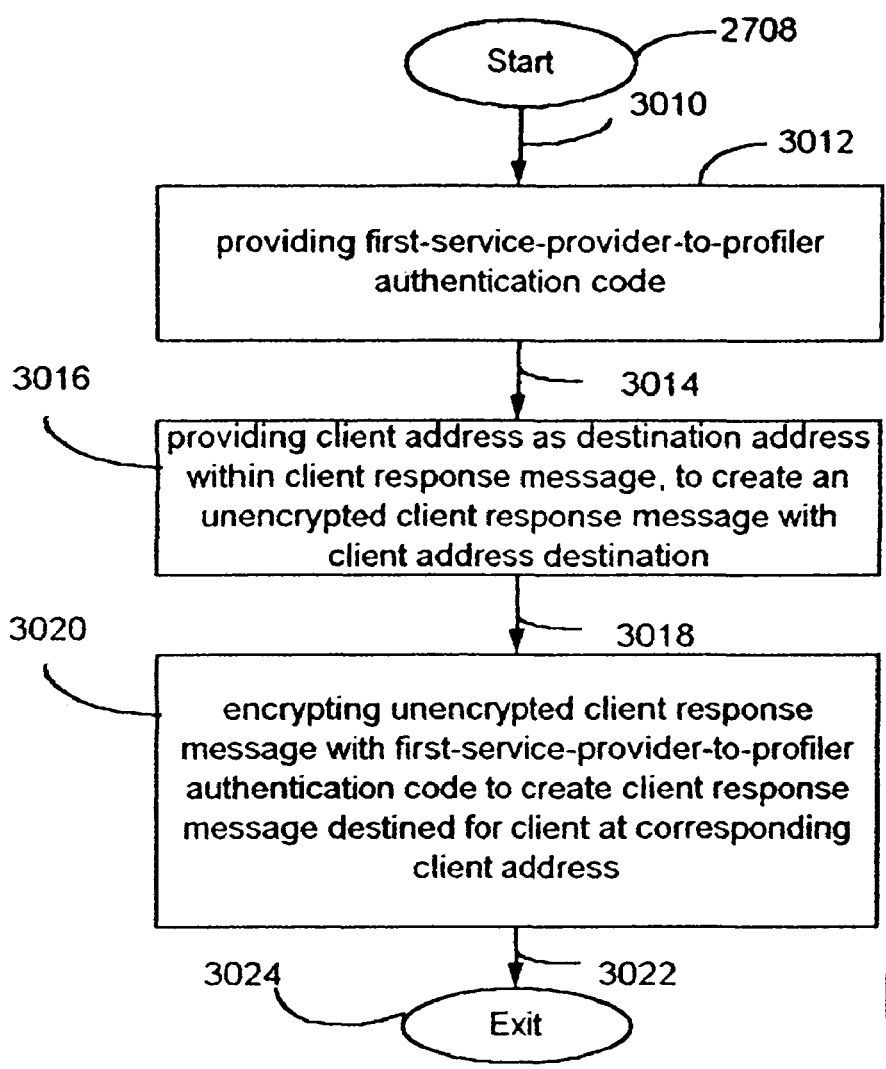
FIG. 68 depicts a flowchart of further details regarding operation 2708, generating the client response message using the second message interface in accordance with embodiments supporting FIG. 56.

FIG. 68 depicts a flowchart of further details regarding operation 2708, generating the client response message using the second message interface in accordance with embodiments supporting FIG. 56. Arrow 3010 directs the flow of execution from starting operation 2708 to operation 3012. Operation 3012 performs providing the first-service-provider-to-profiler authentication code. Arrow 3014 directs execution from operation 3012 to operation 3016. Operation 3016 performs providing the client address as destination address within the client response message, to create an unencrypted client response message with client address destination. Arrow 3018 directs execution from operation 3016 to operation 3020. Operation 3020 performs encrypting the unencrypted client response message with the first-service-provider-to-profiler authentication code to create the client response message destined for the client at the corresponding client address. Arrow 3022 directs execution from operation 3020 to operation 3024. Operation 3024 terminates the operations of this flowchart.

Note that operations 3012 and 3016 in certain alternative embodiments may be performed in reverse order, and in certain further alternative embodiments, may be concurrently performed.

Figure 69:
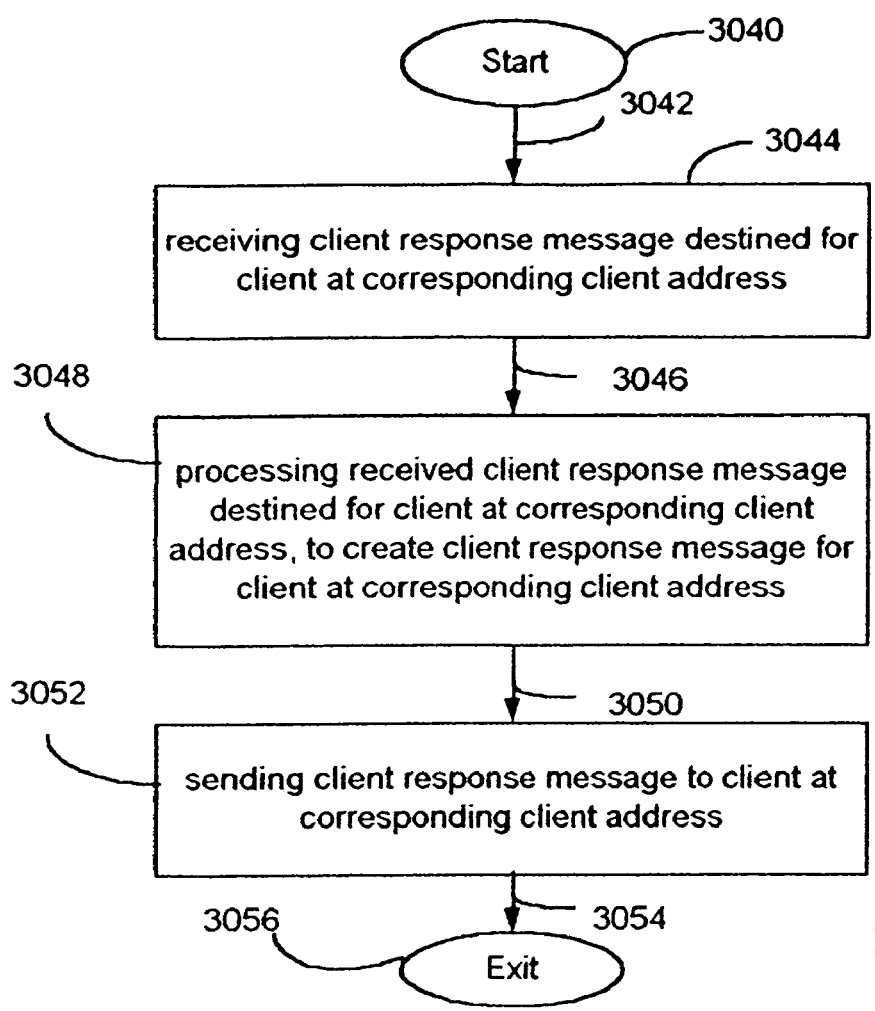
FIG. 69 depicts a flowchart of operations of the service profiler process performed by the service profiler in accordance with alternative embodiments supporting FIG. 52.

FIG. 69 depicts a flowchart of operations of the service profiler process performed by the service-flow engine in accordance with alternative embodiments supporting FIG. 52. Operation 3040 starts the operations of this flowchart. Arrow 3042 directs the flow of execution from operation 3040 to operation 3044. Operation 3044 performs receiving the client response message destined for the client at the corresponding client address. Arrow 3046 directs execution from operation 3044 to operation 3048. Operation 3048 performs processing the received client response message destined for the client at the corresponding client address, to create the client response message for the client at the corresponding client address. Arrow 3050 directs execution from operation 3048 to operation 3052. Operation 3052 performs sending the client response message to the client at the corresponding client address. Arrow 3054 directs execution from operation 3052 to operation 3056. Operation 3056 terminates the operations of this flowchart.

Figure 70:
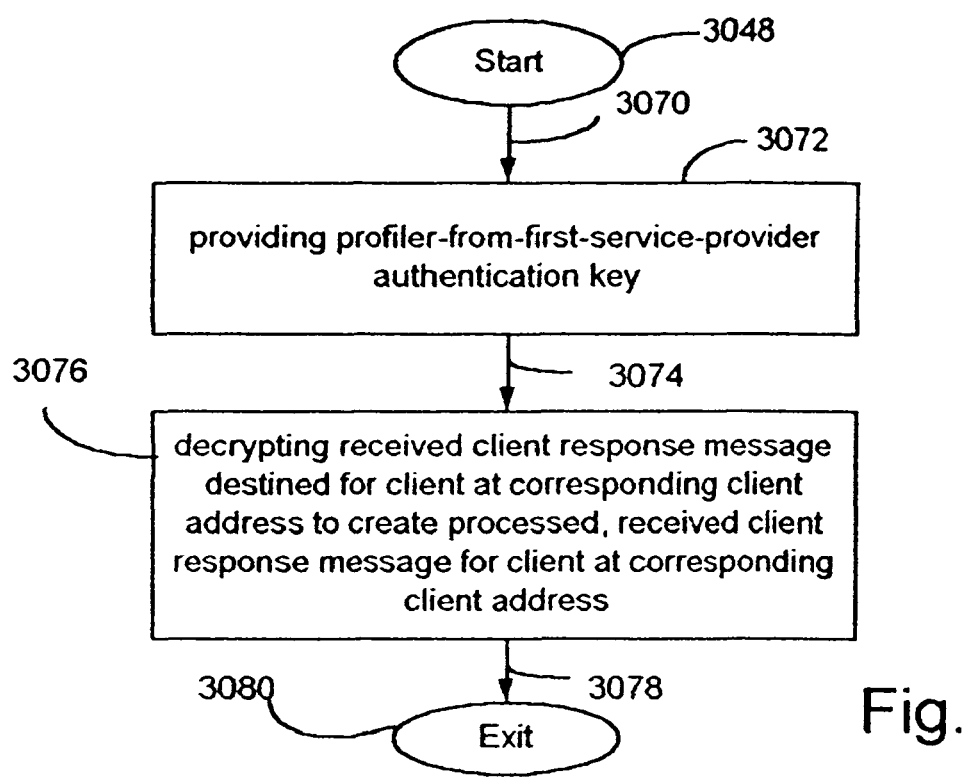
FIG. 70 depicts a flowchart of further details regarding operation 3048, processing the client response message destined for the client using the service profiler process performed by the service profiler in accordance with embodiments supporting FIG. 69.

FIG. 70 depicts a flowchart of further details regarding operation 3048, processing the client response message destined for the client using the service profiler process performed by the service-flow engine in accordance with embodiments supporting FIG. 69. Arrow 3070 directs the flow of execution from starting operation 3048 to operation 3072. Operation 3072 performs providing a profiler-from-first-service-provider authentication key. Arrow 3074 directs execution from operation 3072 to operation 3076. Operation 3076 performs decrypting the received client response message destined for the client at the corresponding client address to create the processed, received client response message for the client at the corresponding client address. Arrow 3078 directs execution from operation 3076 to operation 3080. Operation 3080 terminates the operations of this flowchart.

Figure 71:
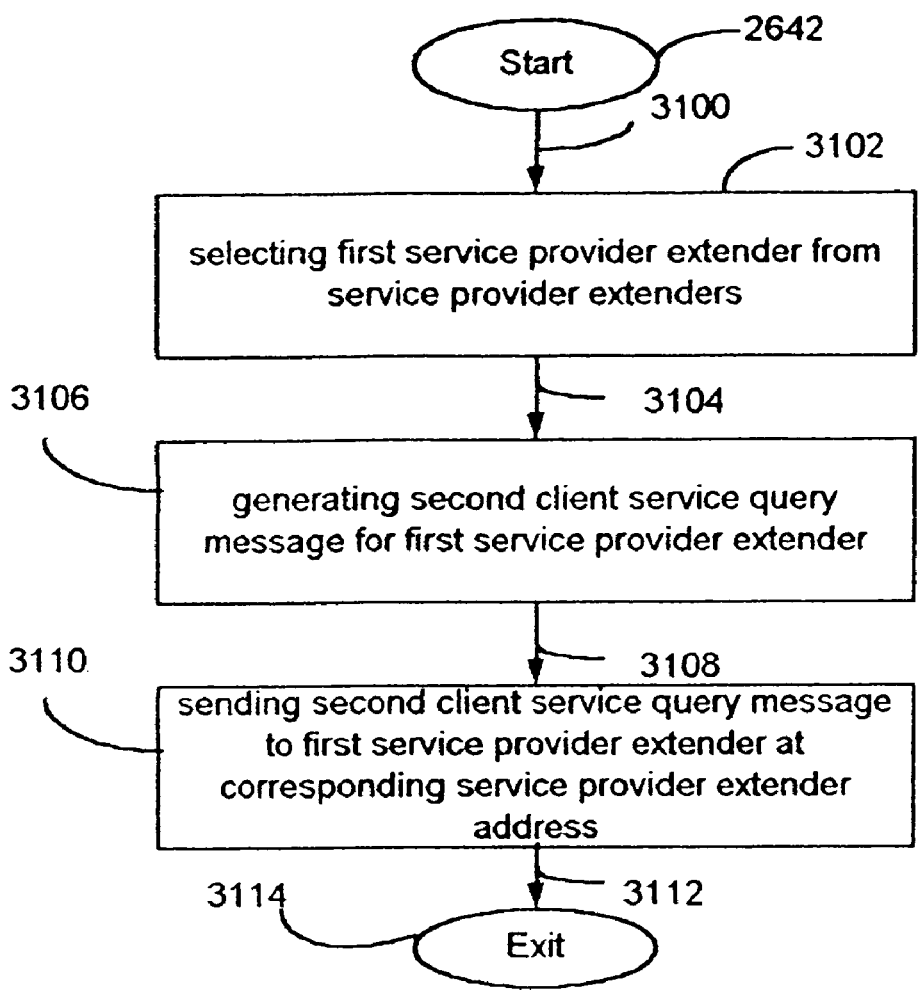
FIG. 71 depicts a flowchart of further details regarding operation 2642, generating a client service query message using the service profiler process performed by the service profiler in accordance with embodiments.

FIG. 71 depicts a flowchart of further details regarding operation 2642, generating a client service query message using the service profiler process performed by the service-flow engine in accordance with embodiments. Arrow 3100 directs the flow of execution from starting operation 2642 to operation 3102. Operation 3102 performs selecting a first service extender from the service extenders. Arrow 3104 directs execution from operation 3102 to operation 3106. Operation 3106 performs generating a second client service query message for the first service extender. Arrow 3108 directs execution from operation 3106 to operation 3110. Operation 3110 performs sending the second client service query message to the first service extender at the corresponding service extender address. Arrow 3112 directs execution from operation 3110 to operation 3114. Operation 3114 terminates the operations of this flowchart.

Note that in certain embodiments, operation 3102 is based upon the received educated query message. In certain further embodiments, operation 3102 is based upon the processed, received educated query message.

Figure 72:
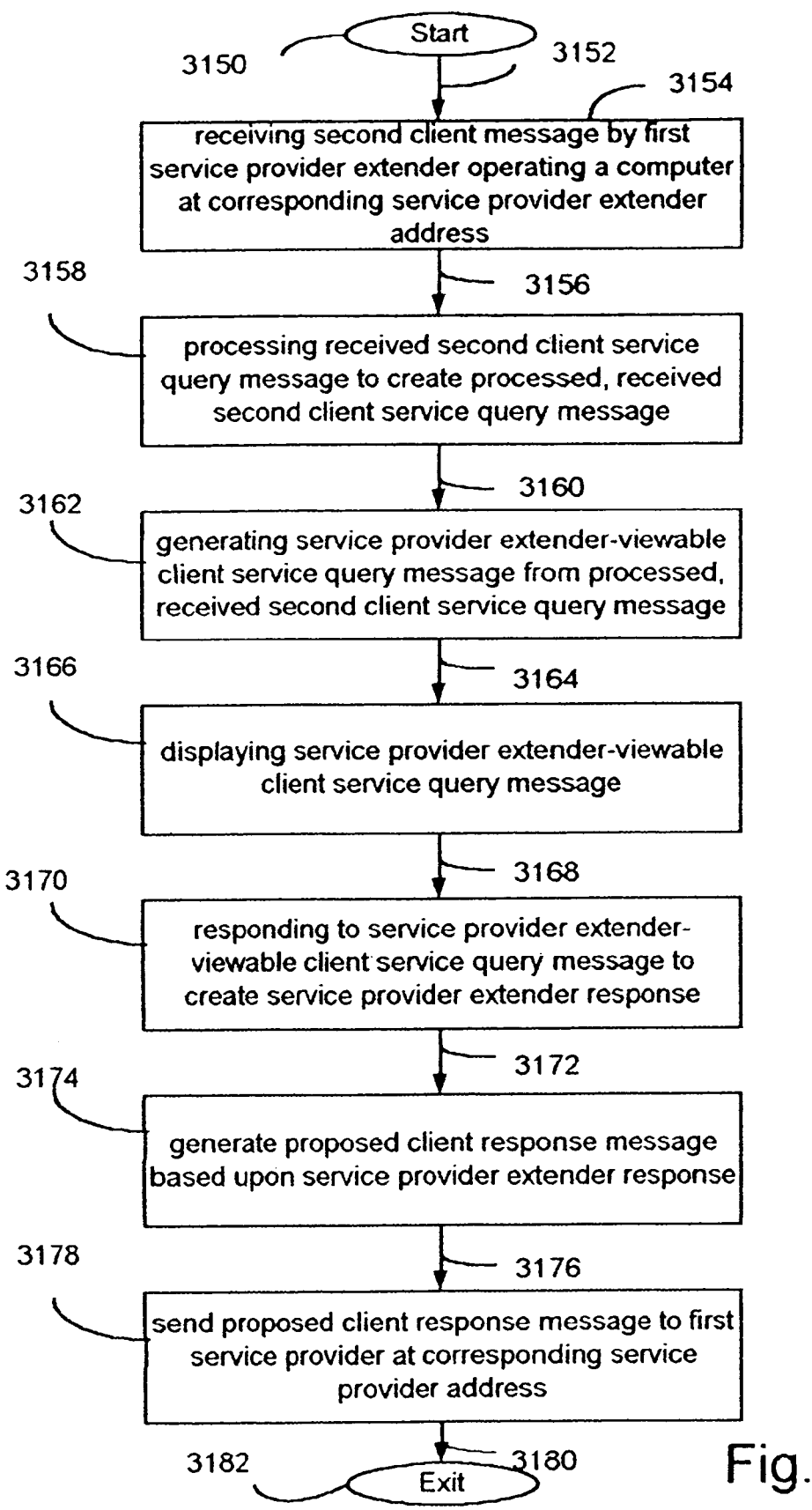
FIG. 72 depicts a flowchart of operations using the third message interface on the service extender computer in accordance with embodiments supporting FIG. 57.

FIG. 72 depicts a flowchart of operations using the third message interface on the service extender computer in accordance with embodiments supporting FIG. 57. Operation 3150 starts the operations of this flowchart. Arrow 3152 directs the flow of execution from operation 3150 to operation 3154. Operation 3154 performs receiving a second client message by first service extender operating a computer at the corresponding service extender address. Arrow 3156 directs execution from operation 3154 to operation 3158. Operation 3158 performs processing the received second client service query message to create a processed, received second client service query message. Arrow 3160 directs execution from operation 3158 to operation 3162. Operation 3162 performs generating a service extender-viewable client service query message from the processed, received second client service query message. Arrow 3164 directs execution from operation 3162 to operation 3166. Operation 3166 performs displaying the service extender-viewable service query message. Arrow 3168 directs execution from operation 3166 to operation 3170. Operation 3170 performs responding to the service extender-viewable service query message to create a service extender response. Arrow 3172 directs execution from operation 3170 to operation 3174. Operation 3174 performs generating the proposed client response message from service extender response. Arrow 3176 directs execution from operation 3174 to operation 3178. Operation 3178 performs sending the proposed client response message to the first service provider at the corresponding service provider address. Arrow 3180 directs execution from operation 3178 to operation 3182. Operation 3182 terminates the operations of this flowchart.

Figure 73:
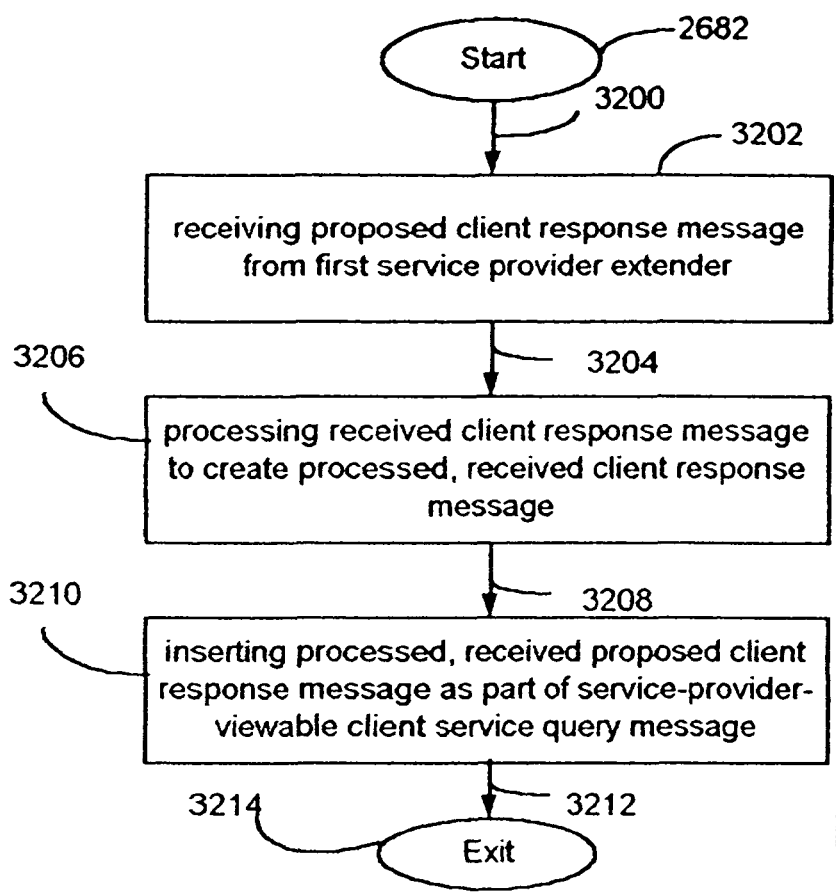
FIG. 73 depicts a flowchart of further details regarding operation 2602, generating the service-provider-viewable client service query message in accordance with embodiments supporting FIG. 55.

FIG. 73 depicts a flowchart of further details regarding operation 2682, generating the service-provider-viewable client service query message in accordance with embodiments supporting FIG. 55. Arrow 3200 directs the flow of execution from starting operation 2682 to operation 3202. Operation 3202 performs receiving proposed client response message from first service extender. Arrow 3204 directs execution from operation 3202 to operation 3206. Operation 3206 performs processing the received client response message to create processed, received client response message. Arrow 3208 directs execution from operation 3206 to operation 3210. Operation 3210 performs inserting the processed, received proposed client response message as part of the service-provider-viewable client service query message. Arrow 3212 directs execution from operation 3210 to operation 3214. Operation 3214 terminates the operations of this flowchart.

Figure 74:
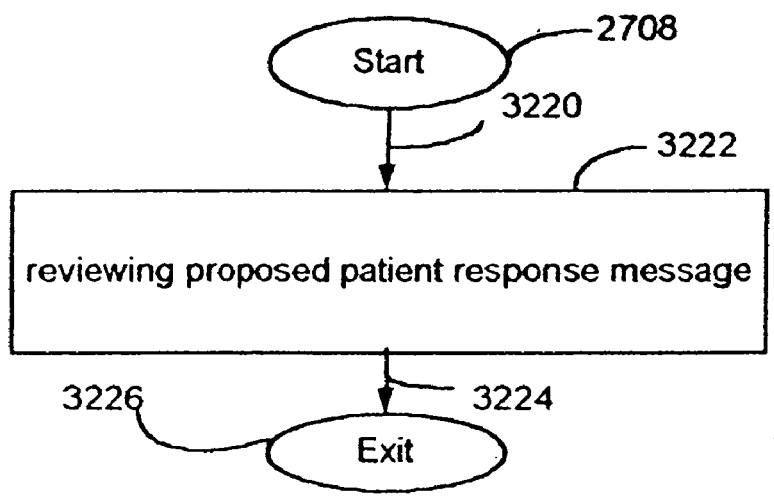
FIG. 74 depicts a flowchart of further details regarding operation 2708, generating the client response message using the second message interface in accordance with embodiments supporting FIG. 56.

FIG. 74 depicts a flowchart of further details regarding operation 2708, generating the client response message using the second message interface in accordance with certain embodiments. Arrow 3220 directs the flow of execution from starting operation 2708 to operation 3222. Operation 3222 performs reviewing the proposed client response message. Arrow 3224 directs execution from operation 3222 to operation 3226. Operation 3226 terminates the operations of this flowchart.

Figure 75:
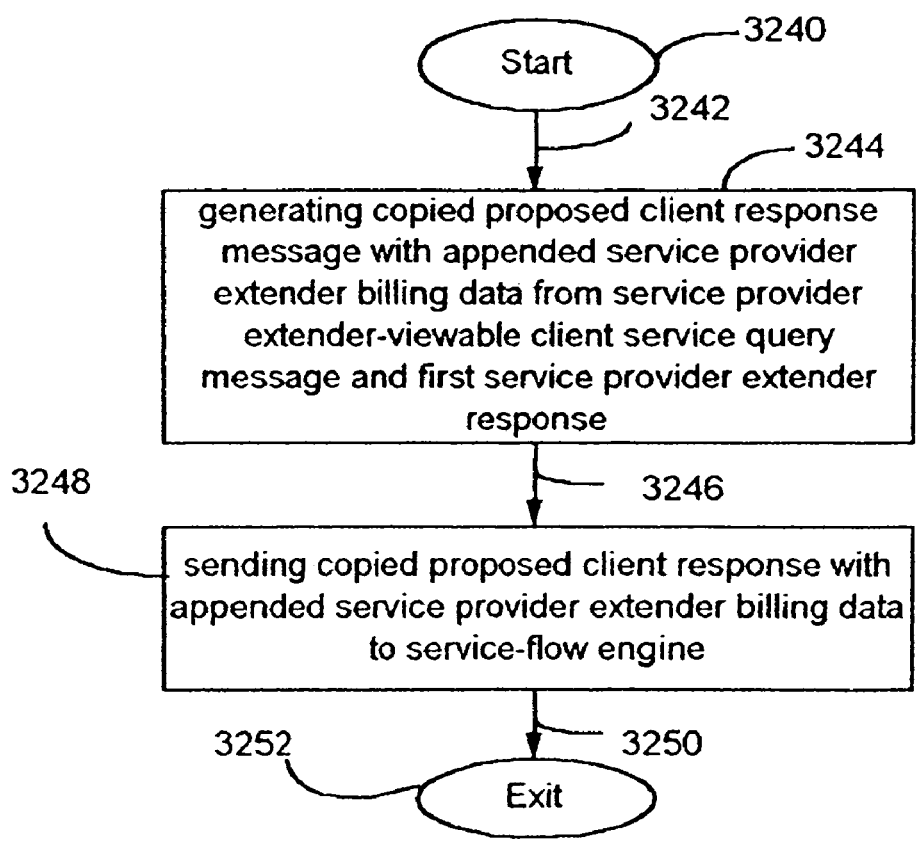
FIG. 75 depicts a flowchart of further operations embodying the third message interface in accordance with certain embodiments.

FIG. 75 depicts a flowchart of further operations embodying the third message interface in accordance with certain embodiments. Arrow 3240 directs the flow of execution from starting operation 3240 to operation 3242. Operation 3242 performs generating a copied proposed client response message with appended service extender billing data from the service extender-viewable client service query message and first service extender response. Arrow 3244 directs execution from operation 3242 to operation 3246. Operation 3246 performs sending copied proposed client response with appended service extender billing data to service-flow engine. Arrow 3248 directs execution from operation 3246 to operation 3250. Operation 3250 terminates the operations of this flowchart.

Figure 76:
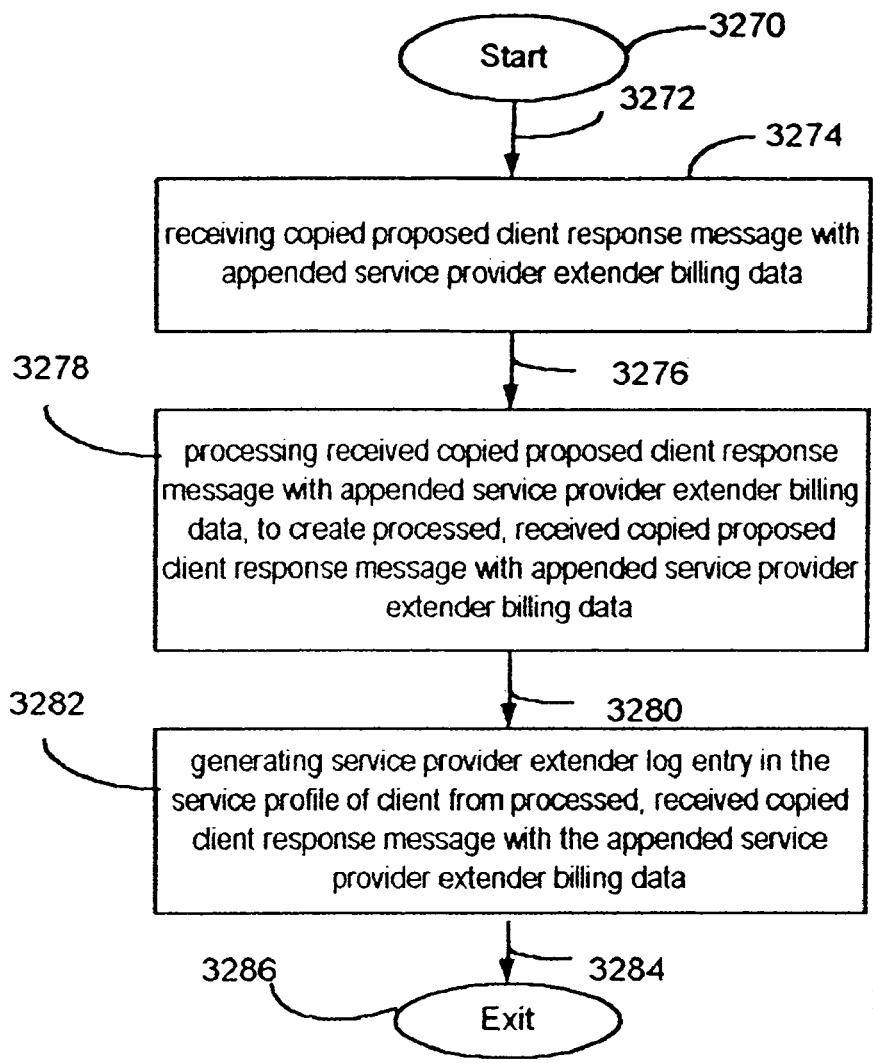
FIG. 76 depicts a flowchart of further operations embodied in the message profiler process in accordance with certain embodiments.

FIG. 76 depicts a flowchart of further operations embodied in the message profiler process in accordance with certain embodiments. Operation 3270 starts the operations of this flowchart. Arrow 3272 directs the flow of execution from operation 3270 to operation 3274. Operation 3274 performs receiving the copied proposed client response message with the appended service extender billing data. Arrow 3276 directs execution from operation 3274 to operation 3278. Operation 3278 performs processing the received copied proposed client response message with the appended service extender billing data, to create a processed, received copied proposed client response message with the appended service extender billing data. Arrow 3280 directs execution from operation 3278 to operation 3282. Operation 3282 performs generating a service extender log entry in the service profile of the client from the processed, received copied client response message with the appended service extender billing data. Arrow 3284 directs execution from operation 3282 to operation 3286. Operation 3286 terminates the operations of this flowchart.

Figure 77:
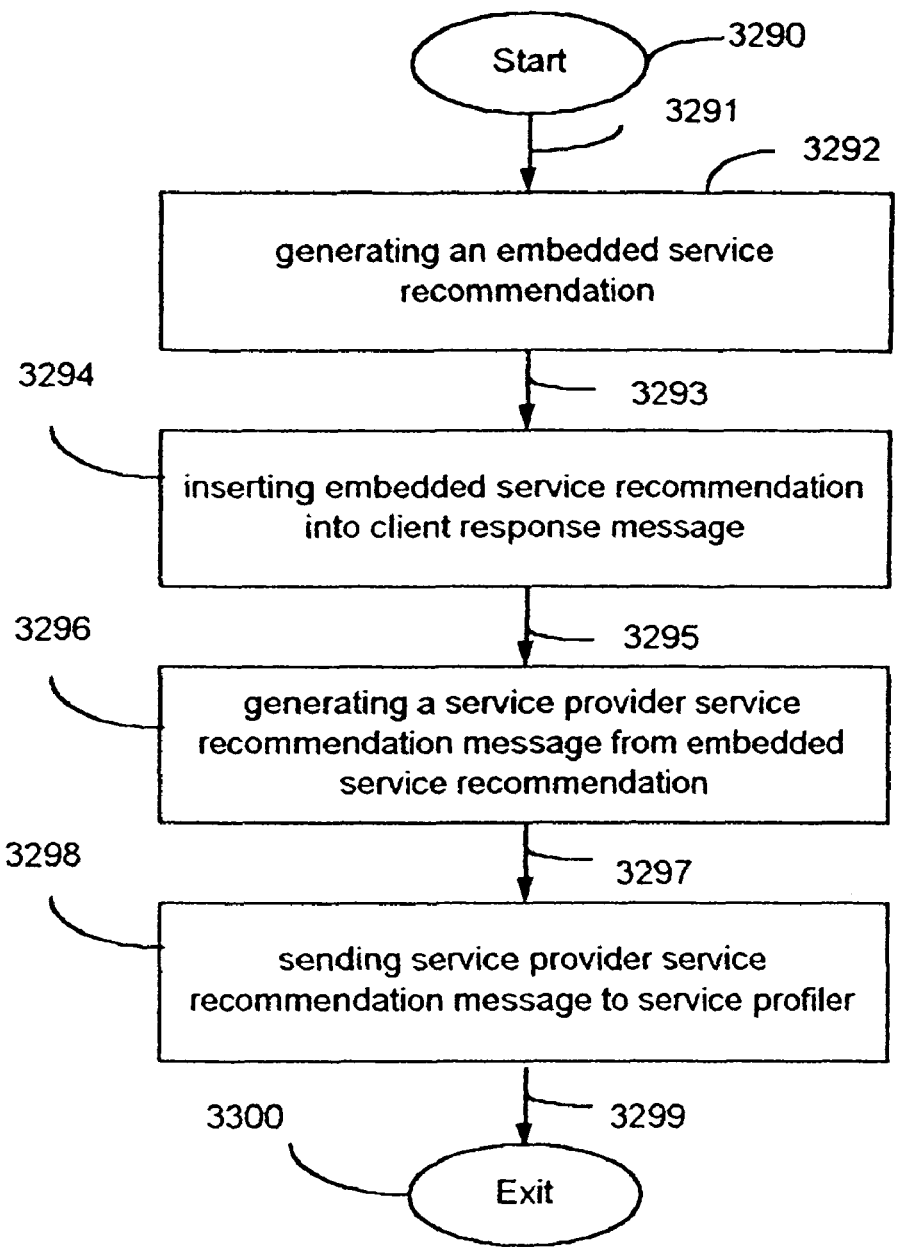
FIG. 77 depicts a flowchart of further operations embodied in a second message interface in accordance with certain embodiments supporting service recommendations.

FIG. 77 depicts a flowchart of further operations embodied in a second message interface in accordance with certain embodiments supporting service recommendations. Operation 3290 starts the operations of this flowchart. Arrow 3291 directs the flow of execution from operation 3290 to operation 3292. Operation 3292 performs generating an embedded service recommendation. Arrow 3293 directs execution from operation 3292 to operation 3294. Operation 3294 performs inserting the embedded service recommendation into client response message. Arrow 3295 directs execution from operation 3294 to operation 3296. Operation 3296 performs generating a service provider service recommendation message from the embedded service recommendation. Arrow 3297 directs execution from operation 3296 to operation 3298. Operation 3298 performs sending the service provider service recommendation message to the service-flow engine. Arrow 3299 directs execution from operation 3298 to operation 3300. Operation 3300 terminates the operations of this flowchart.

Figure 78:
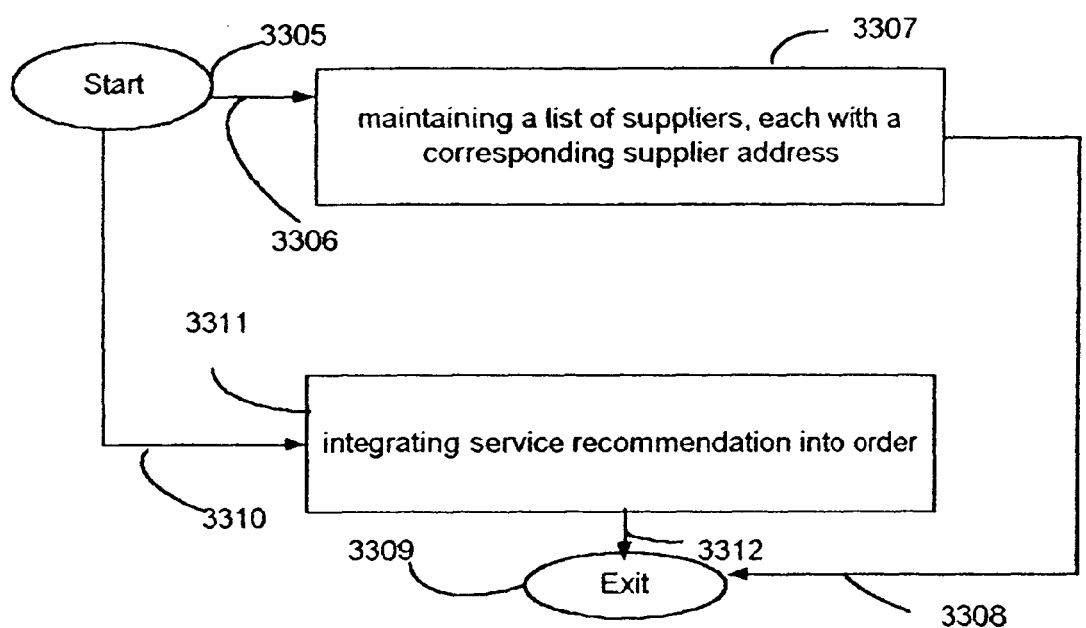
FIG. 78 depicts a flowchart of further operations embodied in a service profiler in accordance with certain embodiments supporting service recommendations.

FIG. 78 depicts a flowchart of further operations embodied in a service profiler in accordance with certain embodiments supporting service recommendations. Operation 3305 starts the operations of this flowchart. Arrow 3306 directs the flow of execution from operation 3305 to operation 3307. Operation 3307 performs maintaining a list of suppliers, each with a corresponding supplier address. Arrow 3308 directs execution from operation 3307 to operation 3309. Operation 3309 terminates the operations of this flowchart.

Arrow 3310 directs the flow of execution from starting operation 3305 to operation 3311. Operation 3311 performs integrating a service order. Arrow 3312 directs execution from operation 3311 to operation 3309. Operation 3309 terminates the operations of this flowchart.

Note that arrows 3306 and 3310 may be concurrently active, the supplier list may be undergoing maintenance operations and the integration of service orders may be performed concurrently on either the same computer or distinct computers according to various embodiments of the invention.

Figure 78A:
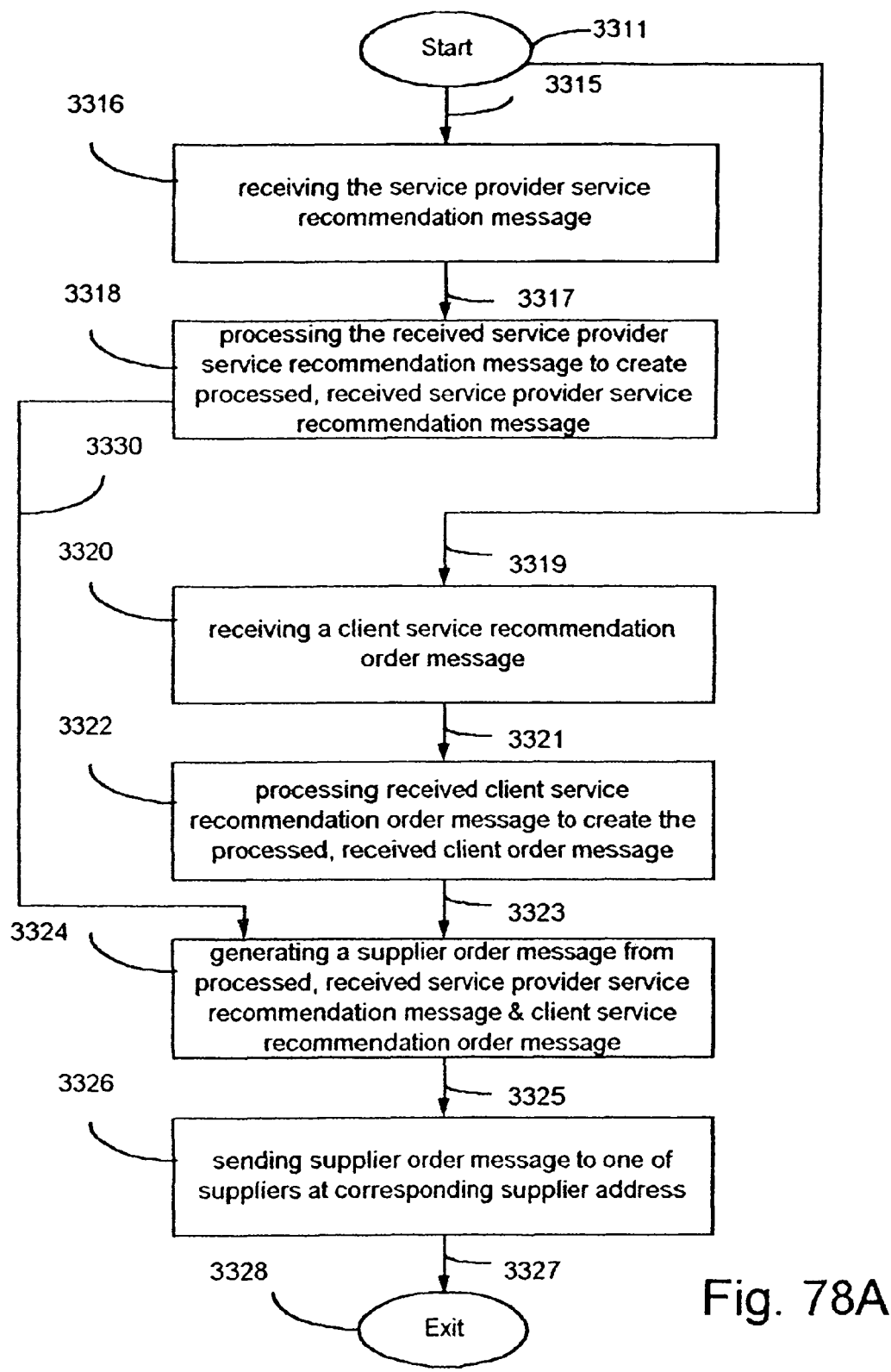
FIG. 78A depicts a flowchart of further details regarding operation 3311, integrating a service order in the service profiler process in accordance with embodiments supporting FIG. 78.

FIG. 78A depicts a flowchart of further details regarding operation 3311, integrating a service order in the service profiler process in accordance with embodiments supporting FIG. 78. Arrow 3315 directs the flow of execution from the starting of operation 3311 to operation 3316. Operation 3316 performs receiving the service provider service recommendation message. Arrow 3317 directs execution from operation 3316 to operation 3318. Operation 3318 performs processing the received service provider service recommendation message, to create a processed, received service provider service recommendation message.

Arrow 3319 directs execution from operation 3311 to operation 3320. Operation 3320 performs receiving a client order message. Arrow 3321 directs execution from operation 3320 to operation 3322. Operation 3322 performs processing the received client order message to create a processed, received client order message.

Arrow 3323 directs execution from operation 3322 to operation 3324. Arrow 3330 directs execution from operation 3318 to operation 3324. Note that in certain embodiments, both arrows 3323 and 3330 must perform their flow of execution before operation 3324 can execute. Operation 3324 performs generating a supplier service order message from the processed, received service provider service recommendation message and the processed, received client order message. Arrow 3325 directs execution from operation 3324 to operation 3326. Operation 3326 performs sending the supplier service order message to one of the suppliers at the corresponding supplier address. Arrow 3327 directs execution from operation 3326 to operation 3328. Operation 3328 terminates the operations of this flowchart.

Figure 79:
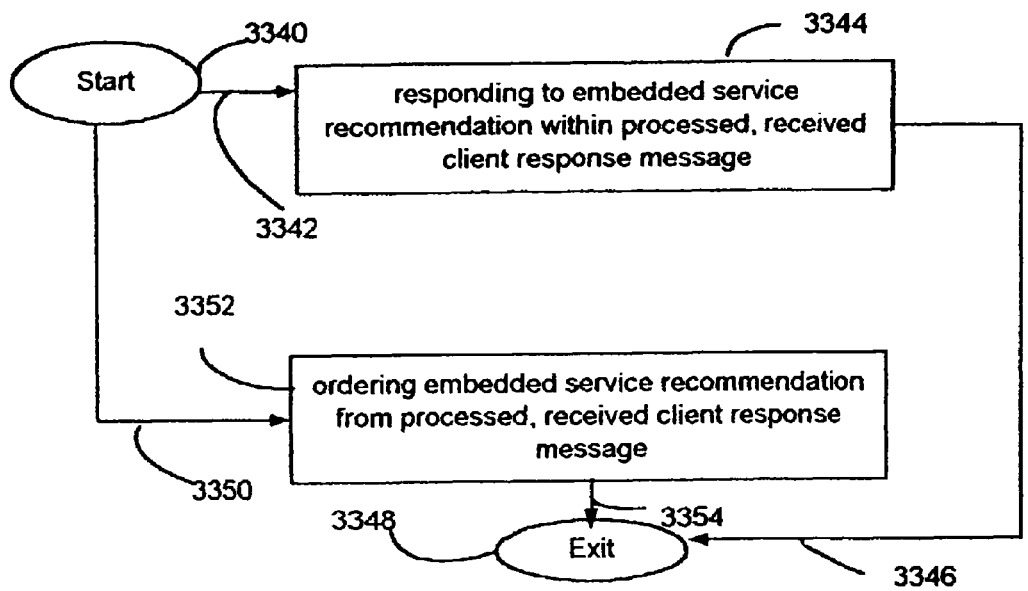
FIG. 79 depicts a flowchart of further operations embodied in the first message interface in accordance with certain embodiments supporting service recommendations.

FIG. 79 depicts a flowchart of further operations embodied in the first message interface in accordance with certain embodiments supporting service recommendations. Operation 3340 starts the operations of this flowchart. Arrow 3342 directs the flow of execution from operation 3340 to operation 3344. Operation 3344 performs responding to the embedded service recommendation within the processed, received client response message. Arrow 3346 directs execution from operation 3344 to operation 3348. Operation 3348 terminates the operations of this flowchart.

Arrow 3350 directs the flow of execution from starting operation 3340 to operation 3352. Operation 3352 performs ordering the embedded service recommendation from the processed, received client response message. Arrow 3354 directs execution from operation 3352 to operation 3348. Operation 3348 terminates the operations of this flowchart.

Note that in certain embodiments, the starting operation may act as a branching mechanism. Such a mechanism can be driven by client choices via a user interface, such as buttons or pull down menus being selected or pushed.

Figure 80:
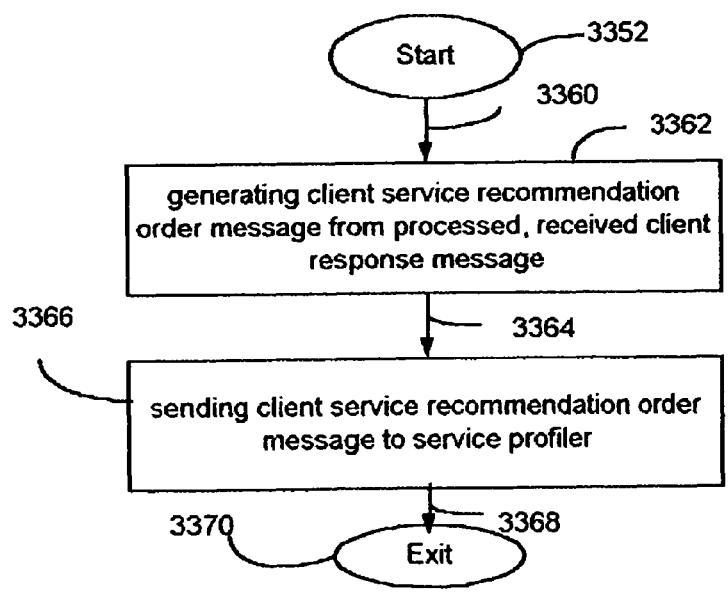
FIG. 80 depicts a flowchart of further details of operation 3352, ordering the embedded service recommendation of FIG. 79.

FIG. 80 depicts a flowchart of further details of operation 3352, ordering the embedded service recommendation of FIG. 79. Arrow 3360 directs the flow of execution from starting operation 3352 to operation 3362. Operation 3362 performs generating a client service recommendation message from the processed, received client response message. Arrow 3364 directs execution from operation 3362 to operation 3366. Operation 3366 performs sending the client service recommendation message to the service-flow engine. Arrow 3368 directs execution from operation 3366 to operation 3370. Operation 3370 terminates the operations of this flowchart.

Figure 81:
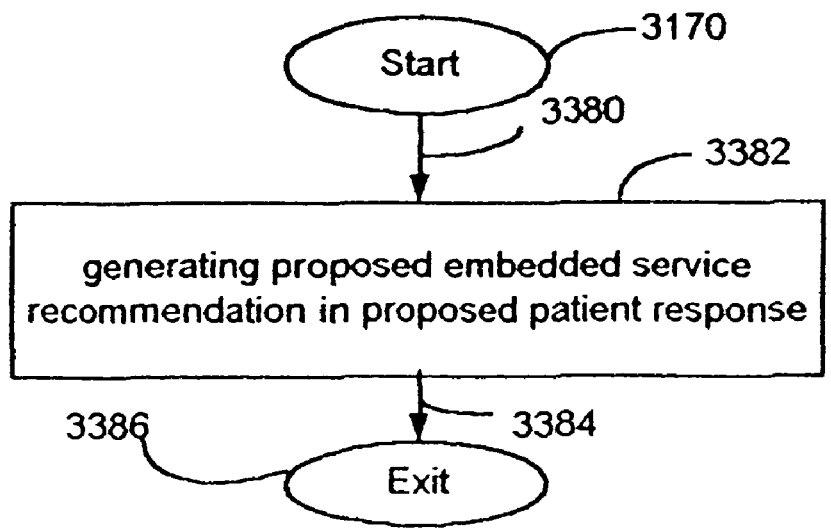
FIG. 81 depicts a flowchart of further details of operation 3170 of FIG. 73.

FIG. 81 depicts a flowchart of further details of operation 3170 of FIG. 73. Arrow 3380 directs the flow of execution from starting operation 3170 to operation 3382. Operation 3382 performs generating a proposed embedded service recommendation refill in the proposed client response. Arrow 3384 directs execution from operation 3382 to operation 3386. Operation 3386 terminates the operations of this flowchart.

Figure 82:
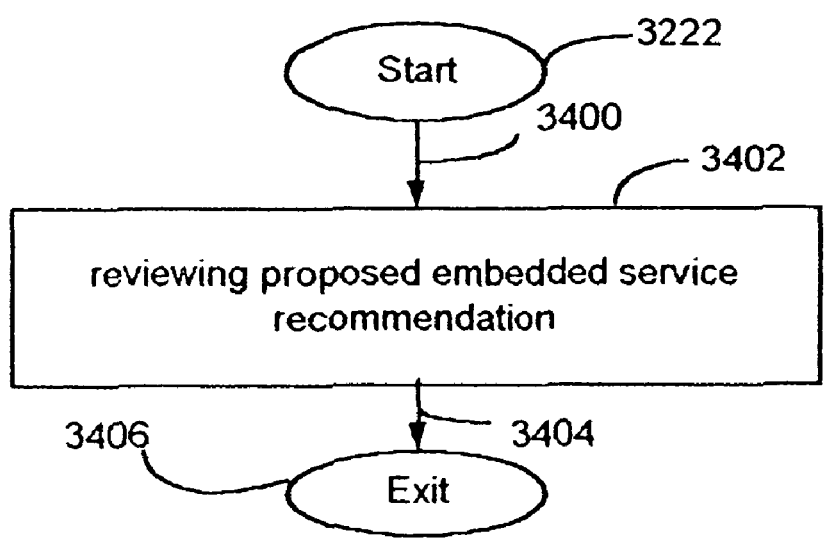
FIG. 82 depicts a flowchart of further details of operation 3222 of FIG. 75.

FIG. 82 depicts a flowchart of further details of operation 3222 of FIG. 75. Arrow 3400 directs the flow of execution from starting operation 3222 to operation 3402. Operation 3402 performs reviewing the proposed embedded service recommendation refill. Arrow 3404 directs execution from operation 3402 to operation 3406. Operation 3406 terminates the operations of this flowchart.

Figure 83:
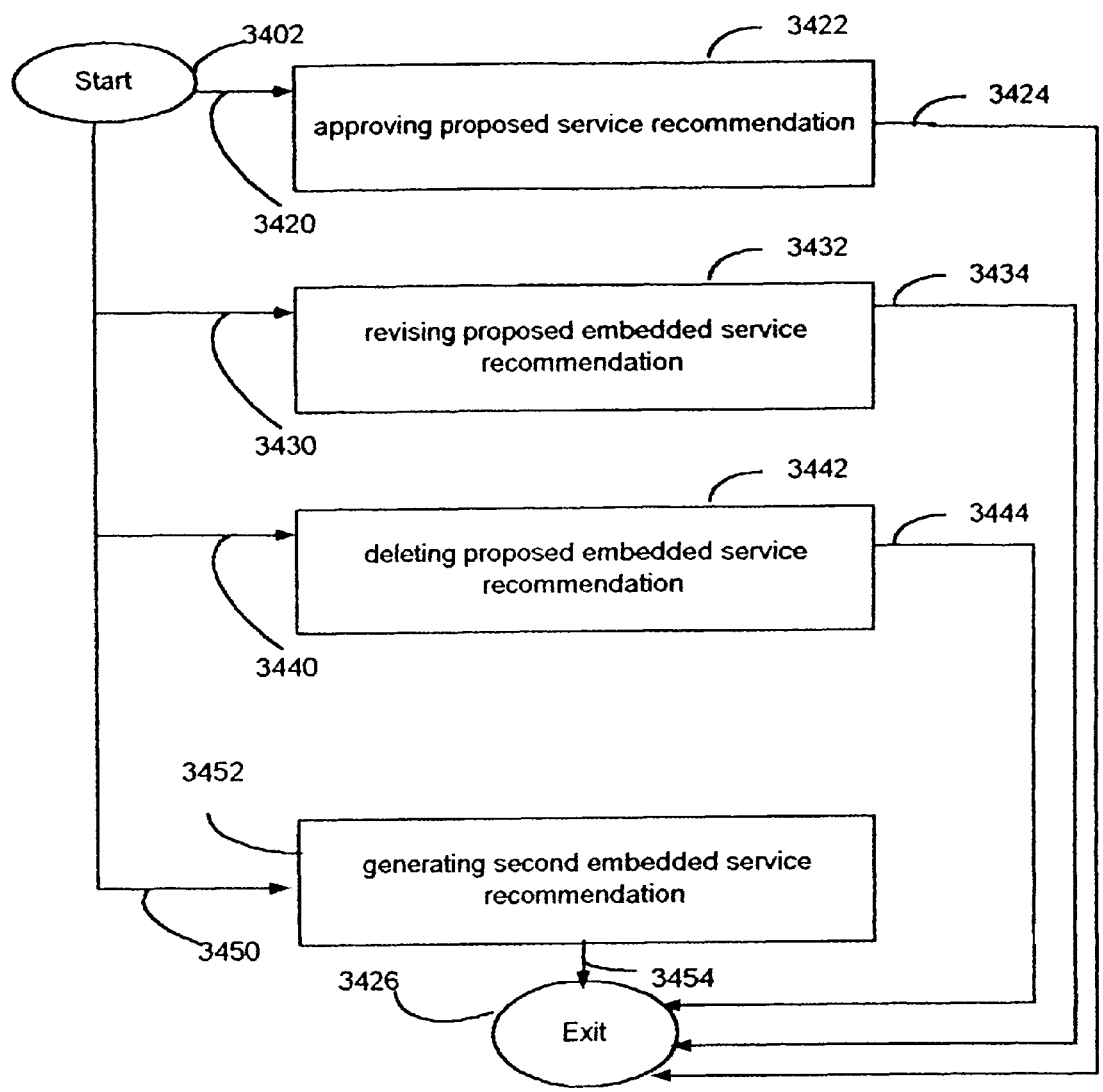
FIG. 83 depicts a flowchart of further details of operation 3402 of FIG. 82.

FIG. 83 depicts a flowchart of further details of operation 3402 of FIG. 82. Arrow 3420 directs the flow of execution from starting operation 3402 to operation 3422. Operation 3422 performs approving the proposed service recommendation refill. Arrow 3424 directs execution from operation 3422 to operation 3426. Operation 3426 terminates the operations of this flowchart.

Arrow 3430 directs the flow of execution from starting operation 3402 to operation 3432. Operation 3432 performs revising the proposed embedded service recommendation refill. Arrow 3434 directs execution from operation 3432 to operation 3426. Operation 3426 terminates the operations of this flowchart.

Arrow 3440 directs the flow of execution from starting operation 3402 to operation 3442. Operation 3442 performs deleting the proposed embedded service recommendation refill. Arrow 3444 directs execution from operation 3442 to operation 3426. Operation 3426 terminates the operations of this flowchart.

Arrow 3450 directs the flow of execution from starting operation 3402 to operation 3452. Operation 3452 performs generating a second embedded service recommendation. Arrow 3454 directs execution from operation 3452 to operation 3426. Operation 3426 terminates the operations of this flowchart.

Note that in certain embodiments, the starting operation may act as a branching mechanism. Such a mechanism can be driven by client choices via a user interface, such as buttons or pull down menus being selected or pushed.

Figure 84:
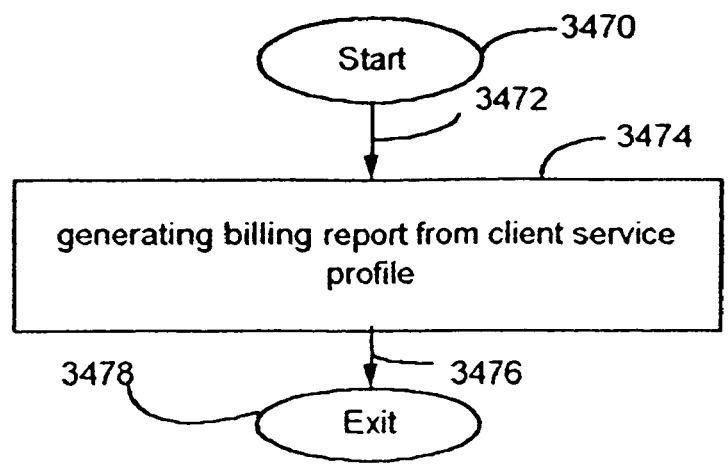
FIG. 84 depicts a flowchart of further operations embodying the message profiler process in accordance with certain embodiments supporting billing clients.

FIG. 84 depicts a flowchart of further operations embodying the message profiler process in accordance with certain embodiments supporting billing clients. Operation 3470 starts the operations of this flowchart. Arrow 3472 directs the flow of execution from operation 3470 to operation 3474. Operation 3474 performs generating a billing report from the client service profile. Arrow 3476 directs execution from operation 3474 to operation 3478. Operation 3478 terminates the operations of this flowchart.

Figure 85:
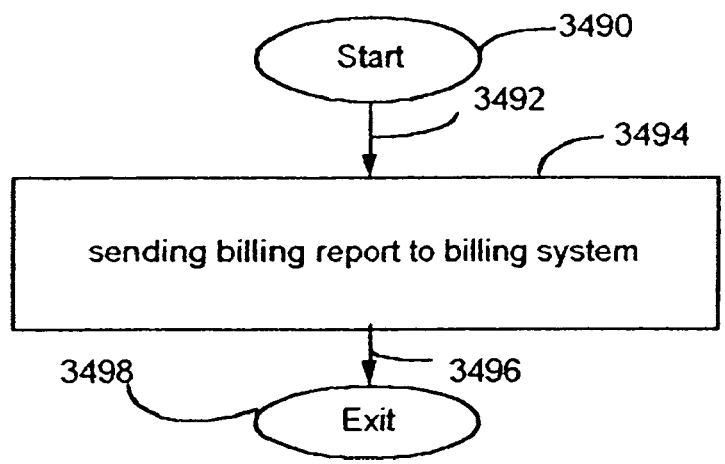
FIG. 85 depicts a flowchart of further operations embodying the message profiler process in accordance with certain embodiments further supporting billing clients.

FIG. 85 depicts a flowchart of further operations embodying the message profiler process in accordance with certain embodiments further supporting billing clients. Operation 3490 starts the operations of this flowchart. Arrow 3492 directs the flow of execution from operation 3490 to operation 3494. Operation 3494 performs sending the billing report to the billing system. Arrow 3496 directs execution from operation 3494 to operation 3498. Operation 3498 terminates the operations of this flowchart.

Figure 86:
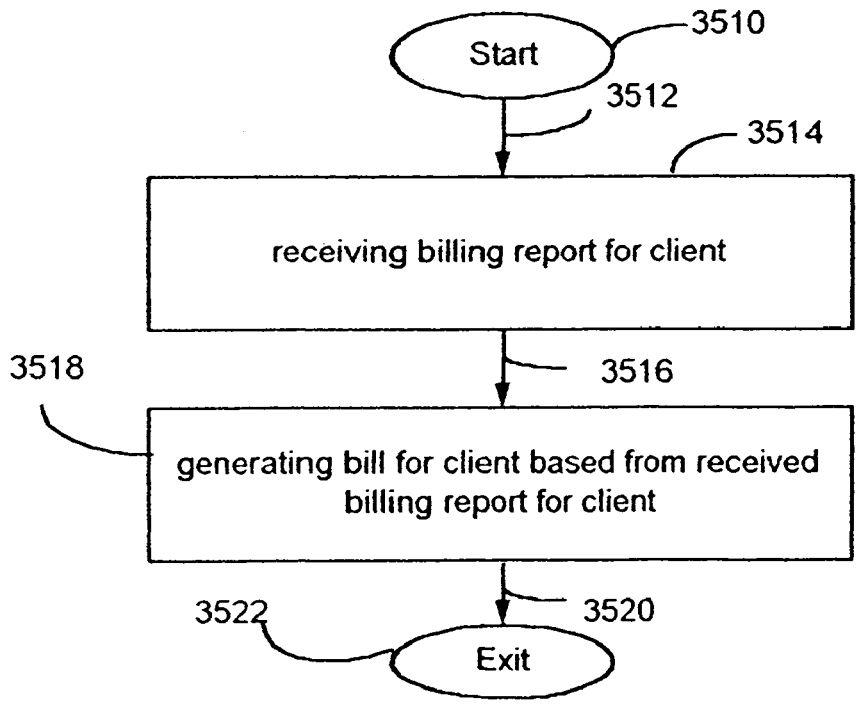
FIG. 86 depicts a flowchart of further operations embodying a billing process in accordance with certain embodiments.

FIG. 86 depicts a flowchart of further operations embodying a billing process in accordance with certain embodiments. Operation 3510 starts the operations of this flowchart. Arrow 3512 directs the flow of execution from operation 3510 to operation 3514. Operation 3514 performs receiving the billing report for the client. Arrow 3516 directs execution from operation 3514 to operation 3518. Operation 3518 performs generating a bill for the client based from the received billing report for the client. Arrow 3520 directs execution from operation 3518 to operation 3522. Operation 3522 terminates the operations of this flowchart.

Figure 87:
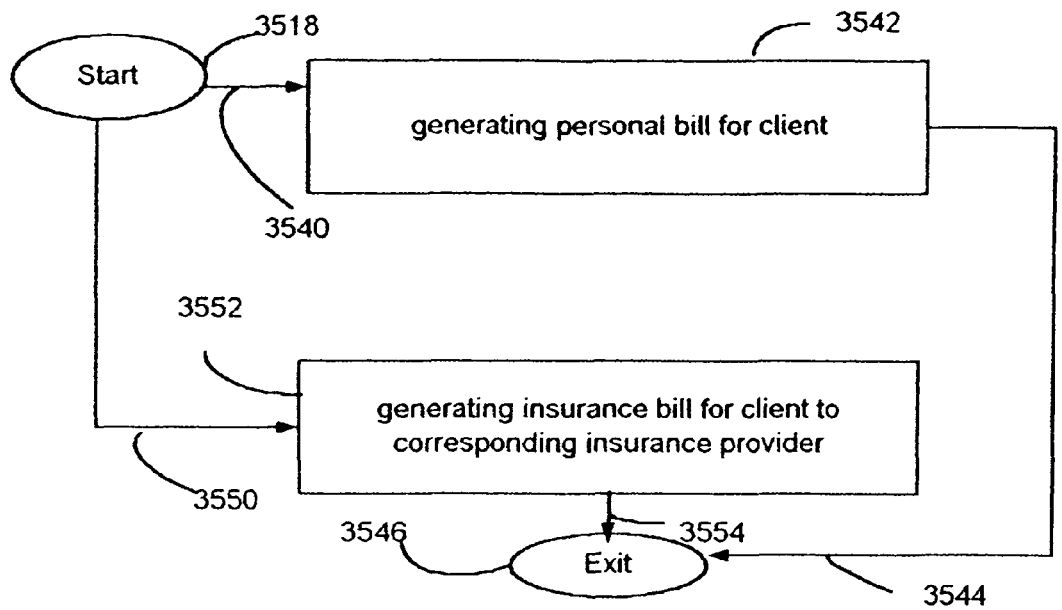
FIG. 87 depicts a flowchart of further details of operation 3518 of FIG. 86.

FIG. 87 depicts a flowchart of further details of operation 3518 of FIG. 86. Arrow 3540 directs the flow of execution from starting operation 3518 to operation 3542. Operation 3542 performs generating a personal bill for the client. Arrow 3544 directs execution from operation 3542 to operation 3546. Operation 3546 terminates the operations of this flowchart.

Arrow 3550 directs the flow of execution from starting operation 3518 to operation 3552. Operation 3552 performs generating an insurance bill for the client to corresponding insurance provider. Arrow 3554 directs execution from operation 3552 to operation 3546. Operation 3546 terminates the operations of this flowchart.

Note that a client may not have insurance, so that in such circumstances, no insurance bills would be generated. Note also, that in certain circumstances, there may be an overall insuring, such as a governmental agency, fully paying for the health costs. In such circumstances, no personal service bill might be generated. In certain alternative embodiments, the performing of these operations might not lead to output of one or the other kinds of service bills.

Figure 88:
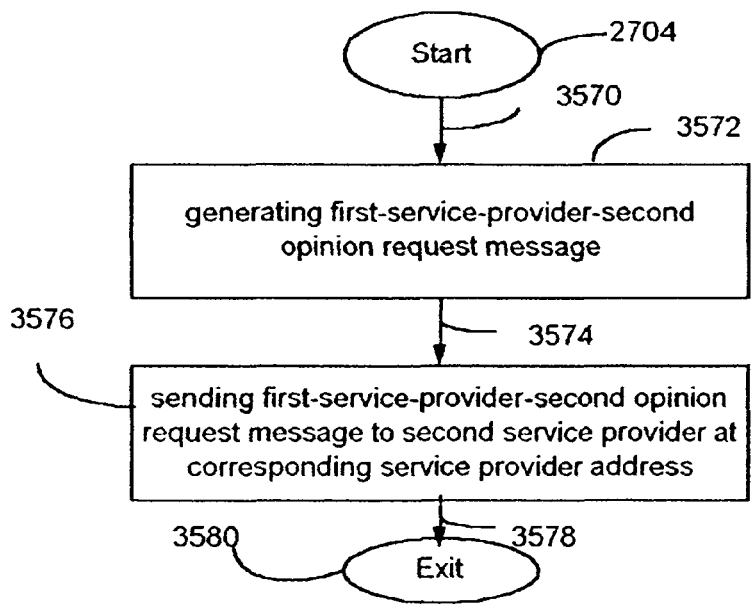
FIG. 88 depicts a flowchart of further details of operation 2704 of FIG. 56 supporting a service provider requesting a second opinion in accordance with certain embodiments.

FIG. 88 depicts a flowchart of further details of operation 2704 of FIG. 56 supporting a service provider requesting a second opinion in accordance with certain embodiments. Arrow 3570 directs the flow of execution from starting operation 2704 to operation 3572. Operation 3572 performs generating a first-service-provider-second opinion request message. Arrow 3574 directs execution from operation 3572 to operation 3576. Operation 3576 performs sending the first-service-provider-second opinion request message to the second service provider at the corresponding service provider address. Arrow 3578 directs execution from operation 3576 to operation 3580. Operation 3580 terminates the operations of this flowchart.

Figure 89:
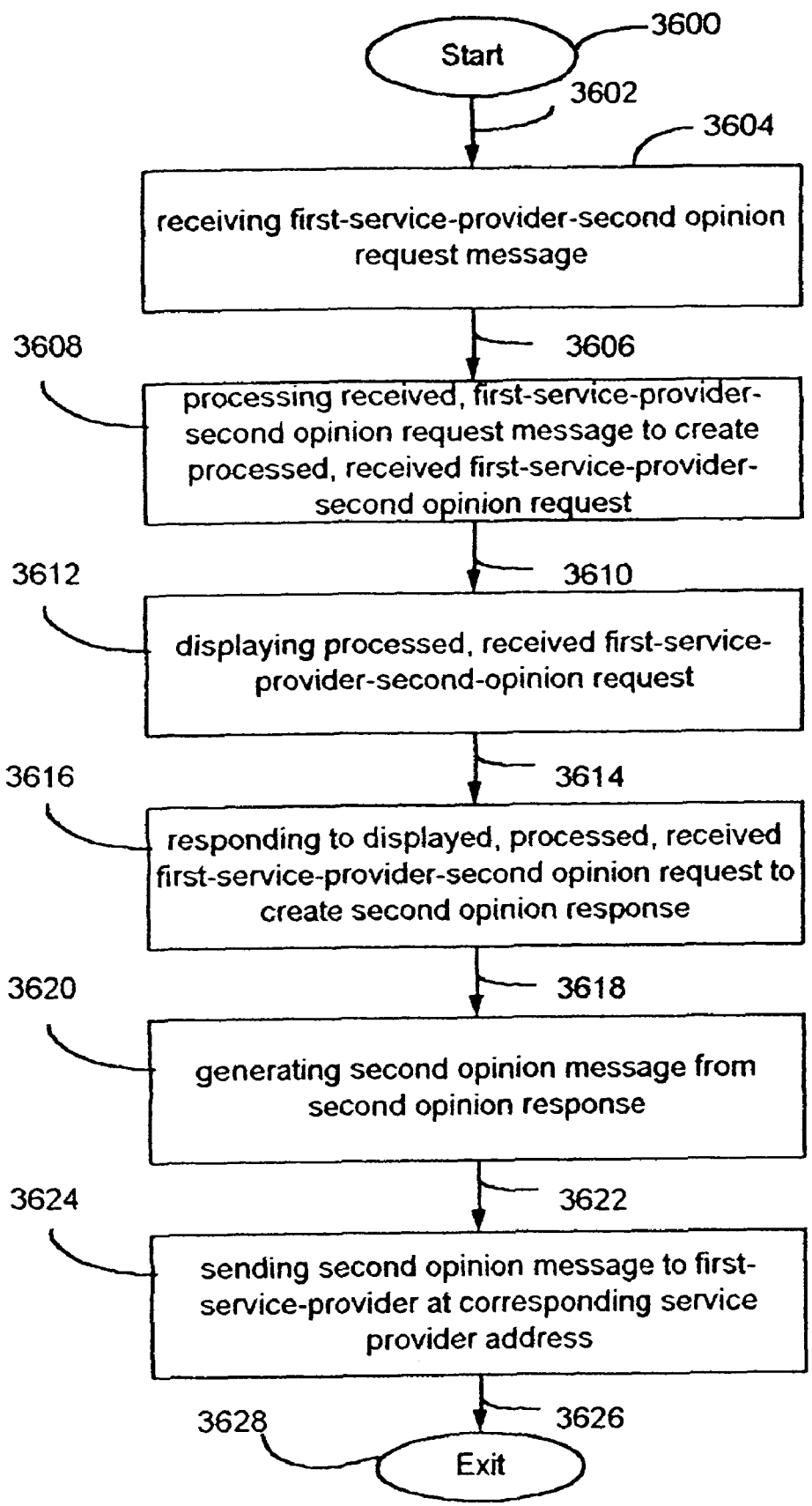
FIG. 89 depicts a flowchart of operations embodied in the second message interface supporting a second service provider and a second opinion request in accordance with certain embodiments.

FIG. 89 depicts a flowchart of operations embodied in the second message interface supporting a second service provider and a second opinion request in accordance with certain embodiments. Operation 3600 starts the operations of this flowchart. Arrow 3602 directs the flow of execution from operation 3600 to operation 3604. Operation 3604 performs receiving the first-service-provider-second opinion request message. Arrow 3606 directs execution from operation 3604 to operation 3608. Operation 3608 performs processing the received, first-service-provider-second opinion request message to create the processed, received first-service-provider-second opinion request. Arrow 3610 directs execution from operation 3608 to operation 3612. Operation 3612 performs displaying the processed, received first-service-provider-second-opinion request. Arrow 3614 directs execution from operation 3612 to operation 3616. Operation 3616 performs responding to the displayed, processed, received first-service-provider-second opinion request to create a second opinion response. Arrow 3618 directs execution from operation 3616 to operation 3620. Operation 3620 performs generating a second opinion message from the second opinion response. Arrow 3622 directs execution from operation 3620 to operation 3624. Operation 3624 performs sending the second opinion message to the first-service-provider at the corresponding service provider address. Arrow 3626 directs execution from operation 3624 to operation 3628. Operation 3628 terminates the operations of this flowchart.

Figure 90:
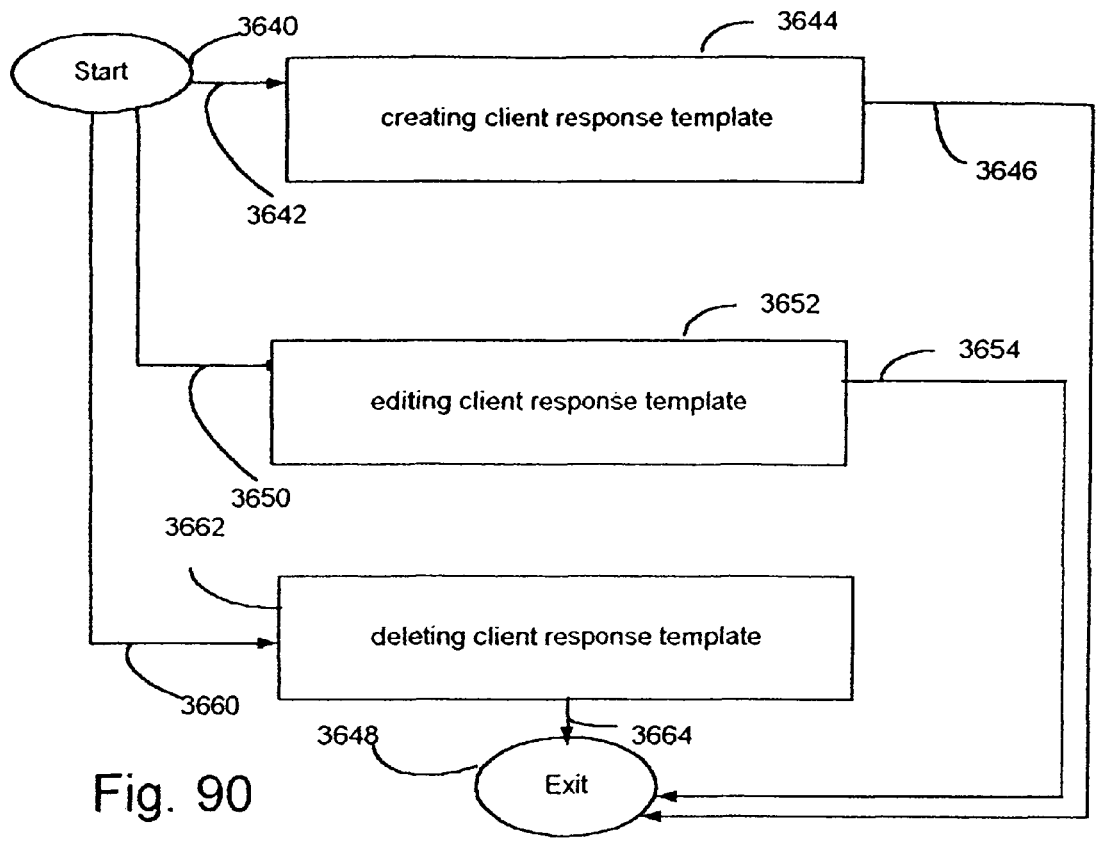
FIG. 90 depicts a flowchart of operations embodied in a second message interface supporting maintaining a collection of client response templates in accordance with certain embodiments.

FIG. 90 depicts a flowchart of operations embodied in a second message interface supporting maintaining a collection of client response templates in accordance with certain embodiments. Operation 3640 starts the operations of this flowchart. Arrow 3642 directs the flow of execution from operation 3640 to operation 3644. Operation 3644 performs creating a client response template. Arrow 3646 directs execution from operation 3644 to operation 3648. Operation 3648 terminates the operations of this flowchart.

Arrow 3650 directs the flow of execution from starting operation 3640 to operation 3652. Operation 3652 performs editing one of the client response templates. Arrow 3654 directs execution from operation 3652 to operation 3648. Operation 3648 terminates the operations of this flowchart.

Arrow 3660 directs the flow of execution from starting operation 3640 to operation 3662. Operation 3662 performs deleting one of the client response templates. Arrow 3664 directs execution from operation 3662 to operation 3648. Operation 3648 terminates the operations of this flowchart.

Note that in certain embodiments, the starting operation may act as a branching mechanism. Such a mechanism can be driven by client choices via a user interface, such as buttons or pull down menus being selected or pushed.

Figure 91:
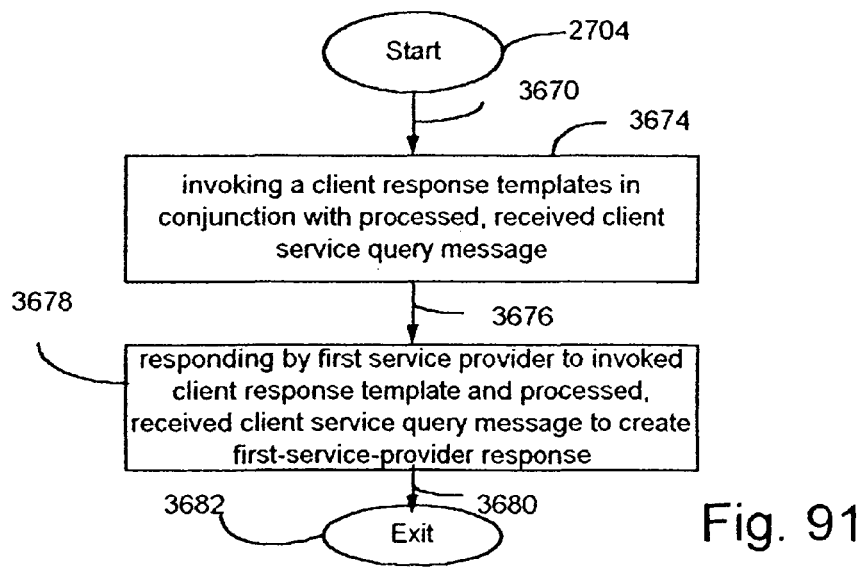
FIG. 91 depicts a flowchart of further details of operation 2704 of FIG. 56 supporting use of a client response template to create a first-service-provider response in accordance with certain embodiments.

FIG. 91 depicts a flowchart of further details of operation 2704 of FIG. 56 supporting use of a client response template to create a first-service-provider response in accordance with certain embodiments. Arrow 3670 directs the flow of execution from starting operation 2704 to operation 3672. Operation 3672 performs invoking one of the client response templates in conjunction with the processed, received client service query message. Arrow 3674 directs execution from operation 3672 to operation 3676. Operation 3676 performs responding by first service provider to invoked client response template and processed, received client service query message to create the first-service-provider response. Arrow 3678 directs execution from operation 3676 to operation 3680. Operation 3680 terminates the operations of this flowchart.

Figure 92:
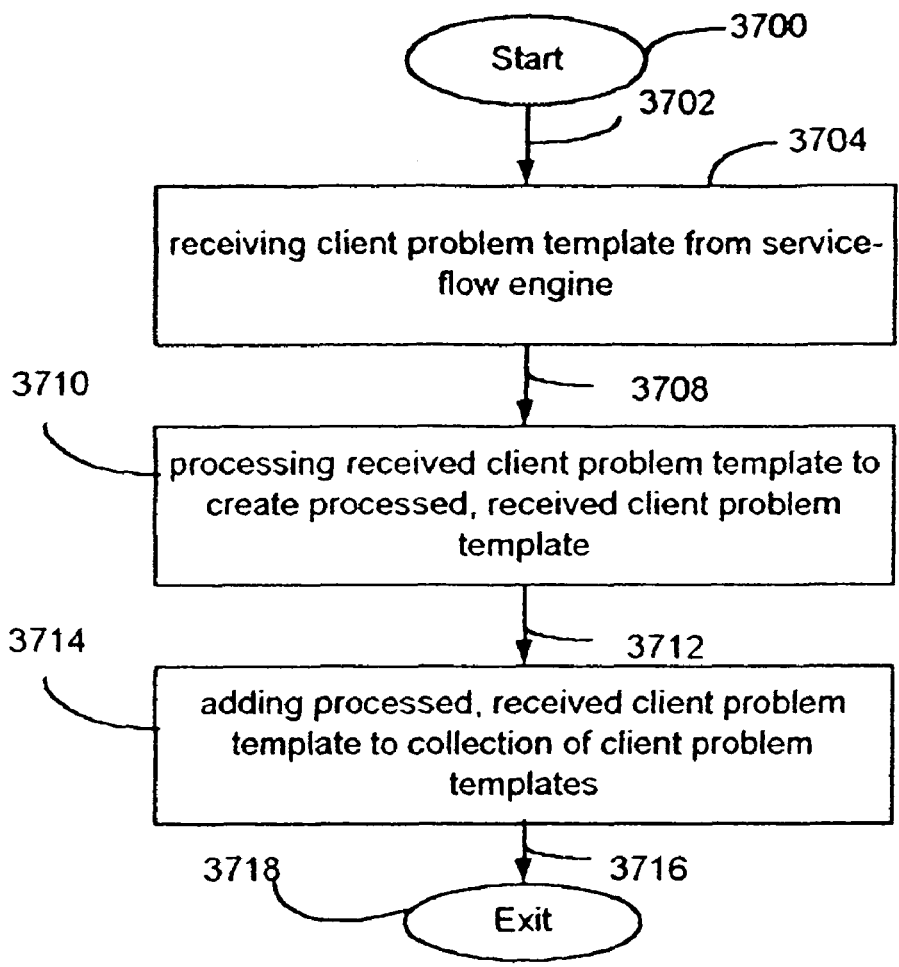
FIG. 92 depicts a flowchart of operations embodied in a first message interface to support maintaining a collection of client problem templates in accordance with certain embodiments.

FIG. 92 depicts a flowchart of operations embodied in a first message interface to support maintaining a collection of client problem templates in accordance with certain embodiments. Operation 3700 starts the operations of this flowchart. Arrow 3702 directs the flow of execution from operation 3700 to operation 3704. Operation 3704 performs receiving the client problem template from service-flow engine. Arrow 3706 directs execution from operation 3704 to operation 3708.

Operation 3708 performs processing the received client problem template to create a processed, received client problem template. Arrow 3710 directs execution from operation 3708 to operation 3712. Operation 3712 performs adding the processed, received client problem template to the collection of client problem templates. Arrow 3714 directs execution from operation 3712 to operation 3716. Operation 3716 terminates the operations of this flowchart.

Figure 93:
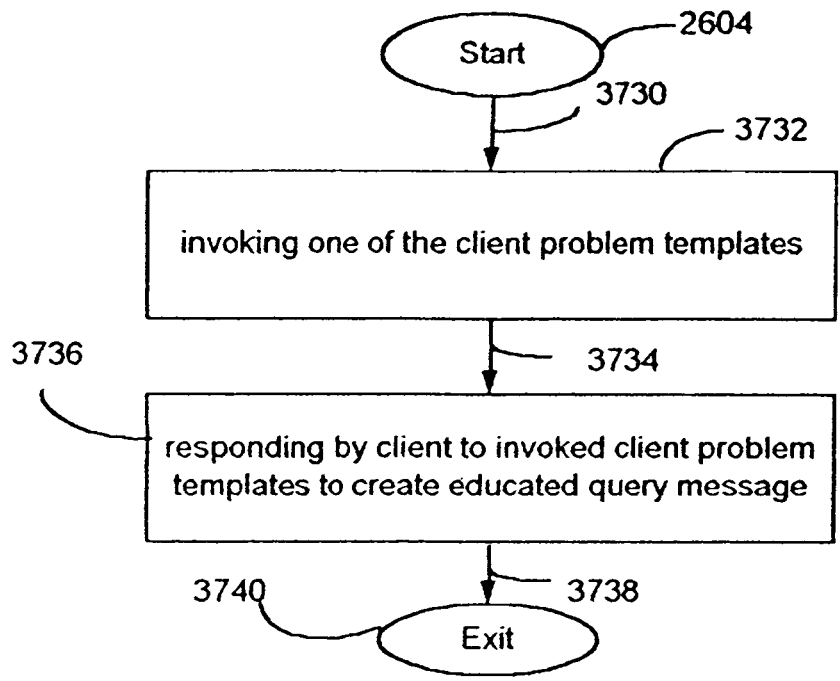
FIG. 93 depicts a flowchart of further details of operation 2604 of FIG. 53 supporting use of a client problem template to create an educated service query using a first service interface in accordance with certain embodiments.

FIG. 93 depicts a flowchart of further details of operation 2604 of FIG. 53 supporting use of a client problem template to create an educated service query using a first service interface in accordance with certain embodiments. Arrow 3730 directs the flow of execution from starting operation 2604 to operation 3732. Operation 3732 performs invoking one of the client problem templates. Arrow 3734 directs execution from operation 3732 to operation 3736. Operation 3736 performs responding by client to invoked client problem templates to create the educated query message. Arrow 3738 directs execution from operation 3736 to operation 3740. Operation 3740 terminates the operations of this flowchart.

Figure 94:
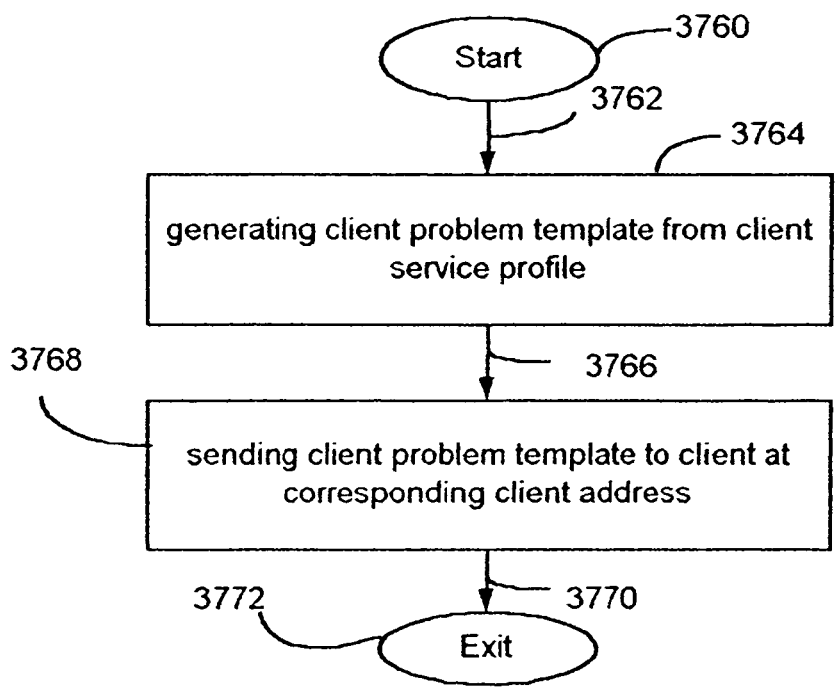
FIG. 94 depicts a flowchart of operations embodied in a service profiler process to generate and send client problem templates to clients in accordance with certain embodiments.

FIG. 94 depicts a flowchart of operations embodied in a service profiler process performed by a service-flow engine to generate and send client problem templates to clients in accordance with certain embodiments. Operation 3760 starts the operations of this flowchart. Arrow 3762 directs the flow of execution from operation 3760 to operation 3764. Operation 3764 performs generating a client problem template from the client service profile. Arrow 3766 directs execution from operation 3764 to operation 3768. Operation 3768 performs sending the client problem template to the client at the corresponding client address. Arrow 3770 directs execution from operation 3768 to operation 3772. Operation 3772 terminates the operations of this flowchart.

Figure 95:
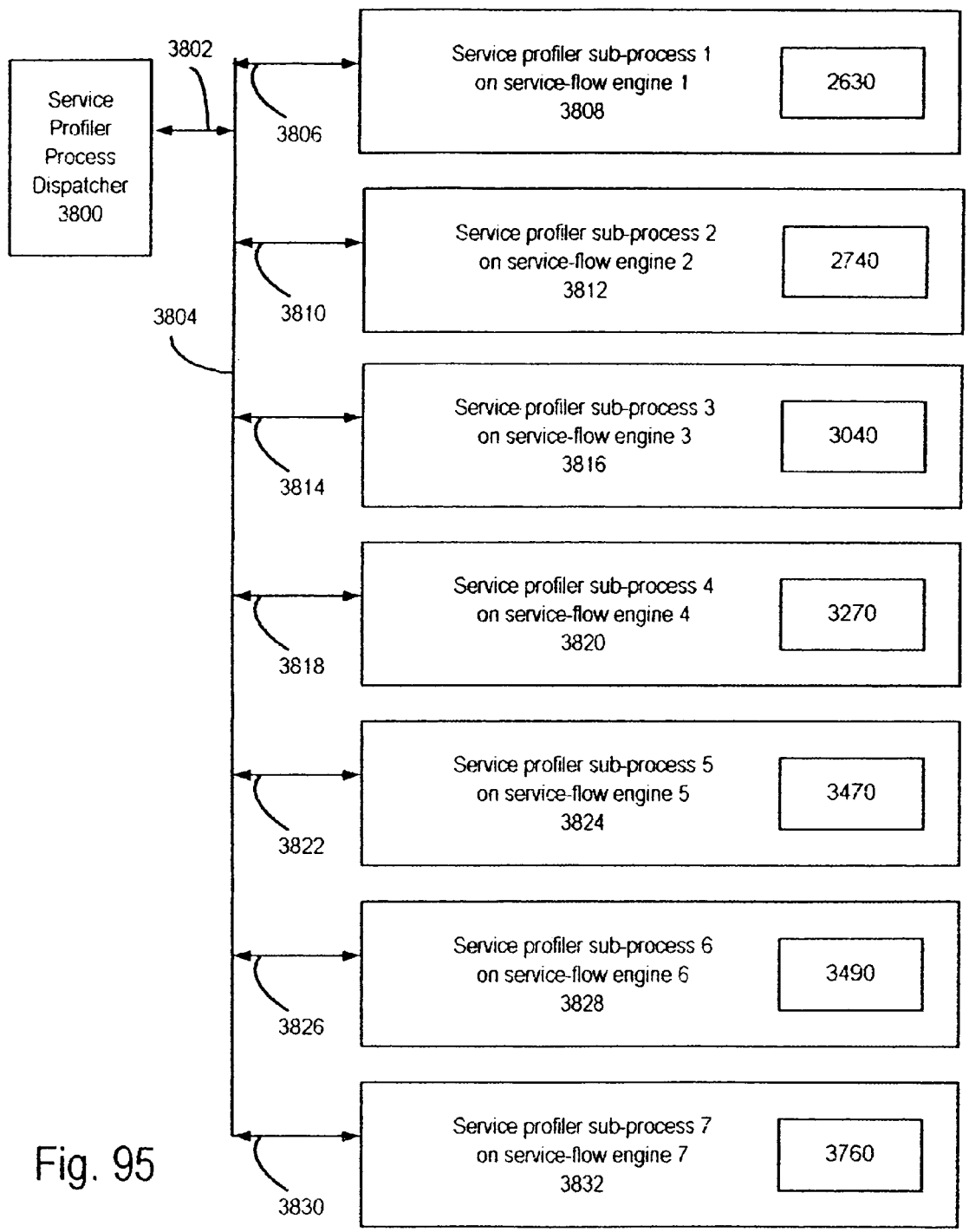
FIG. 95 depicts a flow diagram of a service profiler process in accordance with certain embodiments.

FIG. 95 depicts a flow diagram of a service profiler process in accordance with certain embodiments. Box 3800 designates a Service Profiler Process Dispatcher. This communicates via physical transport mechanism 3802 to network 3804. Box 3808 designates Service profiler sub-process 1 on service-flow engine 1, performing the operation 2630 of FIG. 54. This communicates via physical transport mechanism 3806 to network 3804. Box 3812 designates Service profiler sub-process 2 on service-flow engine 2, performing the operation 2740 of FIG. 57. This communicates via physical transport mechanism 3810 to network 3804. Box 3816 designates Service profiler sub-process 3 on service-flow engine 3, performing the operation 3040 of FIG. 69. This communicates via physical transport mechanism 3814 to network 3804. Box 3820 designates Service profiler sub-process 4 on service-flow engine 4, performing the operation 3270 of FIG. 76. This communicates via physical transport mechanism 3818 to network 3804. Box 3824 designates Service profiler sub-process 5 on service-flow engine 5, performing the operation 3470 of FIG. 84. This communicates via physical transport mechanism 3822 to network 3804. Box 3828 designates Service profiler sub-process 6 on service-flow engine 6, performing the operation 3490 of FIG. 85. This communicates via physical transport mechanism 3826 to network 3804. Box 3832 designates Service profiler sub-process 7 on service-flow engine 7, performing the operation 3760 of FIG. 94. This communicates via physical transport mechanism 3830 to network 3804.

Note that in certain alternative embodiments, collections of these sub-processes may preferably reside on a single service-flow engine. Note that in certain other embodiments, multiple service-flow engines may be performing a given sub-process.

Figure 96:
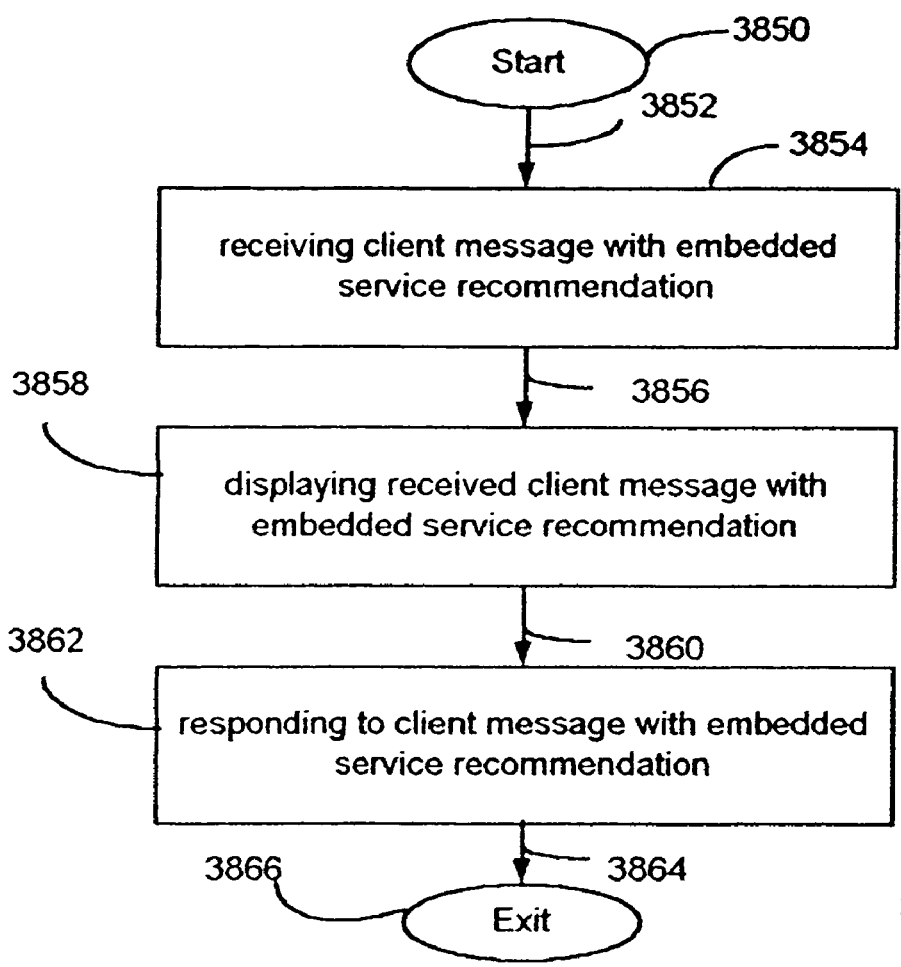
FIG. 96 depicts a flow diagram of a computer program capable of receiving a message from a service provider containing a service recommendation and responding to the message containing the service recommendation by generating and sending a service order message in accordance with certain embodiments in accordance with an aspect of the invention.

FIG. 96 depicts a flow diagram of a computer program capable of receiving a message from a service provider containing a service recommendation and responding to the message containing the service recommendation in accordance with an aspect of the invention. Operation 3850 starts the operations of this flowchart. Arrow 3852 directs the flow of execution from operation 3850 to operation 3854. Operation 3854 performs receiving the client message with an embedded service recommendation. Arrow 3856 directs execution from operation 3854 to operation 3858. Operation 3858 performs displaying the received client message with embedded service recommendation. Arrow 3860 directs execution from operation 3858 to operation 3862. Operation 3862 performs responding to the client message with embedded service recommendation. Arrow 3864 directs execution from operation 3862 to operation 3866. Operation 3866 terminates the operations of this flowchart.

Figure 97:
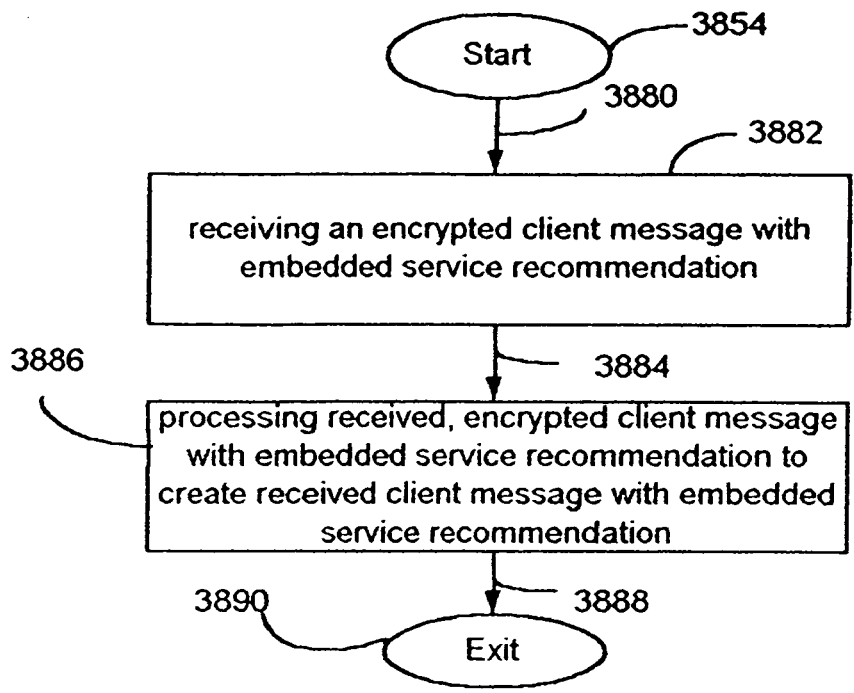
FIG. 97 depicts a flowchart of further details of the code of 3854 of FIG. 96 supporting receiving a client response message with an embedded service recommendation in accordance with certain embodiments.

FIG. 97 depicts a flowchart of further details of the code of 3854 of FIG. 96 supporting receiving a client message with an embedded service recommendation in accordance with certain embodiments. Arrow 3880 directs the flow of execution from starting operation 3854 to operation 3882. Operation 3882 performs receiving an encrypted client message with embedded service recommendation. Arrow 3884 directs execution from operation 3882 to operation 3886. Operation 3886 performs processing the received, encrypted client message with embedded service recommendation to create the received client message with embedded service recommendation. Arrow 3888 directs execution from operation 3886 to operation 3890. Operation 3890 terminates the operations of this flowchart.

Figure 98:
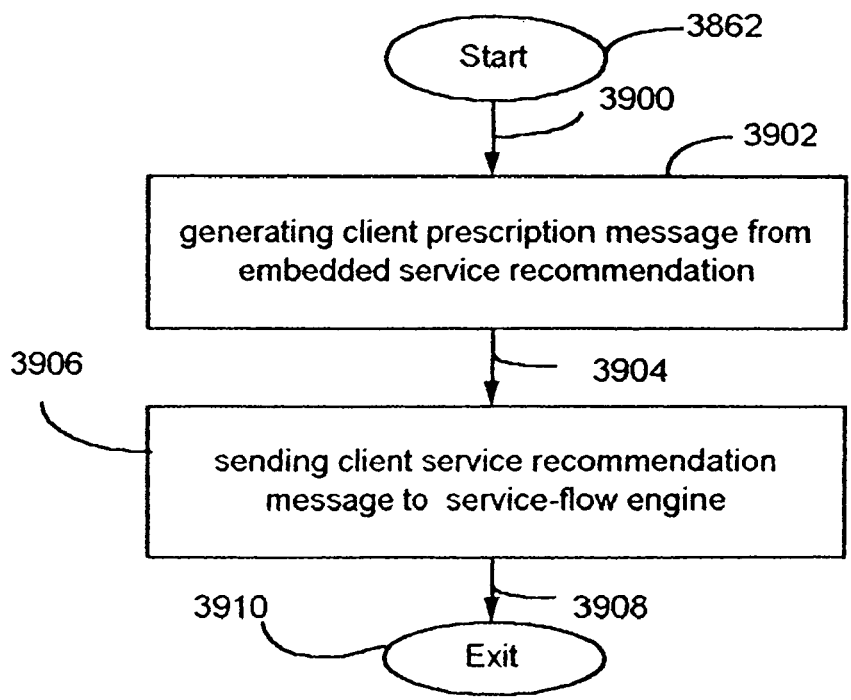
FIG. 98 depicts a flowchart of further details of the code of 3862 of FIG. 96 supporting responding to the client response message in accordance with certain embodiments.

FIG. 98 depicts a flowchart of further details of the code of 3862 of FIG. 96 supporting responding to the client response message in accordance with certain embodiments. Arrow 3900 directs the flow of execution from starting operation 3862 to operation 3902. Operation 3902 performs generating a client service recommendation message from said embedded service recommendation. Arrow 3904 directs execution from operation 3902 to operation 3906. Operation 3906 performs sending said client service recommendation message to said service-flow engine. Arrow 3908 directs execution from operation 3906 to operation 3910. Operation 3910 terminates the operations of this flowchart.

Figure 98A:
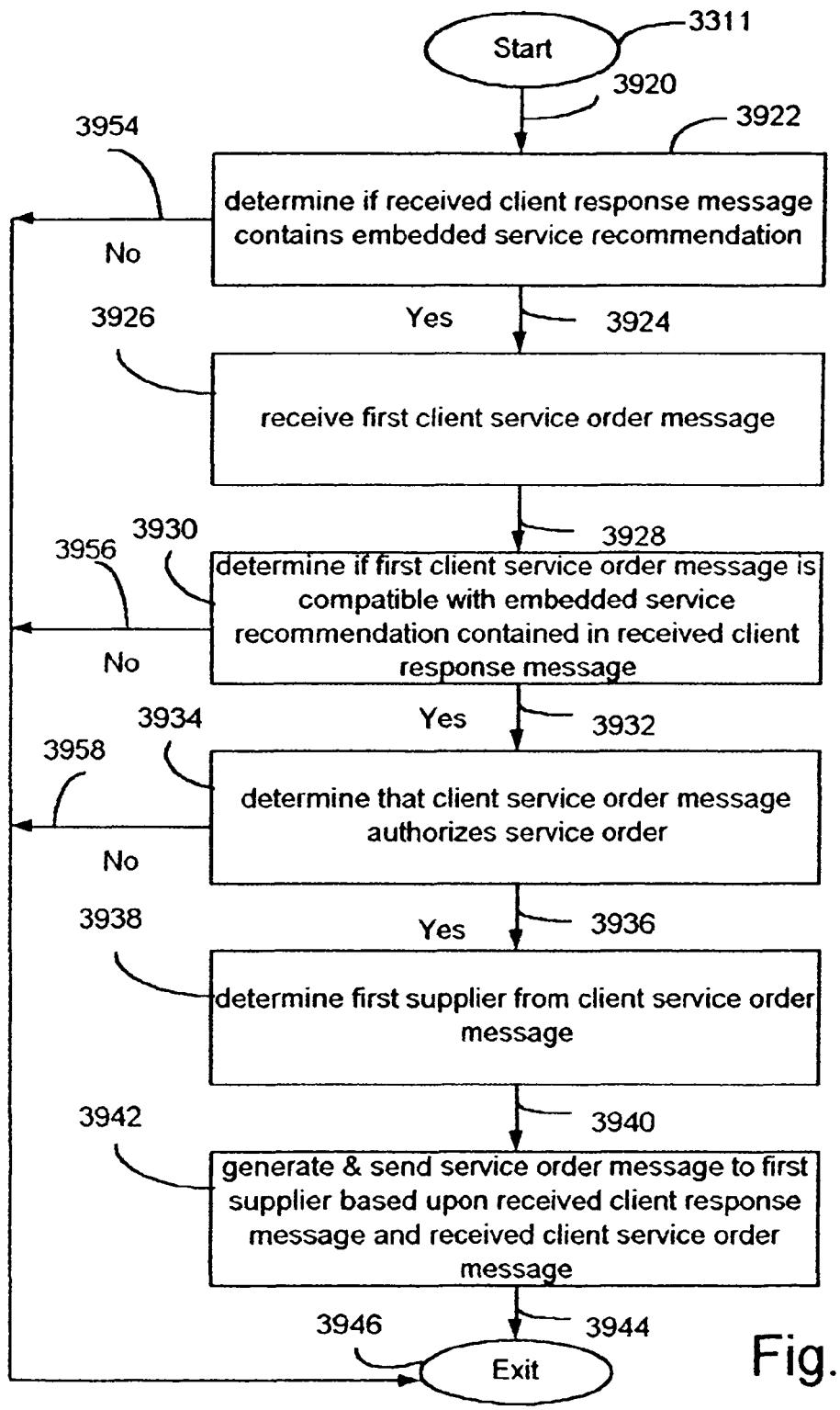
FIG. 98A depicts a flowchart of further details of 3311 of FIG. 78 supporting integrating a service order in accordance with certain embodiments.

FIG. 98A depicts a flowchart of further details of 3311 of FIG. 78 supporting integrating a service order in accordance with certain embodiments.

Arrow 3920 directs the flow of execution from starting operation 3311 to operation 3922. Operation 3922 determines if the received client response message contains an embedded service recommendation. Arrow 3924 directs execution from operation 3922 to operation 3926. Arrow 3924 directs execution when the determination is ☐Yes☐ to operation 3926. Arrow 3954 directs execution when the determination is ☐No☐ to operation 3946.

Operation 3926 performs receiving the client service order message from the first client. Arrow 3928 directs execution from operation 3926 to operation 3930. Operation 3930 determines if the client service order message from the first client is compatible with the embedded service recommendation contained in the received client response message. Arrow 3932 directs execution from operation 3930 to operation 3934. Arrow 3932 directs execution when the determination is ☐Yes☐ to operation 3934. Arrow 3956 directs execution when the determination is ☐No☐ to operation 3946.

Operation 3934 determines if the client service order received from the first client authorizes the service order. Arrow 3936 directs execution from operation 3934 to operation 3938. Arrow 3936 directs execution when the determination is ☐Yes☐ to operation 3938. Arrow 3958 directs execution when the determination is ☐No☐ to operation 3946.

Operation 3938 determines a first pharmacy from the client service order. Arrow 3940 directs execution from operation 3938 to operation 3942. Operation 3942 performs generates and sends the service order message to the first pharmacy based upon the received client response message and the received client service order message. Arrow 3944 directs execution from operation 3942 to operation 3946. Operation 3946 terminates the operations of this flowchart.

Figure 98B:
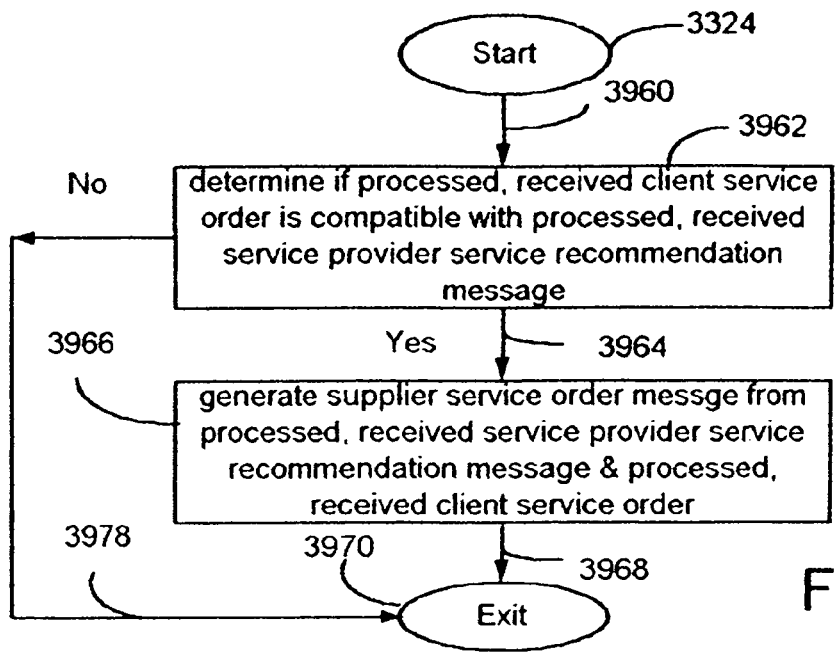
FIG. 98B depicts a flowchart of further details of 3324 of FIG. 78A supporting generating a supplier service order in accordance with certain embodiments.

FIG. 98B depicts a flowchart of further details of 3324 of FIG. 78A supporting generating a pharmacy service order in accordance with certain embodiments.

Arrow 3960 directs the flow of execution from starting operation 1324 to operation 3962. Operation 3962 determines if the processed, received client service order is compatible with the processed, received service provider service recommendation. Arrow 3964 directs execution when the determination is 'Yes' to operation 3966. Arrow 3978 directs usage when the determination is 'No' to operation 3970.

Operation 3966 generates a pharmacy service order message from the processed, received service provider service recommendation message and the processed, received client service order. Arrow 3968 directs execution from operation 3966 to operation 3970. Operation 3970 terminates the operations of this flowchart.

Figure 98C:
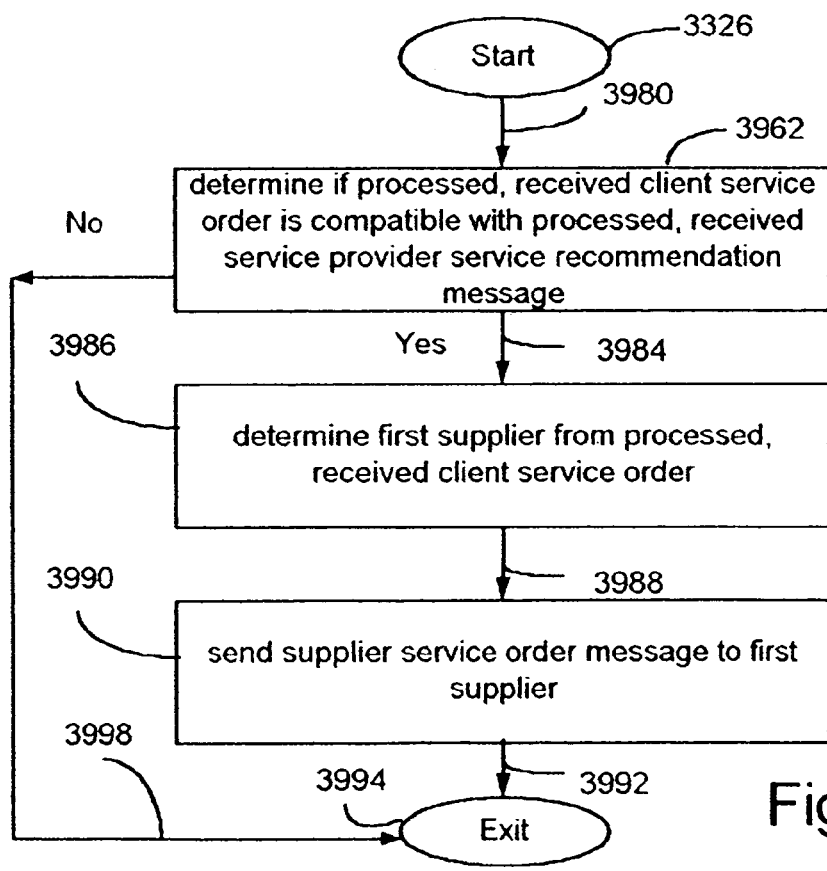
FIG. 98C depicts a flowchart of further details of 3326 of FIG. 78A supporting sending a supplier service order to a supplier in accordance with certain embodiments.

FIG. 98C depicts a flowchart of further details of 3326 of FIG. 78A supporting sending a pharmacy service order to a pharmacy in accordance with certain embodiments.

Arrow 3980 directs the flow of execution from starting operation 3326 to operation 3962. Operation 3962 determines if the processed, received client service order is compatible with the processed, received service provider service recommendation. Arrow 3984 directs execution from operation 3962 to operation 3986. Arrow 3984 directs execution when the determination is ☐Yes☐ to operation 3986. Arrow 3998 directs usage when the determination is ☐No☐ to operation 3994.

Operation 3986 performs determine the first pharmacy from the processed, received client service order. Arrow 3988 directs execution from operation 3986 to operation 3990. Operation 3990 performs sending the pharmacy service order message to the first pharmacy. Arrow 3992 directs execution from operation 3990 to operation 3994. Operation 3994 terminates the operations of this flowchart.

Figure 98D:
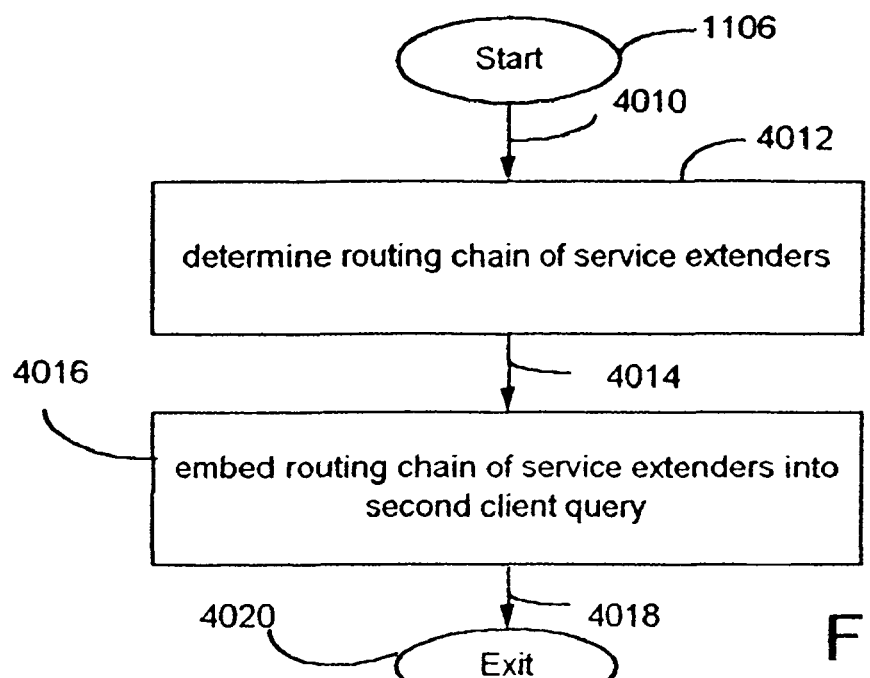
FIG. 98D depicts a flowchart of further details of 3106 of FIG. 71 supporting determining a routing chain of service extenders and embedding the routing chain into a second client query in accordance with certain embodiments.

FIG. 98D depicts a flowchart of further details of 3106 of FIG. 71 supporting determining a routing chain of service extenders and embedding the routing chain into a second client query in accordance with certain embodiments.

Arrow 4010 directs the flow of execution from starting operation 1106 to operation 4012. Operation 4012 determines a routing chain of service extenders. Arrow 4014 directs execution from operation 4012 to operation 4016. Operation 4016 embeds the routing chain of service extenders into the second service query. Arrow 4018 directs execution from operation 4016 to operation 4020. Operation 4020 terminates the operations of this flowchart.

Note that a routing chain of service extenders is a collection of at least one service extender to whom the second client query will be routed after the first service extender has added their proposed response to the client query.

Figure 98E:
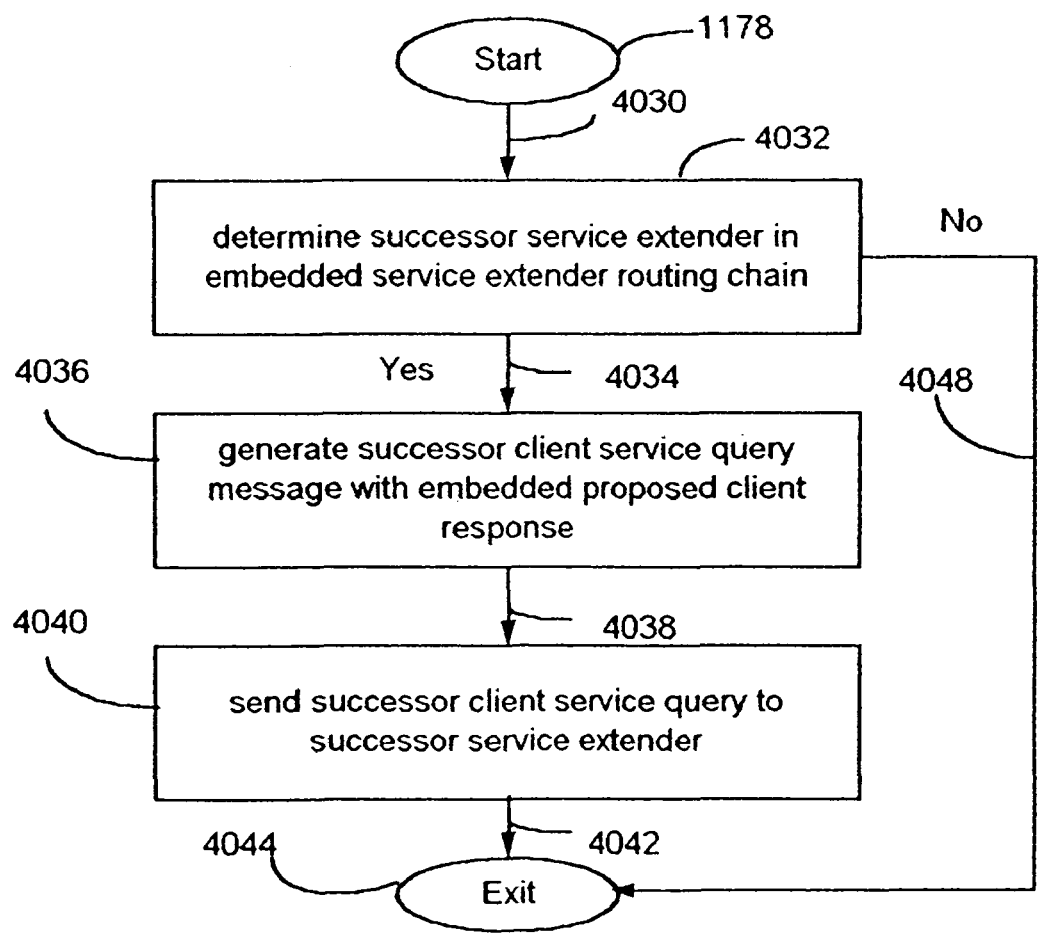
FIG. 98E depicts a flowchart of further details of 3178 of FIG. 72 supporting determining successor service extenders in an embedded service extender routing chain, generating a successor medical query message with embedded proposed client response and sending the successor client medical query to the successor service extender.

FIG. 98E depicts a flowchart of further details of 3178 of FIG. 72 supporting determining successor service extenders in an embedded service extender routing chain, generating a successor service query message with embedded proposed client response and sending the successor client service query to the successor service extender.

Arrow 4030 directs the flow of execution from starting operation 1178 to operation 4032. Operation 4032 determines if there is a successor service extender in the embedded service extender chain. Arrow 4034 directs execution from operation 4032 to operation 4036. Arrow 4034 directs execution when the determination is ☐Yes☐ to operation 4032. Arrow 4048 directs execution when the determination is ☐No☐ to operation 4044.

Operation 4036 generates the successor service query message with the embedded proposed client response. Arrow 4038 directs execution from operation 4036 to operation 4040. Operation 4040 send the successor client service query to the successor service extender. Arrow 4042 directs execution from operation 4040 to operation 4044. Operation 4044 terminates the operations of this flowchart.

Figure 98F:
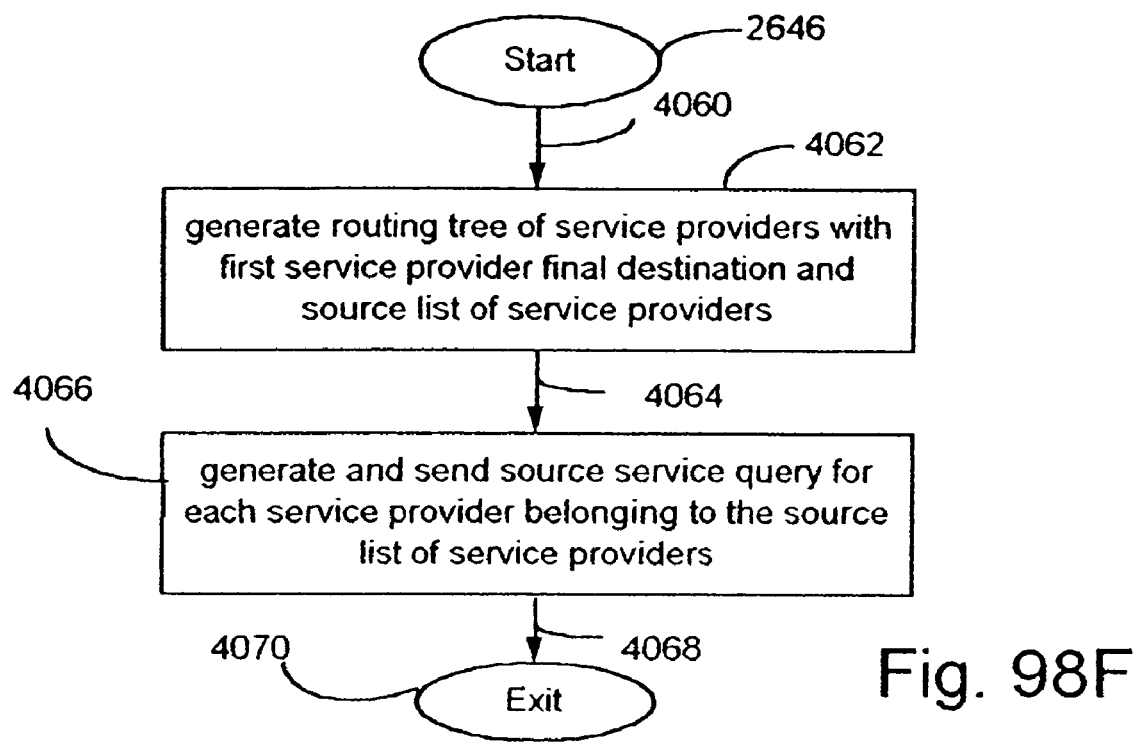
FIG. 98F depicts a flowchart of further details of 2646 of FIG. 53 supporting generating a routing tree of service providers with first service provider final destination and source list of service providers, generating and sending a source medical query to each service provider included in the service provider source list.

FIG. 98F depicts a flowchart of further details of 2646 of FIG. 54 supporting generating a routing tree of service providers with first service provider final destination and source list of service providers, generating and sending a source service query to each service provider included in the service provider source list.

Arrow 4060 directs the flow of execution from starting operation 646 to operation 4062. Operation 4062 performs generating a routing tree of service providers with the first service provider the final destination of the routing tree and a source list of service providers of the routing tree. Arrow 4064 directs execution from operation 4062 to operation 4066. Operation 4066 performs generating and sending a source service query for and to each service provider belonging to the source list of the routing tree. Arrow 4068 directs execution from operation 4066 to operation 4070. Operation 4070 terminates the operations of this flowchart.

This disclosure is provided to reveal a embodiment of the invention and a best mode for practicing the invention. However, one skilled in the art will readily appreciate that other approaches may be substituted for those set forth herein without departing from the spirit and scope of the present invention. Further, additional advantages, applications and modifications of the invention will readily occur to those skilled in the art. Accordingly, the invention should only be limited by the claims included below.

The invention claimed is:

1. A method of messaging upon a network implementing a messaging protocol involving at least one physician, each operating a computer from time to time capable of receiving and sending messages upon said network at a corresponding physician address on said network, at least one patient, each operating a computer from time to time capable of receiving and sending messages upon said network at a corresponding patient address on said network, and a workflow engine accessing said network capable of receiving and sending messages upon said network at least one workflow engine address on said network, and a medical profiler accessing said network with at least one medical profiler address on said network, comprising:

using a first medical message wizard by said patient on said patient operated computer further comprising:
generating a query message;
sending said query message to one of said workflow engine addresses; and
performing a medical profiler process by said workflow engine further comprising
receiving said query message at said workflow engine address;
processing said received query message, to create a processed, received query message;
generating a patient message log entry in a medical profile of said patient from said processed, received query message;
generating a patient medical query message from said processed, received query message;
sending said patient medical query message to a first physician with said corresponding physician address;
using a second medical message wizard by said first physician on said first physician operated computer at said corresponding physician address further comprising:
receiving said patient medical query message;
processing said received patient medical query message, to create a processed, received patient medical query message;
generating a physician-viewable patient medical query message from said processed, received patient medical query message;

displaying said physician-viewable patient medical query message, wherein using said second medical message wizard by said first physician further comprises;
responding to said physician-viewable patient medical query message, to create a first-physician response;
generating a patient response message from said physician-viewable patient medical query message and said first-physician response;
sending said patient response message to said patient at said corresponding patient address;
copying said patient response message with an appended physician billing data to said workflow engine address, and
wherein said medical profiler process further comprises:
receiving said copied patient response message with said appended physician billing data;
processing said received, copied patient response message with said appended physician billing data, generating a processed, received copied patient response message with said appended physician billing data;
generating a patient response log entry in said medical profile of said patient from said processed, received copied patient response message with said appended physician billing data;
using said first message wizard on said patient operated computer at said corresponding patient address further comprises;
receiving said patient response message;
processing said received patient response message to create a processed, received patient response message; and
displaying said processed, received patient response message.

2. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim wherein generating said query message by said first message wizard on said patient operated computer further comprises;
providing patient-to-profiler authentication key; and
encrypting said query message with said patient-to-profiler authentication key; and
wherein processing said received query message by said medical profiler process further comprises;
providing profiler-from-patient authentication key; and
decrypting said received query message with said profiler-from patient authentication key; and
wherein generating said patient medical query message by said medical profiler process further comprises;
providing a profiler-to-first-physician authentication key; and
encrypting said patient medical query message with said profiler-to-first physician authentication key; and
wherein processing said received patient medical query message using said second message wizard further comprises;
providing a first-physician-from-profiler authentication key; and decrypting said received patient medical query message with said first physician-from-profiler authentication key; and
wherein copying said patient response message with an appended physician billing data to said workflow engine address using said second message wizard further comprises;
providing a first-physician-to-profiler authentication key;
encrypting said patient response message with an appended physician billing data with said first-physician-to-profiler authentication key, to create a first-physician-to-profiler encrypted patient response message with an appended physician billing data; and
sending said first-physician-to-profiler encrypted patient response message with an appended physician billing data to said workflow engine as said copied patient response message with an appended physician billing data; and
wherein processing said received, copied patient response message with said appended physician billing data by said medical profiler process further comprises;
providing profiler-from-first-physician authentication key; and
decrypting said received, copied patient response message with said appended physician billing data with said profiler-from-first-physician authentication key, generating said processed, received patient response message with said appended physician billing data.

3. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim 2;
wherein generating said patient response message by said second message wizard on said first physician operated computer further comprises
providing a first-physician-to-patient authentication key;
generating an unencrypted patient response message from said physician viewable patient medical query message and said first-physician response; and
encrypting said unencrypted patient response message with said first physician-to-patient authentication key, to create said patient response message; and
wherein processing said received patient response message using said first message wizard on said patient operated computer further comprises
providing a patient-from-first-physician authentication key; and
decrypting said received patient response message with said patient-from first-physician authentication key, to create said processed, received patient response message.

4. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim 2;
wherein sending said patient response message to said patient at said corresponding patient address using said second message wizard by said first physician further comprises sending a patient response message destined for said patient at said corresponding patient address to said workflow engine address;
wherein generating said patient response message by said second message wizard on said first physician operated computer further comprises
providing a first-physician-to-profiler authentication key;
providing said patient corresponding patient address as a destination address within said patient response message, to create an unencrypted patient response message with said patient corresponding address destination; and encrypting said unencrypted patient response message with said patient corresponding address destination with said first-physician-to-patient authentication key, to create said patient response message destined for said patient at said corresponding patient address; and wherein performing said medical profiler process by said workflow engine further comprises:

receiving said patient response message destined for said patient at said corresponding patient address at said workflow engine address;

processing said received patient response message destined for said patient at said corresponding patient address, to create said processed patient response message for said patient at said corresponding patient address further comprises;

providing a profiler-from-first-physician authentication key; and decrypting said patient response message destined for said patient at said corresponding patient address with said profiler-from-first-physician authentication key, to create processed patient response message for said patient at said corresponding patient address;

sending processed patient response message for said patient at said corresponding patient address to said patient at said corresponding address.

5. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim 2;

wherein there is at least one physician extender operating a computer capable of receiving and sending messages at a corresponding address upon said network; and wherein generating a patient medical query message in said medical profiler process further comprises selecting a first of said physician extenders;

generating a second patient medical query message for said first physician extender; and sending said second patient medical query message to said first physician extender at said corresponding physician extender address; and further comprising using a third medical message wizard by said first physician extender on said first physician extender operated computer further comprising:

receiving said second patient medical query message at said first physician extender corresponding physician extender address;

processing said received second patient medical query message, to create a processed, received second patient medical query message;

generating a physician extender-viewable patient medical query message from said processed, received second patient medical query message;

displaying said physician extender-viewable patient medical query message;

responding to said physician extender-viewable patient medical query message to create a first physician extender response;

generating a proposed patient response message from said physician extender-viewable patient medical query message and said first physician extender response; and sending said proposed patient response message to said first-physician at said corresponding physician address; and generating said physician-viewable patient medical query message using said second message wizard further comprising receiving said proposed patient response message from said first physician extender at said corresponding physician extender address;

processing said received proposed patient response message, to create a processed, received proposed patient response message; and inserting said processed, received proposed patient response message as part of said physician-viewable patient medical query message; and generating said patient response message using said second message wizard further comprising reviewing said proposed patient response message to create said patient response message.

6. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim 5;

wherein at least one of said physician extenders is an administrator.

7. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim 5;

wherein at least one of said physician extenders is a physician assistant.

8. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim 5;

wherein using said third medical message wizard on further comprises:

generating a copied proposed patient response message with an appended physician extender billing data from said physician extender-viewable patient medical query message and said first physician extender response; and sending said copied proposed patient response message sent with an appended physician extender billing data to said workflow engine address; and wherein said medical profiler process further comprises:

receiving said copied proposed patient response message with said appended physician extender billing data;

processing said received copied proposed patient response message with said appended physician extender billing data, to create a processed, received copied proposed patient response message with said appended physician extender billing data; and generating a physician extender log entry in said medical profile of said patient from said processed, received copied patient response message with said appended physician extender billing data.

9. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim 5;
wherein generating said patient response message to said patient address in using said second medical message wizard further comprises:
generating an embedded prescription;
inserting said embedded prescription in said patient response message;
generating a physician prescription message from said embedded prescription;
sending said physician prescription message to said workflow engine;
said medical profiler process performed by said workflow engine further comprising:
integrating a prescription order further comprising:
receiving said physician prescription message;
processing said received physician prescription message to create a processed, received physician prescription message.

10. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim 9
wherein said network further involves at least one pharmacy, each operating a computer from time to time capable of receiving and sending messages upon said network at a corresponding pharmacy address on said network;
wherein generating said patient response message to said patient address in using said second medical message wizard further comprises:
maintaining a list of said pharmacies each with said corresponding pharmacy
address; and
integrating a prescription order further comprising:
receiving a patient prescription order message;
processing said patient prescription message to create a processed, received patient prescription message;
generating a pharmacy prescription order message from said processed, received physician prescription message and said processed, received patient prescription message and said list of said pharmacies; and
sending said pharmacy prescription order message to one of said pharmacies at said corresponding address; and
using said first message wizard on said patient operated computer at said corresponding patient address further comprises:
responding to said patient response message using said first messaging wizard further comprising;
generating a patient prescription message from said embedded prescription; and
sending said patient prescription message to said workflow engine.

11. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim 9
wherein at least one of said physician extenders is a nurse;
wherein generating said proposed patient response message using said third medical message wizard by said nurse further comprises
generating a proposed embedded prescription refill in said proposed patient
response message;
reviewing said proposed patient response message using said second messaging wizard by said first physician further comprises reviewing said proposed embedded prescription refill further comprising at least one of the collection containing;
approving said proposed embedded prescription refill;
revising said proposed embedded prescription refill;
deleting said proposed embedded prescription refill; and
generating a second embedded prescription.

12. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim 5
wherein said third message wizard is implemented as a computer program residing in computer readable media accessible by said physician extender operating said computer.

13. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim
wherein said medical profiler process further comprises generating a billing report from said medical profile of said patient.

14. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim 13
wherein said network further involves a billing system accessing said network at a billing system address on said network; and
wherein said workflow engine process further comprises
sending said billing report from said medical profile of said patient to said billing system address; and
further comprising a billing process performed by said billing system further comprising:
receiving said billing report for said patient sent from said workflow engine process; and
generating a bill for said patient from said received billing report.

15. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim 14
wherein generating said bill for said patient from said received billing report further comprises at least one of the collection comprising:
generating a personal bill for said patient; and
generating at least one insurance bills for said patient to a corresponding insurance provider.

16. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim 15 wherein said corresponding insurance provider includes the United States Government.

17. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim 15 wherein said corresponding insurance provider includes a commercial insurance provider.

18. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim wherein said network involves at least two physicians including a second physician;
wherein responding to said physician-viewable patient medical query message using said second message wizard by said first physician further comprises
generating a first-physician-second opinion request message;
sending said first-physician-second opinion request message to said second physician at said corresponding physician address;
further comprising using said second message wizard by said second physician operating said computer at said corresponding physician address further comprises;
receiving said first-physician-second opinion request message at said second physician corresponding physician address;
processing said received first-physician-second opinion request message, to create a processed, received first-physician-second opinion request;
displaying said processed, received first-physician-second opinion request;
responding to said displayed processed, received first-physician-second opinion request to create a second opinion response;
generating a second opinion message from said second opinion response; and
sending said second opinion message to said first physician at said corresponding physician address.

19. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim
wherein using said second wizard further comprises maintaining a collection of patient response templates, further comprising;
creating one of said patient response templates of said patient response template collection;
editing one of said patient response templates of said patient response template collection;
deleting one of said patient response templates of said patient response template collection,
wherein responding to said patient medical query message using said second wizard further comprises invoking one of said patient response template in conjunction with said processed, received patient medical query message; and
responding to said invoked patient response template and said processed, received patient medical query message to create said first-physician response.

20. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim 1
wherein using said first message wizard further comprises maintaining a collection of patient problem templates, further comprising
receiving a patient problem template from said medical profiler; processing said received patient problem template to create a processed, received patient problem template; and
adding said processed, received patient problem template to said collection of patient problem templates; and
wherein generating an query message using said first message wizard further comprises
invoking one of said patient problem template; and
responding to said invoked patient problem template to generate said query message; and
wherein performing said workflow engine processes further comprises generating a patient problem template from said medical profile of said patient;
sending said generated patient problem template to said patient.

21. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim 1
wherein performing said medical profiler process further comprises maintaining a routing table comprised of at least one routing directive to said first physician;
wherein sending said patient medical query message to a first physician with said corresponding physician address further comprises:
examining said routing table based upon said patient medical query message to find a first of said routing directives to said first physician compatible with said patient medical query message; and finding said first routing directive to said first physician compatible with said patient medical query message.

22. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim 21
wherein maintaining a routing table comprised of at least one routing directive to said first physician comprises;
extracting from said medical profile one of said patients a patient routing extract; and
integrating into the routing table said patient routing extract.

23. A method supporting messaging upon a network implementing a messaging protocol involving at least one physician, each operating a computer at a corresponding physician address on said network, at least one patient, each operating a computer at a corresponding patient address-on said network, and a
medical profiler accessing said network with at least one medical profiler address on said network, as recited in claim 21
wherein maintaining a routing table comprised of at least one routing directive to said first physician comprises;
extracting from said medical profile of at least two of said patients a patient routing pattern;
integrating into the routing table said patient routing pattern.

24. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim 1 wherein said messaging protocol supports email.

25. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim 24 wherein said messaging protocol supports TCPIP.

26. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim 25 wherein said messaging protocol supports the World Wide Web.

27. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim 1 wherein said second message wizard is implemented as a computer program residing on a computer readable medium accessible by said physician operated computer.

28. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim 1 wherein said first message wizard is implemented as a computer program residing on a computer readable medium accessible by said patient operated computer.

29. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim 1
wherein said medical profiler resides on at least one server capable of accessing said network to receive and send messages; and
wherein said workflow engine process is implemented as a program system wherein the various stated operations of said process are implemented as component program which may be concurrently operating.

30. A method supporting messaging upon a network implementing a messaging protocol involving at least one physician, each operating a computer at a corresponding physician address on said network, at least one patient, each operating a computer at a corresponding patient address on said network, and a medical profiler accessing said network with at least one medical profiler address on said network, as recited in claim 29 wherein said workflow engine resides on exactly one server capable of accessing said network to receive and send messages.

31. A method supporting messaging upon a network implementing a messaging
protocol involving at least one physician, each operating a computer at a corresponding physician address on said network, at least one patient, each operating a computer at a corresponding patient address on said network, and a medical profiler accessing said network with at least one medical profiler address on said network, as recited in claim 30;
wherein said medical profiler resides on a first server and a second server coupled to said first server by a second network implementing a second messaging protocol;
wherein said first server capable of accessing said network to receive and send messages and maintaining a firewall to filter all messages received from said network providing at least one of said filtered, received messages from said first network to be received by said second server upon said second network; and
wherein said second server performs at least one of the stated operations of said workflow engine process.

32. A method of messaging upon a network implementing a messaging protocol involving at least one service provider, each operating a computer from time to time capable of receiving and sending messages upon said network at a corresponding service provider address on said network, at least one client, each operating a computer from time to time capable of receiving and sending messages upon said network at a corresponding client address on said network, and a service-flow engine accessing said network capable of receiving and sending messages upon said network at least one service-flow engine address on said network, and a service profiler accessing said network with at least one service profiler address on said network comprising:

using a first service message interface by said client on said client operated computer further comprising:

generating an query message;

sending said query message to one of said service-flow engine addresses; and performing a service profiler process by said service-flow engine further comprising;

receiving said query message at said service-flow engine address;

processing said received query message, to create a processed, received query message;

generating a client message log entry in a service profile of said client from said processed, received query message;

generating a client service query message from said processed, received query message;

sending said client service query message to a first service provider with said corresponding service provider address; and using a second service message interface by said first service provider on said first service provider operated computer at said corresponding service provider address further comprising:

receiving said client service query message;

processing said received client service query message, to create a processed, received client service query message;

generating a service-provider-viewable client service query message from said processed, received client service query message;

displaying said service-provider-viewable client service query message, wherein using said second service message interface by said first service provider further comprises:

responding to said service-provider-viewable client service query message, to create a first-service-provider response;

generating a client response message from said service-provider-viewable client service query message and said first-service-provider response;

sending said client response message to said client at said corresponding client address;

copying said client response message with an appended service provider billing data to said service-flow engine address, and wherein said service profiler process further comprises:

receiving said copied client response message with said appended service provider billing data;

processing said received, copied client response message with said appended service provider billing data, generating a processed, received copied client response message with said appended service provider billing data;

generating a client response log entry in said service profile of said client from said processed, received copied client response message with said appended service provider billing data;

using said first message interface on said client operated computer at said corresponding client address further comprises:

receiving said client response message;

processing said received client response message to create a processed, received client response message; and displaying said processed, received client response message.

33. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 32 wherein generating said query message by said first message interface on said client operated computer further comprises providing client-to-profiler authentication key; and encrypting said query message with said client-to-profiler authentication key; and wherein processing said received query message by said service profiler process further comprises providing profiler-from-client authentication key; and decrypting said received query message with said profiler-from client authentication key; and wherein generating said client service query message by said service profiler process further comprises providing a profiler-to-first-service-provider authentication key; and encrypting said client service query message with said profiler-to-first service provider authentication key; and wherein processing said received client service query message using said second message interface further comprises providing a first-service-provider-from-profiler authentication key; and decrypting said received client service query message with said first service-provider-from-profiler authentication key; and wherein copying said client response message with an appended service provider billing data to said service-flow engine address using said second message interface further comprises providing a first-service-provider-to-profiler authentication key;

encrypting said client response message with an appended service provider billing data with said first-service-provider-to-profiler authentication key, to create a first-service-provider-to-profiler encrypted client response message with an appended service provider billing data; and sending said first-service-provider-to-profiler encrypted client response message with an appended service provider billing data to said service-flow engine as said copied client response message with an appended service provider billing data; and wherein processing said received, copied client response message with said appended service provider billing data by said service profiler process further comprises providing profiler-from-first-service-provider authentication key; and decrypting said received, copied client response message with said appended service provider billing data with said profiler-from-first-service provider authentication key, generating said processed, received client response message with said appended service provider billing data.

34. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 33:

wherein generating said client response message by said second message interface on said first service provider operated computer further comprises
providing a first-service-provider-to-client authentication key;
generating an unencrypted client response message from said service provider
viewable client service query message and said first-service-provider response; and
encrypting said unencrypted client response message with said first service-provider-to-client authentication key, to create said client response message; and
wherein processing said received client response message using said first message interface on said client operated computer further comprises
providing a client-from-first-service-provider authentication key; and
decrypting said received client response message with said client-from first-service-provider authentication key, to create said processed, received client response message.

35. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 33:
wherein sending said client response message to said client at said corresponding client address using said second message interface by said first service provider further comprises sending a client response message destined for said client at said corresponding client address to said service-flow engine address;
wherein generating said client response message by said second message interface on said first service provider operated computer further comprises
providing a first-service-provider-to-profiler authentication key;
providing said client corresponding client address as a destination address within said client response message, to create an unencrypted client response message with said client corresponding address destination; and
encrypting said unencrypted client response message with said client corresponding address destination with said first-service-provider-to-client authentication key, to create said client response message destined for said client at said corresponding client address; and
wherein performing said service profiler process by said service-flow engine further comprises:
receiving said client response message destined for said client at said corresponding client address at said service-flow engine address;
processing said received client response message destined for said client at said corresponding client address, to create said processed client response message for said client at said corresponding client address further comprises
providing a profiler-from-first-service-provider authentication key; and
decrypting said client response message destined for said client at said corresponding client address with said profiler-from-first-service-provider authentication key, to create processed client response message for said client at said corresponding client address;
sending processed client response message for said client at said corresponding client address to said client at said corresponding address.

36. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 33
wherein there is at least one service extender operating a computer capable of receiving and sending messages at a corresponding address upon said network; and
wherein generating a client service query message in said service profiler process further comprises
selecting a first of said service extenders;
generating a second client service query message for said first service provider extender; and
sending said second client service query message to said first service provider
extender at said corresponding service extender address; and
further comprising using a third service message interface by said first service extender on said first service extender operated computer further comprising:
receiving said second client service query message at said first service provider
extender corresponding service extender address;
processing said received second client service query message, to create a processed, received second client service query message;
generating a service extender-viewable client service query message from said processed, received second client service query message;
displaying said service extender-viewable client service query message;
responding to said service extender-viewable client service query message to create a first service extender response;
generating a proposed client response message from said service provider
extender-viewable client service query message and said first service extender response; and
sending said proposed client response message to said first-service-provider at
said corresponding service provider address; and
generating said service-provider-viewable client service query message using said second message interface further comprising
receiving said proposed client response message from said first service provider
extender at said corresponding service extender address;
processing said received proposed client response message, to create a processed, received proposed client response message; and
inserting said processed, received proposed client response message as part of said service-provider-viewable client service query message; and
generating said client response message using said second message interface further comprising reviewing said proposed client response message to create said client response message.

37. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 36;

wherein at least one of said service extenders is an administrator.

38. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 36;

wherein at least one of said service extenders is a service provider assistant.

39. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 36;

wherein using said third service message interface on further comprises:

generating a copied proposed client response message with an appended service extender billing data from said service extender-viewable client service query message and said first service extender response; and sending said copied proposed client response message sent with an appended service extender billing data to said service-flow engine address; and wherein said service profiler process further comprises:

receiving said copied proposed client response message with said appended service extender billing data;

processing said received copied proposed client response message with said appended service extender billing data, to create a processed, received copied proposed client response message with said appended service extender billing data; and generating a service extender log entry in said service profile of said client from said processed, received copied client response message with said appended service extender billing data.

40. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 36;

wherein generating said client response message to said client address in using said second service message interface further comprises:

generating an embedded service recommendation;

inserting said embedded service recommendation in said client response message;

generating a service provider service recommendation message from said embedded service recommendation;

sending said service provider service recommendation message to said service-flow engine;

said service profiler process performed by said service-flow engine further comprising:

integrating a service order further comprising:

receiving said service provider service recommendation message;

processing said received service provider service recommendation message to create a processed, received service provider service recommendation message.

41. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 40;

wherein said network further involves at least one supplier, each operating a computer from time to time capable of receiving and sending messages upon said network at a corresponding supplier address on said network;

wherein generating said client response message to said client address in using said second service message interface further comprises:

maintaining a list of said suppliers each with said corresponding supplier address; and integrating a service order further comprising:

receiving a client order message;

processing said client service recommendation message to create a processed, received client service recommendation message;

generating a supplier service order message from said processed, received service provider service recommendation message and said processed, received client service recommendation message and said list of said suppliers; and sending said supplier service order message to one of said suppliers at said corresponding address; and using said first message interface on said client operated computer at said corresponding client address further comprises:

responding to said client response message using said first messaging interface further comprising:

generating a client service recommendation message from said embedded service recommendation; and sending said client service recommendation message to said service-flow engine.

42. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 40;

wherein at least one of said service extenders is a service assistant;

wherein generating said proposed client response message using said third service message interface by said service assistant further comprises generating a proposed embedded service recommendation refill in said proposed client response message;

reviewing said proposed client response message using said second message interface by said first service provider further comprises reviewing said proposed embedded service recommendation refill further comprising at least one of the collection containing;

approving said proposed embedded service recommendation refill;

revising said proposed embedded service recommendation refill;

deleting said proposed embedded service recommendation refill; and generating a second embedded service recommendation.

43. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 36;

wherein said third message interface is implemented as a computer program residing in computer readable media accessible by said service extender operating said computer.

44. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 32; wherein said service profiler process further comprises generating a billing report from said service profile of said client.

45. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 44;

wherein said network further involves a billing system accessing said network at a billing system address on said network; and wherein said service-flow engine process further comprises sending said billing report from said service profile of said client to said billing system address; and further comprising a billing process performed by said billing system further comprising:

receiving said billing report for said client sent from said service-flow engine process; and generating a bill for said client from said received billing report.

46. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 45;

wherein generating said bill for said client from said received billing report further comprises at least one of the collection comprising:

generating a personal bill for said client; and generating at least one insurance bills for said client to a corresponding insurance provider.

47. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 46 wherein said corresponding insurance provider includes the United States Government.

48. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 46 wherein said corresponding insurance provider includes a commercial insurance provider.

49. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 32;

wherein said network involves at least two service providers including a second service provider;

wherein responding to said service-provider-viewable client service query message using said second message interface by said first service provider further comprises generating a first-service-provider-second opinion request message;

sending said first-service-provider-second opinion request message to said second service provider at said corresponding service provider address;

further comprising using said second message interface by said second service provider operating said computer at said corresponding service provider address further comprises;

receiving said first-service-provider-second opinion request message at said second service provider corresponding service provider address;

processing said received first-service-provider-second opinion request message, to create a processed, received first-service-provider-second opinion request;

displaying said processed, received first-service-provider-second opinion request;

responding to said displayed processed, received first-service-provider-second opinion request to create a second opinion response;

generating a second opinion message from said second opinion response; and sending said second opinion message to said first service provider at said corresponding service provider address.

50. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 32;

wherein using said second message interface further comprises maintaining a collection of client response templates, further comprising;

creating one of said client response templates of said client response template collection;

editing one of said client response templates of said client response template collection;

deleting one of said client response templates of said client response template collection, wherein responding to said client service query message using said second message interface further comprises invoking one of said client response template in conjunction with said processed, received client service query message; and responding to said invoked client response template and said processed, received client service query message to create said first-service-provider response.

51. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 32;

wherein using said first message interface further comprises maintaining a collection of client problem templates, further comprising receiving a client problem template from said service profiler;

processing said received client problem template to create a processed, received client problem template; and adding said processed, received client problem template to said collection of client problem templates; and wherein generating a query message using said first message interface further comprises invoking one of said client problem template; and responding to said invoked client problem template to generate said educated query message; and wherein performing said service-flow engine processes further comprises generating a client problem template from said service profile of said client;

sending said generated client problem template to said client.

52. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 32;

wherein performing said service profiler process further comprises maintaining a routing table comprised of at least one routing directive to said first service provider;

wherein sending said client service query message to a first service provider with said corresponding service provider address further comprises:

examining said routing table based upon said client service query message to find a first of said routing directives to said first service provider compatible with said client service query message; and finding said first routing directive to said first service provider compatible with said client service query message.

53. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 52;

wherein maintaining a routing table comprised of at least one routing directive to said first service provider comprises extracting from said service profile one of said clients a client routing extract;

and integrating into the routing table said client routing extract.

54. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 52;

wherein maintaining a routing table comprised of at least one routing directive to said first service provider comprises extracting from said service profile of at least two of said clients a client routing pattern;

and integrating into the routing table said client routing pattern.

55. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 32 wherein said messaging protocol supports email.

56. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 55 wherein said messaging protocol supports TCPIP.

57. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 56 wherein said messaging protocol supports the World Wide Web.

58. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 32 wherein said second message interface is implemented as a computer program residing on a computer readable medium accessible by said service provider operated computer.

59. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 32 wherein said first message interface is implemented as a computer program residing on a computer readable medium accessible by said client operated computer.

60. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 32;
- wherein said service profiler resides on at least one server capable of accessing said network to receive and send messages; and
- wherein said service-flow engine process is implemented as a program system wherein the various stated operations of said process are implemented as component program which may be concurrently operating.

61. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 60 wherein said service-flow engine resides on exactly one server capable of accessing said network to receive and send messages.

62. A method supporting messaging upon a network implementing a messaging protocol involving at least one service provider, each operating a computer at a corresponding service provider address on said network, at least one client, each operating a computer at a corresponding client address on said network, and a service profiler accessing said network with at least one service profiler address on said network, as recited in claim 61;
- wherein said service profiler resides on a first server and a second server coupled to said first server by a second network implementing a second messaging protocol;
- wherein said first server capable of accessing said network to receive and send messages and maintaining a firewall to filter all messages received from said network providing at least one of said filtered, received messages from said first network to be received by said second server upon said second network; and
- wherein said second server performs at least one of the stated operations of said service-flow engine process.

* * * * *